United States Patent
Zhang et al.

(10) Patent No.: US 11,242,334 B2
(45) Date of Patent: Feb. 8, 2022

(54) HETEROCYCLIC COMPOUNDS AS KINASE INHIBITORS, COMPOSITIONS COMPRISING THE HETEROCYCLIC COMPOUND, AND METHODS OF USE THEREOF

(71) Applicant: JS INNOPHARM (SHANGHAI) LTD, Shanghai (CN)

(72) Inventors: Jintao Zhang, Shanghai (CN); Wen Xu, Shanghai (CN); Shanzhong Jian, Shanghai (CN); Qun Li, Shanghai (CN)

(73) Assignee: JS Innopharm (Shanghai) Ltd., Shanghai (CN)

( * ) Notice: Subject to any disclaimer, the term of this patent is extended or adjusted under 35 U.S.C. 154(b) by 39 days.

(21) Appl. No.: 16/640,813

(22) PCT Filed: Aug. 15, 2018

(86) PCT No.: PCT/CN2018/100685
§ 371 (c)(1),
(2) Date: Feb. 21, 2020

(87) PCT Pub. No.: WO2019/037640
PCT Pub. Date: Feb. 28, 2019

(65) Prior Publication Data
US 2020/0239438 A1    Jul. 30, 2020

(30) Foreign Application Priority Data
Aug. 22, 2017 (CN) .......................... 201710725379.6

(51) Int. Cl.
| | | |
|---|---|---|
| *C07D 401/14* | (2006.01) | |
| *C07D 401/04* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *A61K 45/06* | (2006.01) | |

(52) U.S. Cl.
CPC ......... *C07D 401/14* (2013.01); *C07D 401/04* (2013.01); *C07D 405/14* (2013.01); *C07D 413/14* (2013.01); *C07D 417/14* (2013.01); *C07D 471/04* (2013.01); *A61K 45/06* (2013.01)

(58) Field of Classification Search
CPC .. C07D 401/04; C07D 401/14; C07D 405/14; C07D 413/14; C07D 417/14; C07D 471/04; A61K 45/06
See application file for complete search history.

(56) References Cited

U.S. PATENT DOCUMENTS

2007/0293491 A1* 12/2007 Shafer ................. C07D 403/04
                                                                514/234.5
2014/0031360 A1    1/2014 Wang et al.

FOREIGN PATENT DOCUMENTS

| WO | WO 2005123680 A1 | 12/2005 |
|---|---|---|
| WO | WO 2007048065 A2 | 4/2007 |
| WO | WO 2007/124288 A1 | 11/2007 |
| WO | WO 2007124288 A1 | 11/2007 |
| WO | WO 2008143759 A1 | 11/2008 |
| WO | WO 2009015037 A3 | 1/2009 |
| WO | WO 2013024002 A1 | 2/2013 |
| WO | WO 2013/130976 A1 | 9/2013 |
| WO | WO 2016/026078 A1 | 2/2016 |

OTHER PUBLICATIONS

Crane, E. (2013). The Therapeutic Promise of Anti-Cancer Drugs Against the Ras/Raf/MEK/ERK Pathway. *Topics in Anti-Cancer Research*, vol. 2, pp. 63-94.
International Patent Application No. PCT/CN2018/100685: International Search Report and Written Opinion, dated Nov. 20, 2018 (13 pages).
Adjei, A. (2001). Blocking Oncogenic Ras Signaling for Cancer Therapy. *J. Natl. Cancer Inst.*, 93(14):1062-1074.
Aviel-Ronen, S., et al. (2006). K-ras Mutations in Non-Small-Cell Lung Carcinoma: A Review. *Clin. Lung Cancer*, 8(1):30-38.
Brose, M., et al. (2002). BRAF and RAS Mutations in Human Lung Cancer and Melanoma. *Cancer Res.*, 62(23):6997-7000.
Kolch, W. (2005). Coordinating ERK/MAPK signalling through scaffolds and inhibitors. *Nat. Rev. Mol. Cell Biol.*, 6:827-837.

(Continued)

*Primary Examiner* — D Margaret M Seaman
(74) *Attorney, Agent, or Firm* — Finnegan, Henderson, Farabow, Garrett & Dunner, LLP

(57) ABSTRACT

(I) Disclosed herein are compounds of formula I, and/or a stereoisomer, a stable isotope, or a pharmaceutically acceptable salt thereof; and therapeutic uses of these compounds, which are kinase inhibitors potentially useful in the treatment of diseases treatable, such as cancers, as well as pharmaceutical compositions, comprising a compound of formula I, and/or a stereoisomer, a stable isotope, or a pharmaceutically acceptable salt thereof, and a pharmaceutically acceptable carrier.

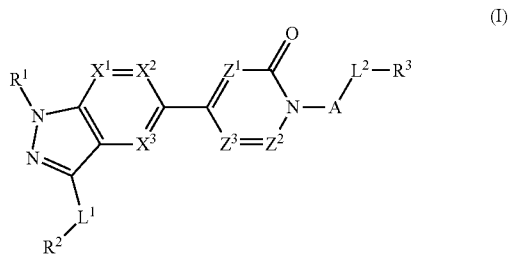

(I)

31 Claims, No Drawings

(56) References Cited

OTHER PUBLICATIONS

Mallon, R., et al. (2004). Identification of 4-anilino-3-quinolinecarbonitrile inhibitors of mitogen-activated protein/extracellular signal-regulated kinase 1 kinase. *Mol. Cancer Ther.*, 3(6):755-762.
Sebolt-Leopold, J. (2004). MEK Inhibitors: A Therapeutic Approach to Targeting the Ras-MAP Kinase Pathway in Tumors. *Curr. Pharm. Des.*, 10(16):1907-1914.
Sebolt-Leopold, J. and Herrera, R. (2004). Targeting the Mitogen-Activated Protein Kinase Cascade to Treat Cancer. *Nat. Rev. Cancer*, 4:937-947.
Sebolt-Leopold, J. (2000). Development of anticancer drugs targeting the MAP kinase pathway. *Oncogene*, 19:6594-6599.
Singer, G., et al. (2003). Mutations in BRAF and KRAS Characterize the Development of Low-Grade Ovarian Serous Carcinoma. *J. Natl. Cancer Inst.*, 95(6):484-486.
Thomas, N. (2006). BRAF somatic mutations in malignant melanoma and melanocytic naevi. *Melanoma Res.*, 16(2):97-103.
Yoon, S. and Seger, R. (2006). The extracellular signal-regulated kinase: Multiple substrates regulate diverse cellular functions. *Growth Factors*, 24(1):21-44.
European Patent Application No. 18848280.6: Extended European Search Report dated Apr. 23, 2021 (9 pages).

\* cited by examiner

HETEROCYCLIC COMPOUNDS AS KINASE INHIBITORS, COMPOSITIONS COMPRISING THE HETEROCYCLIC COMPOUND, AND METHODS OF USE THEREOF

This application is a national stage filing under 35 U.S.C. § 371 of International Application No. PCT/CN2018/100685, filed on Aug. 15, 2018, the content of which is incorporated herein by reference.

BACKGROUND

Disclosed herein are novel heterocyclic compounds that can serve as extracellular signal-regulated kinases (ERK or Erk) inhibitors. Further disclosed herein are pharmaceutical compositions, comprising at least one of such compounds, as well as methods of using at least one of such compounds in treatment of diseases modulated by ERK, such as cancers.

The Ras-Raf-Mek-Erk intracellular signaling cascade is known as a central signaling module that transmits proliferation, survival, growth and differentiation signals into the cell interior from activated receptor tyrosine kinases (RTKs) such as ErbB family, PDGF, FGF, and VEGF (Sebolt-Leopold, J. S. and Herrera, R., *Nat. Rev. Cancer*, 41:937-947, 2004; Kolch, W., *Nat. Rev. Mol. Cell Biol.*, 61:827-837, 2005). This signaling axis includes Ras, Raf, Mek (mitogen-activated protein kinase kinase), and Erk (extracellular signal-regulated kinases) proteins all occurring in highly homologous isoforms. Ras proteins (e.g, H-Ras, N-Ras, and K-Ras) are 21 kDa GTPases that are activated at the proximity sites of the intracellular kinase domains of RTKs. Raf kinases (e.g, RafA, RafB, and RafC) are intermediate downstream effectors of Ras, and activated by binding to GTP-loaded Ras. Raf kinases phosphorylate Meks (Mek1 and Mek2) are on two closely adjacent serine residues, S218 and S222 in the case of Mek1. Meks are dual specificity theroine/tyrosine kinases that phosphorylate threonine and tyrosine residues within the TXY motif of Erks, where T represents threonine, Y represents tyrosine, and X represents any amino acid. Erk proteins (Erk1 and Erk2), also known as MAPKs (mitogen-activated protein kinases), are serine/threonine kinases that phosphorylate more than 100 downstream cytosolic and nuclear target proteins that participate in cellular processes such as division, proliferation, migration, and apoptosis (Yoon, S. and Seger, R., *Growth Factors*, 24:21-44, 2006). These phosphorylations substantially modulate, generally stimulate, the activity of the target proteins and can profoundly alter the physiological status of the cells.

Pathological activation of Ras-Raf-Mek-Erk cascade signaling pathway is known to account for the mechanistic aspects of most human cancers, immune dysfunction, and hyper-inflammatory conditions. Activation of the signaling pathway can occur as the result of autocrine or paracrine production of excessive RTK ligands, or constitutive activation of cell surface receptors by mutation or overexpression, or more commonly through gain-of-function mutations of B-Raf and Ras family members. Oncogenic forms of Ras are reported to be associated with 30% of all human cancers. Mutations in K-Ras occur in 90% of pancreatic cancers and in 25% to 50% of colorectal, mucinous ovarian, and non-small cell lung cancers, whereas mutations in H-Ras are common in bladder, kidney, and thyroid cancers and N-Ras mutations are found in melanoma, hepatocellular carcinoma, and hematologic malignancies (Adjei, A., *J. Natl. Cancer Inst.*, 93:1062-74, 2001; Aviel-Ronen, S., et al, *Clin Lung Cancer*, 8:30-8, 2006). B-Raf mutations occur in 66% to 70% of malignant melanomas, 70% of nonpapillary thyroid cancers, 35% of low-grade ovarian serous tumors as well as a wide range of other cancers including, for example, colorectal, thyroid, lung, breast, and ovarian cancers (Thomas, N., *Melanoma Res*, 16:97-103, 2006; Singer, G., et al, *J. Natl. Cancer Inst.*, 95:484-6, 2003; Brose, M., et al, *Cancer Res.*, 62:6997-7000, 2002).

Inhibition of the activity of Ras-Raf-Mek-Erk signaling pathway has been the focus of drug discovery, particularly for cancer treatment (Sebolt-Leopold, J., *Oncogene*, 19:16564-6599, 2000). Small-molecule inhibitors of B-Raf and Mek have been shown to effectively inhibit Ras and Raf mediated cell transformation, Erk activation and dependent processes, cell proliferation in vitro, and tumor growth in vivo (Mallon, R., et al., *Mol. Cancer Ther.*, 31:755-762, 2004; Sebolt-Leopold, J., *Curr. Pharm. Des.*, 101:1907-1914, 2004; Sebolt-Leopold J. and Herrera, R., *Nat. Rev. Cancer*, 41:937-947, 2004). The demonstration of the clinical efficacy of multiple Raf and Mek small-molecule inhibitors in various types of cancers has provided an ultimate validation of targeting this signaling pathway for cancer treatment (Crane, E. and Wang, K., *Topics Anti-Cancer Res.*, 2:63-94, 2013).

Given Erk proteins' downstream position in the Ras-Raf-Mek-Erk signaling cascade, inhibition of Erks can provide an alternative strategy to modulate down the activity of the pathway. As such, there is a strong rationale to develop Erk small-molecule inhibitors as novel therapeutic agents for a broad spectrum of human cancers originated, for example, from brain, lung, colon, breast, gastric, pancreatic, head and neck, esophageal, renal, kidney, ovarian, skin, prostate, testicular, gynecological or thyroid. In addition, the Erk inhibitors may also be used to treat, for example, non-cancerous hyper-proliferative disorders (e.g., benign hyperplasia of the skin, restenosis, benign prostatic hypertrophy), pancreatitis, kidney disease, pain, diseases related to vasculogenesis or angiogenesis, acute and chronic inflammatory diseases (e.g., rheumatoid arthritis, athero sclerosis, inflammatory bowel disease), skin diseases (e.g., psoriasis, eczema, and scleroderma), diabetes, diabetic retinopathy, retinopathy of prematurity, age-related macular degeneration, asthma, septic shock, T-cell mediated diseases, and chronic obstructive pulmonary disease (COPD).

SUMMARY OF THE DISCLOSURE

Disclosed herein are a series of novel and active ERK kinase inhibitors and methods for their preparation and use thereof. The compounds disclosed herein can have stronge cancer inhibitory effects and can effectively inhibit cancer cells with B-Raf and K-Ras mutations. At the same time, the compounds disclosed herein possess improved drug properties and safety margins compared to known ERK inhibitors.

Disclosed herein are compounds of formula I:

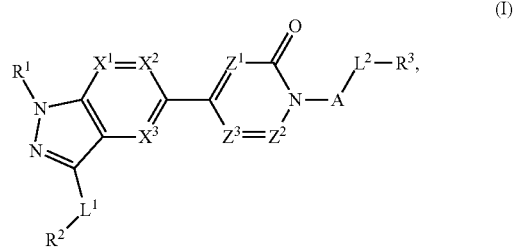

and/or stereoisomers, stable isotopes, or pharmaceutically acceptable salts thereof, wherein $R^1$, $R^2$, $R^3$, A, $L^1$, $L^2$, $X^1$, $X^2$, $X^3$, $Z^1$, $Z^2$ and $Z^3$ are defined below.

$R^1$ is selected from H and C1-C4 alkyl, $R^2$ is selected from H, D, —CN, halo, and an optionally substituted group selected from C1-C6 alkyl, C3-C8 cycloalkyl, C4-8 cycloalkenyl, saturated or unsaturated 4-8 membered heterocyclyl containing 1-2 heteroatoms selected from N, O, and S as ring members, aryl, heteroaryl containing 1-4 heteroatoms selected from N, O, and S as ring members, and wherein the optional substituents for $R^2$ are 1-4 substituents independently selected from D, halo, —OH, =O, —CN, —$N_3$, —$CO_2R^4$, —C(O)N($R^{5a}R^{5b}$), —C(=$NR^6$)N($R^{5a}R^{5b}$), —C(O)$R^4$, —$SO_{0-2}R^7$, —SO(=$NR^6$)$R^7$, —$SO_{1-2}$N($R^{5a}R^{5b}$), —N($R^{5a}R^{5b}$), —N($R^{5a}$)C(O)$R^7$, —N($R^{5a}$)C(=$NR^6$)$R^7$, —N($R^{5a}$)$SO_{1-2}R^7$, —N($R^{5c}$)C(O)N($R^{5a}R^{5b}$), —N($R^{5c}$)C(=$NR^6$)N($R^{5a}R^{5b}$), —N($R^{5c}$)$SO_{1-2}$N($R^{5a}R^{5b}$), —N($R^{5a}$)$CO_2R^7$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, and 4-8 membered heterocyclyl containing 1-2 heteroatoms selected from N, O, and S as ring members, wherein the optional substituents are 1-4 substituents independently selected from D, halo, —$OR^4$, and —N($R^{5c}$)$SO_{1-2}$N($R^{5a}R^{5b}$), wherein $R^4$, $R^{5a}$, $R^{5b}$ and $R^{5c}$ are independently selected from H and C1-C4 alkyl, each of which is optionally substituted with 1-3 groups independently selected from D, halo, —OH, —$NH_2$, —NHMe and —$NMe_2$; $R^6$ is independently selected from H, —CN, —OH, C1-C4 alkyl and C1-C4 alkoxy; $R^7$ is C1-C4 alkyl optionally substituted with 1-3 groups independently selected from D, halo, —OH, —$NH_2$, —NHMe and —$NMe_2$; and two substituents on the same or adjacent carbon atoms of $R^2$ can optionally be taken together to form a 5-6 membered ring that can be saturated or aromatic and optionally contains 1-2 heteroatoms selected from N, O and S and can optionally be substituted with 1-2 groups independently selected from D, -Me, halo, —OH, =O, C1-C4 alkoxy, —$NH_2$, C1-C4 alkylamino and di(C1-C4 alkyl) amino;

$R^3$ is selected from C3-C8 cycloalkyl, 5-8-membered heterocyclyl containing 1-2 heteroatoms selected from N, O, and S as ring members, aryl and heteroaryl containing 1-4 heteroatoms selected from N, O and S as ring members, wherein $R^3$ is optionally substituted with 1-3 substituents selected from D, halo, —OH, =O, —CN, —$N_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —$CO_2R^8$, —C(O)N($R^{9a}R^{9b}$), —C(=$NR^{10}$)N($R^{9a}R^{9b}$), —C(O)$R^8$, —$SO_{0-2}R^{11}$, —SO(=$NR^{10}$)$R^{11}$, —$SO_{1-2}$N($R^{9a}R^{9b}$), —N($R^{9a}R^{9b}$), —N($R^{9a}$)C(O)$R^8$, —N($R^{9a}$)C(=$NR^{10}$)$R^8$, —N($R^{9a}$)$SO_{1-2}R^{11}$, —N($R^{9c}$)C(O)N($R^{9a}R^{9b}$), —N($R^{9c}$)C(=$NR^{10}$)N($R^{9a}R^{9b}$), —N($R^{9c}$)$SO_{1-2}$N($R^{9a}R^{9b}$) and —N($R^{9a}$)$CO_2R^{11}$; wherein $R^8$, $R^{9a}$, $R^{9b}$ and $R^{9c}$ are independently selected from H and C1-C4 alkyl, each of which is optionally substituted with 1-3 groups independently selected from D, halo, —OH, —$NH_2$, —NHMe, —$NMe_2$ and C1-C4 alkoxy; $R^{10}$ is independently selected from H, —CN, —OH, C1-C4 alkyl, and C1-C4 alkoxy; $R^{11}$ is C1-C4 alkyl optionally substituted with 1-3 groups indepently selected from D, halo, —OH, —$NH_2$, —NHMe, —$NMe_2$ and C1-C4 alkoxy;

A is a bond, or can be selected from C1-C4 alkylene, C2-C4 alkenylene, C2-C4 alkynylene, C3-C7 cycloalkyl and 4-7 membered heterocyclyl containing 1-2 heteroatoms selected from N, O, and S as ring members, wherein A is optionally substituted with 1-3 substituents independently selected from D, halo, —OH, =O, —CN, —$N_3$, —$R^{12}$, —$CO_2R^{12}$, —C(O)N($R^{13a}R^{13b}$), —C(=$NR^{14}$)N($R^{13a}R^{13b}$), —C(O)$R^{12}$, —$SO_{0-2}R^{14}$, —SO(=$NR^{15}$)$R^{14}$, —$SO_{1-2}$N($R^{13a}R^{13b}$), —N($R^{13a}R^{13b}$), —N($R^{13a}$)C(O)$R^{12}$, —N($R^{13a}$)C(=$NR^1$)$R^{14}$, —N($R^{13a}$)$SO_{1-2}R^{14}$, —N($R^{13c}$)C(O)N($R^{13a}R^{13b}$), —N($R^{13c}$)C(=$NR^{15}$)N($R^{13a}R^{13b}$), —N($R^{13c}$)$SO_{1-2}$N($R^{13a}R^{13b}$) and —N($R^{13a}$)$CO_2R^{14}$; wherein $R^{14}$ is selected from C1-C4 alkyl optionally substituted with 1-3 groups independently selected from D, halo, —OH, —$NH_2$, —NHMe, —$NMe_2$, —$OPO_3H_2$ and C1-C4 alkoxy; $R^{12}$, $R^{13a}$, $R^{13b}$ and $R^{13c}$ are independently selected from H, C1-C4 alkyl optionally substituted with 1-3 groups independently selected from D, halo, —OH, —$NH_2$, —NHMe, —$NMe_2$, —$OPO_3H_2$ and C1-C4 alkoxy; $R^{15}$ is selected from H, —CN, —OH, C1-C4 alkyl and C1-C4 alkoxy;

$L^1$ and $L^2$ are independently selected from a bond, —N($R^{16}$)—, —O—, —C(O)—, —S(O)$_{0-2}$— and —C($R^{17a}R^{17b}$)—, wherein $R^{16}$, $R^{17a}$, and $R^{17b}$ are independently selected from H and C1-C4 alkyl optionally substituted with 1-3 groups independently selected from D, halo, —OH, —$NH_2$, —NHMe, —$NMe_2$, —$OPO_3H_2$ and C1-C4 alkoxy;

A and $L^2$ can cyclize to form a C5-C7 cycloalkyl ring, a 4-7 membered heterocyclic ring containing 1-2 heteroatoms selected from N, O, and S, phenyl or a 5-6 membered heteroaryl ring containing 1-4 heteroatoms selected from N, O, and S as ring members, wherein the optional ring formed can be optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl, —$CO_2R^{18}$, —CON($R^{19a}R^{19b}$), —$SO_2R^{20}$, —$SO_2$N($R^{19a}R^{19b}$) and —N($R^{19a}R^{19b}$), wherein $R^{18}$, $R^{19a}$ and $R^{19b}$ are independently selected from H and C1-4 alkyl; $R^{20}$ is C1-C4 alkyl;

$X^1$, $X^2$, and $X^3$ are independently selected from N and $CR^{21}$, wherein $R^{21}$ is selected from H, D, halo, —CN, C1-C4 alkyl, C1-C4 haloalkyl, C1-C4 alkoxy and C1-C6 haloalkoxy;

$Z^1$ is selected from N and $CR^{22}$, wherein $R^{22}$ is selected from H, D, —OH, halo, —CN, C1-C4 alkyl, C1-C4 haloalkyl, C1-C4 alkoxy and C1-C6 haloalkoxy;

$Z^2$ is selected from N and $CR^{23}$, wherein $R^{23}$ is selected from H, D, —OH, —CN, C1-C4 alkyl, C1-C4 haloalkyl, C1-C4 alkoxy, C1-C6 haloalkoxy, C3-C8 cycloalkyl, C4-8 cycloalkenyl and saturated and unsaturated 4-8 membered heterocyclyl containing 1-2 heteroatoms selected from N, O, and S as ring members, each of which is optionally substituted with 1-3 groups independently selected from D, halo, —CN, =O, —OH, C1-C4 alkoxy, C1-C4 alkyl, C1-C4 haloalkyl, C1-C4 hydroxyalkyl, C1-C4 haloalkoxy, —$COOR^{24}$, —$SO_2R^{25}$, —N($R^{26a}R^{26b}$), —N($R^{26a}$)C(O)$R^{25}$, —N($R^{26a}$)$SO_2R^{25}$, —N($R^{26a}$)$COOR^{25}$, —CON($R^{26a}R^{26b}$) and —$SO_2$N($R^{26a}R^{26b}$), wherein $R^{24}$, $R^{26a}$ and $R^{26b}$ are independently selected from H and C1-C4 alkyl; $R^{25}$ is C1-C4 alkyl;

$Z^3$ is selected from N and $CR^{27}$, wherein $R^{27}$ is selected from H, D, —OH, halo, —CN, C1-C4 alkyl, C1-C4 haloalkyl, C1-C4 alkoxy and C1-C6 haloalkoxy;

or $R^{23}$ can cyclize with A to form a 5-7 membered heterocyclic ring containing 1-2 heteroatoms selected from N, O, and S, optionally substituted with 1-2 groups independently selected from D, —CN, =O, —OH, C1-C4 alkyl, C1-C4 haloalkyl, C1-C4 alkoxy, C1-C4 haloalkoxy, C1-C4 aminoalkyl, C1-C4 hydroxyalkyl —$CO_2R^{28}$, —CON($R^{29a}R^{29b}$), —$SO_2R^{30}$, —$SO_2$N($R^{29a}R^{29b}$) and —N($R^{29a}R^{29b}$), wherein $R^{28}$, $R^{29a}$ and $R^{29b}$ are independently selected from H and C1-4 alkyl; $R^{30}$ is C1-C4 alkyl;

or $R^{23}$ can cyclize with $R^{27}$ to form a C5-C7 cycloalkyl ring, a 5-7 membered heterocyclic ring containing 1-2 heteroatoms selected from N, O, and S, phenyl or a 5-6 membered heteroaryl containing 1-4 heteroatoms selected from N, O, and S as ring members, wherein the optional ring formed by $R^{23}$ cyclizing with $R^{27}$ can be optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl, —$CO_2R^{31}$, —CON($R^{32a}R^{32b}$), —$SO_2R^{33}$, —$SO_2N$($^{32a}R^{32b}$) and —N($R^{32a}R^{32b}$), wherein $R^{31}$, $R^{32a}$ and $R^{32b}$ are independently selected from H and C1-4 alkyl; $R^{33}$ is C1-C4 alkyl.

Also disclosed herein is a pharmaceutical composition, comprising a compound of formula I and/or a stereoisomer, a stable isotope, or a pharmaceutically acceptable salt thereof disclosed herein and a pharmaceutically acceptable carrier.

Further disclosed herein is a method of inhibiting the activity of Erk comprising contacting the protein Erk with an effective amount of a compound of formula I and/or a stereoisomer, a stable isotope, or a pharmaceutically acceptable salt thereof disclosed herein.

Further disclosed herein is a method of treating a disease treatable by inhibition of Erk in a patient, comprising administering to the patient in recognized need of such treatment, an effective amount of a compound of formula I and/or a stereoisomer, a stable isotope, or a pharmaceutically acceptable salt thereof disclosed herein.

Further disclosed herein is a method of treating a disease treatable by inhibition of Erk in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein, and a pharmaceutically acceptable carrier. In some embodiments, the cancer is colon cancer, gastric cancer, leukemia, lymphoma, melanoma, or pancreatic cancer.

Further disclosed herein is a method of treating an inflammatory disease in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein and a pharmaceutically acceptable carrier. In some embodiments, the inflammatory disease is rheumatoid arthritis, psoriasis, or eczema.

Further disclosed herein is a use of a compound of formula I and/or a stereoisomer, a stable isotope, or a pharmaceutically acceptable salt thereof in preparation of a medication for treating a disease responsive to inhibition of Erk, such as a cancer or an inflammatory disease. In some embodiments, the cancer is colon cancer, gastric cancer, leukemia, lymphoma, melanoma, or pancreatic cancer. In some embodiments, the inflammatory disease is rheumatoid arthritis, psoriasis, or eczema.

Further disclosed herein are compounds of Formula I and the subgenera of Formula I disclosed herein, as well as pharmaceutically acceptable salts of these compounds, and all stereoisomers (including diastereoisomers and enantiomers and enantiomers), and isotopically enriched versions thereof (including deuteroium substitutions). These compounds can be used to treat conditions responsive to ERK inhibition, such as those disclosed herein, and for use in the preparation of a medicament for treating these disorders. The pharmaceutical compositions and methods disclosed herein can also be used with or formulated with a co-therapeutic agent; for example, compounds of formula I and sub-formula thereof can be used with or formulated with at least one agent selected from inhibitors of B-RAF and other therapeutic agents as disclosed herein.

Further disclosed are methods, as well as key intermediate compounds, useful for making the compounds of formula I as disclosed herein.

As used herein, the following words, phrases and symbols are generally intended to have the meanings as set forth below, except to the extent that the context in which they are used indicates otherwise. The following abbreviations and terms have the indicated meanings throughout.

DETAILED DESCRIPTION

The following definitions apply unless otherwise provided or apparent from context:

A dash ("-") that is not between two letters or symbols is used to indicate a point of attachment for a substituent. For example, —$CONR_aR_b$ is attached through the carbon atom.

Unless clearly indicated otherwise, use of the terms "a", "an" and the like refers to one or more.

The term "halogen" or "halo" herein refers to fluorine (F), chlorine (Cl), bromine (Br) or iodine (I). Halogen-substituted groups and moieties, such as alkyl substituted by halogen (haloalkyl) can be mono-, poly-, or per-halogenated. In some embodiments, chloro and fluoro are halo substituents on alkyl or cycloalkyl groups, unless otherwise specified; fluoro, chloro, and bromo are, for example, on aryl or heteroaryl groups, unless otherwise specified.

The term "heteroatoms" or "hetero atoms" as used herein refers to nitrogen (N) or oxygen (O) or sulfur (S) atoms, such as nitrogen or oxygen, unless otherwise specified.

The term "optional" or "optionally" used herein means that the subsequently described event or circumstance may or may not occur, and that the description includes instances where the event or circumstance occurs and instances in which it does not. For example, "alkyl optionally substituted with X" encompasses both "alkyl without substitution of X" and "alkyl substituted with X." It will be understood by those skilled in the art, with respect to any group containing one or more substituents, that such groups are not intended to introduce any substitution or substitution patterns that are sterically impractical, synthetically non-feasible and/or inherently unstable in water at room temperature for at least long enough to be administered as a pharmaceutical agent. When multiple substituents are present, the substituents are selected independently unless otherwise indicated, so where 2 oe 3 substituents are present, for example, those substituents may be the same or different.

In some embodiments, "substituted with at least one group" refers to one hydrogen on the designated atom or group being replaced with one selection from the indicated group of substituents. In some embodiments, "substituted with at least one group" refers to two hydrogens on the designated atom or group being independently replaced with two selections from the indicated group of substituents. In some embodiments, "substituted with at least one group" refers to three hydrogens on the designated atom or group being independently replaced with three selections from the indicated group of substituents. In some embodiments, "substituted with at least one group" refers to four hydrogens on the designated atom or group being independently replaced with four selections from the indicated group of substituents.

The term "alkyl" herein refers to a hydrocarbon group chosen from linear and branched saturated hydrocarbon groups having up to 18 carbon atoms, such as from 1 to 12, further such as from 1 to 8, even further such as from 1 to 6, carbon atoms. Representative examples of alkyl include, but not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octtyl, n-nonyl, n-decyl, and the like.

Unless indicated specifically, alkyl group can be optionally substituted by one or more substituents in place of hydrogen atoms of the unsubstituted alkyl, such as one, two or three substituents, or 1-4 substituents, up to the number of hydrogens present on the unsubstituted alkyl group. Suitable substituents for alkyl groups, if not otherwise specified, may be selected from halogen, D, CN, oxo, hydroxyl, substituted or unsubstituted C1-C4 alkxoy, substituted or unsubstituted C3-C6 cycloalkyl, substituted or unsubstituted 3-7 membered heterocycloalkyl containing 1 or 2 heteroatoms selected from N, O and S as ring members, substituted or unsubstituted aryl, substituted or unsubstituted heteroaryl containing 1 to 4 heteroatoms selected from N, O and S as ring members, amino, —NH(C1-C4 alkyl), —N(C1-C4 alkyl)$_2$, —S(=O)$_{0-2}$(C1-C4 alkyl), —S(=NR)(=O) (C1-C4 alkyl), —C(=O)(C1-C4 alkyl), —C(=NOH)(C1-C4 alkyl), —CO$_2$H, —CO$_2$(C1-C4 alkyl), —S(=O)$_{1-2}$NH$_2$, —S(=O)$_{1-2}$NH(C1-C4 alkyl), —S(=O)$_{1-2}$N(C1-C4 alkyl)$_2$, —CONH$_2$, —C(=O)NH(C1-C4 alkyl), —C(=O)N(C1-C4 alkyl)$_2$, —C(=NOH)NH(C1-C4 alkyl), —OC(=O)(C1-C4 alkyl), —NHC(=O)(C1-C4 alkyl), —NHC(=NOH)(C1-C4 alkyl), —NH(C=O)NH$_2$, —NHC(=O)O (C1-C4 alkyl), —NHC(=O)NH(C1-C4 alkyl), NHC(=NOH)NH(C1-C4 alkyl), —NHS(=O)$_{1-2}$(C1-C4 alkyl), —NHS(=O)$_{1-2}$NH$_2$, and —NHS(=O)$_{1-2}$NH(C1-C4 alkyl); wherein the substituents for substituted C1-C4 alkoxy, substituted C3-C6 cycloalkyl, substituted 3-7 membered heterocycloalkyl, substituted aryl, and substituted heteroaryl are up to three groups independently selected from halogen, D, —CN, C1-C4 alkyl, C1-C4 haloalkyl, oxo, hydroxy, C1-C4 alkoxy, amino, —NH(C1-C4 alkyl), and —N(C1-C4 alkyl)$_2$. In some embodiments, the substituents for alkyl groups, unless otherwise specified, are selected from halogen, CN, oxo, hydroxy, C1-C4 alkoxy, C3-C6 cycloalkyl, phenyl, amino, —NH(C1-C4 alkyl), —N(C1-C4 alkyl)$_2$, C1-C4 alkylthio, C1-C4 alkylsulfonyl, —C(=O)(C1-C4 alkyl), —CO$_2$H, —CO$_2$(C1-C4 alkyl), —OC(=O)(C1-C4 alkyl), —NHC(=O)(C1-C4 alkyl) and —NHC(=O)O(C1-C4 alkyl).

The term "alkoxy" herein refers to a straight or branched alkyl group comprising from 1 to 18 carbon atoms attached through an oxygen bridge such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Typically, alkoxy groups comprise from 1 to 6 carbon atoms, such as 1 to 4 carbon atoms, attached through the oxygen bridge.

Unless indicated specifically, alkoxyl group can be optionally substituted by one or more substituents in place of hydrogen atoms of the unsubstituted alkyl portion of the alkoxyl, such as one, two or three substituents, or 1-4 substituents, up to the number of hydrogens present on the unsubstituted alkoxyl group. Unless otherwise specified, suitable substituents are selected, for example, from the substituents listed above for alkyl groups, except that hydroxyl and amino are not normally present on the carbon that is directly attached to the oxygen of the substituted alkyl-O group.

The term "alkenyl" herein refers to a hydrocarbon group selected from linear and branched hydrocarbon groups, comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, buta-1-enyl, buta-2-enyl, buta-3-enyl, buta-1,3-dienyl, 2-methylbuta-1,3-diene, hex-1-enyl, hex-2-enyl, hex-3-enyl, hex-4-enyl, and hexa-1,3-dienyl groups. The point of attachment can be on the unsaturated carbon or saturated carbon.

Unless indicated specifically, alkenyl group can be optionally substituted by one or more substituents in place of hydrogen atoms of the unsubstituted alkenyl, such as one, two or three substituents, or 1-4 substituents, up to the number of hydrogens present on the unsubstituted alkenyl group. Unless otherwise specified, suitable substituents are selected, for example, from the substituents listed above for alkyl groups.

The term "alkynyl" herein refers to a hydrocarbon group selected from linear and branched hydrocarbon groups, comprising at least one —C≡C— triple bond and from 2 to 18, such as from 2 to 6 carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups. The point of attachment can be on the unsaturated carbon or saturated carbon.

Unless indicated specifically, alkynyl group can be optionally substituted by one or more substituents in place of hydrogen atoms of the unsubstituted alkynyl, such as one, two or three substituents, or 1-4 substituents, up to the number of hydrogens present on the unsubstituted alkynyl group. Unless otherwise specified, suitable substituents are selected, for example, from the substituents listed above for alkyl groups.

The term "alkylene" refers to a divalent alkyl group comprising from 1 to 10 carbon atoms, and two open valences to attach to other molecular components. The two molecular components attached to an alkylene can be on the same carbon atom or on different carbon atoms; thus for example propylene is a 3-carbon alkylene that can be 1,1-disubstituted, 1,2-disubstituted or 1,3-disubstituted. Unless otherwise specified, alkylene refers to moieties comprising from 1 to 6 carbon atoms, such as from 1 to 4 carbon atoms. Examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable substituents are selected, for example, from the substituents listed above for alkyl groups.

Unless indicated specifically, alkylenyl group can be optionally substituted by one or more substituents in place of hydrogen atoms of the unsubstituted alkylenyl, such as one, two or three substituents, or 1-4 substituents, up to the number of hydrogens present on the unsubstituted alkylenyl group. Unless otherwise specified, suitable substituents are selected, for example, from the substituents listed above for alkyl groups.

Similarly, "alkenylene" and "alkynylene" refer to alkylene groups comprising a double bond or a triple bond, respectively; they are, for example, 2-6 and such as 2-4 carbon atoms in length, and can be substituted as discussed above for alkylene groups.

The term "haloalkyl" refers to an alkyl as defined herein, which is substituted by one or more halo groups as defined herein. Unless otherwise specified, the alkyl portion of the haloalkyl comprises 1-4 carbon atoms. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. The polyhaloalkyl comprises, for example, up to 6, or 4, or 3, or 2 halo groups. Examples of haloalkyl include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. In some embodiments, the haloalkyl groups, unless specified otherwise, include monofluoro-, difluoro- and trifluoro-substituted methyl and ethyl groups, e.g. —$CF_3$, —$CF_2H$, —$CFH_2$ and —$CH_2CF_3$.

Unless indicated specifically, haloalkyl group can be optionally substituted by one or more substituents in place of hydrogen atoms of the unsubstituted haloalkyl, such as one, two or three substituents, or 1-4 substituents, up to the number of hydrogens present on the unsubstituted haloalkyl group. Unless otherwise specified, suitable substituents are selected, for example, from the substituents listed above for alkyl groups.

As used herein, the term "haloalkoxy" refers to haloalkyl-O—, wherein haloalkyl is defined above. Examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. In some embodiments, haloalkyloxy groups comprise 1-4 carbon atoms, and up to three halogens, e.g., monofluoro, difluoro and trifluoro substituted methoxy groups and ethoxy groups.

Unless indicated specifically, haloalkoxyl group can be optionally substituted by one or more substituents in place of hydrogen atoms of the unsubstituted alkyl portion of the haloalkoxyl, such as one, two or three substituents, or 1-4 substituents, up to the number of hydrogens present on the unsubstituted haloalkoxyl group. Unless otherwise specified, suitable substituents are selected, for example, from the substituents listed above for alkyl groups, except that hydroxyl and amino are not normally present on the carbon that is directly attached to the oxygen of the substituted haloalkyl-O group.

The term "cycloalkyl" herein refers to a hydrocarbon group selected from saturated and partially unsaturated cyclic hydrocarbon groups comprising from 3 to 20 carbon atoms, such as monocyclic and polycyclic (e.g., bicyclic and tricyclic, admantanyl and spirocycloalkly) groups. Monocycloalkyl groups are cyclic hydrocarbon groups comprising from 3 to 20 carbon atoms, such as from 3 to 8 carbon atoms. Examples of monocyclic cycloalkyl include, but are not limited to, cyclopropyl, cyclobutyl, cyclopentyl, cyclohexyl, cycloheptyl, cyclooctyl, cyclodecanyl, cyclododecanyl, and cyclohexenyl; Bicycloalkyl groups include bridged bicycloalkyl, fused bicycloalkyl and spirocycloalkyls. Bridged bicycloalkyl contains a monocyclic cycloalkyl ring where two non-adjacent carbon atoms of the monocyclic ring are linked by an alkylene bridge of one to three additional carbon atoms (i.e. a bridging group of the form —(CH2)n-, wherein n is 1, 2, or 3). Examples of bridged bicycloalkyl include, but are not limited to, bicyclo[2.2.1]heptenes, bicyclo[3.1.1]heptanes, bicyclo[2.2.1]heptanes, bicyclo[2.2.2]octane, bicyclo[3.2.2]nonane, bicyclo[3.3.1]nonane, and bicycle[4.2.1]nonane. Fused bicycloalkyl contains a monocyclic cycloalkyl ring fused to either a phenyl, a monocyclic cycloalkyl, or a monocyclic heteroaryl. Examples of fused bicycloalkyl include, but are not limited to, bicyclo[4.2.0]octa-1,3,5-triene, 2,3-dihydro-1H-indene, 6,7-dihydro-5H-cyclopenta[b]pyridine, 5,6-dihydro-4H-cyclopenta[b]thiophene, and decahydronaphthalene. Spirocycloalkyl contains two monocyclic ring systems that share a carbon atom forming a biclyclic ring system. Examples of spirocycloalkyls include, but are not limited to,

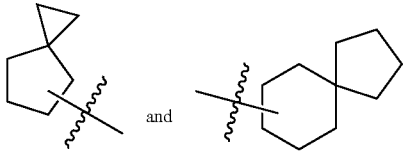

Bicyclic cycloalkyl groups comprise, for example, from 7 to 12 carbon atoms. Monocycloalkyl or bicycloalkyl is attached to the parent molecular moiety through any carbon atom contained within the cycloalkyl ring. Tricycloalkyl groups include bridged tricycloalkyl as used herein referring to 1) a bridged bicycloalkyl ring where two non-adjacent carbon atoms of the bridged bicycloalkyl ring are linked by an alkylene bridge of one to three additional carbon atoms (i.e. a bridging group of the form —$(CH_2)n$-, wherein n is 1, 2, or 3), or 2) a fused bicycloalkyl ring where two unshared ring atoms on each ring are linked by an alkylene bridge of one to three additional carbon atoms (i.e. a bridging group of the form —$(CH_2)n$-, wherein n is 1, 2, or 3), wherein "a fused bicycloalkyl ring" refers to a monocycloalkyl ring fused to a monocycloalkyl ring. Examples of bridged tricycloalkyl groups include, but are not limited to, admantanyl

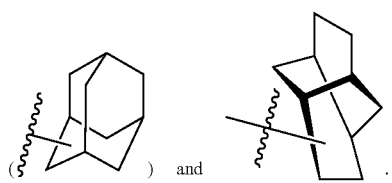

Bridged tricycloalkyl, as used hererin, is appended to the parent molecular moiety through any ring atom. The ring atom disclosed herein refers to the carbon atom on the ring skeleton. The cycloalkyl may be saturated or comprise at least one double bond (i.e. partially unsaturated), but is not fully conjugated, and is not aromatic, as aromatic is defined herein. The cycloalkyl may be substituted with at least one hetero atom selected, for example, from O, S, and N.

Unless indicated specifically, cycloalkyl group can be optionally substituted by one or more substituents in place of hydrogen atoms of the unsubstituted cycloalkyl, such as one, two or three substituents, or 1-4 substituents, up to the number of hydrogens present on the unsubstituted cycloalkyl group. In some embodiments, a substituted cycloalkyl comprises 1-4 such as 1-2 substituents. Unless otherwise specified, suitable substituents are selected, for example, from the substituents listed above for alkyl groups.

The term "heterocycloalkyl," "heterocyclyl," or "heterocyclic" disclosed herein refers to "cycloalkyl" as defined above with at least one ring carbon atom being replaced by a heteroatom independently selected from O, N, and S. Heterocyclyl comprises, for example, 1, 2, 3, or 4 heteroatoms, and the N, C or S can independently be oxidized in the cyclic ring system. The N atom can further be substituted to form tertiary amine or ammonium salts. The point of attachment of heterocyclyl can be on the heteroatom or carbon. "Heterocyclyl" herein also refers to a 5- to 7-membered saturated or partially unsaturated carbocyclic ring comprising at least one heteroatom selected, for example, from N, O, and S (heterocyclic ring) fused with 5-, 6-, and/or 7-membered cycloalkyl, heterocyclic or carbocyclic aromatic ring, provided that the point of attachment is at the heterocyclic ring when the heterocyclic ring is fused with a carbocyclic aromatic ring, and that the point of attachment can be at the cycloalkyl or heterocyclic ring when the heterocylic ring is fused with cycloalkyl. "Heterocyclyl" herein also refers to an aliphatic spirocyclic ring comprising at least one heteroatom selected, for example, from N, O, and S. The rings may be saturated or have at least one double bond (i.e. partially unsaturated). The heterocyclyl may be substituted with, for example, oxo. The point of the attachment may be carbon or heteroatom. A heterocyclyl is not a heteroaryl as defined herein.

Examples of the heterocycle include, but are not limited to, pyrrolidinyl, imidazolidinyl, pyrazolidinyl, piperidinyl, piperidinyl, piperazinyl, pyranyl, morpholinyl, oxiranyl, aziridinyl, thiiranyl, azetidinyl, oxetanyl, thietanyl, dithietanyl, dihydropyridinyl, tetrahydropyridinyl, thiomorpholinyl, thioxanyl, homopiperazinyl, homopiperidinyl, azepanyl, oxepanyl, thiepanyl, oxathianyl, dioxepanyl, oxathiepanyl, oxaazepanyldithiepanyl, thiazepanyl and diazepane, dithianyl, azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, indolinyl, dioxanyl, pyrazolinyl, dithianyl, dithiolanyl, pyrazolidinylimidazolinyl, pyrimidinonyl, 1,1-dioxo-thiomorpholinyl, 3-azabicyclo[3.1.0]hexanyl, 3-azabicyclo[4.1.0]heptanyl and azabicyclo[2.2.2]hexanyl. Substituted heterocycles also include ring systems substituted with one or more oxo moieties, such ac piperidinyl N-oxide morpholinyl-N-oxide 1-oxo-1-thiomorpholinyl 1,1-dioxo-1-thiomorpholinyl,

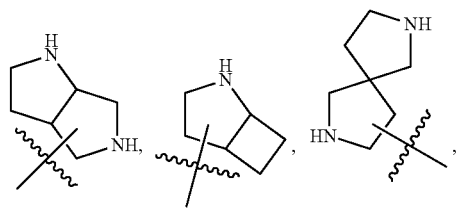

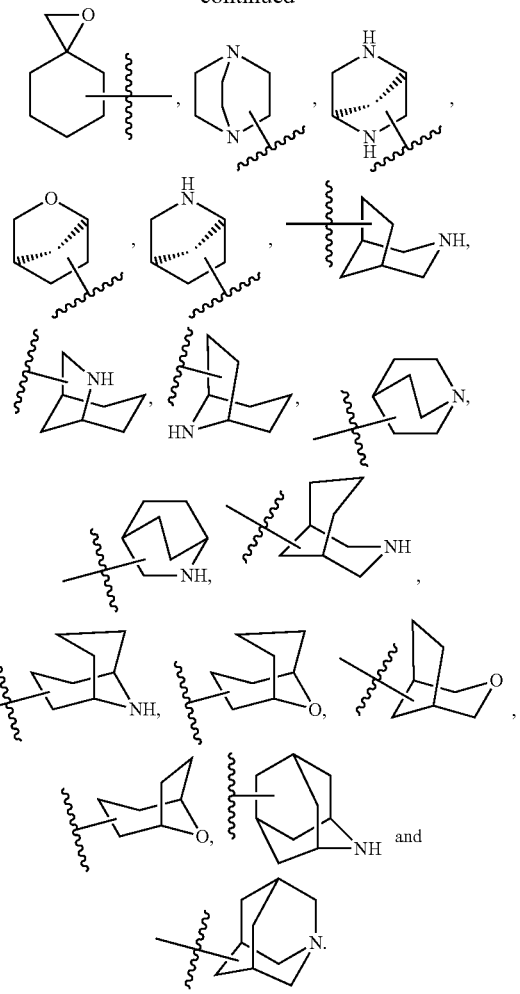

Unless indicated specifically, heterocyclyl group can be optionally substituted by one or more substituents in place of hydrogen atoms of the unsubstituted heterocyclyl, such as one, two or three substituents, or 1-4 substituents, up to the number of hydrogens present on the unsubstituted heterocyclyl group. In some embodiments, a substituted heterocycloalkyl comprises 1-4 such as 1-2 substituents. Unless otherwise specified, suitable substituents are selected, for example, from the substituents listed above for alkyl groups.

The term "aryl" refers to an aromatic hydrocarbon group comprising 5-15 carbon atoms in the ring portion. In some embodiments, aryl refers to a group selected from 5- and 6-membered carbocyclic aromatic rings, for example, phenyl; bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems, wherein at least one ring is carbocyclic and aromatic, for example, fluorene.

In some embodiments, the aryl group is selected from 5 and 6-membered carbocyclic aromatic rings fused to a 5- to 7-membered cycloalkyl or heterocyclic ring (as defined in "heterocyclyl" or "heterocyclic" below) optionally comprising at least one heteroatom selected, for example, from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring (e.g., a heteroaryl as defined below), the resulting ring system is heteroaryl, not aryl, as defined herein.

Unless indicated specifically, aryl group can be optionally substituted by one or more substituents in place of hydrogen atoms of the unsubstituted aryl, such as one, two or three substituents, or 1-4 substituents, up to the number of hydrogens present on the unsubstituted aryl group. In some embodiments, a substituted aryl group comprises 1-5 substituents. Unless otherwise specified, suitable substituents are selected, for example, from the substituents listed above for alkyl groups.

The term "heteroaryl" herein refers to a group selected from 5- to 7-membered aromatic, monocyclic rings comprising at least one heteroatom, for example, from 1 to 4, or, in some embodiments, from 1 to 3, heteroatoms, selected, for example, from N, O, and S, with the remaining ring atoms being carbon; 8- to 12-membered bicyclic rings comprising at least one heteroatom, for example, from 1 to 4, or, in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in the aromatic ring, and with the point of attachment being on any ring and being on either carbon or the heteroatom; and 11- to 14-membered tricyclic rings comprising at least one heteroatom, for example, from 1 to 4, or in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in an aromatic ring, and with the point of attachment being on any ring.

In some embodiments, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

In some embodiments, the heteroaryl group includes a 5- to 7-membered heterocyclic aromatic ring fused to a 5- to 7-membered aryl ring. For such fused, bicyclic heteroaryl ring systems wherein only one of the rings comprises at least one heteroatom, the point of attachment may be at the heteroaromatic ring or at the aryl ring. Non-limiting examples include quinolinyl and quinazolinyl.

In some embodiments, the heteroaryl group includes a 5- to 7-membered heterocyclic aromatic ring fused to another 5- to 7-membered heterocyclic aromatic ring. Non-limiting examples include 1H-pyrazolo[3,4-b]pyridinyl and 1H-pyrrolo[2,3-b]pyridinyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, pyridyl, cinnolinyl, pyrazinyl, pyrimidinyl, imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrimidinyl, pyrrolyl, triazolyl, quinolinyl, isoquinolinyl, pyrazolyl, pyrrolopyridinyl (such as 1H-pyrrolo[2,3-b]pyridin-3-yl), pyrazolopyridinyl (such as1H-pyrazolo[3,4-b]pyridin-3-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

Unless indicated specifically, heteroaryl group can be optionally substituted by one or more substituents in place of hydrogen atoms of the unsubstituted heteroaryl, such as one, two or three substituents, or 1-4 substituents, up to the number of hydrogens present on the unsubstituted heteroaryl group. In some embodiments, a substituted heteroaryl group comprises 1, 2 or 3 substituents. Unless otherwise specified, suitable substituents are selected, for example, from the substituents listed above for alkyl groups.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. It is well-known in the art how to prepare optically active forms, such as by resolution of materials or by asymmetric synthesis. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When the compounds disclosed herein contain olefinic double bonds, unless specified otherwise, such double bonds are meant to include both E and Z geometric isomers.

"A pharmaceutically acceptable salt" includes, but is not limited to, salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" or "alleviation" refers to administering at least one compound and/or at least one stereoisomer thereof, if any, at least one stable isotope thereof, or at least one pharmaceutically acceptable salt thereof disclosed herein to a subject in recognized need thereof that has, for example, cancer.

The term "effective amount" refers to an amount of at least one compound and/or at least one stereoisomer thereof, if any, at least one stable isotope thereof, or at least one pharmaceutically acceptable salt thereof disclosed herein effective to "treat," as defined above, a disease or disorder in a subject.

Various embodiments are disclosed herein. It will be recognized that features specified in each embodiment may be combined with other specified features to provide further embodiments of the present disclosure. The following enumerated embodiments are representative of the present disclosure.

Embodiment 1

Disclosed herein are compounds of formula I:

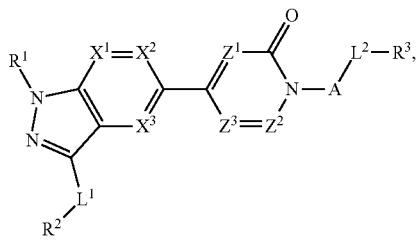

(I)

and/or stereoisomers, stable isotopes, or pharmaceutically acceptable salts thereof, wherein $R^1$, $R^2$, $R^3$, A, $L^1$, $L^2$, $X^1$, $X^2$, $X^3$, $Z^1$, $Z^2$ and $Z^3$ are defined below.

$R^1$ is selected from H and C1-C4 alkyl, $R^2$ is selected from H, D, —CN, halo, and an optionally substituted group selected from C1-C6 alkyl, C3-C8 cycloalkyl, C4-8 cycloalkenyl, saturated or unsaturated 4-8 membered heterocyclyl containing 1-2 heteroatoms selected from N, O, and S as ring members, aryl, and heteroaryl containing 1-4 heteroatoms selected from N, O, and S as ring members, wherein the optional substituents for $R^2$ are 1-4 substituents independently selected from D, halo, —OH, =O, —CN, —N$_3$, —CO$_2$R$^4$, —C(O)N(R$^{5a}$R$^{5b}$), —C(=NR$^6$)N(R$^{5a}$R$^{5b}$), —C(O)R$^4$, —SO$_{0\text{-}2}$R$^7$, —SO(=NR$^6$)R$^7$, —SO$_{1\text{-}2}$N(R$^{5a}$R$^{5b}$), —N(R$^{5a}$R$^{5b}$), —N(R$^{5a}$)C(O)R$^7$, —N(R$^{5a}$)C(=NR$^6$)R$^7$, —N(R$^{5a}$)SO$_{1\text{-}2}$R$^7$, —N(R$^{5c}$)C(O)N(R$^{5a}$R$^{5b}$), —N(R$^{5c}$)C(=NR$^6$)N(R$^{5a}$R$^{5b}$), —N(R$^{5c}$)SO$_{1\text{-}2}$N(R$^{5a}$R$^{5b}$), —N(R$^{5a}$)CO$_2$R$^7$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, wherein the optional substituents are 1-4 substituents independently selected from D, halo, —OR$^4$, and —N(R$^{5c}$)SO$_{1\text{-}2}$N(R$^{5a}$R$^{5b}$), wherein R$^4$, R$^{5a}$, R$^{5b}$ and R$^{5c}$ are independently selected from H and C1-C4 alkyl optionally substituted with 1-3 groups independently selected from D, halo, —OH, —NH$_2$, —NHMe and —NMe$_2$; R$^6$ is independently selected from H, —CN, —OH, C1-C4 alkyl and C1-C4 alkoxy; R$^7$ is C1-C4 alkyl optionally substituted with 1-3 groups independently selected from D, halo, —OH, —NH$_2$, —NHMe and —NMe$_2$; and two substituents on the same or adjacent carbon atoms of R$^2$ can optionally be taken together to form a 5-6 membered ring that can be saturated or aromatic and optionally contains 1-2 heteroatoms selected from N, O and S and can optionally be substituted with 1-2 groups independently selected from D, -Me, halo, —OH, =O, C1-C4 alkoxy, —NH$_2$, C1-C4 alkylamino and di(C1-C4 alkyl) amino;

R$^3$ is selected from C3-C8 cycloalkyl, 5-8-membered heterocyclyl containing 1-2 heteroatoms selected from N, O, and S as ring members, aryl and heteroaryl containing 1-4 heteroatoms selected from N, O and S as ring members, wherein R$^3$ is optionally substituted with 1-3 substituents selected from D, halo, —OH, =O, —CN, —N$_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —CO$_2$R$^8$, —C(O)N(R$^{9a}$R$^{9b}$), —C(=NR$^{10}$)N(R$^{9a}$R$^{9b}$), —C(O)R$^8$, —SO$_{0\text{-}2}$R$^{11}$, —SO(=NR$^{10}$)R$^{11}$, —SO$_{1\text{-}2}$N(R$^{9a}$R$^{9b}$), —N(R$^{9a}$R$^{9b}$), —N(R$^{9a}$)C(O)R$^8$, —N(R$^{9a}$)C(=NR$^{10}$)R$^8$, —N(R$^{9a}$)S$_{1\text{-}2}$R$^{11}$, —N(R$^{9c}$)C(O)N(R$^{9a}$R$^{9b}$), —N(R$^{9c}$)C(=NR$^{10}$)N(R$^{9a}$R$^{9b}$), —N(R$^{9c}$)SO$_{1\text{-}2}$N(R$^{9a}$R$^{9b}$) and —N(R$^{9a}$)CO2R$^{11}$; wherein R$^8$, R$^{9a}$, R$^{9b}$ and R$^{9c}$ are independently selected from H and C1-C4 alkyl, each of which is optionally substituted with 1-3 groups independently selected from D, halo, —OH, —NH$_2$, —NHMe, —NMe$_2$ and C1-C4 alkoxy; R$^{10}$ is independently selected from H, —CN, —OH, C1-C4 alkyl, and C1-C4 alkoxy; R$^{11}$ is C1-C4 alkyl optionally substituted with 1-3 groups independently selected from D, halo, —OH, —NH$_2$, —NHMe, —NMe$_2$ and C1-C4 alkoxy;

A is a bond, or can be selected from C1-C4 alkylene, C2-C4 alkenylene, C2-C4 alkynylene, C3-C7 cycloalkyl and 4-7 membered heterocyclyl containing 1-2 heteroatoms selected from N, O, and S as ring members, wherein A is optionally substituted with 1-3 substituents independently selected from D, halo, —OH, =O, —CN, —N$_3$, —R$^{12}$, —CO$_2$R$^{12}$, —C(O)N(R$^{13a}$R$^{13b}$), —C(=NR$^{14}$)N(R$^{13a}$R$^{13b}$), —C(O)R$^{12}$, —SO$_{0\text{-}2}$R$^{14}$, —SO(=NR$^{15}$)R$^{14}$, —SO$_{1\text{-}2}$N(R$^{13a}$R$^{13b}$), —N(R$^{13a}$R$^{13b}$), —N(R$^{13a}$)C(O)R$^{12}$, —N(R$^{13a}$)C(=NR$^{15}$)R$^{14}$, —N(R$^{13a}$)SO$_{1\text{-}2}$R$^{14}$, —N(R$^{13c}$)C(O)N(R$^{13a}$R$^{13b}$), —N(R$^{13c}$)C(=NR$^1$)N(R$^{13a}$R$^{13b}$), N(R$^{13c}$)SO$_{1\text{-}2}$N(R$^{13a}$R$^{13b}$) and —N(R$^{13a}$)CO$_2$R$^{14}$; wherein R$^{14}$ is selected from C1-C4 alkyl optionally substituted with 1-3 groups independently selected from D, halo, —OH, —NH$_2$, —NHMe, —NMe$_2$, —OPO$_3$H$_2$ and C1-C4 alkoxy; R$^{12}$, R$^{13a}$, R$^{13b}$ and R$^{13c}$ are independently selected from H and C1-C4 alkyl optionally substituted with 1-3 groups independently selected from D, halo, —OH, —NH$_2$, —NHMe, —NMe$_2$, —OPO$_3$H$_2$ and C1-C4 alkoxy; R$^{15}$ is selected from H, —CN, —OH, C1-C4 alkyl and C1-C4 alkoxy;

L$^1$ and L$^2$ are selected from a bond, —N(R$^{16}$)—, —O—, —C(O)—, —S(O)$_{0\text{-}2}$— and —C(R$^{17a}$R$^{17b}$)—, wherein R$^{16}$, R$^{17a}$, and R$^{17b}$ are independently selected from H and C1-C4 alkyl optionally substituted with 1-3 groups independently selected from D, halo, —OH, —NH$_2$, —NHMe, —NMe$_2$, —OPO$_3$H$_2$ and C1-C4 alkoxy;

A and $L^2$ can cyclize to form a C5-C7 cycloalkyl ring, a 4-7 membered heterocyclic ring containing 1-2 heteroatoms selected from N, O, and S, phenyl or a 5-6 membered heteroaryl ring containing 1-4 heteroatoms selected from N, O, and S as ring members, wherein the optional ring formed can be optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl, —$CO_2R^{18}$, —$CON(R^{19a}R^{19b})$, —$SO_2R^{20}$, —$SO_2N(^{19a}R^{19b})$ and —$N(R^{19a}R^{19b})$, wherein $R^{18}$, $R^{19a}$ and $R^{19b}$ are independently H or C1-4 alkyl; $R^{20}$ is C1-C4 alkyl;

$X^1$, $X^2$, and $X^3$ are independently selected from N and $CR^{21}$, wherein $R^{21}$ is selected from H, D, halo, —CN, C1-C4 alkyl, C1-C4 haloalkyl, C1-C4 alkoxy and C1-C6 haloalkoxy;

$Z^1$ is selected from N and $CR^{22}$, wherein $R^{22}$ is selected from H, D, OH, halo, CN, C1-C4 alkyl, C1-C4 haloalkyl, C1-C4 alkoxy and C1-C6 haloalkoxy;

$Z^2$ is selected from N and $CR^{23}$, wherein $R^{23}$ is selected from H, D, —OH, —CN, C1-C4 alkyl, C1-C4 haloalkyl, C1-C4 alkoxy, C1-C6 haloalkoxy, C3-C8 cycloalkyl, C4-8 cycloalkenyl and saturated and unsaturated 4-8 membered heterocyclyl containing 1-2 heteroatoms selected from N, O, and S as ring members, each of which is optionally substituted with 1-3 groups independently selected from D, halo, —CN, =O, —OH, C1-C4 alkoxy, C1-C4 alkyl, C1-C4 haloalkyl, C1-C4 hydroxyalkyl, C1-C4 haloalkoxy, —$COOR^{24}$, —$SO_2R^{25}$, —$N(R^{26a}R^{26b})$, —$N(R^{26a})C(O)R^{25}$, —$N(R^{26a})SO_2R^{25}$, —$N(R^{26a})COOR^{25}$, —$CON(R^{26a}R^{26b})$ and —$SO_2N(^{26a}R^{26b})$, wherein $R^{24}$, $R^{26a}$ and $R^{26b}$ are independently selected from H and C1-C4 alkyl; $R^{25}$ is C1-C4 alkyl;

$Z^3$ is selected from N and $CR^{27}$, wherein $R^{27}$ is selected from H, D, —OH, halo, —CN, C1-C4 alkyl, C1-C4 haloalkyl, C1-C4 alkoxy and C1-C6 haloalkoxy;

or $R^{23}$ can cyclize with A to form a 5-7 membered heterocyclic ring containing 1-2 heteroatoms selected from N, O, and S, optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl —$CO_2R^{28}$, —$CON(R^{29a}R^{29b})$, —$SO_2R^{30}$, —$SO_2N(^{29a}R^{29b})$ and —$N(R^{29a}R^{29b})$, wherein $R^{28}$, $R^{29a}$ and $R^{29b}$ are independently selected from H and C1-C4 alkyl; $R^{30}$ is C1-C4 alkyl;

or $R^{23}$ can cyclize with $R^{27}$ to form a a C5-C7 cycloalkyl ring, a 5-7 membered heterocyclic ring containing 1-2 heteroatoms selected from N, O, and S, phenyl or a 5-6 membered heteroaryl containing 1-4 heteroatoms selected from N, O, and S as ring members, wherein the optional ring formed by $R^{23}$ cyclizing with $R^{27}$ can be optionally substituted with 1-2 groups independently selected from D, —CN, =O, —OH, C1-C4 alkyl, C1-C4 haloalkyl, C1-C4 alkoxy, C1-C4 haloalkoxy, C1-C4 aminoalkyl, C1-C4 hydroxyalkyl, —$CO_2R^{31}$, —$CON(R^{32a}R^{32b})$, —$SO_2R^{33}$, —$SO_2N(^{32a}R^{32b})$ and —$N(R^{32a}R^{32b})$, wherein $R^{31}$, $R^{32a}$ and $R^{32b}$ are independently selected from H and C1-C4 alkyl; $R^{33}$ is C1-C4 alkyl.

Embodiment 2

The compound according to embodiment 1, and/or a stereoisomer, a stable isotope, or a pharmaceutically acceptable salt thereof, wherein $X^1$, $X^2$, and $X^3$ are CH.

Embodiment 3

The compound according to embodiment 1, and/or a stereoisomer, a stable isotope, or a pharmaceutically acceptable salt thereof, wherein $X^1$, $X^2$, and $X^3$ are N.

Embodiment 4

The compound according to embodiment 1, and/or a stereoisomer, a stable isotope, or a pharmaceutically acceptable salt thereof, wherein $X^1$ is N, $X^2$ and $X^3$ are CH.

Embodiment 5

The compound according to embodiment 1, and/or a stereoisomer, a stable isotope, or a pharmaceutically acceptable salt thereof, wherein $X^2$ is N, $X^1$ and $X^3$ are CH.

Embodiment 6

The compound according to embodiment 1, and/or a stereoisomer, a stable isotope, or a pharmaceutically acceptable salt thereof, wherein X is N, X and X are CH.

Embodiment 7

The compound according to embodiment 1, and/or a stereoisomer, a stable isotope, or a pharmaceutically acceptable salt thereof, wherein $Z^1$, $Z^2$, and $Z^3$ are CH.

Embodiment 8

The compound according to any one of embodiments 1-7, and/or a stereoisomer, a stable isotope, or a pharmaceutically acceptable salt thereof, wherein $R^1$ is H.

Embodiment 9

The compound according to any one of embodiments 1-8, and/or a stereoisomer, a stable isotope, or a pharmaceutically acceptable salt thereof, wherein $L^1$ is a bond.

Embodiment 10

The compound according to any one of embodiments 1-9, and/or a stereoisomer, a stable isotope, or a pharmaceutically acceptable salt thereof, wherein $R^2$ is selected from C3-C8 cycloalkyl, 5-8 membered heterocyclyl containing 1-2 heteroatoms selected from N, O, and S as ring members, phenyl, and 5-6 memered heteroaryl containing 1-3 heteroatoms selected from N, O, and S as ring members, and is optionally substituted with 1-3 groups independently selected from =O, D, halo, —CN, —OH, C1-C4 alkoxy, C1-C4 alkyl, C1-C4 haloalkyl, C1-C4 hydroxyalkyl, C1-C4 haloalkoxy, —$COOR^{34}$, —$SO_2R^{35}$, —$N(R^{36a}R^{36b})$, —$N(R^{36a})C(O)R^{35}$, —$N(R^{36a})SO_2R^{35}$, —$N(R^{36a})COOR^{35}$, —$CON(R^{36a}R^{36b})$ and —$SO_2N(R^{36a}R^{36b})$, where $R^{34}$, $R^{36a}$ and $R^{36b}$ are independently selected from H and C1-C4 alkyl; $R^{35}$ is C1-C4 alkyl.

Embodiment 11

The compound according to any one of embodiments 1-10, and/or a stereoisomer, a stable isotope, or a pharmaceutically acceptable salt thereof, wherein $R^2$ is selected from phenyl, pyridine, pyridone, pyrazine, pyridazine, pyrazole, triazole, tetrazole, thiazole, oxazole, imidazole, isothiazole, isoxazole, furan, 1,2,5-oxadiazole, and thiophene, each of which is optionally substituted with one or two groups independently selected from =O, D, halo, —CN, hydroxy, C1-C4 alkoxy, C1-C4 alkyl, C1-C4 haloalkyl, C1-C4 hydroxyalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —N(R$^{36a}$)SO$_2$R$^{35}$, —N(R$^{36a}$)COOR$^{35}$, —CON(R$^{36a}$R$^{36b}$) and —SO$_2$N(R$^{36a}$R$^{36b}$), wherein R$^{34}$, R$^{36a}$ and R$^{36b}$ are independently selected from H and C1-C4 alkyl; R$^{35}$ is C1-C4 alkyl.

Embodiment 12

The compound according to any one of embodiments 1-11, and/or a stereoisomer, a stable isotope, or a pharmaceutically acceptable salt thereof, wherein R$^2$ is selected from cyclobutyl, cyclopentyl, cyclohexyl, cyclohexenyl, tetrahydropyran, dihydropyran, tetrahydrofuran, oxetane, azetidine, pyrrolidine, piperidine, piperazine, morpholine, tetrahydrothiopyran, and tetrahydrothiofuran, each of which is optionally substituted with one or two groups independently selected from =O, D, halo, —CN, —OH, C1-C4 alkoxy, C1-C4 alkyl, C1-C4 haloalkyl, C1-C4 hydroxyalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —N(R$^{36a}$)SO$_2$R$^{35}$, —N(R$^{36a}$)COOR$^{35}$, —CON(R$^{36a}$R$^{36b}$) and —SO$_2$N(R$^{36a}$R$^{36b}$), wherein R$^{34}$, R$^{36a}$ and R$^{36b}$ are independently selected from H and C1-C4 alkyl; R$^{35}$ is C1-C4 alkyl.

Embodiment 13

The compound of any one of embodiments 1-12, and/or a stereoisomer, a stable isotope, or a pharmaceutically acceptable salt thereof, wherein R$^3$ is phenyl and is optionally substituted with up to three groups independently selected from halo, D, —CN, C1-C4 alkoxy, C1-C4 alkyl, C1-C4 haloalkyl, C1-C4 haloalkoxy, —SR$^{35}$, —SO$_2$R$^{35}$, —N(R$^{36a}$R$^{36b}$), —N(R$^{36a}$)C(O)R$^{35}$ and —SO$_2$N(R$^{36a}$R$^{36b}$), wherein R$^{36a}$ and R$^{36b}$ are independently selected from H, C1-C4 alkyl and C1-C4 haloalkyl; R$^{35}$ is C1-C4 alkyl.

Embodiment 14

The compound of any one of embodiments 1-12, and/or a stereoisomer, a stable isotope, or a pharmaceutically acceptable salt thereof, wherein R$^3$ is oxazolyl, isoxazolyl, thiophenyl, thiazolyl, pyridinyl, pyrimidinyl, pyrazinyl or pyridazinyl, and is optionally substituted with up to three groups independently selected from D, halo, —CN, C1-C4 alkoxy, C1-C4 alkyl, C1—C4 haloalkyl, C1-C4 haloalkoxy, —SO$_2$R$^{35}$, —N(R$^{36a}$R$^{36b}$), —N(R$^{36a}$)C(O)R$^{35}$ and —SO$_2$N(R$^{36a}$R$^{36b}$), wherein R$^{36a}$ and R$^{36b}$ are independently selected from H, C1-C4 alkyl and C1-C4 haloalkyl; R$^{35}$ is C1-C4 alkyl.

Embodiment 15

The compound according to any one of embodiments 1 to 14, and/or a stereoisomer, a stable isotope, or a pharmaceutically acceptable salt thereof, wherein A is selected from cyclopropane-1,1-diyl, cyclopropane-1,2-diyl, —CHR$^{37}$— and —C(R$^{37}$)$_2$—, wherein R$^{37}$ is selected from H, D and C1-C2 alkyl optionally substituted with up to three groups independently selected from D, —OH, halo, —NH$_2$, C1-C2 alkylamino, di(C1-C2 alky)amino and C1-C4 alkoxy.

Embodiment 16

The compound of embodiment 15, and/or a stereoisomer, a stable isotope, or a pharmaceutically acceptable salt thereof, wherein A is

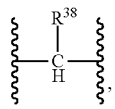

wherein R$^{38}$ is methyl or ethyl, and is optionally substituted with at least one substituent selected from fluoro, amino, hydroxy, methylamino, ethylamino, dimethylamino, —OP(O)(OH)$_2$, methoxy and ethoxy.

Embodiment 17

The compound of embodiment 15, and/or a stereoisomer, a stable isotope, or a pharmaceutically acceptable salt thereof, wherein A is —C(R$^{39}$)$_2$—, wherein R$^{39}$ is H or D.

Embodiment 18

The compound of any one of embodiments 1-17, and/or a stereoisomer, a stable isotope, or a pharmaceutically acceptable salt thereof, wherein Z$^2$ is CR$^{23}$, wherein R$^{23}$ is selected from H, C1-C4 alkyl, C3-C7 cycloalkyl and 5-8 membered heterocyclyl containing 1-2 heteroatoms selected from N, O, and S as ring members, and is optionally substituted with up to three groups independently selected from halo, —CN, C1-C4 alkoxy, C1-C4 alkyl, C1-C4 haloalkyl, C1-C4 haloalkoxy, —SO$_2$R$^{35}$, —N(R$^{36a}$R$^{36b}$), —N(R$^{36a}$)C(O)R$^{35}$, —SO$_2$N(R$^{36a}$R$^{36b}$) and —N(R$^{36a}$)SO$_2$R$^{35}$ wherein R$^{36a}$ and R$^{36b}$ are independently selected from H, C1-C4 alkyl and C1-C4 haloalkyl; R$^{35}$ is C1-C4 alkyl.

Embodiment 19

The compound of any one of embodiments 1-18, and/or a stereoisomer, a stable isotope, or a pharmaceutically acceptable salt thereof, wherein Z$^1$, Z$^2$, and Z$^3$ are CR$^{38}$, wherein CR$^{38}$ is independently selected from H, methyl and halo.

Embodiment 20

The compound of embodiment 1, which is a compound of Formula IA, and/or a stereoisomer, a stable isotope, or a pharmaceutically acceptable salt thereof:

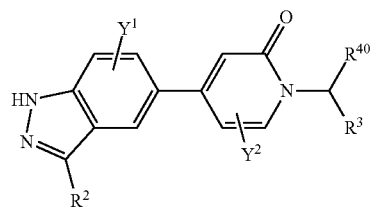

(IA)

wherein R$^2$ is phenyl, pyridinyl, pyrimidinyl, triazinyl, pyrazolyl, imidazolyl, isoxazolyl, isothiazolyl, oxazolyl, oxadizolyl, triazolyl or thiazolyl, which can be substituted with up to two groups independently selected from D, F, Cl, Br, —CN, -Me, -Et, —Pr, i-Pr, butyl, isobutyl, sec-butyl, t-butyl, —CHF$_2$ CF$_3$, cyclopropyl, —OMe, —OEt, —Pr$^i$, —OPr, —OBu, —OBu$^i$, —OBu$^s$, —OBu$^t$, —OCF$_3$, —O(cyclopropyl), —(CH$_2$)$_2$OH, —(CH$_2$)$_2$OMe, —(CH$_2$)C(OH)CH$_2$OH, —(CH$_2$)$_2$NHSO$_2$NH$_2$, —C(OH)(CH$_3$)$_3$, —O(CH$_2$)$_2$OH, —O(CH$_2$)$_2$OMe, —O(CH$_2$)C(OH)CH$_2$OH and —O(CH$_2$)$_2$NHSO$_2$NH$_2$;

or R$^2$ is a non-aromatic cycloalkyl or heterocyclic group such as cyclohexyl, cyclopentyl, tetrahydropyranyl (e.g., 4-tetrahydropyranyl), 3-oxetanyl, 3- or 4-piperidinyl, 4- or 3-piperidin-2-onyl, 3- or 4-thiacyclopentanyl, 3-thiacyclohexanyl, 3-tetrahydrofuranyl, and the like, wherein a ring sulfur can be oxidized to sulfoxide or sulfone oxidation state, and each of these rings may be substituted with 1-3 groups groups independently selected from D, F, Cl, —CN, —NH$_2$, —NHMe, —NMe$_2$, -Me, -Et, —Pr$^i$, —NHSO$_2$Me, —NHCOMe, =O, —OH, —OMe, —CH$_2$OH, and —CF$_3$. The 1,4-disubstituted cyclohexyl can have either a cis or trans relative stereochemistry between the groups attached at positions 1 and 4, for example, a trans relative orientation between these groups;

Y$^1$ and Y$^2$ are independently H, F, Cl or Me;

wherein R$^3$ is phenyl, pyridine or thienyl, optionally substituted with 1-2 groups independently selected from D, —NH$_2$, halo, —CN, C1-C4 alkyl, C1-C4 alkoxy, C1-C4 haloalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —SO$_2$N(R$^{36a}$R$^{36b}$) and —N(R$^{36a}$)SO$_2$R$^{35}$, wherein R$^{34}$, R$^{36a}$ and R$^{36b}$ are independently selected from H and C1-C4 alkyl; R$^{35}$ is C1-C4 alkyl;

R$^{40}$ is selected from H, D and —CH$_2$R*, wherein R* is selected from H, —OH, F, —NH$_2$, —NHMe, —NMe$_2$, —OP(O)(OH)$_2$ and —OMe.

Embodiment 21

The compound of embodiment 1, which is a compound of Formula IB, and/or a stereoisomer, a stable isotope, or a pharmaceutically acceptable salt thereof:

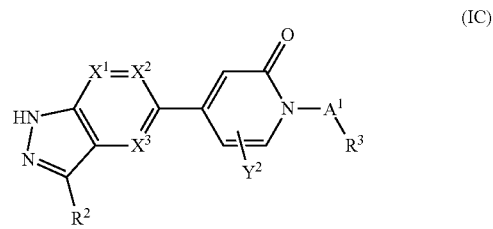
(IB)

wherein X$^1$, X$^2$ and X$^3$ are independently selected from CH and N. Examples of X$^1$, X$^2$ and X$^3$ together forming the structure

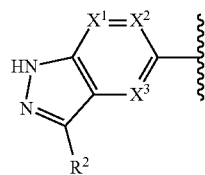

are selected from:

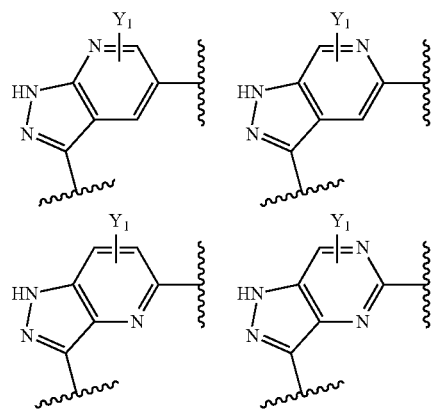

wherein Y$^2$ is H, F, Cl, or Me;
R$^2$, R$^3$, R$^{40}$ and Y$^1$ are as defined in embodiment 20.

Embodiment 22

The compound of embodiment 1, which is a compound of Formula IC, and/or a stereoisomer, a stable isotope, or a pharmaceutically acceptable salt thereof:

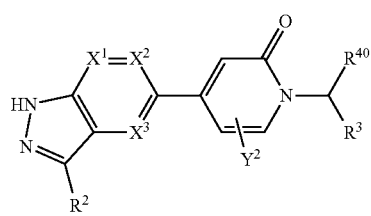
(IC)

wherein A$^1$ is selected from —CR$^{41}$R$^{42}$—, where R$^{41}$ and R$^{42}$ are independently selected from H, D, F, —CH$_3$, —CD$_3$, -Et, and —Pr;

wherein R$^2$, R$^3$, X$^1$, X$^2$, X$^3$, Y$^1$ and Y$^2$ are as defined in embodiments 20 and 21.

Embodiment 23

The compound of any one of embodiments 20-22, and/or a stereoisomer, a stable isotope, or a pharmaceutically acceptable salt thereof, wherein R$^2$ is selected from:

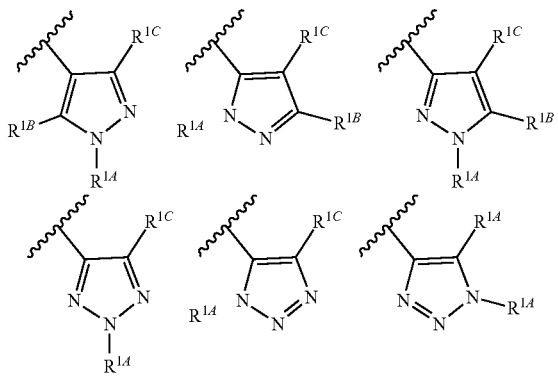

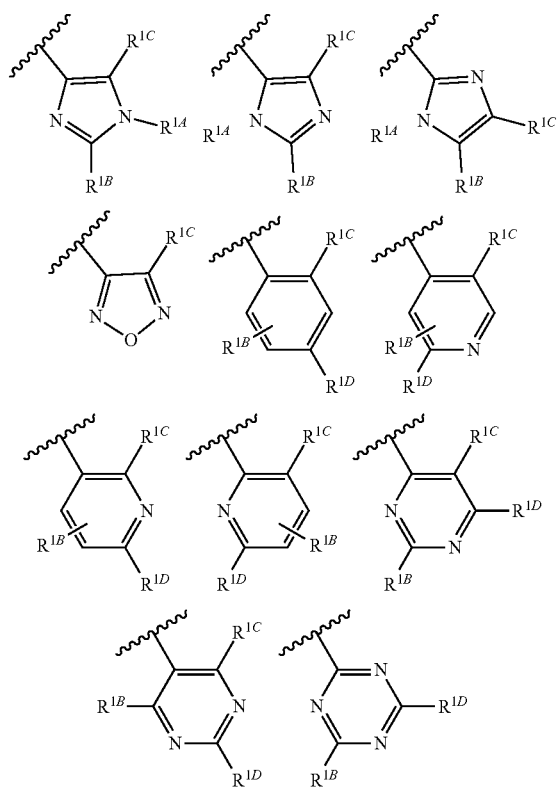

wherein $R^{1A}$ is independently selected from H, D, Me, Et, propyl, isopropyl, butyl, isobutyl, sec-butyl, t-butyl, —CH$_2$F—CF$_2$H, —CF$_3$, cyclopropyl;

$R^{1B}$, $R^{1C}$ and $R^{1D}$ are independently selected from H, D, Me, Et, propyl, isopropyl, butyl, isobutyl, sec-butyl, t-butyl, —CH$_2$F—CF$_2$H, —CF$_3$, cyclopropyl, —OMe, —OEt, —OPr, —OPr$^i$, —OBu, —OBu$^i$, —OBu$^s$, —OBu$^t$, —OCF$_3$, —O(cyclopropyl), —C(OH)Me$_2$, —CN, Cl and F.

Embodiment 24

The compound of any one of embodiments 20-22, and/or a stereoisomer, a stable isotope, or a pharmaceutically acceptable salt thereof, wherein $R^2$ is selected from:

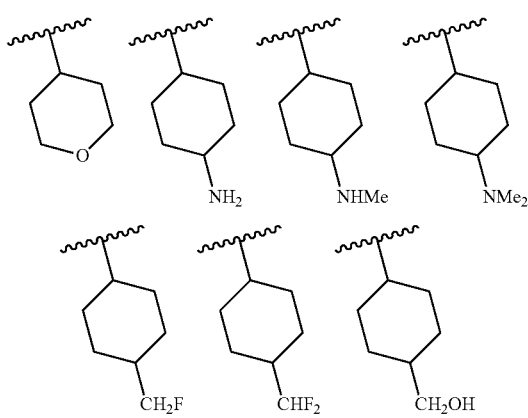

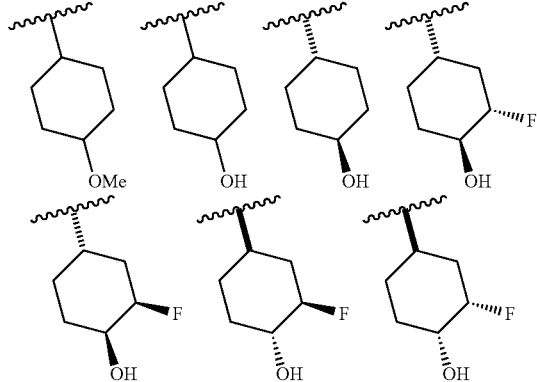

Embodiment 25

The compound of embodiment 1, which is selected from the following compounds and pharmaceutically acceptable salts thereof:

(S)-1-(1-(3-chlorophenyl)-2-hydroxyethyl)-4-(3-(2-methylpyridin-4-yl)-1H-indazol-5-yl)pyridin-2(1H)-one,
(S)-1-(1-(4-chloro-3-fluorophenyl)-2-hydroxyethyl)-4-(3-(2-methylpyridin-4-yl)-1H-indazol-5-yl)pyridin-2(1H)-one,
(S)-1-(1-(3-chlorophenyl)-2-hydroxyethyl)-4-(3-(tetrahydro-2H-pyran-4-yl)-1H-indazol-5-yl)pyridin-2(1H)-one,
(S)-1-(1-(3-chlorophenyl)-2-hydroxyethyl)-4-(3-(1,3-dimethyl-1H-pyrazol-4-yl)-1H-indazol-5-yl)pyridin-2(1H)-one,
(S)-1-(1-(3-chlorophenyl)-2-hydroxyethyl)-4-(3-(6-isopropoxypyridin-3-yl)-1H-indazol-5-yl)pyridin-2(1H)-one,
(S)-1-(1-(3-chlorophenyl)-2-hydroxyethyl)-4-(3-(1-methyl-1H-pyrazol-4-yl)-1H-indazol-5-yl)pyridin-2(1H)-one,
(S)-1-(1-(3-chlorophenyl)-2-hydroxyethyl)-4-(3-(2-isopropoxypyridin-4-yl)-1H-indazol-5-yl)pyridin-2(1H)-one,
(S)-1-(1-(3-chloro-4-fluorophenyl)-2-hydroxyethyl)-4-(3-(6-(2-hydroxypropan-2-yl)pyridin-3-yl)-1H-indazol-5-yl)pyridin-2(1H)-one,
(S)-1-(1-(3-chloro-4-fluorophenyl)-2-hydroxyethyl)-4-(3-(2-(2-hydroxypropan-2-yl)pyridin-4-yl)-1H-indazol,
(S)-1-(1-(3-chlorophenyl)-2-hydroxyethyl)-4-(3-methyl-1H-indazol-5 yl)pyridin-2(1H)-one,
(S)-1-(1-(3-chlorophenyl)-2-hydroxyethyl)-4-(1H-indazol-5-yl)pyridin-2(1H)-one,
(S)-1-(1-(3-chlorophenyl)-2-hydroxyethyl)-4-(3-ethyl-1H-indazol-5-yl)pyridin-2(1H)-one,
(S)-4-(3-amino-1H-indazol-5-yl)-1-(1-(3-chlorophenyl)-2-hydroxyethyl)pyridin-2(1H)-one,
(S)-1-(1-(3-chlorophenyl)-2-hydroxyethyl)-4-(3-(2-methylpyridin-4-yl)-1H-pyrazolo[3,4-b]pyridin-5-yl)pyridin-2(1H)-one,
(S)-1-(1-(4-chloro-3-fluorophenyl)-2-hydroxyethyl)-4-(3-(2-methylpyridin-4-yl)-1H-pyrazolo[3,4-b]pyridin-5-yl)pyridin-2(1H)-one,
(S)-1-(1-(3-bromo-5-fluorophenyl)-2-hydroxyethyl)-4-(3-(2-methylpyridin-4-yl)-1H-indazol-5-yl)pyridin-2(1H)-one,
(S)-1-(1-(3-chlorophenyl)-2-hydroxyethyl)-4-(3-(methylamino)-1H-indazol-5-yl)pyridin-2(1H)-one, 1-((S)-1-(3-chlorophenyl)-2-hydroxyethyl)-4-(3-(3-hydroxypyrrolidin-1-yl)-1H-indazol-5-yl)pyridin-2(1H)-one,
(S)-1-(1-(3-chlorophenyl)-2-hydroxyethyl)-4-(3-((1-methyl-1H-pyrazol-5-yl)amino)-1H-indazol-5-yl)pyridin-2(1H)-one,
(S)-1-(1-(3-bromophenyl)-2-hydroxyethyl)-4-(3-(2-methylpyridin-4-yl)-1H-indazol-5-yl)pyridin-2(1H)-one,
(S)-1-(1-(5-chloro-2-fluorophenyl)-2-hydroxyethyl)-4-(3-(2-methylpyridin-4-yl)-1H-indazol-5-yl)pyridin-2(1H)-one,
(S)-1-(1-(3-chloro-4-fluorophenyl)-2-hydroxyethyl)-4-(3-(2-methylpyridin-4-yl)-1H-indazol-5-yl)pyridin-2(1H)-one,
(R)-1-(1-(3-chlorophenyl)-2-hydroxyethyl)-4-(3-(2-methylpyridin-4-yl)-1H-indazol-5-yl)pyridin-2(1H)-one,
(S)-1-(1-(4-chlorophenyl)-2-hydroxyethyl)-4-(3-(2-methylpyridin-4-yl)-1H-indazol-5-yl)pyridin-2(1H)-one,
(S)-1-(1-(3-fluoro-5-(trifluoromethyl)phenyl)-2-hydroxyethyl)-4-(3-(2-methylpyridin-4-yl)-1H-indazol-5-yl)pyridin-2(1H)-one,
(S)-1-(1-(3-chloro-4-fluorophenyl)-2-hydroxyethyl)-4-(3-(6-isopropoxypyridin-3-yl)-1H-indazol-5-yl)pyridin-2(1H)-one,
(S)-1-(1-(3-chloro-2-fluorophenyl)-2-hydroxyethyl)-4-(3-(2-methylpyridin-4-yl)-1H-indazol-5-yl)pyridin-2(1H)-one,
(S)-1-(1-(3-bromo-4-fluorophenyl)-2-hydroxyethyl)-4-(3-(2-methylpyridin-4-yl)-1H-indazol-5-yl)pyridin-2(1H)-one,
(S)-1-(1-(3-chloro-4-fluorophenyl)-2-hydroxyethyl)-4-(3-(1-methyl-1H-pyrazol-4-yl)-1H-indazol-5-yl)pyridin-2(1H)-one,
(S)-1-(1-(4-chloro-3-fluorophenyl)-2-hydroxyethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(6-isopropoxypyridin-3-yl)-1H-indazol-5-yl)pyridin-2(1H)-one,
(S)-1-(1-(3-fluoro-5-(trifluoromethyl)phenyl)-2-hydroxyethyl)-4-(3-(1-methyl-1H-pyrazol-4-yl)-1H-indazol-5-yl)pyridin-2(1H)-one,
(S)-1-(2-hydroxy-1-(3-(trifluoromethyl)phenyl)ethyl)-4-(3-(1-methyl-1H-pyrazol-4-yl)-1H-indazol-5-yl)pyridin-2(1H)-one,
(S)-1-(2-hydroxy-1-(3-(trifluoromethyl)phenyl)ethyl)-4-(3-(6-isopropoxypyridin-3-yl)-1H-indazol-5-yl)pyridin-2(1H)-one,
(S)-1-(1-(3-bromophenyl)-2-hydroxyethyl)-4-(3-(6-isopropoxypyridin-3-yl)-1H-indazol-5-yl)pyridin-2(1H)-one,
(S)-1-(1-(3-bromophenyl)-2-hydroxyethyl)-4-(3-(1-methyl-1H-pyrazol-4-yl)-1H-indazol-5-yl)pyridin-2(1H)-one,
(S)-1-(1-(3-bromo-4-fluorophenyl)-2-hydroxyethyl)-4-(3-(1-methyl-1H-pyrazol-4-yl)-1H-indazol-5-yl)pyridin-2(1H)-one,
(S)-1-(2-hydroxy-1-(3-iodophenyl)ethyl)-4-(3-(1-methyl-1H-pyrazol-4-yl)-1H-indazol-5-yl)pyridin-2(1H)-one,
(S)-1-(2-hydroxy-1-(3-iodophenyl)ethyl)-4-(3-(6-isopropoxypyridin-3-yl)-1H-indazol-5-yl)pyridin-2(1H)-one,
(S)-1-(2-hydroxy-1-(3-iodophenyl)ethyl)-4-(3-(2-methylpyridin-4-yl)-1H-indazol-5-yl)pyridin-2(1H)-one,
(S)-1-(1-(3-chlorophenyl)-2-hydroxyethyl)-4-(3-(1-methyl-1H-pyrazol-5-yl)-1H-indazol-5-yl)pyridin-2(1H)-one,
(S)-1-(1-(3-chlorophenyl)-2-hydroxyethyl)-4-(3-(1,5-dimethyl-1H-pyrazol-4-yl)-1H-indazol-5-yl)pyridin-2(1H)-one,
(S)-1-(1-(3-chlorophenyl)-2-hydroxyethyl)-4-(4-fluoro-3-(2-methyl-pyridin-4-yl)-1H-indazol-5-yl)pyridin-2(1H)-one,
(S)-1-(1-(3-chlorophenyl)-2-hydroxyethyl)-4-(6-fluoro-3-(2-methylpyridin-4-yl)-1H-indazol-5-yl)pyridin-2(1H)-one,
1-(3-bromo-5-fluorobenzyl)-4-(3-(2-methylpyridin-4-yl)-1H-indazol-5-yl)pyridin-2(1H)-one,
1-(3-chlorobenzyl)-4-(3-(2-methylpyridin-4-yl)-1H-indazol-5-yl)pyridin-2(1H)-one,
1-(5-bromo-2-fluorobenzyl)-4-(3-(2-methylpyridin-4-yl)-1H-indazol-5-yl)pyridin-2(1H)-one,
1-(3-bromo-4-fluorobenzyl)-4-(3-(2-methylpyridin-4-yl)-1H-indazol-5-yl)pyridin-2(1H)-one,
1-(3-iodobenzyl)-4-(3-(2-methylpyridin-4-yl)-1H-indazol-5-yl)pyridin-2(1H)-one
1-(3-chloro-5-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(2-(trifluoromethyl)benzyl)pyridin-2(1H)-one,
1-benzyl-4-(3-(2-methylpyridin-4-yl)-1H-indazol-5-yl)pyridin-2(1H)-one,
1-(3,4-difluorobenzyl)-4-(3-(2-methylpyridin-4-yl)-1H-indazol-5-yl)pyridin-2(1H)-one,
1-(4-chloro-3-fluorobenzyl)-4-(3-(2-methylpyridin-4-yl)-1H-indazol-5-yl)pyridin-2(1H)-one,
1-(3-chloro-2-fluorobenzyl)-4-(3-(2-methylpyridin-4-yl)-1H-indazol-5-yl)pyridin-2(1H)-one,
4-((4-(3-(2-methylpyridin-4-yl)-1H-indazol-5-yl)-2-oxopyridin-1 (2H)-yl)methyl)benzonitrile,
1-(3-chloro-4-fluorobenzyl)-4-(3-(2-methylpyridin-4-yl)-1H-indazol-5-yl)pyridin-2(1H)-one,
1-(5-chloro-2-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3-(trifluoromethoxy)benzyl)pyridin-2(1H)-one,
1-(3-fluorobenzyl)-4-(3-(2-methylpyridin-4-yl)-1H-indazol-5-yl)pyridin-2(1H)-one,
1-(4-bromo-3-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3-(trifluoromethyl)benzyl)pyridin-2(1H)-one,
3-((4-(3-(2-methylpyridin-4-yl)-1H-indazol-5-yl)-2-oxopyridin-1 (2H)-yl)methyl)benzonitrile,
1-(2,5-difluorobenzyl)-4-(3-(2-methylpyridin-4-yl)-1H-indazol-5-yl)pyridin-2(1H)-one,
1-(3-fluoro-5-(trifluoromethyl)benzyl)-4-(3-(2-methylpyridin-4-yl)-1H-indazol-5-yl)pyridin-2(1H)-one,
1-(1-(3-bromo-5-fluorophenyl)ethyl)-4-(3-(2-methylpyridin-4-yl)-1H-indazol-5-yl)pyridin-2(1H)-one,
1-(3-bromo-2-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3,4,5-trifluorobenzyl)pyridin-2(1H)-one,
1-(4-fluoro-3-(trifluoromethyl)benzyl)-4-(3-(2-methylpyridin-4-yl)-1H-indazol-5-yl)pyridin-2(1H)-one,
1-(4-fluoro-3-(trifluoromethoxy)benzyl)-4-(3-(2-methylpyridin-4-yl)-1H-indazol-5-yl)pyridin-2(1H)-one,
1-(3,5-difluorobenzyl)-4-(3-(2-methylpyridin-4-yl)-1H-indazol-5-yl)pyridin-2(1H)-one,
1-(2-fluoro-3-(trifluoromethyl)benzyl)-4-(3-(2-methylpyridin-4-yl)-1H-indazol-5-yl)pyridin-2(1H)-one, 1-(2,3-difluorobenzyl)-4-(3-(2-methylpyridin-4-yl)-1H-indazol-5-yl)pyridin-2(1H)-one,
1-(2-amino-3-fluorobenzyl)-4-(3-(2-methylpyridin-4-yl)-1H-indazol-5-yl)pyridin-2(1H)-one,
N-(2-fluoro-6-((4-(3-(2-methylpyridin-4-yl)-1H-indazol-5-yl)-2-oxopyridin-1 (2H)-yl)methyl)phenyl)methanesulfonamide,
1-(3-chloro-4-fluorobenzyl)-4-(3-(1-methyl-1H-pyrazol-4-yl)-1H-indazol-5-yl)pyridin-2(1H)-one,
1-(5-bromo-2-fluorobenzyl)-4-(3-(1-methyl-1H-pyrazol-4-yl)-1H-indazol-5-yl)pyridin-2(1H)-one,
1-(3-bromo-5-fluorobenzyl)-4-(3-(1-methyl-1H-pyrazol-4-yl)-1H-indazol-5-yl)pyridin-2(1H)-one,
1-(2-fluoro-6-((4-(3-(2-methylpyridin-4-yl)-1H-indazol-5-yl)-2-oxopyridin-1(2H)-yl)methyl)phenyl)urea,
N-(2-fluoro-6-((4-(3-(2-methylpyridin-4-yl)-1H-indazol-5-yl)-2-oxopyridin-1 (2H)-yl)methyl)phenyl)acetamide,
4-(3-(2-methylpyridin-4-yl)-1H-indazol-5-yl)-1-((2-(trifluoromethyl)pyridin-4-yl)methyl)pyridin-2(1H)-one,
1-(3-bromobenzyl)-4-(3-(1-methyl-1H-pyrazol-4-yl)-1H-indazol-5-yl)pyridin-2(1H)-one,
4-(3-(1-methyl-1H-pyrazol-4-yl)-1H-indazol-5-yl)-1-(3-(trifluoromethyl)benzyl)pyridin-2(1H)-one,
1-(3-fluoro-5-(trifluoromethyl)benzyl)-4-(3-(1-methyl-1H-pyrazol-4-yl)-1H-indazol-5-yl)pyridin-2(1H)-one,
1-(3-iodobenzyl)-4-(3-(1-methyl-1H-pyrazol-4-yl)-1H-indazol-5-yl)pyridin-2(1H)-one,
1-((1H-indazol-6-yl)methyl)-4-(3-(2-methylpyridin-4-yl)-1H-indazol-5-yl)pyridin-2(1H)-one,
4-(3-(1-methyl-1H-pyrazol-4-yl)-1H-indazol-5-yl)-1-((2-(trifluoromethyl)pyridin-4-yl)methyl)pyridin-2(1H)-one,
1-(1-(3-bromo-5-fluorophenyl)ethyl)-4-(3-(1-methyl-1H-pyrazol-4-yl)-1H-indazol-5-yl)pyridin-2(1H)-one,
1-(1-(3-chloro-4-fluorophenyl)ethyl)-4-(3-(1-methyl-1H-pyrazol-4-yl)-1H-indazol-5-yl)pyridin-2(1H)-one,
1-(1-(3-chlorophenyl)-2-(methylamino)ethyl)-4-(3-(1-methyl-1H-pyrazol-4-yl)-1H-indazol-5-yl)pyridin-2(1H)-one,
(S)-1-(1-(3-chlorophenyl)-2-hydroxyethyl)-4-(3-(2-methylpyridin-4-yl)-1H-pyrazolo[4,3-b]pyridin-5-yl)pyridin-2 (1H)-one,
(S)-1-(1-(3-chlorophenyl)-2-hydroxyethyl)-4-(3-(2-methylpyridin-4-yl)-1H-pyrazolo[3,4-c]pyridin-5-yl)pyridin-2 (1H)-one,
1-(3-bromo-5-fluorobenzyl)-4-(3-(2-isopropoxypyridin-4-yl)-1H-indazol-5-yl)pyridin-2(1H)-one,
1-(3-bromo-5-fluorobenzyl)-4-(3-(6-isopropoxypyridin-3-yl)-1H-indazol-5-yl)pyridin-2(1H)-one,
(S)-1-(1-(4-chloro-3-fluorophenyl)-2-hydroxyethyl)-4-(3-(6-isopropoxypyridin-3-yl)-1H-indazol-5-yl)pyridin-2 (1H)-one,
4-(3-(2-methylpyridin-4-yl)-1H-indazol-5-yl)pyridin-2 (1H)-one,
4-(3-(2-methylpyridin-4-yl)-1H-indazol-5-yl)-1-(2-morpholinoethyl)pyridin-2(1H)-one,
(S)-1-(1-(3-chloro-4-fluorophenyl)-2-hydroxyethyl)-4-(3-(tetrahydro-2H-pyran-4-yl)-1H-indazol-5-yl)pyridin-2 (1H)-one,
(S)-1-(1-(3-chloro-4-fluorophenyl)-2-hydroxyethyl)-4-(3-(1-cyclopropyl-1H-pyrazol-4-yl)-1H-indazol-5-yl)pyridin-2(1H)-one,
(S)-1-(1-(3-chloro-4-fluorophenyl)-2-hydroxyethyl)-4-(3-(1-(difluoromethyl)-1H-pyrazol-4-yl)-1H-indazol-5-yl)pyridin-2(1H)-one,
(S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one,
(S)-1-(1-(3-chloro-4-fluorophenyl)-2-hydroxyethyl)-4-(3-(1-(2-methoxyethyl)-1H-pyrazol-4-yl)-1H-indazol-5-yl)pyridin-2(1H)-one,
(S)-1-(1-(3-bromo-5-fluorophenyl)-2-hydroxyethyl)-4-(3-(6-ethoxypyridin-3-yl)-1H-indazol-5-yl)pyridin-2(1H)-one,
(S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one,
(S)-1-(1-(3-bromo-5-fluorophenyl)-2-hydroxyethyl)-4-(3-(6-ethoxypyridin-3-yl)-1H-indazol-5-yl)pyridin-2(1H)-one,
(S)-1-(1-(3-bromo-5-fluorophenyl)-2-hydroxyethyl)-4-(3-(6-methoxypyridin-3-yl)-1H-indazol-5-yl)pyridin-2(1H)-one,
4-(3-(2-methylpyridin-4-yl)-1H-pyrazolo[3,4-b]pyridin-5-yl)-1-((2-(trifluoromethyl)pyridin-4-yl)methyl)pyridin-2 (1H)-one,
1-(1-(3-bromo-5-fluorophenyl)ethyl)-4-(3-(2-methylpyridin-4-yl)-1H-pyrazolo[3,4-b]pyridin-5-yl)pyridin-2(1H)-one,
(S)-1-(1-(3-bromo-5-fluorophenyl)-2-hydroxyethyl)-4-(3-(1-methyl-1H-pyrazol-4-yl)-1H-pyrazolo[3,4-b]pyridin-5-yl)pyridin-2(1H)-one,
1-(1-(3-chloro-4-fluorophenyl)-2-(methylamino)ethyl)-4-(3-(2-methylpyridin-4-yl)-1H-indazol-5-yl)pyridin-2 (1H)-one,
(S)-1-(1-(3-chloro-4-fluorophenyl)-2-hydroxyethyl)-4-(3-(1-methyl-1H-pyrazol-4-yl)-1H-pyrazolo[3,4-b]pyridin-5-yl)pyridin-2(1H)-one,
(S)-1-(1-(3-chloro-4-fluorophenyl)-2-hydroxyethyl)-4-(3-(1-(2-hydroxyethyl)-1H-pyrazol-4-yl)-1H-indazol-5-yl)pyridin-2(1H)-one,
(S)-1-(1-(3-bromo-5-fluorophenyl)-2-hydroxyethyl)-4-(3-(6-ethoxypyridin-3-yl)-1H-pyrazolo[3,4-b]pyridin-5-yl)pyridin-2(1H)-one,
(S)-1-(1-(3-bromo-5-fluorophenyl)-2-hydroxyethyl)-4-(3-(4-fluorophenyl)-1H-indazol-5-yl)pyridin-2(1H)-one,
4-(3-(2-methylpyridin-4-yl)-1H-pyrazolo[4,3-b]pyridin-5-yl)-1-((2-(trifluoromethyl)pyridin-4-yl)methyl)pyridin-2 (1H)-one,
(S)-1-(1-(3-bromo-5-fluorophenyl)-2-hydroxyethyl)-4-(2'-methyl-1H,2'H-[3,5'-biindazol]-5-yl)pyridin-2(1H)-one,
(S)-4-(3-(benzo[d]thiazol-6-yl)-1H-indazol-5-yl)-1-(1-(3-bromo-5-fluorophenyl)-2-hydroxyethyl)pyridin-2(1H)-one,
(S)-1-(1-(3-bromo-5-fluorophenyl)-2-hydroxyethyl)-4-(3-(2-methoxypyridin-4-yl)-1H-indazol-5-yl)pyridin-2(1H)-one,
4-(3-(6-methoxypyridin-3-yl)-1H-indazol-5-yl)-1-((2-(trifluoromethyl)pyridin-4-yl)methyl)pyridin-2(1H)-one,
4-(3-(4-fluorophenyl)-1H-indazol-5-yl)-1-((2-(trifluoromethyl)pyridin-4-yl)methyl)pyridin-2(1H)-one,
(S)-1-(1-(3-bromo-5-fluorophenyl)-2-hydroxyethyl)-4-(3-(6-cyclopropoxypyridin-3-yl)-1H-indazol-5-yl)pyridin-2 (1H)-one,
(S)-1-(1-(3-bromo-5-fluorophenyl)-2-hydroxyethyl)-4-(3-(2-ethoxypyridin-4-yl)-1H-indazol-5-yl)pyridin-2(1H)-one,
(S)-1-(1-(3-bromo-5-fluorophenyl)-2-hydroxyethyl)-4-(3-(1-methyl-6-oxo-1,6-dihydropyridin-3-yl)-1H-indazol-5-yl)pyridin-2(1H)-one,
(S)-1-(1-(3-bromo-5-fluorophenyl)-2-hydroxyethyl)-4-(3-(1-methyl-2-oxo-1,2-dihydropyridin-4-yl)-1H-indazol-5-yl)pyridin-2(1H)-one, (S)-1-(1-(3-bromo-5-fluorophenyl)-2-hydroxyethyl)-4-(3-(6-methoxypyridin-3-yl)-1H-pyrazolo[4,3-b]pyridin-5-yl)pyridin-2(1H)-one,
4-(3-(5-fluoropyridin-2-yl)-1H-indazol-5-yl)-1-((2-(trifluoromethyl)pyridin-4-yl)methyl)pyridin-2(1H)-one,
(S)-1-(1-(3-bromo-5-fluorophenyl)-2-hydroxyethyl)-4-(3-(6-methoxypyridin-3-yl)-1H-pyrazolo[3,4-c]pyridin-5-yl)pyridin-2(1H)-one,
(S)-1-(1-(3-bromo-5-fluorophenyl)-2-hydroxyethyl)-4-(3-(5-fluoropyridin-2-yl)-1H-indazol-5-yl)pyridin-2(1H)-one,
4-(3-(2-(trifluoromethyl)pyridin-4-yl)-1H-indazol-5-yl)-1-((2-(trifluoromethyl)pyridin-4-yl)methyl)pyridin-2(1H)-one,
4-(3-(2-methylpyridin-4-yl)-1H-indazol-5-yl)-1-((2-methylpyridin-4-yl)methyl)pyridin-2(1H)-one,
(S)-4-(3-([1,2,4]triazolo[1,5-a]pyridin-6-yl)-1H-indazol-5-yl)-1-(1-(3-bromo-5-fluorophenyl)-2-hydroxyethyl)pyridin-2(1H)-one,
(S)-1-(1-(3-bromo-5-fluorophenyl)-2-hydroxyethyl)-4-(3-(imidazo[1,2-a]pyridin-6-yl)-1H-indazol-5-yl)pyridin-2(1H)-one,
(S)-1-(1-(3-bromo-5-fluorophenyl)-2-hydroxyethyl)-4-(3-(2-methyl-[1,2,4]triazolo[1,5-a]pyridin-6-yl)-1H-indazol-5-yl)pyridin-2(1H)-one,
4-(3-(2-methylpyridin-4-yl)-1H-indazol-5-yl)-1-((6-(trifluoromethyl)pyridin-3-yl)methyl)pyridin-2(1H)-one,
4-(3-(2-ethylpyridin-4-yl)-1H-indazol-5-yl)-1-((2-(trifluoromethyl)pyridin-4-yl)methyl)pyridin-2(1H)-one,
4-(3-(2-cyclopropylpyridin-4-yl)-1H-indazol-5-yl)-1-((2-(trifluoromethyl)pyridin-4-yl)methyl)pyridin-2(1H)-one,
(S)-1-(2-hydroxy-1-(2-(trifluoromethyl)pyridin-4-yl)ethyl)-4-(3-(2-methylpyridin-4-yl)-1H-indazol-5-yl)pyridin-2(1H)-one,
4-(3-(2-methylpyridin-4-yl)-1H-indazol-5-yl)-1-((4-(trifluoromethyl)thiazol-2-yl)methyl)pyridin-2(1H)-one,
4-(3-(2-methylpyridin-4-yl)-1H-indazol-5-yl)-1-((2-(trifluoromethyl)pyridin-3-yl)methyl)pyridin-2(1H)-one,
4-(3-(2-methylpyridin-4-yl)-1H-indazol-5-yl)-1-((6-(trifluoromethyl)pyridin-2-yl)methyl)pyridin-2(1H)-one,
(S)-1-(1-(3-bromo-5-fluorophenyl)-2-hydroxyethyl)-4-(3-(1,3-dimethyl-1H-pyrazol-4-yl)-1H-indazol-5-yl)pyridin-2(1H)-one,
4-(3-(2-methylpyridin-4-yl)-1H-indazol-5-yl)-1-((3-(trifluoromethyl)isoxazol-5-yl)methyl)pyridin-2(1H)-one,
1-(1-(3-bromo-5-fluorophenyl)ethyl)-4-(3-((1r,4r)-4-hydroxycyclohexyl)-1H-indazol-5-yl)pyridin-2(1H)-one,
(S)-1-(1-(3-bromo-5-fluorophenyl)-2-hydroxyethyl)-4-(3-(methylamino)-1H-indazol-5-yl)pyridin-2(1H)-one,
4-(3-(2-methylpyridin-4-yl)-1H-indazol-5-yl)-1-(1-(2-(trifluoromethyl)pyridin-4-yl)ethyl)pyridin-2(1H)-one,
(S)-4-(3-(2-methylpyridin-4-yl)-1H-indazol-5-yl)-1-(1-(2-(trifluoromethyl)pyridin-4-yl)ethyl)pyridin-2(1H)-one,
(R)-4-(3-(2-methylpyridin-4-yl)-1H-indazol-5-yl)-1-(1-(2-(trifluoromethyl)pyridin-4-yl)ethyl)pyridin-2(1H)-one,
6-methyl-4-(3-(2-methylpyridin-4-yl)-1H-indazol-5-yl)-1-((2-(trifluoromethyl)pyridin-4-yl)methyl)pyridin-2(1H)-one,
4-(3-(2-methylpyridin-4-yl)-1H-pyrazolo[3,4-c]pyridin-5-yl)-1-((2-(trifluoromethyl)pyridin-4-yl)methyl)pyridin-2(1H)-one,
(S)-1-(1-(3-bromo-5-fluorophenyl)ethyl)-4-(3-(1-methyl-1H-pyrazol-4-yl)-1H-indazol-5-yl)pyridin-2(1H)-one,
(R)-1-(1-(3-bromo-5-fluorophenyl)ethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(tetrahydro-2H-pyran-4-yl)-1H-indazol-5-yl)pyridin-2(1H)-one,
1-(1-(3-bromo-5-fluorophenyl)ethyl)-4-(3-(tetrahydro-2H-pyran-4-yl)-1H-indazol-5-yl)pyridin-2(1H)-one,
4-(3-(tetrahydro-2H-pyran-4-yl)-1H-indazol-5-yl)-1-((2-(trifluoromethyl)pyridin-4-yl)methyl)pyridin-2(1H)-one,
4-(3-((1r,4r)-4-hydroxycyclohexyl)-1H-indazol-5-yl)-1-((2-(trifluoromethyl)pyridin-4-yl)methyl)pyridin-2(1H)-one,
4-(3-((1s,4s)-4-hydroxycyclohexyl)-1H-indazol-5-yl)-1-((2-(trifluoromethyl)pyridin-4-yl)methyl)pyridin-2(1H)-one,
1-((S)-1-(3-bromo-5-fluorophenyl)-2-hydroxyethyl)-4-(3-(tetrahydrofuran-3-yl)-1H-indazol-5-yl)pyridin-2(1H)-one, and
1-((S)-1-(3-bromo-5-fluorophenyl)-2-hydroxyethyl)-4-(3-(3-hydroxypyrrolidin-1-yl)-1H-indazol-5-yl)pyridin-2(1H)-one.

Embodiment 26

A pharmaceutical composition comprising a compound according to any one of embodiments 1-25, a stereoisomer, a stable isotope and/or a pharmaceutically acceptable salt thereof, admixed with at least one pharmaceutically acceptable carrier.

Embodiment 27

The pharmaceutical composition of embodiment 26, further comprising at least one therapeutic co-agent.

Embodiment 28

The pharmaceutical composition of embodiment 27, wherein the at least one therapeutic co-agent is selected from anticancer compounds, analgesics, and anti-inflammatory compounds.

Embodiment 29

A method to treat cancer, comprising administering to a subject in need of such treatment a therapeutically effective amount of a compound according to any one of embodiments 1-25, and/or a stereoisomer, a stable isotope, or a pharmaceutically acceptable salt thereof, or a pharmaceutical composition of any one of embodiments 26-28.

Embodiment 30

The method of embodiment 29, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer.

Embodiment 31

A compound according to any one of embodiments 1-25 for use as a medicament.

Embodiment 32

Use of a compound according to any one of embodiments 1-25, and/or a stereoisomer, a stable isotope, or a pharmaceutically acceptable salt thereof in the manufacture of a medicament for the treatment of cancer; or use of a compound according to any one of embodiments 1-25, and/or a stereoisomer, a stable isotope, or a pharmaceutically acceptable salt thereof in medicine, especially for treatment of a cancer such as those named in embodiment 30.

Embodiment 33

A method to treat an inflammatory disease in a patient comprising administering to a subject in need of such treatment a therapeutically effective amount of a compound according to any of embodiments 1-25, and/or a stereoisomer, a stable isotope, or a pharmaceutically acceptable salt thereof, or a pharmaceutical composition of any of embodiments 26-28, wherein the inflammatory disease is selected from rheumatoid arthritis, psoriasis, and eczema.

In some embodiments of the compounds of Formula I and other embodiments disclosed above, $R^1$ is H or alkyl. Further in some embodiments, $R^1$ is H.

In some embodiments of the compounds of Formula I and other embodiments disclosed above, $L^1$ and $L^2$ are independently selected from a bond, —NH—, —O— and —CH$_2$—. Further in some embodiments, $L^1$ and $L^2$ are a bond.

In certain of the foregoing embodiments, L is a bond and A is a C1-4 alkylene, which may be straight chain or branched, and can be unsubstituted or substituted with 1-3 groups as described for Formula I. In some embodiments, A is —CH(R)—, wherein R is a C1-C3 alkyl or a C1-C2 alkyl and is optionally substituted with 1-3 groups as described for Formula I. In some embodiments, A is C1-C2 alkyl and is substituted by 1 or 2 groups independently selected from —OH, halo, —OMe, -MH$_2$, —NHMe, —NMe$_2$, and —OP(O)(OH)$_2$. In some embodiments, where $R^3$ is an aryl or heteroaryl group, A is —CH$_2$— or a substituted alkylene of the formula —CH(CH$_2$R*)— wherein R* is H, Me, —OH, F, —NH$_2$, —NHMe, —N(Me)$_2$, —OP(O)(OH)$_2$ or OMe. In other embodiments, A is —CH$_2$CH$_2$—. When A is substituted, it is often substituted with methyl, hydroxymethyl, aminomethyl, methylamino, methylaminomethyl, fluoromethyl, or methoxymethyl.

In embodiments where A is substituted alkylene (e.g., a group of formula —CHR*— as described herein), A contains a chiral center; in certain of these embodiments, A has this stereochemistry:

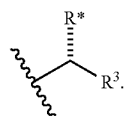

For example, R* is —CH$_3$, —CH$_2$OH, —CH$_2$NH$_2$, —CH$_2$NHMe, —CH$_2$NMe$_2$, —CH$_2$F, —CH$_2$OMe, —CH(OH)Me, —CH$_2$OP(O)(H)$_2$ or —CH(OH)CH$_2$OH.

In some embodiments, the compound of Formula I (such as Formula IA, IB and IC), comprises A having the chiral configuration shown in excess over its enantiomer, so the compound is optically active. For example, such compounds disclosed herein are substantially free of the opposite enantiomer, i.e., at least 95% of the compound has the chirality shown above.

In some embodiments of the foregoing compounds, $R^3$ is aryl or heteroaryl, optionally substituted as described below. For example, $R^3$ is an optionally substituted group selected from phenyl, thienyl, thiazolyl, pyridinyl, pyridazinyl, pyrazinyl, and pyrimidinyl. In some embodiments, $R^3$ is substituted phenyl.

In some embodiments, $R^3$ is substituted with at least one group selected from those set forth in the embodiments above. In some embodiments, $R^3$ is phenyl, 3-thienyl, 2-thiazolyl, 2-pyridinyl, 3-pyridinyl, or 4-pyridinyl that is unsubstituted or is substituted with 1-2 groups independently selected from halo (F, Cl, Br or I), methyl, methoxy, —SMe, methylsulfonyl, cyano, and cyclopropyl. In some embodiments, $R^3$ is phenyl and is substituted in at least one position at meta position relative to A that is attached with F, Cl, Br, I, SMe, —CH$_2$F, —CHF$_2$, or methylsulfonyl.

In some embodiments, the -A-$L^2$-$R^3$ portion of the structure in Formula (I) has the following formula:

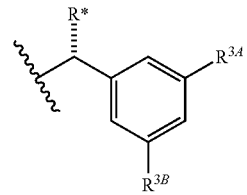

wherein R* is H, —CH$_3$, —CH$_2$OH, —CH$_2$NH$_2$, —CH$_2$NHMe, —CH$_2$NMe$_2$, —CH$_2$OMe, —CH$_2$F, or —CH$_2$OP(O)(OH)$_2$; $R^{3A}$ and $R^{3B}$ are independingly selected from H, F, Cl, CN, —SO$_2$Me, -Me, —OMe, Br, I, —CH$_2$F, —CF$_2$H, CF$_3$, and SMe.

In these embodiments, at least one of $R^{3A}$ and $R^{3B}$ is other than H. For example, at least one of $R^{3A}$ and $R^{3B}$ is halo, such as Cl, Br or I.

In some embodiments, the -A-$L^2$-$R^3$ portion of the structure in Formula (I) has the following formula:

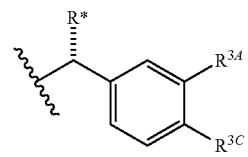

wherein R* is H, —CH$_3$, —CH$_2$OH, —CH$_2$NH$_2$, —CH$_2$NHMe, —CH$_2$NMe$_2$, —CH$_2$OMe, —CH$_2$F, or C—H$_2$OP(O)(OH)$_2$; $R^{3A}$ and $R^{3c}$ are independently selected from H, F, Cl, —CN, —SO$_2$Me, -Me, —OMe, Br, I, —CH$_2$F, CF$_2$H, CF$_3$, and SMe.

In these embodiments, at least one of $R^{3A}$ and $R^{3c}$ is other than H. For example, at least one of $R^{3A}$ and $R^{3c}$ is halo, such as Cl, Br or I.

In some embodiments, the -A-$L^2$-$R^3$ portion of the structure in Formula (I) has the following formula:

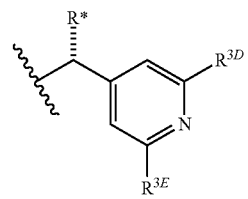

wherein R* is H, —CH₃, —CH₂OH, —CH₂NH₂, —CH₂NHMe, —CH₂NMe₂, —CH₂OMe, —CH₂F, or —CH₂OP(O)(OH)₂; $R^{3D}$ and $R^{3E}$ are independently selected from H, F, —CN, —SO₂Me, Me, —OMe, —OCF₃, —CH₂F, —CF₂H, —CF₃, and SMe.

In these embodiments, at least one of $R^{3D}$ and $R^{3E}$ is other than H. For example, at least one of $R^{3D}$ and $R^{3\backslash E}$ is CF₃.

Also disclosed herein is a pharmaceutical composition comprising a compound of Formula I (such as Formula IA, IB and IC), and/or a stereoisomer, a stable isotope, or a pharmaceutically acceptable salt thereof, and a pharmaceutically acceptable carrier.

Further disclosed herein is a method of inhibiting the activity of ERK comprising contacting the protein Erk with an effective amount of a compound of Formula I (such as Formula IA, IB and IC), and/or a stereoisomer, a stable isotope, or a pharmaceutically acceptable salt thereof disclosed herein.

Further disclosed herein is a method of treating a disease treatable by inhibition of ERK in a patient, comprising administering to the patient in recognized need of such treatment, an effective amount of a compound of Formula I (such as Formula IA, IB and IC), and/or a stereoisomer, a stable isotope, or a pharmaceutically acceptable salt thereof disclosed herein.

Further disclosed herein is a method of treating a disease treatable by inhibition of Erk in a patient, comprising administering to the patient in recognized need of such treatment, an effective amount of a pharmaceutical composition comprising a compound of Formula I (such as Formula IA, IB and IC), and/or a stereoisomer, a stable isotope, or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of Formula I (such as Formula IA, IB and IC), and/or a stereoisomer, a stable isotope, or a pharmaceutically acceptable salt thereof disclosed herein and a pharmaceutically acceptable carrier. In some embodiments, the cancer is colon cancer, gastric cancer, leukemia, lymphoma, melanoma, or pancreatic cancer.

Further disclosed herein is a method of treating an inflammatory disease in a patient, comprising administering to the patient in recognized need of such treatment, an effective amount of a pharmaceutical composition comprising a compound of Formula I (such as Formula IA, IB and IC), and/or a stereoisomer, a stable isotope, or a pharmaceutically acceptable salt thereof disclosed herein and a pharmaceutically acceptable carrier. In some embodiments, the inflammatory disease is rheumatoid arthritis, psoriasis, or eczema.

Further disclosed herein is a use of a compound of Formula I (such as Formula IA, IB and IC), and/or a stereoisomer, a stable isotope, or a pharmaceutically acceptable salt thereof in preparation of a medication for treating a disease responsive to inhibition of Erk, such as a cancer or an inflammatory disease. In some embodiments, the cancer is colon cancer, gastric cancer, leukemia, lymphoma, melanoma, or pancreatic cancer. In some embodiments, the inflammatory disease is rheumatoid arthritis, psoriasis, or eczema.

The pharmaceutical composition comprising a compound of Formula I (such as Formula IA, IB and IC), and/or a stereoisomer, a stable isotope, or a pharmaceutically acceptable salt thereof, and a pharmaceutically acceptable carrier, can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound of Formula I (such as Formula IA, IB and IC), and/or a stereoisomer, a stable isotope, or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound of Formula I (such as Formula IA, IB and IC), and/or a stereoisomer, a stable isotope, or a pharmaceutically acceptable salt thereof can also be administered parenterally, in sterile liquid dosage forms, such as dispersions, suspensions or solutions. Other dosages forms that can also be used to administer the compound of Formula I (such as Formula IA, IB and IC), and/or a stereoisomer, a stable isotope, or a pharmaceutically acceptable salt thereof include ointment, cream, drops, transdermal patch or powder for topical administration, an ophthalmic solution or suspension formation, i.e., eye drops, for ocular administration, an aerosol spray or powder composition for inhalation or intranasal administration, or a cream, ointment, spray or suppository for rectal or vaginal administration.

Gelatin capsules containing the compound of Formula I (such as Formula IA, IB and IC), and/or a stereoisomer, a stable isotope, or a pharmaceutically acceptable salt thereof and at least one powdered carrier selected, for example, from lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound disclosed herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the pharmaceutical composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in *Remington's Pharmaceutical Sciences*, A. Osol, a standard reference text in the art.

The compound of Formula I (such as Formula IA, IB and IC), and/or a stereoisomer, a stable isotope, or a pharmaceutically acceptable salt thereof can be examined for efficacy in treating cancer by in vivo assays. For example, the compound of Formula I (such as Formula IA, IB and IC), and/or a stereoisomer, a stable isotope, or a pharmaceutically acceptable salt thereof can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound of Formula I (such as Formula IA, IB and IC), and/or a stereoisomer, a stable isotope, or a pharmaceutically acceptable salt thereof may be conveniently delivered in the form of an aerosol spray presentation from pressurized packs or nebulisers. The compound of Formula I (such as Formula IA, IB and IC), and/or a stereoisomer, a stable isotope, or a pharmaceutically acceptable salt thereof may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound of Formula I (such as Formula IA, IB and IC), and/or a stereoisomer, a stable isotope, or a pharmaceutically acceptable salt thereof in at least one suitable propellant, selected, for example, from fluorocarbons and hydrocarbons.

For ocular administration, an ophthalmic preparation may be formulated with an appropriate weight percentage of a solution or suspension of the compound of Formula I (such as Formula IA, IB and IC), and/or a stereoisomer, a stable isotope, or a pharmaceutically acceptable salt thereof in an appropriate ophthalmic vehicle, such that the compound of Formula I (such as Formula IA, IB and IC), and/or a stereoisomer, a stable isotope, or a pharmaceutically acceptable salt thereof is maintained in contact with the ocular surface for a sufficient time period to allow the compound to penetrate the corneal and internal regions of the eye.

Useful pharmaceutical dosage-forms for administration of the compound of Formula I (such as Formula IA, IB and IC), and/or a stereoisomer, a stable isotope, or a pharmaceutically acceptable salt thereof include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, the compound of Formula I (such as Formula IA, IB and IC), and/or a stereoisomer, a stable isotope, or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

In some embodiments, a large number of unit capsules can be prepared by filling standard two-piece hard gelatin capsules each with, for example, 100 milligrams of the compound of Formula I (such as Formula IA, IB and IC), and/or a stereoisomer, a stable isotope, or a pharmaceutically acceptable salt thereof in powder, 150 milligrams of lactose, 50 milligrams of cellulose, and 6 milligrams magnesium stearate.

In some embodiments, a mixture of the compound of Formula I (such as Formula IA, IB and IC), and/or a stereoisomer, a stable isotope, or a pharmaceutically acceptable salt thereof and a digestible oil such as soybean oil, cottonseed oil or olive oil can be prepared and injected by means of a positive displacement pump into gelatin to form soft gelatin capsules containing 75 or 100 milligrams of the active ingredient. The capsules are washed and dried.

In some embodiments, the compound of Formula I (such as Formula IA, IB and IC), and/or a stereoisomer, a stable isotope, or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet.

In some embodiments, a large number of tablets can be prepared by conventional procedures so that the dosage unit comprises, for example, 100 milligrams of the compound of Formula I (such as Formula IA, IB and IC), and/or a stereoisomer, a stable isotope, or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may, for example, be applied to increase palatability or delay absorption.

In some embodiments, a parenteral composition suitable for administration by injection can be prepared by stirring 1.5% by weight of a compound of Formula I (such as Formula IA, IB and IC), and/or a stereoisomer, a stable isotope, or a pharmaceutically acceptable salt thereof in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound of Formula I (such as Formula IA, IB and IC), and/or a stereoisomer, a stable isotope, or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound of Formula I (such as Formula IA, IB and IC), and/or a stereoisomer, a stable isotope, or a pharmaceutically acceptable salt thereof are administered stepwise or in conjunction with at least one other therapeutic agent. When drugs are administered in physical combination, the dosage form and administration route should be selected depending on the compatibility of the combined drugs. Thus, the term "co-administration" is understood to include the administration of at least two agents concomitantly or sequentially, or alternatively as a fixed dose combination of the at least two active components.

The compound of Formula I (such as Formula IA, IB and IC), and/or a stereoisomer, a stable isotope, or a pharmaceutically acceptable salt thereof can be administered as the sole active ingredient or in combination with at least one second active ingredient, selected, for example, from other active ingredients known to be useful for treating the target disease, such as cancers including, for example, colon cancer, gastric cancer, leukemia, lymphoma, melanoma, and pancreate cancer in a patient.

As used herein, the term "optical isomer" or "stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. The invention includes enantiomers, diastereomers or racemates of the compounds. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 1R-SJ system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present disclosure is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E orZ configuration unless specified. If the compound contains a di-substituted cycloalkyl, the cycloalkyl substituent may have a cis- or trans-configuration, unless otherwise specified.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, adipate, aluminum, ascorbate, aspartate, benzoate, besylate, bromide/hydrobromide, bicarbonate/carbonate, bisulfate/sulfate, camphorsulfonate, caproate, chloride/hydrochloride, chloroprocaine, chlortheophyllonate, citrate, edetate, calcium edetate, ethandisulfonate, ethylsulfonate, ethylene diamine, fumarate, galactarate (mucate), gluceptate, gluconate, glucuronate, glutamate, glycolate, hexyl resorcinate, hippurate, hydroiodide/iodide, hydroxynapthoate (xinafoate), isethionate, lactate, lactobionate, laurylsulfate, lithium, malate, maleate, malonate, mandelate, mesylate, methylsulphate, naphthoate, napsylate, nicotinate, nitrate, octadecanoate, oleate, oxalate, palmitate, pamoate, pantothenate, phosphate/hydrogen phosphate/dihydrogen phosphate, polygalacturonate, procaine, propionate, salicylate, sebacate, stearate, subacetate, succinate, sulfate, sulfosalicylate, tannate, tartrate, bitartrate, tosylate, triphenylacetate, and trifluoroacetate salts. Lists of additional suitable salts can be found, e.g., in REMINGTON'S PHARMACEUTICAL SCIENCES, 20th ed., Mack Publishing Company, Easton, Pa., (1985); and in HANDBOOK OF PHARMACEUTICAL SALTS: PROPERTIES, SELECTION, AND USE, by Stahl and Wermuth (Wiley-VCH, Weinheim, Germany, 2002). Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is intended to represent unlabeled forms (i.e., compounds wherein all atoms are present at natural isotopic abundances and not isotopically enriched) as well as isotopically enriched or labeled forms of the compounds. Isotopically enriched or labeled compounds have structures depicted by the formulas given herein except that at least one atom of the compound is replaced by an atom of the same element but having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I) if it is incorporated at substantially above the level of natural isotopic abundance. The invention includes isotopically enriched versions of the compounds, e.g., deuterated versions as well as non-deuterated versions. Deuterated versions may be deuterated at a single site, or at multiple sites.

The degree of incorporation of such an isotope in an isotopically-enriched compound, particularly deuterium, may be defined by the isotopic enrichment factor. The term "isotopic enrichment factor" as used herein means the ratio between the isotopic abundance of a specified isotope in a sample, and the natural abundance of the isotope in a non-enriched sample. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, REMINGTON'S PHARMACEUTICAL SCIENCES, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "therapeutically effective amount" refers to the amount of the compound of the present invention that, when administered to a subject, is effective to (1) at least partially alleviate, inhibit, prevent and/or ameliorate a condition, or a disorder or a disease (i) mediated by a kinase such as ERK1/2 or (ii) associated with activity of a kinase such as ERK1/2, or (iii) characterized by activity (normal or abnormal) of ERK1/2; or (2) reduce or inhibit the activity of ERKJ/2 or (3) reduce or inhibit the expression of ERK1/2.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of ERK1/2, or at least partially reduce or inhibit the expression of ERK1/2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, activity, effect, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "Treat", "treating" or "treatment" refers to alleviating or ameliorating at least one physical parameter including those which may not be discernible by the patient. In yet another embodiment, "Treat", "treating" or "treatment" refers to modulating the disease or disorder, either physically, (e.g., stabilization of a discernible symptom), physiologically, (e.g., stabilization of a physical parameter), or both. In yet another embodiment, "Treat", "treating" or "treatment" refers to delaying the development or progression of the disease or disorder.

As used herein, a subject is "in need of" a treatment if such subject would be expected to benefit biologically, medically or in quality of life from such treatment.

As used herein, the term "a" "an" "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer.

Substituents at atoms with carbon-carbon double bonds may, where possible, be present in cis-(Z)-ortrans-(E)-form, and both are included in the invention unless otherwise indicated.

Accordingly, as used herein a compound of the present invention can be in the form of one of the possible isomers, rotamers, atropisomers, or as a mixture thereof, for example, as substantially pure geometric (cis or trans) isomers, diastereomers, optical isomers (antipodes), racemates or mixtures thereof. 'Substantially pure' or 'substantially free of other isomers" as used herein means the product contains less than 5%, and preferably less than 2%, of other isomers relative to the amount of the preferred isomer, by weight.

the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds of formula I can be made by general synthetic method as illustrated in Scheme 1. Indazoles 1 can be converted to 3-idodoindazole 2 by reacting with iodine. The desired $R^2L^1$ group substituted indazole intermediate 3 can be introduced by reaction of iodoindazole 2 with appropriate intermediates ($R^2$—$B(OR)_2$, $R^2NH_2$, $R^2OH$, etc.) using palladium catalyzed chemistry. Coupling of indazole 3 and pyridone bronic acid or esters 6, which can be made from bromo-pyridone 5 catalyzed by palladium, under well-known palladium-assisted conditions to form compounds of formula 7, which are compounds of Formula I.

Alternatively, indazole 3 can be converted to indazole bronic acid or esters 4, and then coupled with bromo-pyridone 5 to form compounds of formula 7 using palladium catalyzed chemistry.

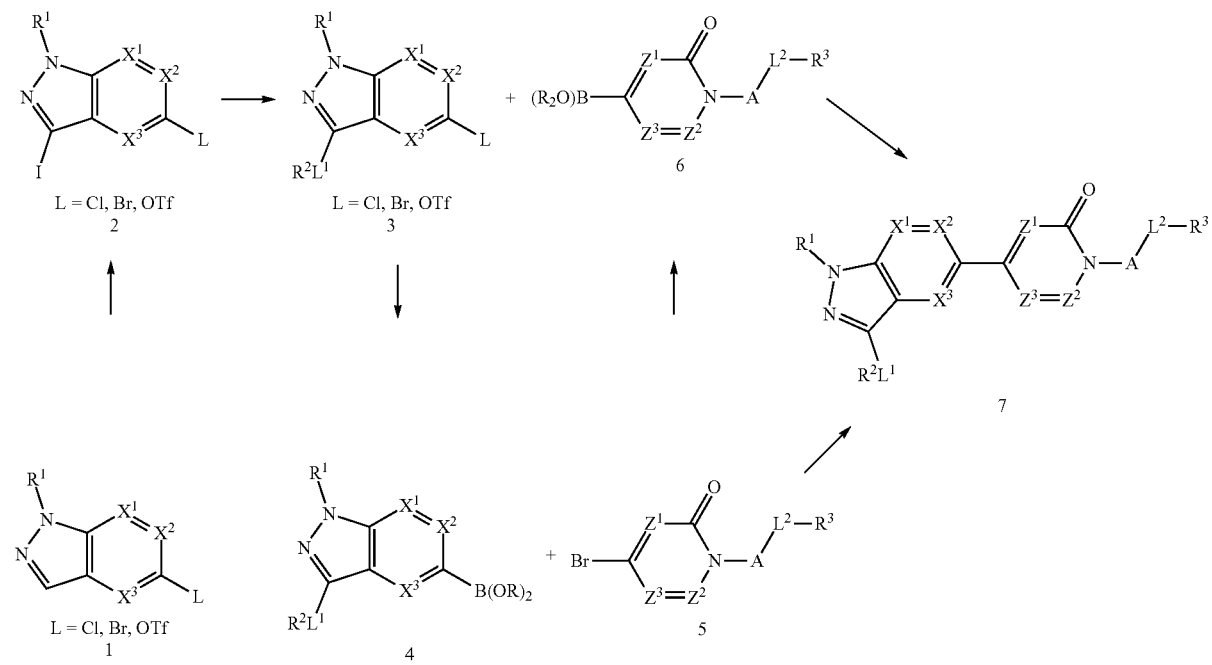

Scheme 1

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating The Schemes 2-4 in some instances illustrate preparation of compounds wherein A is a bond, $Z^1$, $Z^2$, and $Z^3$ are CH, and $L^2$ is methylene or a substituted alkylene group, but methods for preparing suitable pyridones where A and $L^2$ are other options encompassed by Formula I are readily apparent to the skilled person in view of the many known methods for making the requisite indazole and pyridones intermediates, so these methods are equally applicable to preparation of compounds with other embodiments of A and $L^2$.

Scheme 2

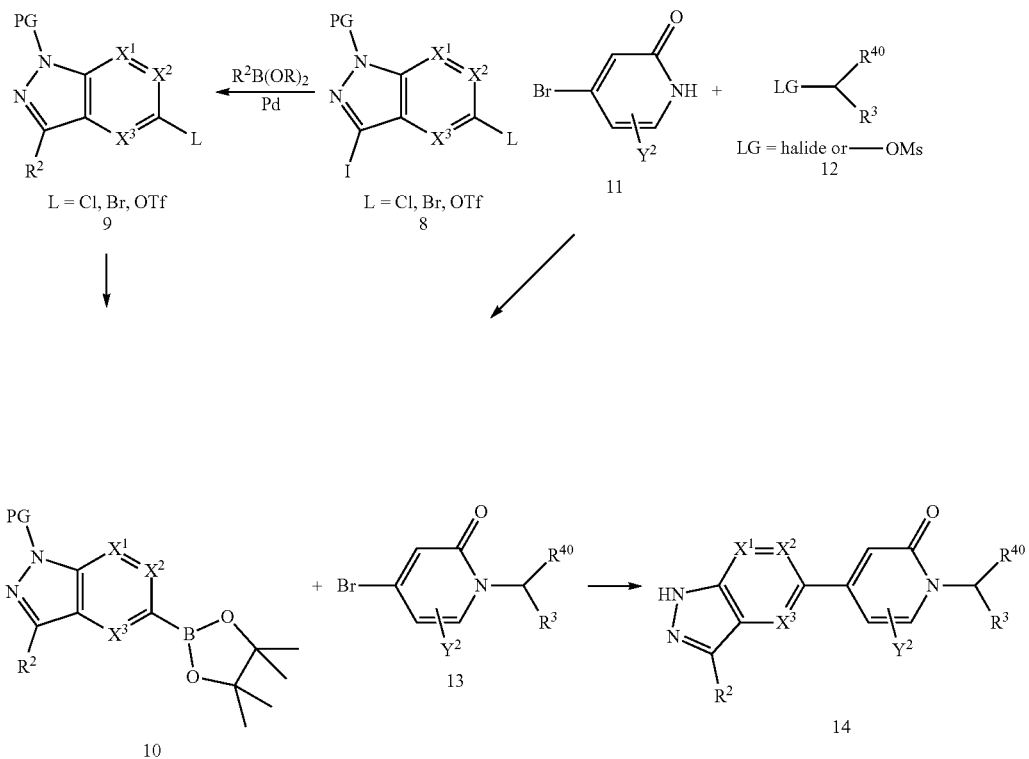

The intermediate 8 and pyridine 11, as shown in Scheme 2, can be made by many known methods to the skilled person. The iodoindazole 8 can be selectively converted to the boric acid or esters of intermediate 10 using palladium-catalyzed chemistry. N-alkylation of pyridone 11 with apropiate allylating agent 12 provides intermidate 13, which upon coupling with boric acid or esters 10 under palladium catalyzed reaction conditions and subsequent deprotection of the protective group PG to form target compounds of formula 14, which are compounds of formula IA. $R^2$ groups of compounds of Formula 14 may require further modifications such as hydrogenation and reduction by conventional methods leading to the desired substituents. This option is illustrated in Scheme 3, where preparations of compounds having 4-tetrahydropyranyl (15) and 4-hydroxylcyclohexyl (16) as $R^2$ are shown.

Scheme 4 illustrates another synthetic method to compound 14, where the groups corresponding to $R^3$ and $R^{40}$ in Formula IA are attached after indazole and pyridine is coupled. Intermediate 9 can be coupled with 2-fluoropyridine-4-boronic ester intermediate 17 under palladium catalyzed reaction conditions to form intermediate 18, which can be hydrolyzed to 2-pyridone intermediate 19. Alternatively, intermediate 19 can be obtained by coupling of intermediate 10 and intermidate 11 under palladium catalyzed reaction conditions. N-alkylation of pyridone 19 with Scheme 3

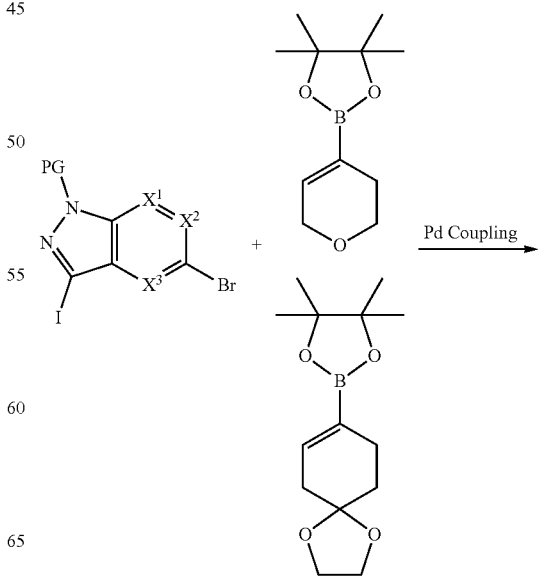

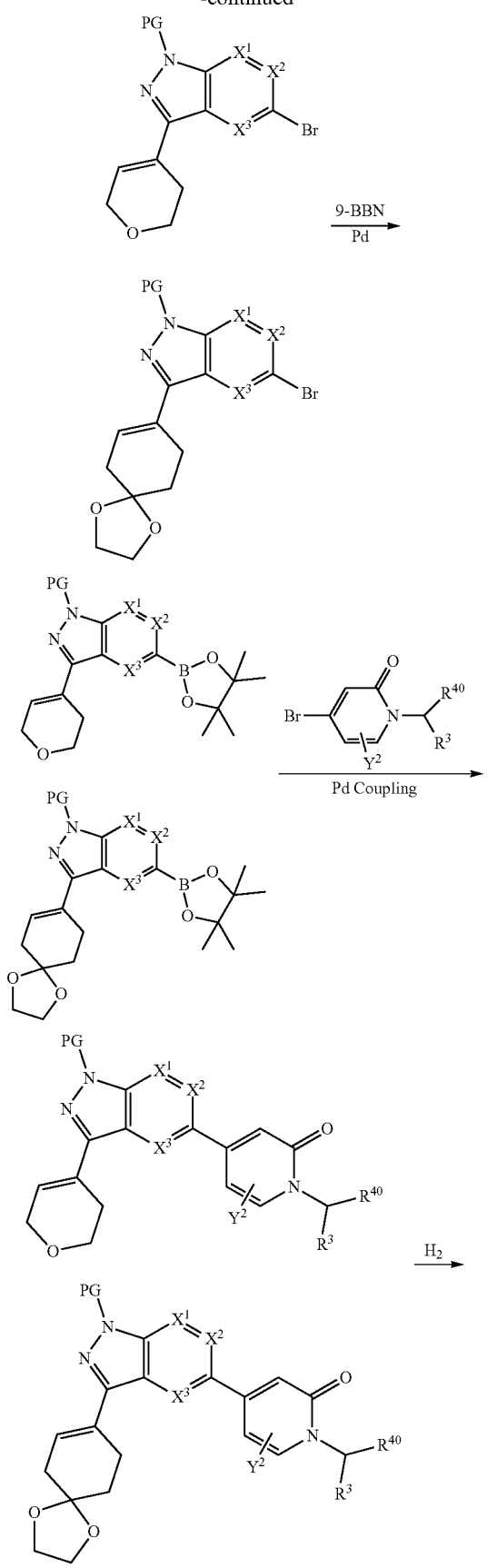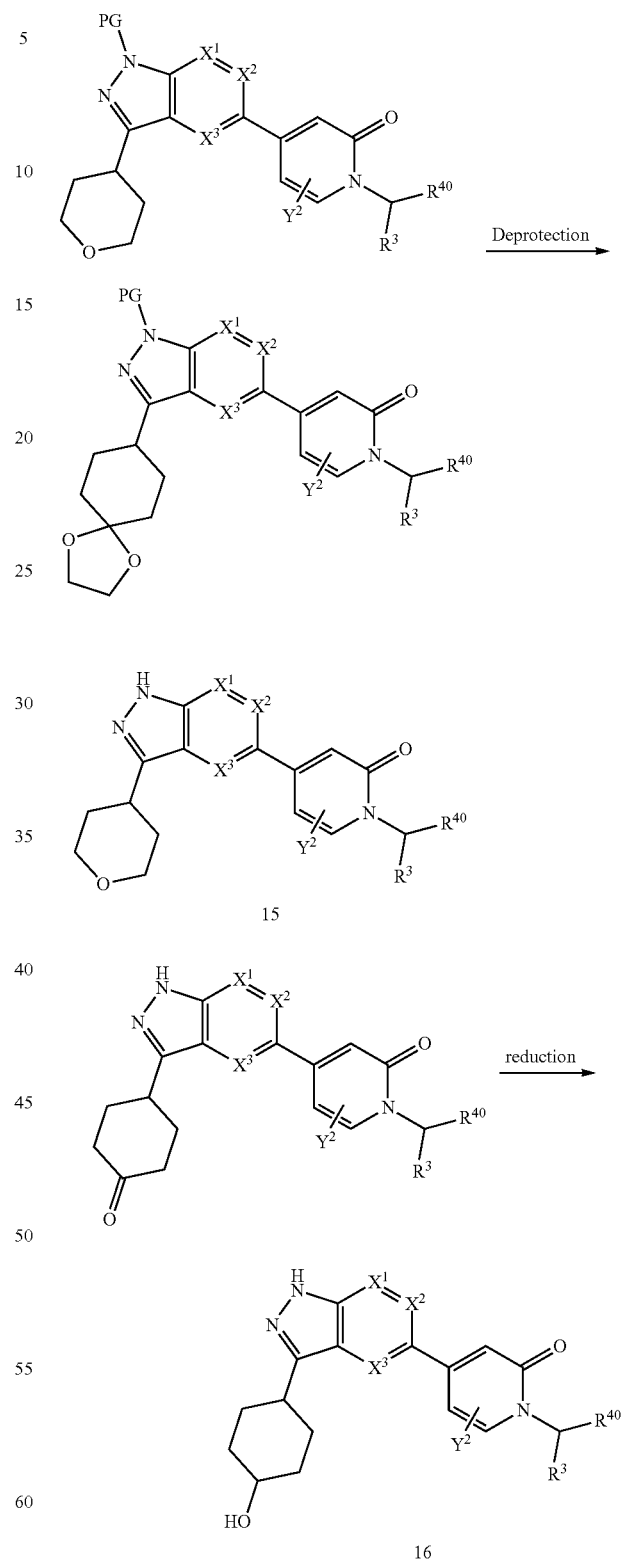
an appropriate allylating agent 12 provides intermediate 20, and subsequent deprotection of the protective group PG to form target compound of formula 14.

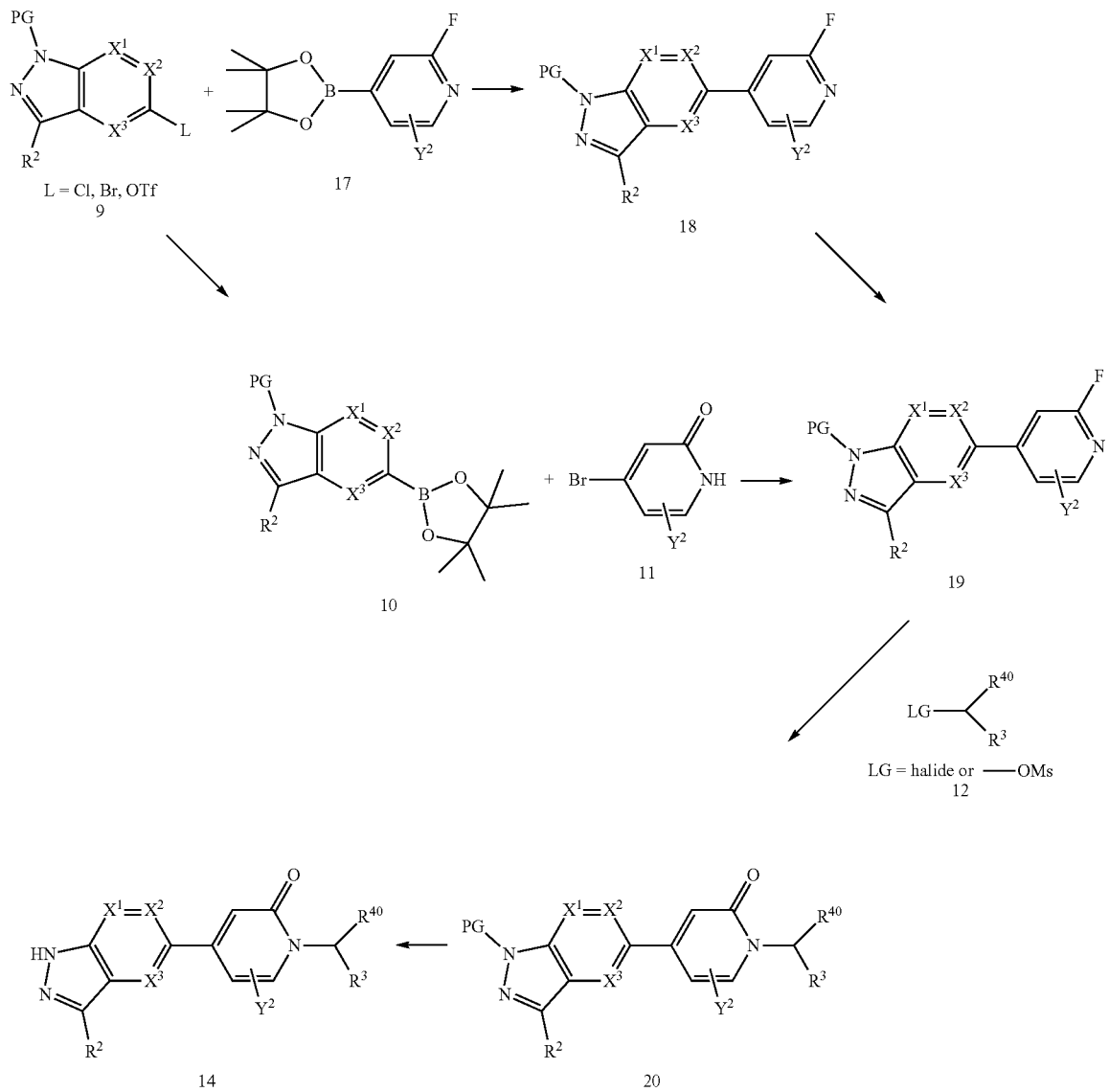

Scheme 4

EXAMPLES

The following examples illustrate certain embodiments of the disclosue and how to make and use them. They are not intended to limit the scope of the disclosure.

In the following examples, the abbreviations below are used:
B₂Pin₂ Bis(pinacolato)diboron
DCM Dichloromethane
DIPEA di-isopropylethylamine
DMAP 4-Dimethylaminopyridine
DMF Dimethylformamide
DMSO Diemthylsulfoxide
EDTA Ethylenediaminetetraacetic acid
EtOAc ethyl acetate
HATU 1-[Bis(dimethylamino)methylene]-1H-1,2,3-triazolo[4,5-b]pyridinium 3-oxid hexafluorophosphate
KHMDS Potassium hexamethyldisilazane
LG Leaving group
MeOH Methanol
PdPd₂dba₃ Tris(dibenzylideneacetone)palladium
PdPd(dppf)Cl₂ [1,1'Bis(diphenylphosphino)ferrocene]dichloropalladium(II)
PE Petroleum ether
PG Protecting group
PPTS Pyridinium p-toluenesulfonate
TBSCl t-Butyldimethylsilyl chloride
TLC Thin layer chromatography
TEA Triethylamine
TES Triethylsilyl
TFA Trifluoacetic acid
Tf₂O Trifluoromethanesulfonic anhydride
THF Tetrahydrofuran
Xantphos 4,5-Bis(diphenylphosphino)-9,9-dimethylxanthene

Example 1 (Method 1)

Preparation of (S)-1-(1-(3-chlorophenyl)-2-hydroxyethyl)-4-(3-(2-methyl-pyridin-4-yl)-1H-indazol-5-yl)pyridin-2(1H)-one

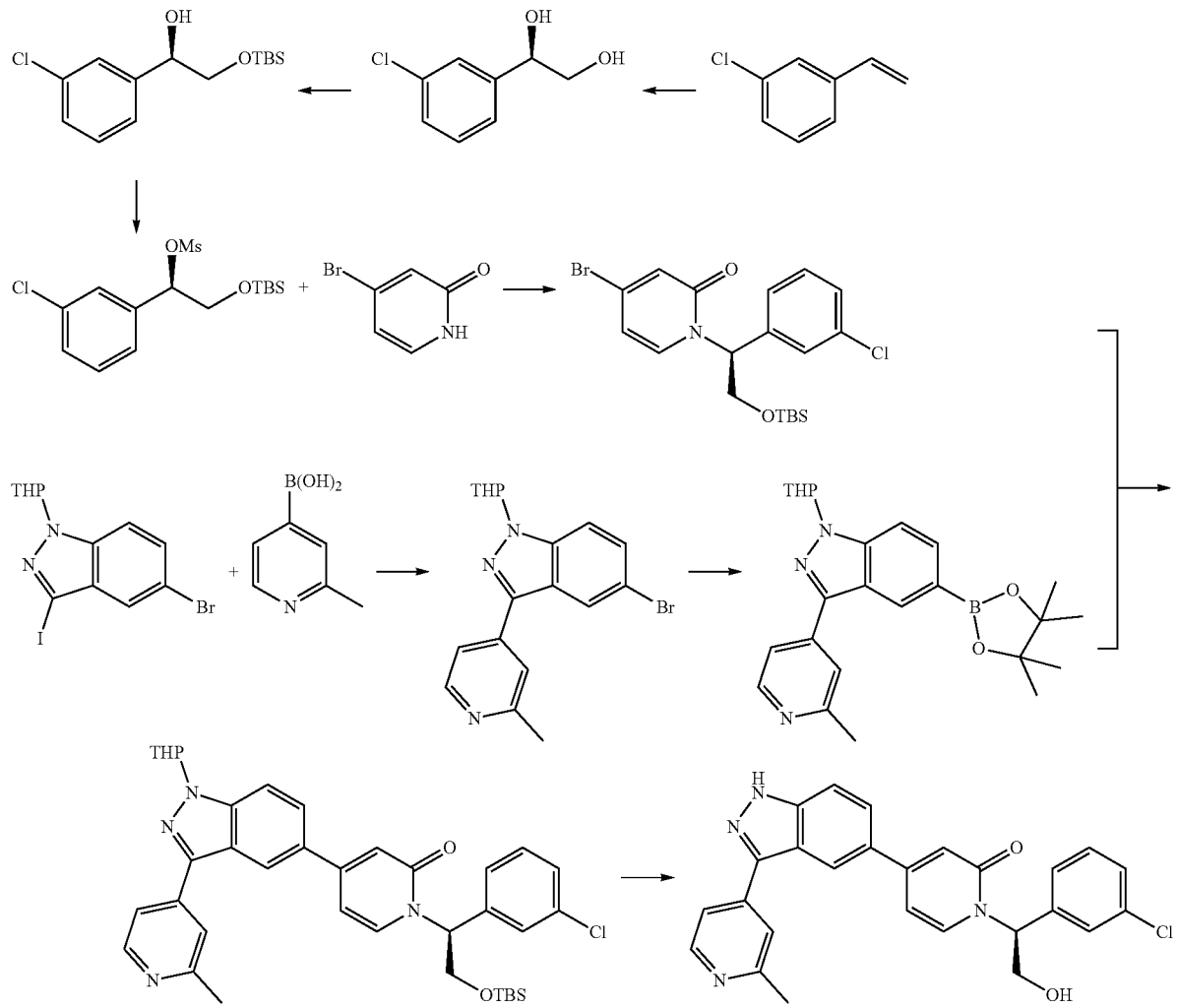

Step 1. (R)-1-(3-chlorophenyl)ethane-1,2-diol

To mixture of AD-mix-Beta (50 g) in t-BuOH/H2O (1:1, 300 mL) was added 1-chloro-3-vinylbenzene (5 g, 36 mmol) at 0° C. The mixture was stirred at room temperature overnight and quenched with saturated aqueous NaHSO₃, extracted with EtOAc (1000 mL). The organic layer was dried over anhydrous Na₂SO₄, filtered off, and concentrated in vacuo. The crude product was purified by silica gel flash column chromatography eluting with ethyl acetate to give the title compound (5.55 g, 90%).

Step 2. (R)-2-((tert-butyldimethylsilyl)oxy)-1-(3-chlorophenyl)ethanol

To a solution of (R)-1-(3-chlorophenyl)ethane-1,2-diol (5.55 g, 32.2 mmol) and imidazole (5.47 g, 80.5 mmol) in DCM (50 mL) was added TBSCl (4.864 g, 32.2 mmol) at 0° C. The mixture was stirred at 0° C. for 1 h and diluted with DCM (200 mL), washed with saturated NaHCO₃ (100 mL) and H₂O (100 mL). The organic layer was dried over anhydrous Na₂SO₄, filtered off, and concentrated in vacuo. The crude product was purified by silica gel flash column chromatography eluting with (PE:EA=4:1) to give the title compound (7.8 g, 85%).

Step 3. (R)-2-((tert-butyldimethylsilyl)oxy)-1-(3-chlorophenyl)ethyl-ethanesulfonate To mixture of (R)-2-((tert-butyldimethylsilyl)oxy)-1-(3-chlorophenyl)-ethanol (7.8 g, 27.3 mmol) and Et₃N (5.7 ml, 40.9 mmol) in DCM (273 mL) was added MsCl (2.6 g, 32.8 mmol) at 0° C. The mixture was stirred at 0° C. for 2 h and then washed with H₂O (100 mL) and saturated NaHCO₃ (100 mL). The organic layer was dried over anhydrous Na₂SO₄, filtered off, and concentrated in vacuo to give the title compound (10 g, 96%).

Step 4. 5-bromo-3-(2-methylpyridin-4-yl)-1-(tetrahydro-2H-pyran-2-yl)-1H-indazole A solution of 5-bromo-3-iodo-1-(tetrahydro-2H-pyran-2-yl)-1H-indazole (55 g, 135 mmol), (2-methylpyridin-4-yl)boronic acid (20.3 g, 148 mmol), Pd(dppf)Cl₂-DCM (5.5 g, 6.75 mmol) and Na₂CO₃ (28.6 g, 270 mmol) in dioxane (500 mL)/H₂O (100 mL) was stirred at 65° C. under N₂ protection overnight. The mixture was then cooled to room temperature and diluted with H₂O (300 mL), extracted with EA (300 mL×3). The combined organic layers were washed with H₂O (200 mL) and brine (200 mL), dried over anhydrous Na₂SO₄, filtered off, and concentrated in vacuo. The crude product was purified by silica gel flash column chromatography to give the title compound (35.5 g, 71% yield).

Step 5. 3-(2-methylpyridin-4-yl)-1-(tetra-hydro-2H-pyran-2-yl)-5-(4,4,5,5-tetramethyl-1,3,2-dioxaborolan-2-yl)-1H-indazole A mixture of 5-bromo-3-(2-methylpyridin-4-yl)-1-(tetrahydro-2H-pyran-2-yl)-1H-indazole (0.75 g, 2.0 mmol), bis(pinacolato)diboron (0.61 g, 2.4 mmol), Pd(dppf)Cl₂-DCM (0.15 g, 0.2 mmol) and KOAc (0.39 g, 4.0 mmol) in DMF (10 ml) was degassed with N₂ and stirred at 85° C. for 2 h. The mixture was cooled to room temperature and diluted with EA (100 mL), washed by H₂O (30 mL×2) and brine (30 mL). The organic layer was dried over anhydrous Na₂SO₄, filtered off, and concentrated in vacuo. The residue was purified by silica gel flash column chromatography (PE/EA=2/1-1/2) to give the title compound (0.61 g, 74% yield).

Step 6. (S)-4-bromo-1-(2-((tert-butyldimethylsilyl)oxy)-1-(3-chloro-phenyl)-ethyl)pyridin-2(1H)-one To a solution of 4-bromopyridin-2(1H)-one (870 mg, 5.0 mmol) in dry THF (25 mL) was added KHMDS (1M in THF, 5.5 mL) at room temperature. The mixture was stirred at room temperature for 0.5 h, followed by the addition of (R)-2-((tert-butyl-dimethylsilyl)-oxy)-1-(3-chlorophenyl) ethyl methanesulfonate (5.5 mL, 5.5 mmol) in one portion. The mixture was transferred to a capped vial and stirred at 85° C. for 18 h. The reaction mixture was cooled to room temperature and diluted with EtOAc (50 mL), washed with brine (20 mL). The organic layer was dried over anhydrous Na₂SO₄, filtered off and concentrated in vacuo. The residue was purified by silica gel flash column chromatography (PE:EtOAc=100:1 to 10:1) to give the title compound (1.33 g, yield: 56%).

Step 7. 1-((S)-2-((tert-butyldimethylsilyl)-oxy)-1-(3-chlorophenyl)-ethyl)-4-(3-(2-methylpyridin-4-yl)-1-(tetra-hydro-2H-pyran-2-yl)-1H-indazol-5-yl) pyridin-2(1H)-one A solution of 4-bromo-1-(2-(tert-butyldimethylsilyloxy)-1-(3-chlorophenyl)ethyl)-pyridine-2(1H)-one (240 mg, 0.543 mmol), 3-(2-methylpyridin-4-yl)-1-(tetrahydro-2H-pyran-2-yl)-5-(4,4,5,5-tetramethyl-1,3,2-dioxaborolan-2-yl)-1H-indazole (250 mg, 0.598 mmol), Pd(dppf)Cl₂-DCM (40 mg, 0.054 mmol) and Na₂CO₃ (115 mg, 1.086 mmol) in dioxane/H₂O (4:1, 10 ml) was degassed with N₂ and stirred at 80° C. for 3 h. The mixture was cooled to room temperature and diluted with EA (100 mL), washed by H₂O (30 mL×2) and brine (30 mL). The organic layer was dried over anhydrous Na₂SO₄, filtered off and concentrated in vacuo. The residue was purified by silica gel flash column chromatography (PE/EA=1/1) to give the title compound (300 mg, 84% yield).

Step 8. (S)-1-(1-(3-chlorophenyl)-2-hydroxyethyl)-4-(3-(2-methyl-pyridin-4-yl)-1H-indazol-5-yl)pyridin-2(1H)-one A solution of 1-(2-(tert-butyldimethylsilyloxy)-1-(3-chlorophenyl)ethyl)-4-(3-(2-methylpyridin-4-yl)-1-(tetrahydro-2H-pyran-2-yl)-1H-indazol-5-yl)pyridin-2(1H)-one (300 mg, 0.458 mmol) in HCl (6.0 N, 10 mL) was stirred at 50° C. overnight. The reaction mixture was then cooled to room temperature and concentrated. The residue was dissolved with H₂O (50 mL) and cooled in ice-water bath. Saturated aqueous Na₂CO₃ was added to adjust PH to 8-9. The resulting solution was extracted with DCM/MeOH (10:1, 50 mL×3). The combined organic layers were washed with brine (50 mL) and dried over anhydrous Na₂SO₄, filtered off, and concentrated in vacuo. The crude product was purified by prep-TLC (DCM/MeOH=10/1) to give the title compound (140 mg, 67% yield). MS (ESI) m/z: 457.1 [M+1]⁺; ¹H NMR (400 MHz, CD₃OD) δ/ppm: 8.49 (s, 1H), 8.33 (d, J=4.7 Hz, 1H), 7.95-7.62 (m, 5H), 7.48-7.25 (m, 4H), 6.95-6.79 (m, 2H), 6.17 (dd, J=7.4, 5.4 Hz, 1H), 4.26 (ddd, J=17.3, 12.1, 6.5 Hz, 2H), 2.62 (s, 3H).

Example 2 (Method 2)

Preparation of (S)-1-(1-(3-chlorophenyl)-2-hydroxyethyl)-4-(3-(tetrahydro-2H-pyran-4-yl)-1H-indazol-5-yl)pyridin-2(1H)-one

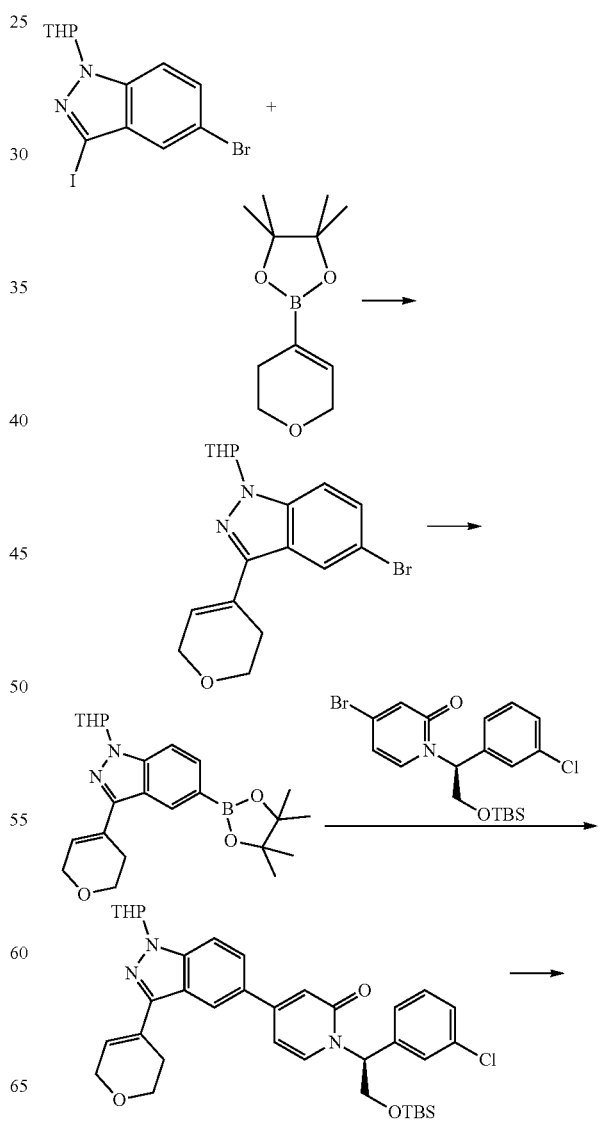

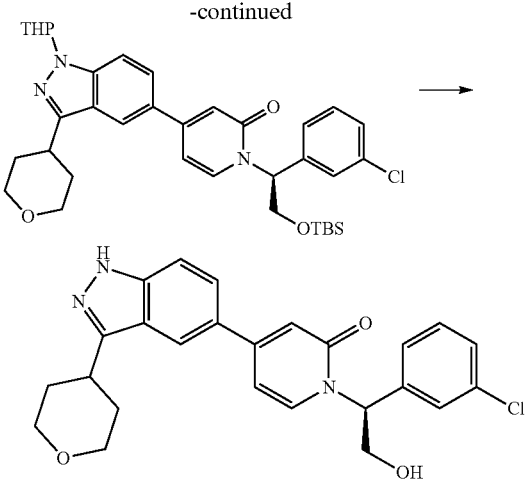

Step 1. 5-bromo-3-(3,6-dihydro-2H-pyran-4-yl)-1-(tetrahydro-2H-pyran-2-yl)-1H-indazole The mixture of 5-bromo-3-iodo-1-(tetrahydro-2H-pyran-2-yl)-1H-indazole (406 mg, 1.0 mmol), 2-(3,6-dihydro-2H-pyran-4-yl)-4,4,5,5-tetramethyl-1,3,2-dioxaborolane (231 mg, 1.1 mmol), Pd(dppf)Cl$_2$-DCM (40 mg, 0.05 mmol) and Na$_2$CO$_3$ (212 mg, 2.0 mmol) in dioxane (5.0 ml)/water (1.0 ml) was degassed with N$_2$ and stirred at 65° C. overnight. The mixture was cooled to temperature and diluted with EA (50 ml), washed by H$_2$O (20 ml×2) and brine (20 ml). The organic layer was dried over anhydrous Na$_2$SO$_4$, filtered off, and concentrated in vacuo. The residue was purified by silica gel flash column chromatography (DCM/MeOH=100/1-50/1) to give the title compound (0.3 g, 82% yield).

Step 2. 3-(3,6-dihydro-2H-pyran-4-yl)-1-(tetrahydro-2H-pyran-2-yl)-5-(4,4,5,5-tetramethyl-1,3,2-dioxaborolan-2-yl)-1H-indazole The mixture of 5-bromo-3-(3,6-dihydro-2H-pyran-4-yl)-1-(tetrahydro-2H-pyran-2-yl)-1H-indazole (150 mg, 0.413 mmol), 4,4,4',4',5,5,5',5'-octamethyl-2,2'-bi(1,3,2-dioxaborolane) (125 mg, 0.496 mmol), Pd(dppf)Cl$_2$-DCM (33 mg, 0.0413 mmol) and KOAc (81 mg, 0.826 mmol) in DMF (2.0 ml) was degassed with N$_2$ and stirred at 85° C. for 3 h. The mixture was cooled to room temperature and diluted with EA (50 ml), washed by H$_2$O (20 ml×2) and brine (20 ml). The organic layer was dried over anhydrous Na$_2$SO$_4$, filtered off, and concentrated in vacuo. The residue was purified by silica gel flash column chromatography (PE/EA=2/1-1/2) to give the title compound (93 mg, 55% yield).

Step 3. 1-((S)-2-((tert-butyldimethylsilyl)oxy)-1-(3-chlorophenyl)ethyl)-4-(3-(3,6-dihydro-2H-pyran-4-yl)-1-(tetrahydro-2H-pyran-2-yl)-1H-indazol-5-yl)pyridin-2(1H)-one The solution of 3-(3,6-dihydro-2H-pyran-4-yl)-1-(tetrahydro-2H-pyran-2-yl)-5-(4,4,5,5-tetramethyl-1,3,2-dioxaborolan-2-yl)-1H-indazole (93 mg, 0.227 mmol), (S)-4-bromo-1-(2-((tert-butyldimethylsilyl)oxy)-1-(3-chlorophenyl)ethyl)pyridin-2(1H)-one (104.7 mg, 0.250 mmol), Pd(dppf)Cl$_2$-DCM (18.6 mg, 0.0227 mmol) and Na$_2$CO$_3$ (48.1 mg, 0.454 mmol) in dioxane (2.0 ml)/H$_2$O (1 ml) was degassed with N$_2$ and stirred at 80° C. overnight. The mixture was cooled to room temperature and diluted with EA (50 ml), washed by H$_2$O (20 ml×2) and brine (20 ml). The organic layer was dried over anhydrous Na$_2$SO$_4$, filtered off, and concentrated in vacuo. The residue was purified by Prep-TLC (DCM/MeOH=20/1) to give the title compound (100 mg, 68% yield).

Step 4. 1-((S)-2-((tert-butyldimethylsilyl)oxy)-1-(3-chlorophenyl)ethyl)-4-(1-(tetrahydro-2H-pyran-2-yl)-3-(tetrahydro-2H-pyran-4-yl)-1H-indazol-5-yl)pyridin-2(1H)-one The mixture of 1-((S)-2-((tert-butyldimethylsilyl)oxy)-1-(3-chlorophenyl)ethyl)-4-(3-(3,6-dihydro-2H-pyran-4-yl)-1-(tetrahydro-2H-pyran-2-yl)-1H-indazol-5-yl)pyridin-2(1H)-one (100 mg, 0.154 mmol) and Pd/C (10%) in EtOAc (3.0 ml) was stirred under H$_2$ balloon at room temperature for 48 h. The solid was removed by filtration. The filtrate was concentrated in vacuo and purified by Prep-TLC (DCM/MeOH=20/1) to give the title compound (22 mg, 22% yield).

Step 5. (S)-1-(1-(3-chlorophenyl)-2-hydroxyethyl)-4-(3-(tetrahydro-2H-pyran-4-yl)-1H-indazol-5-yl)pyridin-2(1H)-one The mixture of 1-((S)-2-((tert-butyldimethylsilyl)oxy)-1-(3-chlorophenyl)ethyl)-4-(1-(tetrahydro-2H-pyran-2-yl)-3-(tetrahydro-2H-pyran-4-yl)-1H-indazol-5-yl)pyridin-2(1H)-one (22 mg, 0.0034 mmol) in HCl (6.0 N, 3.0 ml)/MeOH (1.0 ml) was stirred at room temperature overnight. The reaction mixture was concentrated. The residue was dissolved with H$_2$O (30 mL) and cooled in ice-water bath. Saturated aqueous Na$_2$CO$_3$ was added to adjust PH to 8-9. The resulting solution was extracted with DCM/MeOH (10:1, 30 mL×3). The combined organic layers were washed with brine (50 mL) and dried over anhydrous Na$_2$SO$_4$, filtered off, and concentrated. The crude product was purification by Prep-TLC (DCM/MeOH=10/1) to give the title compound (10 mg, 66% yield). MS (ESI) m/z: 450.0 [M+1]+; $^1$H NMR (400 MHz, CD$_3$OD) δ 8.16 (s, 1H), 7.80 (d, J=7.1 Hz, 1H), 7.71 (dd, J=8.8, 1.4 Hz, 1H), 7.57 (d, J=8.8 Hz, 1H), 7.43 (s, 1H), 7.39-7.30 (m, 4H), 6.84-6.81 (m, 2H), 6.17-6.14 (m, 1H), 4.30 (dd, J=12.1, 7.7 Hz, 1H), 4.21 (dd, J=12.1, 5.2 Hz, 1H), 4.09-4.06 (m, 2H), 3.69-3.64 (m, 2H), 3.48-3.41 (m, 1H), 2.18-1.90 (m, 4H).

Example 3 (Method 3)

Preparation of (S)-1-(1-(3-chlorophenyl)-2-hydroxyethyl)-4-(3-methyl-1H-indazol-5-yl)pyridin-2(1H)-one

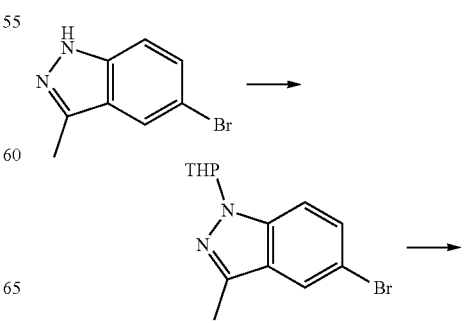

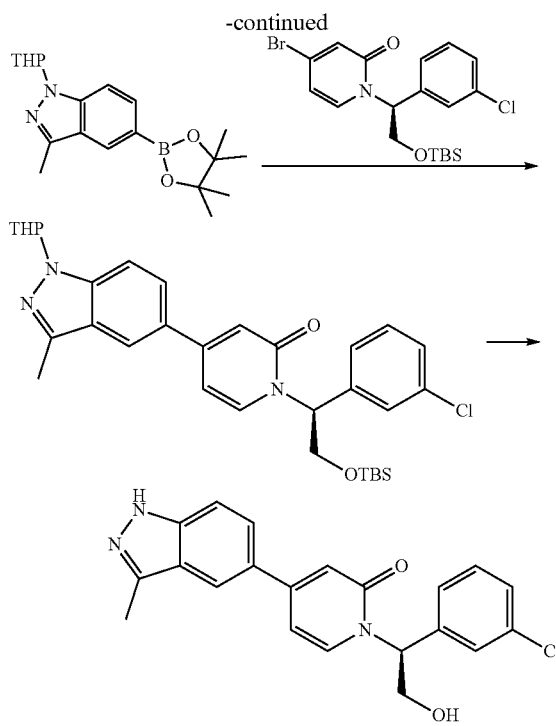

Step 1. 5-bromo-3-methyl-1-(tetrahydro-2H-pyran-2-yl)-1H-indazole

A solution of 5-bromo-3-methyl-1H-indazole (0.63 g, 3.0 mmol), 3,6-dihydro-2H-pyran (0.76 g, 9.0 mmol) and PPTS (75 mg, 0.3 mmol) in THF (20 ml) was stirred at 50° C. for 2 h. The mixture was cooled to room temperature and diluted with EA (100 mL), washed by $H_2O$ (50 mL×2) and brine (50 mL). The organic layer was dried over anhydrous $Na_2SO_4$, filtered off, and concentrated in vacuo to give the title compound (0.87 g, 98% crude yield).

Step 2. 3-methyl-1-(tetrahydro-2H-pyran-2-yl)-5-(4,4,5,5-tetramethyl-1,3,2-dioxaborolan-2-yl)-1H-indazole A solution of 5-bromo-3-methyl-1-(tetrahydro-2H-pyran-2-yl)-1H-indazole (0.87 g, 3.0 mmol), bis(pinacolato)diboron (0.92 g, 3.6 mmol), Pd(dppf)$Cl_2$-DCM (0.22 g, 0.3 mmol) and KOAc (0.59 g, 6.0 mmol) in DMF (10 ml) was stirred at 85° C. under $N_2$ protection for 2 h. The mixture was cooled to room temperature and diluted with EA (100 mL), washed by $H_2O$ (50 mL×2) and brine (50 mL). The organic layer was dried over anhydrous $Na_2SO_4$, filtered off, and concentrated in vacuo. The residue was purified by silica gel flash column chromatography (PE/EA=5/1-3/1) to give the title compound (0.92 g, 90% yield).

Step 3. 1-((S)-2-((tert-butyldimethylsilyl)oxy)-1-(3-chlorophenyl)ethyl)-4-(3-methyl-1-(tetrahydro-2H-pyran-2-yl)-1H-indazol-5-yl)pyridin-2(1H)-one A solution of (S)-4-bromo-1-(2-((tert-butyldimethylsilyl)oxy)-1-(3-chlorophenyl)-ethyl)pyridin-2(1H)-one (100 mg, 0.23 mmol), 3-methyl-1-(tetrahydro-2H-pyran-2-yl)-5-(4,4,5,5-tetramethyl-1,3,2-dioxaborolan-2-yl)-1H-indazole (85 mg, 0.25 mmol), Pd(dppf)$Cl_2$-DCM (15 mg, 0.02 mmol) and $Na_2CO_3$ (49 mg, 0.46 mmol) in dioxane/$H_2O$ (4:1, 10 ml) was stirred at 80° C. under $N_2$ protection for 3 h. The mixture was cooled to room temperature and diluted with EA (100 mL), washed by $H_2O$ (30 mL×2) and brine (30 mL). The organic layer was dried over anhydrous $Na_2SO_4$, filtered off, and concentrated in vacuo. The crude product was purified by Prep-TLC (PE/EA=1/1) to give the title compound (100 mg, 75% yield).

Step 4. Preparation of (S)-1-(1-(3-chlorophenyl)-2-hydroxyethyl)-4-(3-methyl-1H-indazol-5-yl)pyridin-2(1H)-one A solution of 1-((S)-2-((tert-butyldimethylsilyl)oxy)-1-(3-chlorophenyl)ethyl)-4-(3-methyl-1-(tetrahydro-2H-pyran-2-yl)-1H-indazol-5-yl)pyridin-2(1H)-one (100 mg, 0.173 mmol) in HCl (6.0 N, 5 mL) was stirred at 50° C. for 2 h. The reaction mixture was then cooled to room temperature and concentrated. The residue was dissolved with $H_2O$ (10 mL) and cooled in ice-water bath. Saturated aqueous $Na_2CO_3$ was added to adjust PH to 8-9. The resulting solution was extracted with DCM/MeOH (10:1, 50 mL×3). The organic layer was dried over anhydrous $Na_2SO_4$, filtered off, and concentrated in vacuo. The crude product was purified by prep-TLC (DCM/MeOH=10/1) gave the title compound (35 mg, 54% yield). MS (ESI) m/z: 380.0 $[M+1]^+$; $^1$H NMR (400 MHz, $CD_3OD$) δ 8.08 (s, 1H), 7.78 (t, J=9.2 Hz, 1H), 7.71 (d, J=8.8 Hz, 1H), 7.55 (d, J=8.8 Hz, 1H), 7.45-7.28 (m, 4H), 6.94-6.74 (m, 2H), 6.16 (dd, J=7.3, 5.4 Hz, 1H), 4.25 (ddd, J=17.4, 12.1, 6.4 Hz, 2H), 2.60 (s, 3H).

Example 4 (Method 4)

Preparation of 1-(1-(3-chlorophenyl)-2-hydroxyethyl)-4-(3-(2-methylpyridin-4-yl)-1H-pyrazolo[3,4-b]pyridin-5-yl)pyridin-2(1H)-one

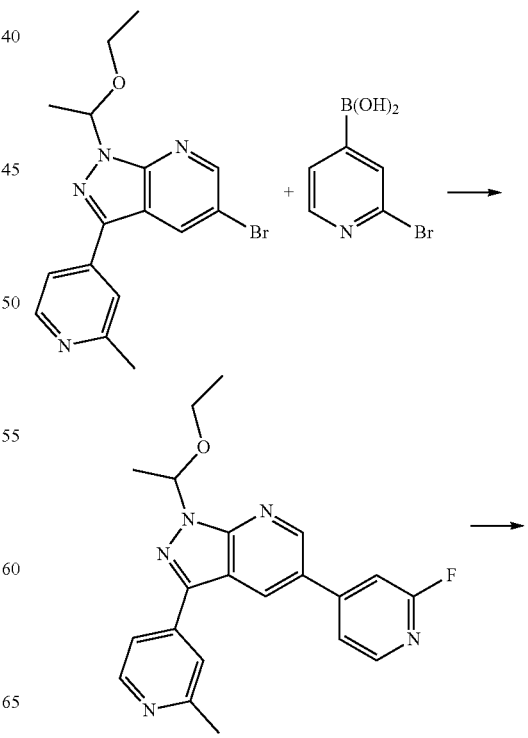

-continued

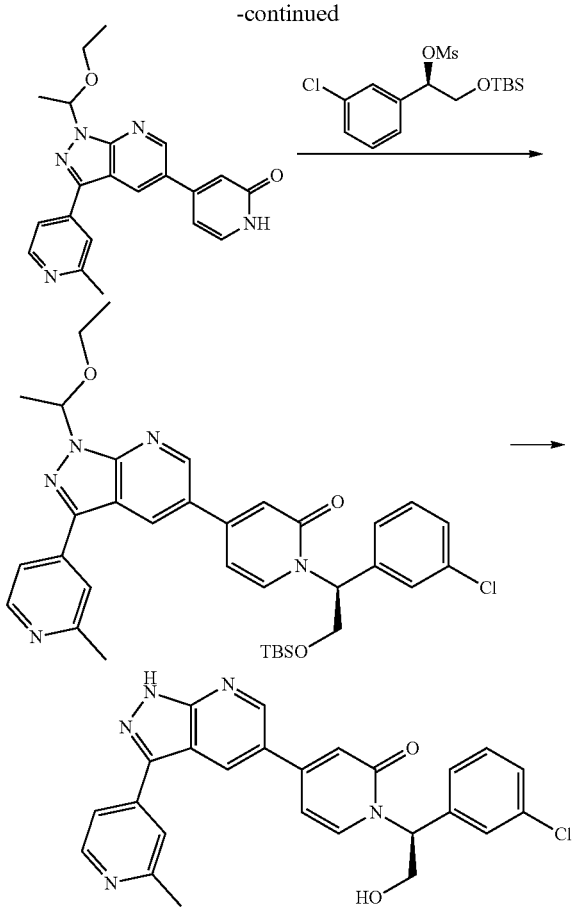

Step 1. 1-(1-ethoxyethyl)-5-(2-fluoropyridin-4-yl)-3-(2-methylpyridin-4-yl)-1H-pyrazolo-[3,4-b]pyridine A mixture of 5-bromo-1-(1-ethoxyethyl)-3-(2-methylpyridin-4-yl)-1H-pyrazolo-[3,4-b]pyridine (320 mg, 0.89 mmol), (2-fluoropyridin-4-yl)boronic acid (150 mg, 1.06 mmol), Pd(dppf)Cl$_2$.DCM (36 mg, 0.04 mmol) and Na$_2$CO$_3$ (284 mg, 2.67 mmol) in dioxane (4 mL)/H$_2$O (2 mL) was stirred at 85° C. under N$_2$ protection for 5 h. The mixture was cooled to room temperature and diluted with EtOAc (30 mL) washed with water (10 mL), brine (10 mL). The organic layer was dried over anhydrous Na$_2$SO$_4$, filtered off, and concentrated in vacuo. The crude product was purified by silica gel flash column chromatography eluting with ethyl acetate in hexane (20 percent) to give the title compound (210 mg, 63%).

Step 2. Preparation of 4-(1-(1-ethoxyethyl)-3-(2-methylpyridin-4-yl)-1H-pyrazolo[3,4-b]-pyridin-5-yl)-pyridin-2(1H)-one A solution of 1-(1-ethoxyethyl)-5-(2-fluoropyridin-4-yl)-3-(2-methylpyridin-4-yl)-1H-pyrazolo[3,4-b]pyridine (210 mg, 0.56 mmol) in 4N NaOH (6 mL) was stirred at 150° C. overnight and then cooled to room temperature. 2N HCl was added to adjust PH to 7. The resulting mixture was extracted with EA (100 mL), washed with water (30 mL) and brine (30 mL). The organic layer was dried over anhydrous Na$_2$SO$_4$, filtered off, and concentrated in vacuo to give the title compound (115 mg, yield: 54%).

Step 3. 1-((S)-2-((tert-butyldimethylsilyl)oxy)-1-(3-chlorophenyl)ethyl)-4-(1-(1-ethoxyethyl)-3-(2-methylpyridin-4-yl)-1H-pyrazolo[3,4-b]pyridin-5-yl)pyridin-2(1H)-one To a solution of 4-(1-(1-ethoxyethyl)-3-(2-methylpyridin-4-yl)-1H-pyrazolo-[3,4-b]-pyridin-5-yl)pyridin-2(1H)-one (115 mg, 0.31 mmol) in dry THF (3 mL) was added KHMDS (1M in THF, 0.46 ml; 0.46 mmol) at 0° C. The mixture was stirred at room temperature for 20 minutes, followed by the addition of (R)-2-((tert-butyldimethyl-silyl)oxy)-1-(3-chlorophenyl)ethyl methanesulfonate (106 mg, 0.372 mmol) in one portion. The mixture was transferred to a capped vial and stirred at 85° C. overnight. The reaction mixture was cooled to room temperature and diluted with EtOAc (30 mL), washed with brine (20 mL). The organic layer was dried over anhydrous Na$_2$SO$_4$, filtered off, and concentrated in vacuo. The crude product was purified by prep-TLC to afford the title compound (103 mg, yield: 52%).

Step 4. (S)-1-(1-(3-chlorophenyl)-2-hydroxyethyl)-4-(3-(2-methylpyridin-4-yl)-1H-pyrazolo[3,4-b]pyridin-5-yl)pyridin-2(1H)-one A solution of 1-((S)-2-((tert-butyldimethylsilyl)oxy)-1-(3-chlorophenyl)ethyl)-4-(1-(1-ethoxyethyl)-3-(2-methylpyridin-4-yl)-1H-pyrazolo[3,4-b]pyridin-5-yl)pyridin-2(1H)-one (103 mg, 0.16 mmol) in EA (3 mL) was treated with 4N HCl in dioxane (1.0 mL). The mixture was stirred at room temperature for 3 h and then concentrated to remove the solvent. The solid obtained was washed with EA and Et$_2$O, and dried under vacuum to give the title compound (30 mg, 41%). MS-ESI: 458.0 (M+1)+; $^1$H NMR (400 MHz, CD$_3$OD) δ/ppm: 9.05 (s, 1H), 8.99 (d, J=1.4 Hz, 1H), 8.73 (d, J=6.3 Hz, 1H), 8.66 (s, 1H), 8.62 (d, J=6.1 Hz, 1H), 7.95 (d, J=7.1 Hz, 1H), 7.65 (s, 1H), 7.43 (s, 1H), 7.40-7.33 (m, 3H), 7.06 (s, 1H), 6.98 (d, J=6.8 Hz, 1H), 6.24-6.13 (m, 1H), 4.34 (dd, J=12.2, 7.6 Hz, 1H), 4.24 (dd, J=12.1, 4.8 Hz, 1H), 2.90 (s, 3H).

Example 5 (Method 5)

Preparation of (S)-1-(1-(3-chlorophenyl)-2-hydroxyethyl)-4-(3-(methyl-amino)-1H-indazol-5-yl)pyridin-2(1H)-one

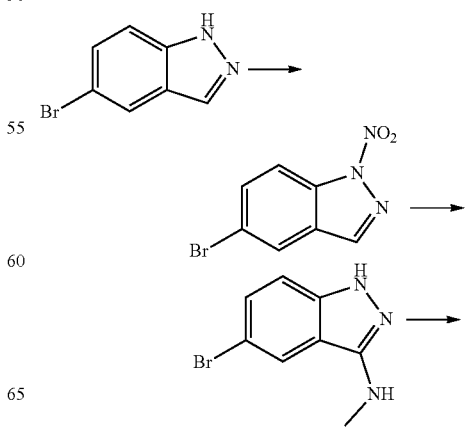

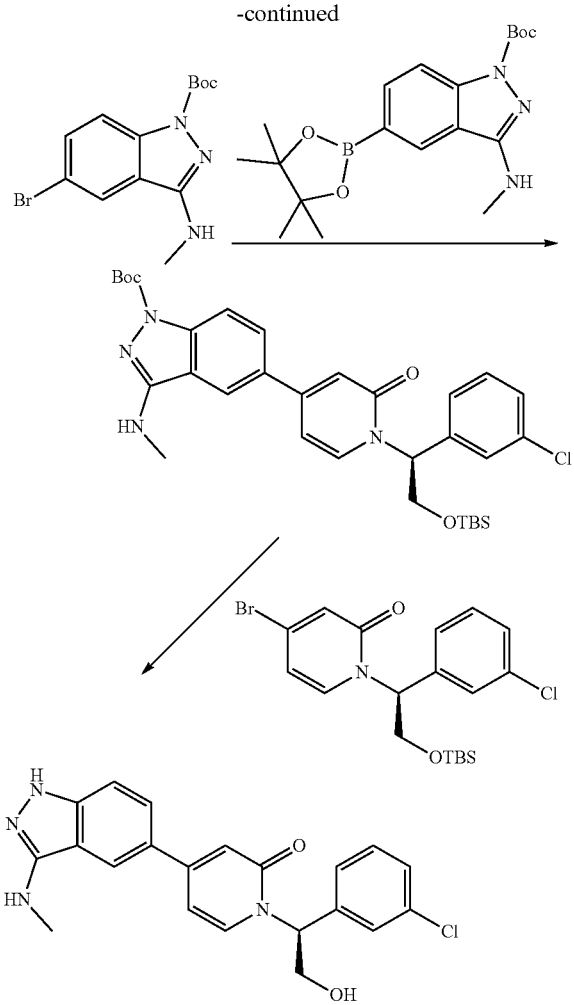

Step 1. 5-bromo-1-nitro-1H-indazole

To Ac$_2$O (18.6 ml) in a flask cooled in ice-water bath, fuming nitric acid (8 ml) was added slowly, followed by addition dropwise of AcOH (40 ml). Then 5-bromo-1H-indazole (5.9 g, 30 mmol) added in portions under 0° C. The resulting mixture was stirred at 0° C. for 2 h and poured into ice water (100 mL) under stirring. The solid formed was collected by filtration, washed with H$_2$O (50 mL×2), and dried in vacuo to give the title compound (4.5 g, 61% yield).

Step 2. 5-bromo-N-methyl-1H-indazol-3-amine

A solution of 5-bromo-1-nitro-1H-indazole (2 g, 8.26 mmol) in CH$_3$NH$_2$-THF (20 ml) was stirred at 65° C. overnight. The mixture was cooled to room temperature and was diluted with EA (100 mL), washed by H$_2$O (50 mL×2) and brine (50 mL). The organic layer was dried over anhydrous Na$_2$SO$_4$, filtered off, and concentrated in vacuo. The crude product was purified by silica gel flash column chromatography (PE/EA=3/1-1/1) to give the title compound (785 mg, 42% yield).

Step 3. tert-butyl 5-bromo-3-(methylamino)-1H-indazole-1-carboxylate

A solution of 5-bromo-N-methyl-1H-indazol-3-amine (226 mg, 1 mmol), Boc$_2$O (240 mg, 1.1 mmol), DMAP (25 mg, 0.2 mmol) and TEA (151 mg, 1.5 mmol) in THF (5 ml) was stirred at room temperature overnight. The mixture was diluted with EA (50 mL) and washed by H$_2$O (20 mL×2) and brine (20 mL). The organic layer was dried over anhydrous Na$_2$SO$_4$, filtered off, and concentrated in vacuo. The crude product was purified by silica gel flash column chromatography (PE/EA=5/1) to give the title compound (250 mg, 76% yield).

Step 4. tert-butyl 3-(methylamino)-5-(4,4,5,5-tetramethyl-1,3,2-dioxa-borolan-2-yl)-1H-indazole-1-carboxylate A solution of tert-butyl 5-bromo-3-(methylamino)-1H-indazole-1-carboxylate (250 mg, 0.76 mmol), bis(pinacolato)diboron (195 mg, 0.76 mmol), Pd(dppf)Cl$_2$-DCM (62 mg, 0.076 mmol) and KOAc (300 mg, 3 mmol) in Dioxane (5 ml) was stirred at 80° C. under N$_2$ protection overnight. The mixture was cooled to room temperature and diluted with EA (50 mL), washed by H$_2$O (20 mL×2) and brine (20 mL). The organic layer was dried over anhydrous Na$_2$SO$_4$, filtered off, and concentrated in vacuo. The crude product was purified by silica gel flash column chromatography (PE/EA=3/1) to give the title compound (171 mg, 60% yield).

Step 5. (S)-tert-butyl 5-(1-(2-((tert-butyldimethylsilyl)-oxy)-1-(3-chloro-phenyl)ethyl)-2-oxo-1,2-dihydropyridin-4-yl)-3-(methylamino)-1H-indazole-1-carboxylate A solution of tert-butyl 3-(methylamino)-5-(4,4,5,5-tetramethyl-1,3,2-dioxaborolan-2-yl)-1H-indazole-1-carboxylate (170 mg, 0.45 mmol), (S)-4-bromo-1-(2-((tert-butyldimethylsilyl)oxy)-1-(3-chlorophenyl)-ethyl)-pyridin-2(1H)-one (202 mg, 0.45 mmol), Pd(dppf)Cl$_2$-DCM (37 mg, 0.045 mmol) and Na$_2$CO$_3$ (97 mg, 0.91 mmol) in dioxane/H$_2$O (5:1, 6 ml) was stirred at 80° C. under N$_2$ protection for 3 h. The mixture was cooled to room temperature and diluted with EA (50 mL), washed by H$_2$O (20 mL×2) and brine (20 mL). The organic layer was dried over anhydrous Na$_2$SO$_4$, filtered off, and concentrated in vacuo. The crude product was purified by prep-TLC to give the title compound (169 mg, 61% yield).

Step 6. (S)-1-(1-(3-chlorophenyl)-2-hydroxyethyl)-4-(3-(methylamino)-1H-indazol-5-yl)pyridin-2(1H)-one A solution of (S)-tert-butyl 5-(1-(2-((tert-butyldimethylsilyl)oxy)-1-(3-chloro-phenyl)-ethyl)-2-oxo-1,2-dihydropyridin-4-yl)-3-(methylamino)-1H-indazole-1-carboxylate (169 mg, 0.277 mmol) in HCl (6.0 N, 1.5 mL)/MeOH (0.7 ml) was stirred at 50° C. overnight. The mixture was cooled to room temperature and concentrated. The residue was dissolved in H2O (10 mL) and basified with saturated aqueous Na$_2$CO$_3$ to PH=8-9 in ice-water bath, extracted with DCM/MeOH (10:1, 20 mL×3). The combined organic layer was dried over anhydrous Na$_2$SO$_4$, filtered off, and concentrated in vacuo. The crude product was purified by prep-TLC (DCM/MeOH=10/1) to give the title compound (75 mg, 68% yield). MS (ESI) m/z: 395 [M+1]$^+$; $^1$HNMR (400 MHz, CD$_3$OD) δ/ppm: 8.05 (d, J=0.7 Hz, 1H), 7.76 (d, J=7.3 Hz, 1H), 7.65 (dt, J=9.1, 4.5 Hz, 1H), 7.42 (s, 1H), 7.39-7.27 (m, 4H), 6.84 (d, J=1.8 Hz, 1H), 6.80 (dd, J=7.3, 2.0 Hz, 1H), 6.15 (dd, J=7.2, 5.5 Hz, 1H), 4.28 (dd, J=12.1, 7.6 Hz, 1H), 4.20 (dd, J=12.1, 5.3 Hz, 1H), 2.99 (s, 3H).

Example 6 (Method 6)

Preparation of (S)-1-(1-(3-bromophenyl)-2-hydroxyethyl)-4-(3-(2-methyl-pyridin-4-yl)-1H-indazol-5-yl)pyridin-2(1H)-one

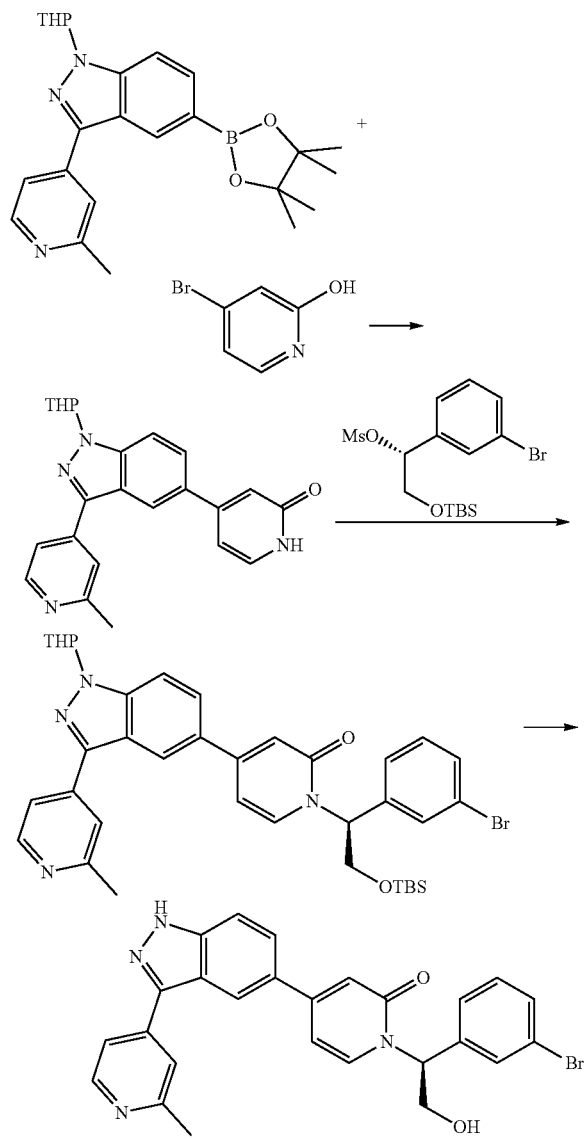

Step 1. 4-(3-(2-methylpyridin-4-yl)-1-(tetrahydro-2H-pyran-2-yl)-1H-indazol-5-yl)pyridin-2(1H)-one A solution of 4-bromopyridin-2-ol (1.0 g, 5.7 mmol), 3-(2-methylpyridin-4-yl)-1-(tetrahydro-2H-pyran-2-yl)-5-(4,4,5,5-tetramethyl-1,3,2-dioxaborolan-2-yl)-1H-indazole (2.7 g, 6.3 mmol), Pd(dppf)Cl$_2$.DCM (233 mg, 0.28 mmol) and Na$_2$CO$_3$ (1.2 g, 11.4 mmol) in dioxane (30 mL)/H$_2$O (8 ml) was stirred at 80° C. under N$_2$ protection for 3 h. The mixture was cooled to room temperature and diluted with EA (100 mL), washed by H$_2$O (50 mL×2) and brine (50 mL). The organic layer was dried over anhydrous Na$_2$SO$_4$, filtered off, and concentrated in vacuo. The crude product was purified by silica gel flash column chromatography (DCM/MeOH=10/1) to give the title compound (1.8 g, 82% yield).

Step 2. 1-((S)-1-(3-bromophenyl)-2-((tert-butyldimethylsilyl)oxy)-ethyl)-4-(3-(2-methylpyridin-4-yl)-1-(tetrahydro-2H-pyran-2-yl)-1H-indazol-5-yl)pyridin-2(1H)-one To the solution of 4-(3-(2-methylpyridin-4-yl)-1-(tetrahydro-2H-pyran-2-yl)-1H-indazol-5-yl)pyridin-2(1H)-one (100 mg, 0.26 mmol) in dry THF cooled by ice-water, KHMDS in THF (1 N, 0.31 mL, 0.31 mmol) was added. The resulting mixture was stirred at room temperature for 0.5 h and (R)-1-(3-bromophenyl)-2-((tert-butyldimethylsilyl)oxy)ethyl methanesulfonate (128 mg, 0.31 mmol) was added. The mixture was stirred at 85° C. overnight and then cooled to room temperature, diluted with EA (100 mL), washed by H$_2$O (50 mL×2) and brine (50 mL). The organic layer was dried over anhydrous Na$_2$SO$_4$, filtered off, and concentrated in vacuo. The residue was purified by prep-TLC (DCM/EA=1/1) to give the title compound (102 mg, 56% yield).

Step 3. (S)-1-(1-(3-bromophenyl)-2-hydroxyethyl)-4-(3-(2-methylpyridin-4-yl)-1H-indazol-5-yl)pyridin-2(1H)-one A solution of 1-((S)-1-(3-bromophenyl)-2-((tert-butyldimethylsilyl)oxy)ethyl)-4-(3-(2-methylpyridin-4-yl)-1-(tetrahydro-2H-pyran-2-yl)-1H-indazol-5-yl)pyridin-2(1H)-one (102 mg, 0.15 mmol) in HCl (6.0 N, 10 mL)/MeOH (5 mL) was stirred at 50° C. for 2 h. The mixture was cooled to room temperature and concentrated in vacuum to remove the solvent. The residue was dissolved in H$_2$O (10 mL) and basified with saturated aqueous Na$_2$CO$_3$ to PH=8-9 cooled in ice-water bath, extracted with DCM/MeOH (10:1, 50 mL×3). The combined organic layers were dried over anhydrous Na$_2$SO$_4$, filtered off, and concentrated in vacuo. The crude product was purified by prep-TLC (DCM/MeOH=10/1) to give the title compound (50 mg, 66% yield). MS (ESI) m/z: 501.0 [M+1]$^+$; $^1$HNMR (400 MHz, CD$_3$OD) δ/ppm: 8.48 (d, J=5.3 Hz, 1H), 8.32 (d, J=20.4 Hz, 1H), 7.86 (d, J=15.4 Hz, 1H), 7.85-7.76 (m, 2H), 7.72 (d, J=8.8 Hz, 1H), 7.68-7.61 (m, 1H), 7.59 (s, 1H), 7.48 (d, J=7.8 Hz, 1H), 7.37 (d, J=7.8 Hz, 1H), 7.30 (t, J=7.8 Hz, 1H), 6.93-6.79 (m, 2H), 6.17 (dd, J=13.5, 8.0 Hz, 1H), 4.26 (ddd, J=17.3, 12.1, 6.5 Hz, 2H), 2.50 (s, 3H).

Example 7 (Method 7)

Preparation of (S)-1-(1-(3-chlorophenyl)-2-hydroxyethyl)-4-(3-(1-methyl-1H-pyrazol-5-yl)-1H-indazol-5-yl)pyridin-2(1H)-one

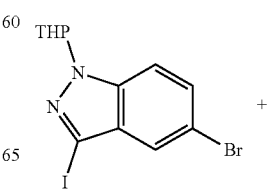

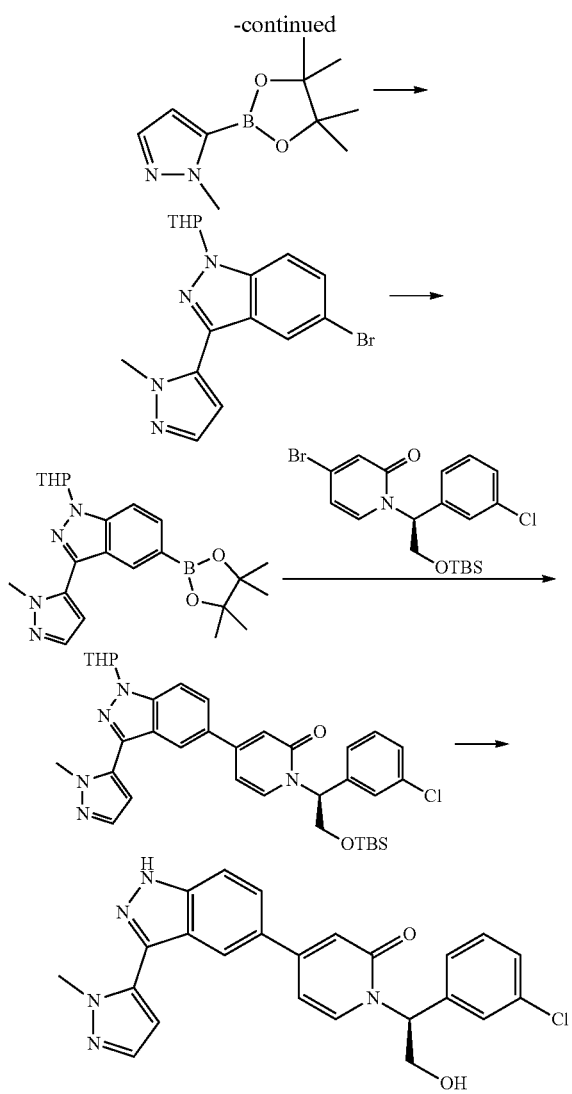

Step 1. 5-bromo-3-(1-methyl-1H-pyrazol-5-yl)-1-(tetrahydro-2H-pyran-2-yl)-1H-indazole A solution of 5-bromo-3-iodo-1-(tetrahydro-2H-pyran-2-yl)-1H-indazole (300 mg, 0.735 mmol), 1-methyl-5-(4,4,5,5-tetramethyl-1,3,2-dioxaborolan-2-yl)-1H-pyrazole (153 mg, 0.735 mmol), Pd(dppf)Cl$_2$-DCM (60 mg, 0.073 mmol) and Na$_2$CO$_3$ (156 mg, 1.47 mmol) in dioxane/H$_2$O (5:1 m, 6 ml) was stirred at 80° C. under N$_2$ protection for 3 h. The mixture was cooled to room temperature and diluted with EA (50 mL), washed by H$_2$O (20 mL×2) and brine (20 mL). The organic layer was dried over anhydrous Na$_2$SO$_4$, filtered off, and concentrated in vacuo. The crude product was purified by silica gel flash column chromatography (PE/EA=2/1) to give the title compound (150 mg, 56% yield).

Step 2. 1-((S)-2-((tert-butyldimethylsilyl)oxy)-1-(3-chlorophenyl)-ethyl)-4-(3-(1-methyl-1H-pyrazol-5-yl)-1-(tetrahydro-2H-pyran-2-yl)-1H-indazol-5-yl)pyridin-2(1H)-one A solution of 5-bromo-3-(1-methyl-1H-pyrazol-5-yl)-1-(tetrahydro-2H-pyran-2-yl)-1H-indazole (150 mg, 0.415 mmol), bis(pinacolato)diboron (105 mg, 0.415 mmol), Pd(dppf)Cl$_2$-DCM (34 mg, 0.041 mmol) and KOAc (163 mg, 1.66 mmol) in dioxane (2.5 ml) was stirred at 80° C. under N$_2$ protection overnight. After cooling to room temperature, a mixture (S)-4-bromo-1-(2-((tert-butyldimethylsilyl)oxy)-1-(3-chlorophenyl)ethyl)-pyridin-2(1H)-one (147 mg, 0.332 mmol) and Na$_2$CO$_3$ (88 mg, 0.83 mmol) was added. The resulting solution was stirred at 80° C. for 3 h and then cooled to room temperature, diluted with EA (50 mL), washed by H$_2$O (20 mL×2) and brine (20 mL). The organic layer was dried over anhydrous Na$_2$SO$_4$, filtered off, and concentrated in vacuo. The crude product was purified by prep-TLC to give the title compound (150 mg, 70% yield).

Step 3. (S)-1-(1-(3-chlorophenyl)-2-hydroxyethyl)-4-(3-(1-methyl-1H-pyrazol-5-yl)-1H-indazol-5-yl)pyridin-2(1H)-one A solution of 1-((S)-2-((tert-butyldimethylsilyl)oxy)-1-(3-chlorophenyl)ethyl)-4-(3-(1-methyl-1H-pyrazol-5-yl)-1-(tetrahydro-2H-pyran-2-yl)-1H-indazol-5-yl)pyridin-2(1H)-one (150 mg, 0.23 mmol) in HCl (6.0 N, 1.5 mL)/MeOH (1 mL) was stirred at 50° C. overnight. The reaction mixture was then cooled to room temperature and concentrated. The residue was dissolved with H2O (10 mL) and cooled in ice-water bath. Saturated aqueous Na$_2$CO$_3$ was added to adjust PH to 8-9. The resulting solution was extracted with DCM/MeOH (10:1, 20 mL×3). The combined organic layers were washed with brine (20 mL), dried over anhydrous Na$_2$SO$_4$, and concentrated in vacuo. The crude product was purified by prep-TLC (DCM/MeOH=10/1) to give the title compound (65 mg, 62.5% yield). MS (ESI) m/z: 446 [M+1]$^+$; $^1$HNMR (400 MHz, CD$_3$OD) δ/ppm: 8.09 (s, 1H), 7.79 (d, J=7.3 Hz, 1H), 7.74 (dd, J=8.8, 1.5 Hz, 1H), 7.66 (d, J=8.7 Hz, 1H), 7.60 (d, J=2.0 Hz, 1H), 7.43 (s, 1H), 7.38-7.28 (m, 3H), 6.86 (s, 2H), 6.81 (dd, J=7.3, 2.0 Hz, 1H), 6.16 (dd, J=7.4, 5.4 Hz, 1H), 4.29 (dd, J=12.1, 7.6 Hz, 1H), 4.23-4.17 (m, 1H), 4.14 (s, 3H).

Example 8 (Method 8)

Preparation of 1-(3-bromo-5-fluorobenzyl)-4-(3-(2-methylpyridin-4-yl)-1H-indazol-5-yl)pyridin-2(1H)-one

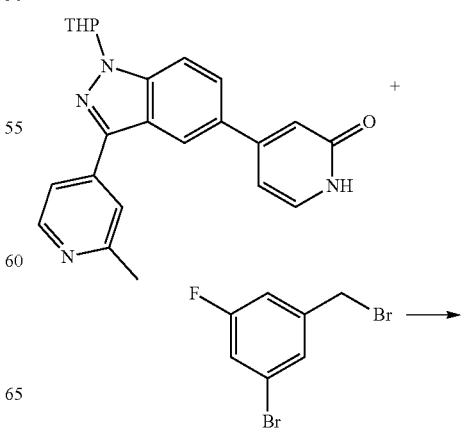

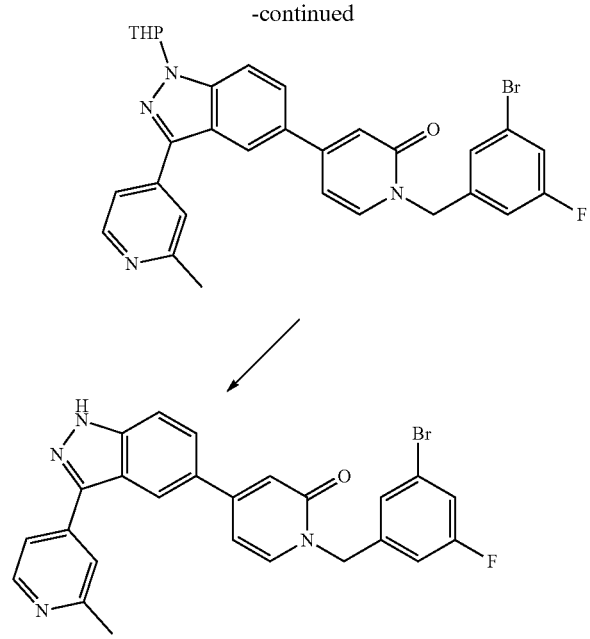

Step 1. 1-(3-bromo-5-fluorobenzyl)-4-(3-(2-methylpyridin-4-yl)-1-(tetrahydro-2H-pyran-2-yl)-1H-indazol-5-yl)pyridin-2(1H)-one A solution of 4-(3-(2-methylpyridin-4-yl)-1-(tetrahydro-2H-pyran-2-yl)-1H-indazol-5-yl)pyridin-2(1H)-one (77 mg, 0.2 mmol), 1-bromo-3-(bromomethyl)-5-fluorobenzene (59 mg, 0.22 mmol) and $K_2CO_3$ (55 mg, 0.4 mmol) in DMF (10 ml) was stirred at room temperature overnight. The mixture was diluted with EA (50 mL), washed by $H_2O$ (15 mL×2) and brine (15 mL). The organic layer was dried over anhydrous $Na_2SO_4$, filtered off, and concentrated in vacuo. The crude product was purified by prep-TLC (DCM/EA=1/1) to give the title compound (89 mg, 78% yield).

Step 2. 1-(3-bromo-5-fluorobenzyl)-4-(3-(2-methylpyridin-4-yl)-1H-indazol-5-yl)pyridin-2(1H)-one A solution of 1-(3-bromo-5-fluorobenzyl)-4-(3-(2-methylpyridin-4-yl)-1-(tetra-hydro-2H-pyran-2-yl)-1H-indazol-5-yl)pyridin-2(1H)-one (89 mg, 0.16 mmol) in HCl (6.0 N, 5 mL)/MeOH (5 mL) was stirred at 50° C. overnight. The reaction mixture was then cooled to room temperature and concentrated. The residue was dissolved with $H_2O$ (20 mL) and cooled in an ice-water bath. Saturated aqueous $Na_2CO_3$ was added to adjust PH to 8-9. The resulting solution was extracted with DCM/MeOH (10:1, 50 mL×3). The combined organic layers were washed with brine (50 mL), dried over anhydrous $Na_2SO_4$ and drived in vacuo. The crude product was purified by prep-TLC (DCM/MeOH=10/1) to give the title compound (35 mg, 45% yield). MS (ESI) m/z: 489 [M+1]$^+$; $^1$HNMR (400 MHz, CD$_3$OD) δ/ppm: 8.51 (d, J=5.3 Hz, 1H), 8.31 (s, 1H), 7.88 (s, 1H), 7.83 (d, J=5.2 Hz, 1H), 7.72 (dt, J=16.9, 8.0 Hz, 3H), 7.36 (s, 1H), 7.27-7.19 (m, 1H), 7.09 (d, J=9.1 Hz, 1H), 6.89 (d, J=1.7 Hz, 1H), 6.83 (dd, J=7.1, 2.0 Hz, 1H), 5.20 (s, 2H), 2.64 (s, 3H).

Example 9 (Method 9)

Preparation of (S)-1-(1-(3-chlorophenyl)-2-hydroxyethyl)-4-(3-(2-methyl-pyridin-4-yl)-1H-pyrazolo[4,3-b]pyridin-5-yl)pyridin-2(1H)-one

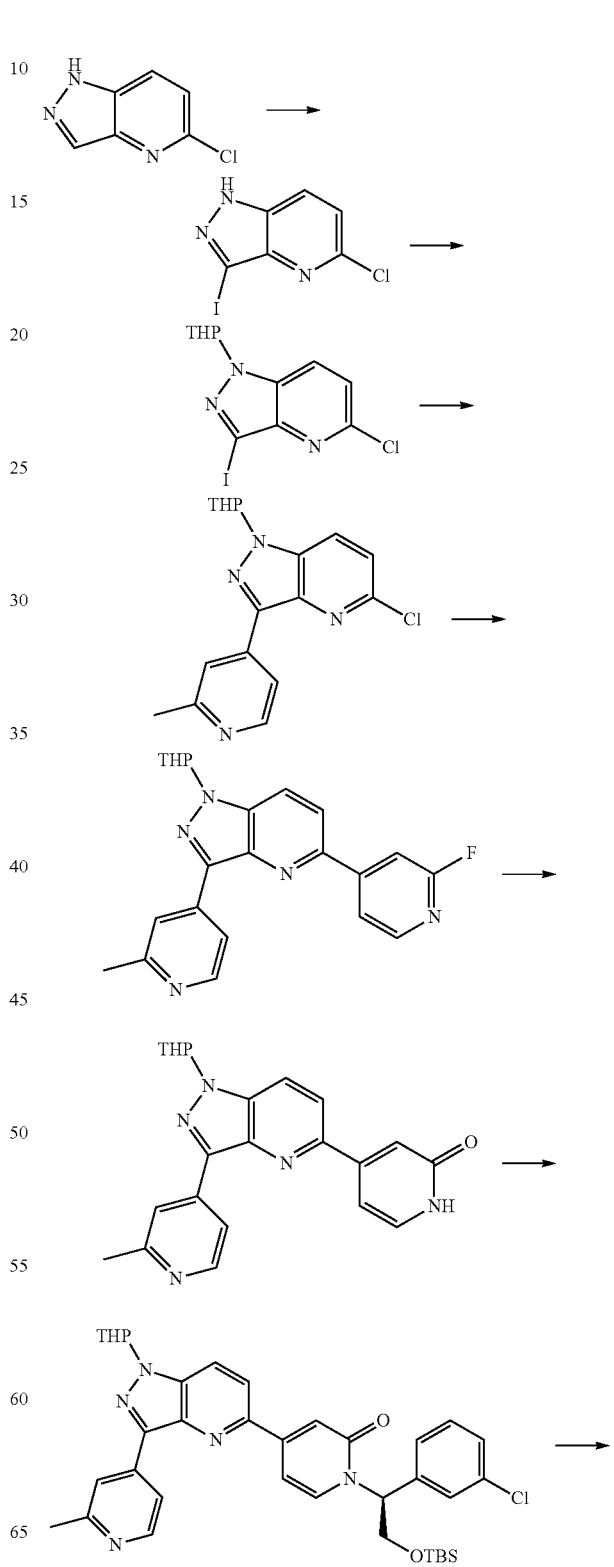

-continued

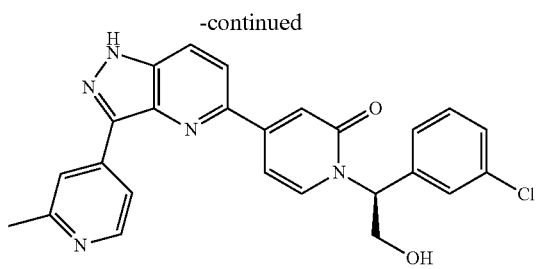

Step 1. 5-chloro-3-iodo-1H-pyrazolo[4,3-b]pyridine

The mixture of 5-chloro-1H-pyrazolo[4,3-b]pyridine (2.0 g, 13.02 mmol), iodine (13.0 g, 52.1 mmol) and NaOH (12M, 11 mL, 130 mmol) in dioxane (20 mL) was stirred at 90° C. for 18 h. The reaction mixture was cooled to room temperature and extracted with ethyl acetate (20 mL×3). The combined organic layers were washed with 10% aqueous $Na_2S_2O_3$ (20 mL×2), brine (20 mL), dried over anhydrous $Na_2SO_4$, filtered off, and concentrated in vacuo. The crude product was purified by silica gel flash column chromatography eluting with hexanes/ethyl acetate (4:1-1:1) to give the title compound (3.3 g, 91% yield).

Step 2. 5-chloro-3-iodo-1-(tetrahydro-2H-pyran-2-yl)-1H-pyrazolo[4,3-b]pyridine The mixture of 5-chloro-3-iodo-1H-pyrazolo[4,3-b]pyridine (2.2 g, 7.89 mmol), 3,4-dihydro-2H-pyran (2.0 g, 23.67 mmol) and pyridinium p-toluene sulfonate (198 mg, 0.79 mmol) in THF (40 mL) was stirred at 70° C. overnight. The reaction mixture was cooled to room temperature and diluted with EA (75 mL), washed with brine (20 mL×2), dried over anhydrous $Na_2SO_4$, filtered off, and concentrated in vacuo. The crude product was purified by silica gel flash column chromatography eluting with hexanes/ethyl acetate (20:1-4:1) to give the title compound (2.2 g, 77% yield).

Step 3. 5-chloro-3-(2-methylpyridin-4-yl)-1-(tetrahydro-2H-pyran-2-yl)-1H-pyrazolo[4,3-b]pyridine The mixture of 5-chloro-3-iodo-1-(tetrahydro-2H-pyran-2-yl)-1H-pyrazolo[4,3-b]-pyridine (2.85 g, 7.86 mmol), (2-methylpyridin-4-yl)boronic acid (1.13 g, 8.26 mmol), $Na_2CO_3$ (1.67 g, 15.73 mmol) and Pd(dppf)Cl$_2$-DCM (644 mg, 0.79 mmol) in dioxane (30 mL)/H$_2$O (6 mL) was stirred at 65° C. overnight under $N_2$ protection. The reaction mixture was cooled to room temperature and diluted with EA (90 mL), washed with brine (20 mL×2), dried over anhydrous $Na_2SO_4$, filtered off, and concentrated in vacuo. The crude product was purified by silica gel flash column chromatography eluting with hexanes/ethyl acetate (4:1-1:2) to give the title compound (1.72 g, 66% yield).

Step 4. 5-(2-fluoropyridin-4-yl)-3-(2-methylpyridin-4-yl)-1-(tetrahydro-2H-pyran-2-yl)-1H-pyrazolo[4,3-b]pyridine The mixture of 5-chloro-3-(2-methylpyridin-4-yl)-1-(tetrahydro-2H-pyran-2-yl)-1H-pyrazolo[4,3-b]pyridine (500 mg, 1.5 mmol), (2-fluoropyridin-4-yl)boronic acid (260 mg, 1.8 mmol), $Cs_2CO_3$ (1.22 g, 3.8 mmol) and Pd(dppf)Cl$_2$-DCM (120 mg, 0.15 mmol) in dioxane (20 mL)/H$_2$O (4 mL) was stirred at 110° C. overnight under $N_2$ protection. The reaction mixture was cooled to room temperature and diluted with EA (30 mL), washed with brine (10 mL×2), dried over anhydrous $Na_2SO_4$, filtered off, and concentrated in vacuo. The crude product was purified by silica gel flash column chromatography eluting with DCM/MeOH (20:1) to give the title compound (226 mg, 39% yield).

Step 5. 4-(3-(2-methylpyridin-4-yl)-1-(tetrahydro-2H-pyran-2-yl)-1H-pyrazolo[4,3-b]pyridin-5-yl) pyridin-2(1H)-one The mixture of 5-(2-fluoropyridin-4-yl)-3-(2-methylpyridin-4-yl)-1-(tetrahydro-2H-pyran-2-yl)-1H-pyrazolo[4,3-b] pyridine (226 mg, 0.58 mmol) in acetic acid (20 mL)/H$_2$O (2 mL) was stirred at 90° C. for 2 days under $N_2$ protection. The reaction mixture was cooled to room temperature and concentrated under vacuum to remove the solvents. The residue was diluted with methanol:DCM=1:10 (10 mL×3), washed with saturated aqueous $Na_2CO_3$ (10 mL×2), brine (10 mL), dried over anhydrous $Na_2SO_4$, filtered off, and concentrated in vacuo. The crude product was purified by prep-TLC to give the title compound (86 mg, 38% yield).

Step 6. 1-((S)-2-((tert-butyldimethylsilyl)oxy)-1-(3-chlorophenyl)ethyl)-4-(3-(2-methylpyridin-4-yl)-1-(tetrahydro-2H-pyran-2-yl)-1H-pyrazolo[4,3-b]pyridin-5-yl)pyridin-2(1H)-one To the solution of 4-(3-(2-methylpyridin-4-yl)-1-(tetrahydro-2H-pyran-2-yl)-1H-pyrazolo[4,3-b]pyridin-5-yl) pyridin-2(1H)-one (86 mg, 0.22 mmol) in THF (3 mL) was added KHMDS (1M, 0.27 mL; 0.27 mmol) at 0° C. under $N_2$. The mixture was stirred at room temperature for 20 min. Then (S)-2-((tert-butyldimethylsilyl)oxy)-1-(3-chlorophenyl)ethyl methanesulfonate (102 mg, 0.27 mmol) was added. The reaction mixture was stirred at 90° C. overnight. The mixture was cooled to room temperature, diluted with water (2 mL), extracted with ethyl acetate (10 mL×3). The combined organic layers were washed with brine (10 mL×2), dried over anhydrous $Na_2SO_4$, filtered off, and concentrated in vacuo. The crude product was purified by prep-TLC to give the title compound (45 mg, 32% yield).

Step 7. (S)-1-(1-(3-chlorophenyl)-2-hydroxyethyl)-4-(3-(2-methylpyridin-4-yl)-1H-pyrazolo[4,3-b]pyridin-5-yl)pyridin-2(1H)-one To the solution of 1-((S)-2-((tert-butyldimethylsilyl)oxy)-1-(3-chlorophenyl)ethyl)-4-(3-(2-methylpyridin-4-yl)-1-(tetrahydro-2H-pyran-2-yl)-1H-pyrazolo[4,3-b]pyridin-5-yl)pyridin-2(1H)-one (45 mg, 0.068 mmol) in methanol (3 mL) was added HCl (6M, 3 mL; 18 mmol) at room temperature under $N_2$ protection. The mixture was stirred at 50° C. for 2 h and then cooled to room temperature, neutralized with saturated aqueous $Na_2CO_3$ (10 mL), extracted with methanol/DCM (1:10, 10 mL×3). The combined organic layers were washed with brine (10 mL×2), dried over anhydrous $Na_2SO_4$, filtered off, and concentrated in vacuo. The crude product was purified by prep-TLC to give the title compound (12 mg, 35% yield). MS (ESI) m/z: 458.2 [M+1]$^+$; $^1$HNMR (400 MHz, CD$_3$OD) δ/ppm: 8.58-8.37 (m, 3H), 8.11 (d, J=8.9 Hz, 1H), 8.01 (d, J=8.9 Hz, 1H), 7.90 (d, J=7.2 Hz, 1H), 7.47 (s, 1H), 7.42-7.29 (m, 5H), 6.20 (dd, J=7.4, 5.4 Hz, 1H), 4.34 (dd, J=12.1, 7.7 Hz, 1H), 4.24 (dd, J=12.2, 5.2 Hz, 1H), 2.64 (s, 3H).

Example 10 (Method 10)

Preparation of 1-(3-bromo-5-fluorobenzyl)-4-(3-(2-isopropoxypyridin-4-yl)-1H-indazol-5-yl)pyridin-2(1H)-one

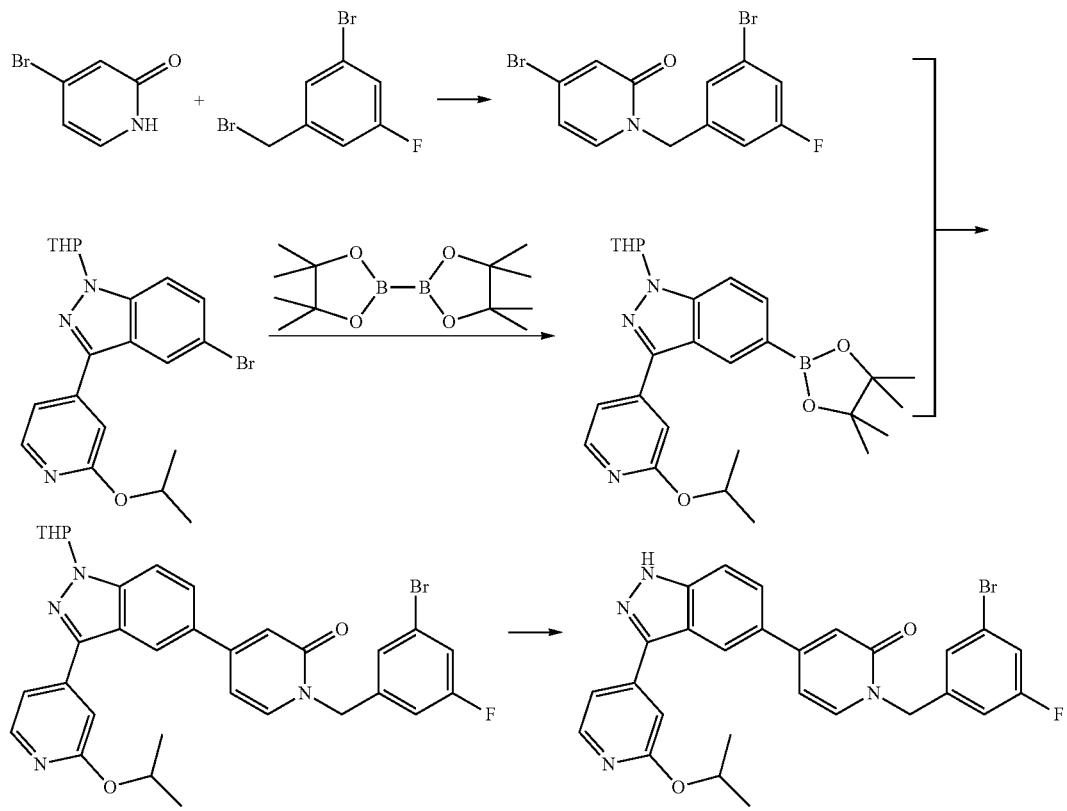

Step 1. 4-bromo-1-(3-bromo-5-fluorobenzyl)pyridin-2(1H)-one

A solution of 4-bromopyridin-2(1H)-one (147 mg, 0.848 mmol), 1-bromo-3-(bromomethyl)-5-fluorobenzene (250 mg, 0.932 mmol) and K$_2$CO$_3$ (234 mg, 1.696 mmol) in DMF (5 mL) was stirred and room temperature overnight. The mixture was diluted with EA (60 mL), which was washed with water (20 mL×2) and brine (20 mL). The organic layer was dried over anhydrous Na$_2$SO$_4$, filtered off, and concentrated in vacuo to give the title compound (300 mg, 98% yield).

Step 2. 1-(3-bromo-5-fluorobenzyl)-4-(3-(2-isopropoxypyridin-4-yl)-1-(tetrahydro-2H-pyran-2-yl)-1H-indazol-5-yl)pyridin-2(1H)-one A mixture of 5-bromo-3-(2-isopropoxypyridin-4-yl)-1-(tetrahydro-2H-pyran-2-yl)-1H-indazole (220 mg, 0.528 mmol), bis(pinacolato)diboron (134 mg, 0.528 mmol), Pd(dppf)Cl$_2$-DCM (42.5 mg, 0.052 mmol), and KOAc (155 mg, 1.58 mmol) in dixoane (5 mL) was stirred at 100° C. under N$_2$ protection overnight. The mixture was cooled to 50° C., followed by the addition of 4-bromo-1-(3-bromo-5-fluorobenzyl)pyridin-2(1H)-one (143 mg, 0.396 mmol), Na$_2$CO$_3$ (112 mg, 1.056 mmol) and water (1 mL). The resulting mixture was stirred at 100° C. for 6 h under N$_2$ protection and then cooled to room temperature, diluted with DCM (30 mL). The organic layer was washed with water (15 mL), brine (10 mL), dried over anhydrous Na$_2$SO$_4$, filtered off, and concentrated in vacuo. The crude product was purified by prep-TLC (DCM:MeOH=10:1) to give the title compound (100 mg, yield: 40%).

Step 3. 1-(3-bromo-5-fluorobenzyl)-4-(3-(2-isopropoxypyridin-4-yl)-1H-indazol-5-yl)pyridin-2(1H)-one A solution of 1-(3-bromo-5-fluorobenzyl)-4-(3-(2-isopropoxypyridin-4-yl)-1-(tetrahydro-2H-pyran-2-yl)-1H-indazol-5-yl)pyridin-2(1H)-one (100 mg, 0.16 mmol) in HCl (6.0 N, 3 mL)/MeOH (1.5 mL) was stirred at 50° C. overnight. The reaction mixture was then cooled to room temperature and concentrated. The residue was dissolved with H$_2$O (20 mL) and cooled in ice-water bath. Saturated aqueous Na$_2$CO$_3$ was added to adjust PH to 8-9. The resulting solution was extracted with DCM/MeOH (10:1, 30 mL×3). The combined organic layers were washed with brine (30 mL), dried over anhydrous Na$_2$SO$_4$, filtered off, and concentrated in vacuo. The crude product was purified by prep-TLC (DCM/MeOH=10/1) gave the title compound (25 mg, 29% yield). MS (ESI) m/z: 532.8 [M+1]$^+$; $^1$HNMR (400 MHz, CD$_3$OD) δ/ppm: 8.33 (s, 1H), 8.22 (d, J=5.3 Hz, 1H), 7.81 (d, J=7.0 Hz, 1H), 7.78 (dd, J=8.8, 1.3 Hz, 1H), 7.70 (d, J=8.8 Hz, 1H), 7.56 (dd, J=5.3, 1.2 Hz, 1H), 7.39 (s, 1H), 7.33-7.27 (m, 2H), 7.13 (d, J=9.2 Hz, 1H), 6.90 (s, 1H), 6.88 (dd, J=7.1, 2.0 Hz, 1H), 5.35-5.26 (m, 1H), 5.22 (s, 2H), 1.38 (d, J=6.2 Hz, 6H).

Example 11

Preparation of (S)-4-(3-amino-1H-indazol-5-yl)-1-(1-(3-chlorophenyl)-2-hydroxyethyl)pyridin-2(1H)-one

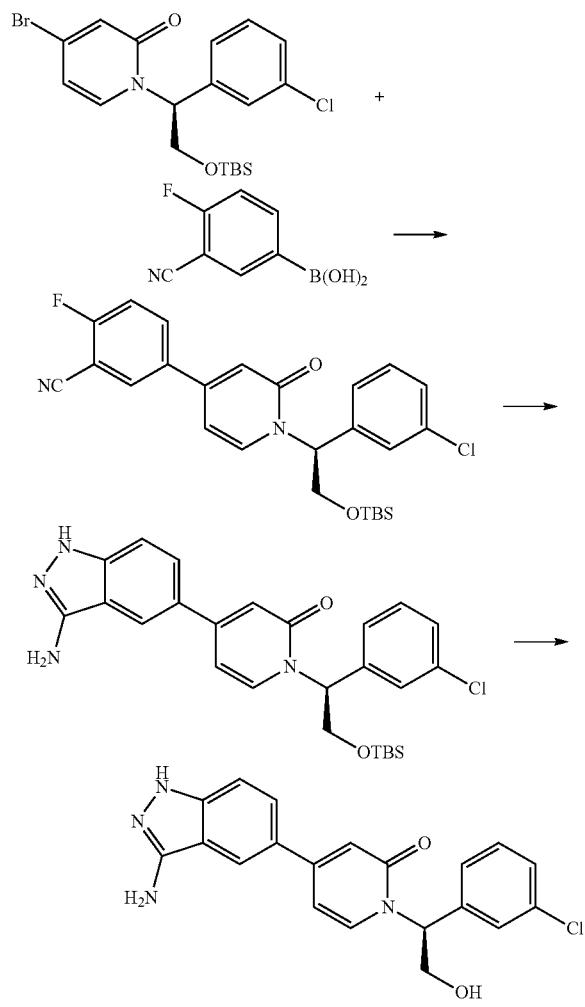

Step 1. (S)-5-(1-(2-((tert-butyldimethylsilyl)oxy)-1-(3-chlorophenyl)ethyl)-2-oxo-1,2-dihydropyridin-4-yl)-2-fluorobenzonitrile A solution of (S)-4-bromo-1-(2-((tert-butyldimethylsilyl)oxy)-1-(3-chloro-phenyl)ethyl)pyridin-2(1H)-one (135 mg, 0.305 mmol), (3-cyano-4-fluorophenyl)-boronic acid (50 mg, 0.305 mmol), Pd(dppf)Cl₂-DCM (25 mg, 0.03 mmol) and Na₂CO₃ (64.66 mg, 0.61 mmol) in dioxane/H₂O (5:1, 2.4 ml) was stirred at 80° C. under N₂ protection for 2 h. The mixture was cooled to room temperature and diluted with EA (100 mL), washed with H₂O (30 mL×2) and brine (30 mL). The organic layer was dried over anhydrous Na₂SO₄, filtered off, and concentrated in vacuo. The residue was purified by prep-TLC (PE/EA=2/1) to give the title compound (60 mg, 40% yield).

Step 2. (S)-4-(3-amino-1H-indazol-5-yl)-1-(2-((tert-butyldimethylsilyl)oxy)-1-(3-chlorophenyl)ethyl)pyridin-2(1H)-one To the solution of (S)-5-(1-(2-((tert-butyldimethylsilyl)oxy)-1-(3-chlorophenyl)-ethyl)-2-oxo-1,2-dihydropyridin-4-yl)-2-fluorobenzonitrile (60 mg, 0.124 mmol) in EtOH, hydrazine hydrate (20 mg, 0.620 mmol) was added. The resulting mixture was stirred at 105° C. in a sealed tube overnight and then cooled to room temperature, diluted with EA (50 mL), washed by H₂O (20 mL×2) and brine (20 mL). The organic layer was dried over anhydrous Na₂SO₄, filtered off, and concentrated in vacuo to give the crude title compound which was used in the next step without further purification.

Step 3. (S)-4-(3-amino-1H-indazol-5-yl)-1-(1-(3-chlorophenyl)-2-hydroxy-ethyl)pyridin-2(1H)-one A solution of (S)-4-(3-amino-1H-indazol-5-yl)-1-(2-((tert-butyldimethylsilyl)-oxy)-1-(3-chlorophenyl)ethyl)pyridin-2(1H)-one in HCl/dioxane (4N, 0.5 ml) and EA (1 ml) was stirred at room temperature for 1.5 h. The precipitate formed in the mixture was collected by filtration and washed with EA, dried under vacuum to give the title compound (30 mg, 65% yield). MS (ESI) m/z: 381.0 [M+1]⁺; ¹HNMR (400 MHz, DMSO-d6) δ/ppm: 8.52 (d, J=12.3 Hz, 1H), 7.93-7.82 (m, 2H), 7.48 (d, J=8.9 Hz, 1H), 7.44-7.35 (m, 3H), 7.28 (d, J=7.0 Hz, 1H), 6.71 (d, J=1.9 Hz, 1H), 6.65 (dd, J=7.3, 2.0 Hz, 1H), 5.98 (dd, J=7.8, 5.7 Hz, 1H), 4.16 (dd, J=11.7, 8.2 Hz, 1H), 4.08-3.99 (m, 1H), 3.55 (s, 1H).

Example 12

Preparation of (S)-1-(1-(3-chlorophenyl)-2-hydroxy-ethyl)-4-(3-((1-methyl-1H-pyrazol-5-yl)amino)-1H-indazol-5-yl)pyridin-2(1H)-one

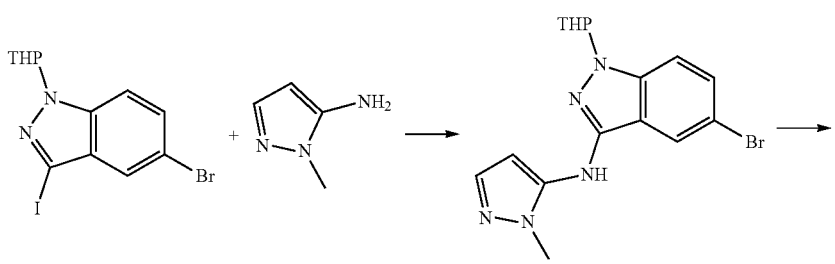

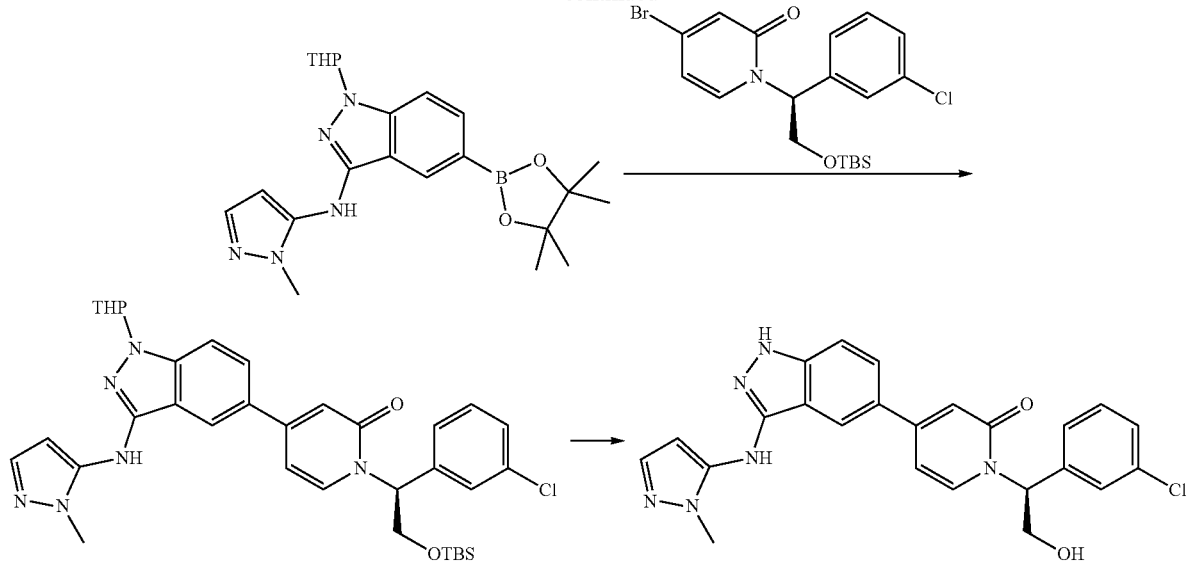

Step 1. 5-bromo-N-(1-methyl-1H-pyrazol-5-yl)-1-(tetrahydro-2H-pyran-2-yl)-1H-indazol-3-amine A mixture of 5-bromo-3-iodo-1-(tetrahydro-2H-pyran-2-yl)-1H-indazole (408 mg, 1.0 mmol), 1-methyl-1H-pyrazol-5-amine (97 mg, 1.0 mmol), Xantphos (86 mg, 0.15 mmol), Pd₂dba₃ (45 mg, 0.005 mmol) and Cs₂CO₃ (651 mg, 2.0 mmol) in dioxane was stirred at 80° C. under N₂ protection for 18 h. The mixture was cooled to room temperature and diluted with DCM (30 mL), washed with water (15 mL) and brine (15 mL). The organic layer was dried over anhydrous Na₂SO₄, filtered off, and concentrated in vacuo. The residue was purified by silica gel flash column chromatography (DCM:MeOH=100:1-10:1) to give the title compound (150 mg, yield: 40%).

Step 2. 1-((S)-2-((tert-butyldimethylsilyl)oxy)-1-(3-chloro-phenyl)-ethyl)-4-(3-((1-methyl-1H-pyrazol-5-yl)amino)-1-(tetrahydro-2H-pyran-2-yl)-1H-indazol-5-yl)pyridin-2(1H)-one A mixture of 5-bromo-N-(1-methyl-1H-pyrazol-5-yl)-1-(tetrahydro-2H-pyran-2-yl)-1H-indazol-3-amine (150 mg, 0.4 mmol), bis(pinacolato)diboron (101 mg, 0.4 mmol), Pd(dppf)Cl₂-DCM (16 mg, 0.02 mmol), and KOAc (117 mg, 1.2 mmol) in dixoane (2 mL) was stirred at 80° C. under N₂ protection for 8 h. The mixture was cooled to 50° C., followed by addition of (S)-4-bromo-1-(2-((tert-butyldimethyl-silyl)oxy)-1-(3-chlorophenyl)ethyl)pyridin-2(1H)-one (177 mg, 0.4 mmol), Cs₂CO₃ (260 mg, 0.8 mmol) and water (0.4 mL). The resulting mixture was stirred at 80° C. for 4 h under N₂ protection and then cooled to room temperature, diluted with DCM (30 mL). The organic layer was washed with water (15 mL), brine (10 mL), dried over anhydrous Na₂SO₄, filtered off, and concentrated in vacuo. The crude product was purified by prep-TLC (DCM:MeOH=10:1) gave the title compound (150 mg, yield: 56%).

Step 3. (S)-1-(1-(3-chlorophenyl)-2-hydroxyethyl)-4-(3-((1-methyl-1H-pyrazol-5-yl)amino)-1H-indazol-5-yl)pyridin-2(1H)-one To a solution of 1-((S)-2-((tert-butyldimethylsilyl)oxy)-1-(3-chlorophenyl)-ethyl)-4-(3-((1-methyl-1H-pyrazol-5-yl)amino)-1-(tetrahydro-2H-pyran-2-yl)-1H-indazol-5-yl)pyridin-2(1H)-one (150 mg, 0.227 mmol) in MeOH (1.5 mL) was added 6N hydrochloric acid (2 mL). The mixture was stirred at 50° C. for 18 h and then cooled to room temperature, neutralized with solid NaHCO₃, extracted with DCM (25 mL×2). The combined organic layers were washed with brine (20 mL), dried over anhydrous Na₂SO₄, filtered off, and concentrated in vacuo. The residue was purified by prep-TLC to give the title compound (25 mg, yield: 23%). MS-ESI: 461.0 (M+1)+; ¹HNMR (400 MHz, CD₃OD) δ/ppm: 8.10 (s, 1H), 7.79 (d, J=7.3 Hz, 1H), 7.71 (dd, J=8.8, 1.6 Hz, 1H), 7.47 (d, J=8.9 Hz, 1H), 7.43 (s, 1H), 7.39 (d, J=2.1 Hz, 1H), 7.38-7.29 (m, 3H), 6.85 (d, J=1.9 Hz, 1H), 6.79 (dd, J=7.3, 2.1 Hz, 1H), 6.25 (d, J=2.0 Hz, 1H), 6.15 (dd, J=7.4, 5.4 Hz, 1H), 4.29 (dd, J=12.1, 7.6 Hz, 1H), 4.20 (dd, J=12.1, 5.3 Hz, 1H), 3.80 (s, 3H).

Example 13

Preparation of (S)-1-(1-(3-chlorophenyl)-2-hydroxy-ethyl)-4-(4-fluoro-3-(2-methylpyridin-4-yl)-1H-indazol-5-yl)pyridin-2(1H)-one

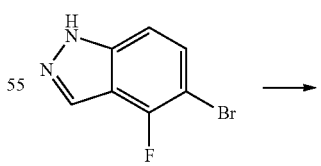

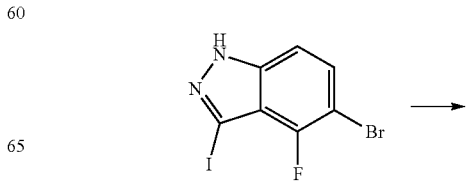

-continued

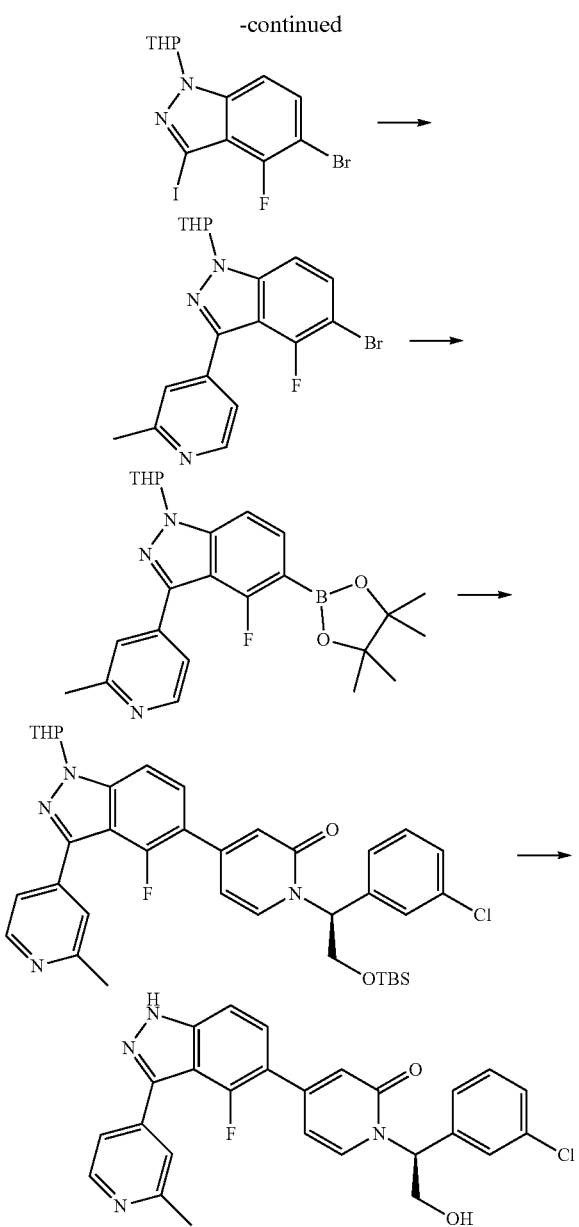

Step 1. 5-bromo-4-fluoro-3-iodo-1H-indazole

The mixture of 5-bromo-4-fluoro-1H-indazole (1.0 g, 4.65 mmol), iodine (2.36 g, 9.30 mmol) and KOH (783 mg, 13.95 mmol) in DMF (10 mL) was stirred at 70° C. for 6 h under $N_2$ protection. The reaction mixture was cooled to room temperature and diluted with ethyl acetate (150 mL), washed with 10% $Na_2S_2O_3$ (50 mL) and brine (50 mL). The organic layer was dried over anhydrous $Na_2SO_4$, filtered off, and concentrated in vacuo. The residue was purified by silica gel flash column chromatography eluting with hexanes/ethyl acetate (4:1-2:1) to give the title compound (1.54 g, 97% yield).

Step 2. 5-bromo-4-fluoro-3-iodo-1-(tetrahydro-2H-pyran-2-yl)-1H-indazole

The mixture of 5-bromo-4-fluoro-3-iodo-1H-indazole (1.538 g, 4.5 mmol), 3,4-dihydro-2H-pyran (1.14 g, 13.5 mmol) and pyridinium p-toluenesulfonate (113 mg, 0.45 mmol) in THF (30 mL) was stirred at 70° C. overnight. The reaction mixture was cooled to room temperature and diluted with ethyl acetate (90 mL), washed with brine (20 mL×2). The organic layer was dried over anhydrous $Na_2SO_4$, filtered off, and concentrated in vacuo. The residue was purified by silica gel flash column chromatography eluting with hexanes/ethyl acetate (10:1) to give the title compound (1.47 g, 77% yield).

Step 3. 5-bromo-4-fluoro-3-(2-methylpyridin-4-yl)-1-(tetrahydro-2H-pyran-2-yl)-1H-indazole The mixture of 5-bromo-4-fluoro-3-iodo-1-(tetrahydro-2H-pyran-2-yl)-1H-indazole (1.47 g, 3.46 mmol), (2-methylpyridin-4-yl)boronic acid (497.5 mg, 3.63 mmol), $Na_2CO_3$ (733.5 mg, 6.92 mmol) and Pd(dppf)$Cl_2$-DCM (282 mg, 0.35 mmol) in dioxane (15 mL)/$H_2O$ (3 mL) was stirred at 65° C. overnight under $N_2$ protection. The reaction mixture was cooled to room temperature and diluted with ethyl acetate (100 mL), washed with brine (20 mL×2). The organic layer was dried over anhydrous $Na_2SO_4$, filtered off, and concentrated in vacuo. The residue was purified by silica gel flash column chromatography eluting with hexanes/ethyl acetate (4:1-1:1) to give the title compound (470 mg, 35% yield).

Step 4. 1-((S)-2-((tert-butyldimethylsilyl)oxy)-1-(3-chlorophenyl)ethyl)-4-(4-fluoro-3-(2-methylpyridin-4-yl)-1-(tetrahydro-2H-pyran-2-yl)-1H-indazol-5-yl)pyridin-2(1H)-one The mixture of 5-bromo-4-fluoro-3-(2-methylpyridin-4-yl)-1-(tetrahydro-2H-pyran-2-yl)-1H-indazole (100 mg, 0.256 mmol), bis(pinacolato)diboron (65 mg, 0.256 mmol), potassium acetate (75 mg, 0.768 mmol) and Pd(dppf)$Cl_2$-DCM (21 mg, 0.026 mmol) in dioxane (1 mL) was stirred at 90° C. overnight under $N_2$ protection. Then to the cooled reaction mixture (S)-4-bromo-1-(2-((tert-butyldimethylsilyl)oxy)-1-(3-chlorophenyl)ethyl)pyridin-2(1H)-one (113 mg, 0.256 mmol), $Cs_2CO_3$ (167 mg, 0.512 mmol) and $H_2O$ (0.5 mL) was added. The resulting mixture was stirred at 85° C. overnight and then cooled to room temperature, diluted with EA (30 mL), washed by brine (10 mL×2). The organic layer was dried over anhydrous $Na_2SO_4$, filtered off, and concentrated in vacuo. The residue was purified by by prep-TLC gave the title compound (86 mg, 50% yield).

Step 5. (S)-1-(1-(3-chlorophenyl)-2-hydroxyethyl)-4-(4-fluoro-3-(2-methyl-pyridin-4-yl)-1H-indazol-5-yl)pyridin-2(1H)-one To the solution of 1-((S)-2-((tert-butyldimethylsilyl)oxy)-1-(3-chlorophen yl)ethyl)-4-(4-fluoro-3-(2-methylpyridin-4-yl)-1-(tetrahydro-2H-pyran-2-yl)-1H-indazol-5-yl)pyridin-2(1H)-one (86 mg, 0.128 mmol) in methanol (2 mL) was added HCl (6M, 2 mL; 12 mmol) at room temperature. The mixture was stirred at 60° C. for 2 h and then cooled to room temperature, concentrated in vacuum to remove the solvents. The residue was diluted with DCM/MeOH (10:1, 30 mL), washed with saturated aqueous $Na_2CO_3$ (10 mL) and brine (10 mL). The organic layer was dried over anhydrous $Na_2SO_4$, filtered off, and concentrated in vacuo. The residue was purified by by prep-TLC (DCM/MeOH=10/1) to give the title compound (31 mg, 51% yield). MS (ESI) m/z: 474.6 [M+1]$^+$; $^1$HNMR (400 MHz, $CD_3OD$) δ/ppm: 8.50 (d, J=5.3 Hz, 1H), 7.88 (s, 1H), 7.84-7.77 (m, 2H), 7.60 (m, 1H), 7.52

(m, 1H), 7.45 (s, 1H), 7.35 (m, 3H), 6.83 (s, 1H), 6.74 (m, 1H), 6.17 (m, 1H), 4.26 (m, 2H), 2.62 (s, 3H).

Example 14

Preparation of (S)-1-(1-(3-chlorophenyl)-2-hydroxyethyl)-4-(6-fluoro-3-(2-methylpyridin-4-yl)-1H-indazol-5-yl)pyridin-2(1H)-one

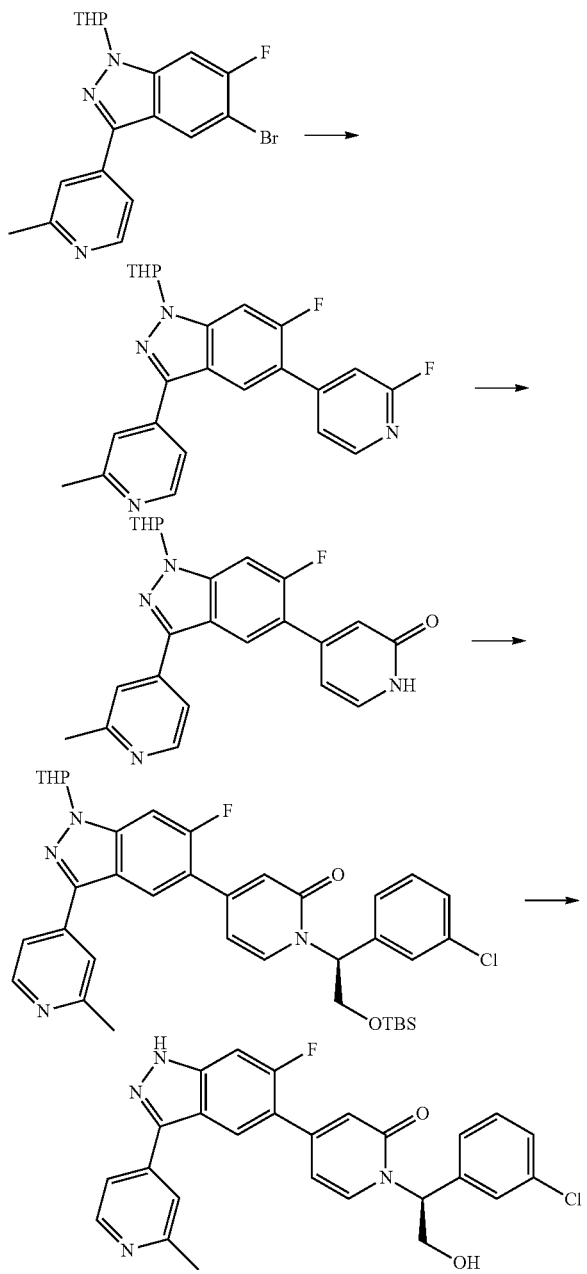

Step 1. 6-fluoro-5-(2-fluoropyridin-4-yl)-3-(2-methylpyridin-4-yl)-1-(tetrahydro-2H-pyran-2-yl)-1H-indazole A solution of 5-bromo-6-fluoro-3-(2-methylpyridin-4-yl)-1-(tetrahydro-2H-pyran-2-yl)-1H-indazole (250 mg, 0.64 mmol), (2-fluoropyridin-4-yl)boronic acid (90 mg, 0.64 mmol) Pd(dppf)Cl$_2$-DCM (52 mg, 0.064 mmol) and Na$_2$CO$_3$ (135 mg, 1.28 mmol) in dioxane/H$_2$O (5/1 ml) was stirred at 80° C. under N$_2$ protection for 3 h. The mixture was cooled to room temperature and diluted with EA (50 mL), washed by H$_2$O (20 mL×2) and brine (20 mL). The organic layer was dried over anhydrous Na$_2$SO$_4$, filtered off, and concentrated in vacuo. The residue was purified by silica gel flash column chromatography (PE/EA=1/1) to give the title compound (200 mg, 76% yield).

Step 2. 4-(6-fluoro-3-(2-methylpyridin-4-yl)-1-(tetrahydro-2H-pyran-2-yl)-1H-indazol-5-yl)pyridin-2(1H)-one A solution of 6-fluoro-5-(2-fluoropyridin-4-yl)-3-(2-methylpyridin-4-yl)-1-(tetrahydro-2H-pyran-2-yl)-1H-indazole (200 mg, 0.49 mmol) in AcOH (20 ml) and H$_2$O (2 ml) was stirred at 85° C. for 22 h. The reaction mixture was then cooled to room temperature and concentrated. The residue was dissolved with H$_2$O (20 mL) and cooled in ice-water bath. Saturated aqueous Na$_2$CO$_3$ was added to adjust PH to 8-9. The resulting solution was extracted with DCM/MeOH (10:1, 30 mL×3). The combined organic layers were washed with brine (20 mL), dried over anhydrous Na$_2$SO$_4$, filtered off, and concentrated in vacuo. The residue was purified by Prep-TLC to give the title compound (82 mg, 41% yield).

Step 3. 1-((S)-2-((tert-butyldimethylsilyl)oxy)-1-(3-chlorophenyl)ethyl)-4-(6-fluoro-3-(2-methylpyridin-4-yl)-1-(tetrahydro-2H-pyran-2-yl)-1H-indazol-5-yl)pyridin-2(1H)-one To a solution of 4-(6-fluoro-3-(2-methylpyridin-4-yl)-1-(tetrahydro-2H-pyran-2-yl)-1H-indazol-5-yl)pyridin-2(1H)-one (82 mg, 0.2 mmol) in THF (2.5 mL), 1N KHMDS (0.24 ml, 0.243 mmol) was added slowly at room temperature. The resulting mixture was stirred at room temperature for 30 min. Then (R)-2-((tert-butyldimethyl-silyl)oxy)-1-(3-chlorophenyl)ethyl methanesulfonate (89 mg, 0.243 mmol) was added. The mixture was stirred at 85° C. overnight and then cooled to room temperature and concentrated under vacuum. The residue was diluted with EA (50 mL), washed by H$_2$O (20 mL×2) and brine (20 mL). The organic layer was dried over anhydrous Na$_2$SO$_4$, filtered off, and concentrated in vacuo. The residue was purified by by prep-TLC to give the title compound (80 mg, 58% yield).

Step 4. (S)-1-(1-(3-chlorophenyl)-2-hydroxyethyl)-4-(6-fluoro-3-(2-methylpyridin-4-yl)-1H-indazol-5-yl)pyridin-2(1H)-one A solution of 1-((S)-2-((tert-butyldimethylsilyl)oxy)-1-(3-chlorophenyl)ethyl)-4-(6-fluoro-3-(2-methylpyridin-4-yl)-1-(tetrahydro-2H-pyran-2-yl)-1H-indazol-5-yl)pyridin-2(1H)-one (80 mg, 0.118 mmol) in HCl (6.0 N, 1.5 mL)/MeOH (0.7 ml) was stirred at 60° C. for 3 h. The reaction mixture was then cooled to room temperature and concentrated. The residue was dissolved with H$_2$O (10 mL) and cooled in ice-water bath. Saturated aqueous Na$_2$CO$_3$ was added to adjust PH to 8-9. The resulting solution was extracted with DCM/MeOH (10:1, 20 mL×3). The combined organic layers were washed with brine (20 mL), dried over anhydrous Na$_2$SO$_4$, filtered off, and concentrated in vacuo. The residue was purified by prep-TLC (DCM/MeOH=10/1) to give the title compound (40 mg, 70% yield). MS (ESI) m/z: 474.8 [M+1]$^+$; $^1$HNMR (400 MHz, CD$_3$OD) δ/ppm: 8.47 (d, J=5.3 Hz, 1H), 8.17 (d, J=6.9 Hz, 1H), 7.85 (s, 1H), 7.80 (d, J=7.3 Hz, 2H), 7.44 (s, 1H), 7.42-7.29 (m, 4H), 6.83 (s, 1H), 6.70 (d, J=7.2 Hz, 1H), 6.18 (dd, J=7.2, 5.4 Hz, 1H), 4.31 (dd, J=12.1, 7.7 Hz, 1H), 4.21 (dd, J=12.1, 5.2 Hz, 1H), 2.59 (s, 3H).

Table 1 lists examples that were prepared according to the procedures as described in methods 1-10 as indicated below the structure of each example by using the corresponding intermediates and reagents under appropriate conditions that could be accomplished by the skilled persons.

TABLE 1

| Example | Structure (Synthetic Method) | Chemical Name | LC/MS [M + H]$^+$ | 1H-NMR (400 MHz) |
|---|---|---|---|---|
| 15 | (Method 1) | (S)-1-(1-(4-chloro-3-fluorophenyl)-2-hydroxyethyl)-4-(3-(2-methylpyridin-4-yl)-1H-indazol-5-yl)pyridin-2(1H)-one | 474.9 | $^1$H NMR (400 MHz, CD$_3$OD) δ/ppm: 8.52 (d, J = 5.3 Hz, 1H), 8.36 (s, 1H), 7.93 (s, 1H), 7.87 (d, J = 5.2 Hz, 1H), 7.82 (d, J = 7.2 Hz, 1H), 7.77 (dd, J = 8.8, 1.3 Hz, 1H), 7.70 (d, J = 8.8 Hz, 1H), 7.49 (t, J = 8.0 Hz, 1H), 7.33 (dd, J = 10.3, 1.8 Hz, 1H), 7.23-7.16 (m, 1H), 6.93-6.85 (m, 2H), 6.18-6.10 (m, 1H), 4.30 (dd, J = 12.1, 7.4 Hz, 1H), 4.21 (dd, J = 12.1, 5.2 Hz, 1H), 2.63 (s, 3H). |
| 16 | (Method 1) | (S)-1-(1-(3-chlorophenyl)-2-hydroxyethyl)-4-(3-(1,3-dimethyl-1H-pyrazol-4-yl)-1H-indazol-5-yl)pyridin-2(1H)-one | 459.9 | $^1$H NMR (400 MHz, CD$_3$OD) δ/ppm: 8.16 (s, 1H), 8.12 (s, 1H), 7.80 (d, J = 7.2 Hz, 1H), 7.75 (d, J = 8.8 Hz, 1H), 7.63 (d, J = 8.8 Hz, 1H), 7.43 (s, 1H), 7.37-7.30 (m, 3H), 6.89 (s, 1H) 6.88 (dd, J = 7.6 Hz, 2H), 6.16 (dd, J = 7.4, 5.4 Hz, 1H), 4.30 (dd, J = 12.1, 7.6 Hz, 1H), 4.21 (dd, J = 12.1, 5.3 Hz, 1H), 3.93 (s, 3H), 2.47 (s, 3H). |
| 17 | (Method 1) | (S)-1-(1-(3-chlorophenyl)-2-hydroxyethyl)-4-(3-(6-isopropoxypyridin-3-yl)-1H-indazol-5-yl)pyridin-2(1H)-one | 501.1 | 1H NMR (400 MHz, CD$_3$OD) δ/ppm: 8.68 (d, J = 2.1 Hz, 1H), 8.22-8.17 (m, 2H), 7.78 (d, J = 7.3 Hz, 1H), 7.72 (dd, J = 8.8, 1.2 Hz, 1H), 7.63 (d, J = 8.8 Hz, 1H), 7.43 (s, 1H), 7.39-7.28 (m, 3H), 6.91-6.79 (m, 3H), 6.16 (dd, J = 7.1, 5.5 Hz, 1H), 5.31 (dp, J = 12.3, 6.1 Hz, 1H), 4.29 (dd, J = 12.1, 7.6 Hz, 1H), 4.20 (dd, J = 12.1, 5.2 Hz, 1H), 1.37 (d, J = 6.1 Hz, 6H). |
| 18 | (Method 1) | (S)-1-(1-(3-chlorophenyl)-2-hydroxyethyl)-4-(3-(1-methyl-1H-pyrazol-4-yl)-1H-indazol-5-yl)pyridin-2(1H)-one | 446.2 | $^1$H NMR (400 MHz, CD$_3$OD) δ/ppm: 8.28 (s, 1H), 8.21 (s, 1H), 8.05 (s, 1H), 7.79 (d, J = 7.2 Hz, 1H), 7.71 (dd, J = 8.8, 1.3 Hz, 1H), 7.59 (d, J = 8.8 Hz, 1H), 7.43 (s, 1H), 7.33 (ddd, J = 10.0, 7.3, 3.2 Hz, 3H), 6.90 (d, J = 1.7 Hz, 1H), 6.86 (dd, J = 7.3, 2.0 Hz, 1H), 6.16 (dd, J = 7.2, 5.5 Hz, 1H), 4.30 (dd, J = 12.1, 7.6 Hz, 1H), 4.21 (dd, J = 12.1, 5.2 Hz, 1H), 3.99 (s, 3H). |

TABLE 1-continued

| Example | Structure (Synthetic Method) | Chemical Name | LC/MS [M + H]⁺ | 1H-NMR (400 MHz) |
|---|---|---|---|---|
| 19 | (Method 1) | (S)-1-(1-(3-chlorophenyl)-2-hydroxyethyl)-4-(3-(2-isopropoxypyridin-4-yl)-1H-indazol-5-yl)pyridin-2(1H)-one | 523.4 [M + Na]⁺ | $^1$H NMR (400 MHz, CD$_3$OD) δ/ppm: 8.28 (s, 1H), 8.21 (d, J = 5.3 Hz, 1H), 7.80 (d, J = 7.3 Hz, 1H), 7.74 (dd, J = 8.8, 1.2 Hz, 1H), 7.67 (d, J = 8.8 Hz, 1H), 7.55-7.50 (m, 1H), 7.44 (s, 1H), 7.35 (dq, J = 9.4, 7.6 Hz, 3H), 7.28 (s, 1H), 6.88 (d, J = 1.7 Hz, 1H), 6.84 (dd, J = 7.2, 1.9 Hz, 1H), 6.19-6.11 (m, 1H), 5.29 (dt, J = 12.3, 6.2 Hz, 1H), 4.30 (dd, J = 12.1, 7.6 Hz, 1H), 4.21 (dd, J = 12.1, 5.2 Hz, 1H), 1.36 (t, J = 9.2 Hz, 6H). |
| 20 | (Method 1) | (S)-1-(1-(3-chloro-4-fluorophenyl)-2-hydroxyethyl)-4-(3-(6-(2-hydroxypropan-2-yl)pyridin-3-yl)-1H-indazol-5-yl)pyridin-2(1H)-one | 519.3 | $^1$H NMR (400 MHz, DMSO-d6) δ 13.52 (s, 1H), 9.16 (d, J = 1.6 Hz, 1H), 8.42 (m, 1H), 8.36 (s, 1H), 7.90-7.73 (m, 3H), 7.69 (m, 1H), 7.61 (m, 1H), 7.38 (m, 2H), 6.84 (m, 1H), 6.81-6.76 (m, 1H), 6.03-5.94 (m, 1H), 5.31 (t, J = 5.1 Hz, 1H), 5.29 (s, 1H), 4.11 (m, 2H), 1.50 (s, 6H). |
| 21 | (Method 1) | (S)-1-(1-(3-chloro-4-fluorophenyl)-2-hydroxyethyl)-4-(3-(2-(2-hydroxypropan-2-yl)pyridin-4-yl)-1H-indazol | 519.2 | $^1$H NMR (400 MHz, CD$_3$OD) δ 8.61 (d, J = 5.2 Hz, 1H), 8.42 (s, 1H), 8.36 (s, 1H), 7.94-7.88 (m, 1H), 7.85-7.70 (m, 3H), 7.57 (dd, J = 6.9, 2.2 Hz, 1H), 7.42-7.34 (m, 1H), 7.31-7.22 (m, 1H), 6.93-6.85 (m, 2H), 6.17-6.10 (m, 1H), 4.30 (dd, J = 12.0, 7.5 Hz, 1H), 4.20 (dd, J = 12.1, 5.3 Hz, 1H), 1.62 (s, 6H). |
| 22 | (Method 3) | (S)-1-(1-(3-chlorophenyl)-2-hydroxyethyl)-4-(1H-indazol-5-yl)pyridin-2(1H)-one | 365.9 | $^1$H NMR (400 MHz, CD$_3$OD) δ/ppm: 8.13 (t, J = 9.6 Hz, 2H), 7.79 (d, J = 7.3 Hz, 1H), 7.73 (dd, J = 8.8, 1.6 Hz, 1H), 7.64 (d, J = 8.8 Hz, 1H), 7.46-7.28 (m, 4H), 6.90-6.77 (m, 2H), 6.16 (dd, J = 7.3, 5.4 Hz, 1H), 4.25 (ddd, J = 17.4, 12.1, 6.4 Hz, 2H). |
| 23 | (Method 3) | (S)-1-(1-(3-chlorophenyl)-2-hydroxyethyl)-4-(3-ethyl-1H-indazol-5-yl)pyridin-2(1H)-one | 393.9 | $^1$H NMR (400 MHz, CD$_3$OD) δ/ppm: 8.09 (s, 1H), 7.80 (d, J = 7.1 Hz, 1H), 7.70 (d, J = 8.2 Hz, 1H), 7.56 (d, J = 8.7 Hz, 1H), 7.43 (s, 1H), 7.40-7.23 (m, 3H), 6.85 (d, J = 9.7 Hz, 2H), 6.23-6.08 (m, 1H), 4.25 (ddd, J = 17.1, 12.0, 6.5 Hz, 2H), 3.04 (dd, J = 15.1, 7.5 Hz, 2H), 1.40 (t, J = 7.6 Hz, 3H). |

TABLE 1-continued

| Example | Structure (Synthetic Method) | Chemical Name | LC/MS [M + H]+ | 1H-NMR (400 MHz) |
|---|---|---|---|---|
| 24 | 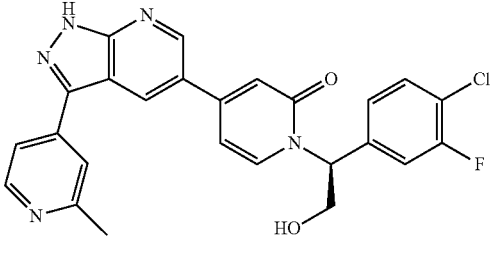<br>(Method 4) | (S)-1-(1-(4-chloro-3-fluorophenyl)-2-hydroxyethyl)-4-(3-(2-methylpyridin-4-yl)-1H-pyrazolo[3,4-b]pyridin-5-yl)pyridin-2(1H)-one | 476.1 | $^1$H NMR (400 MHz, CD$_3$OD) δ/ppm: 9.10 (d, J = 2.0 Hz, 1H), 8.99 (d, J = 1.9 Hz, 1H), 8.73 (d, J = 6.2 Hz, 1H), 8.65 (s, 1H), 8.62 (d, J = 6.4 Hz, 1H), 8.03 (d, J = 7.0 Hz, 1H), 7.67-7.53 (m, 1H), 7.52-7.47 (m, 1H), 7.34 (dd, J = 10.1, 2.0 Hz, 1H), 7.23 (d, J = 8.5 Hz, 1H), 7.18-7.11 (m, 2H), 6.23-6.15 (m, 1H), 4.35 (dd, J = 12.2, 7.7 Hz, 1H), 4.24 (dd, J = 12.2, 5.0 Hz, 1H), 2.90 (s, 3H). |
| 25 | 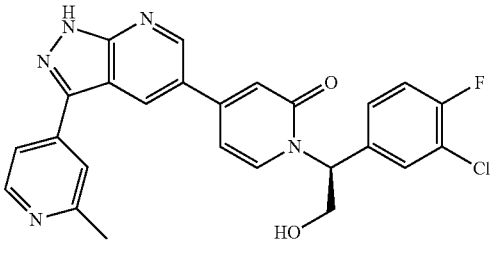<br>(Method 4) | (S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one | 476.0 | 1H NMR (400 MHz, DMSO-d6) δ 14.28 (s, 1H), 8.91 (d, J = 12.1 Hz, 2H), 8.54 (d, J = 5.0 Hz, 1H), 7.94 (s, 1H), 7.91 (d, J = 7.2 Hz, 2H), 7.61 (d, J = 6.0 Hz, 1H), 7.45-7.33 (m, 2H), 6.96 (s, 1H), 6.84 (d, J = 6.1 Hz, 1H), 6.04-5.94 (m, 1H), 5.32 (s, 1H), 4.26-4.13 (m, 1H), 4.10-4.00 (m, 1H), 2.45 (s, 3H). |
| 26 | 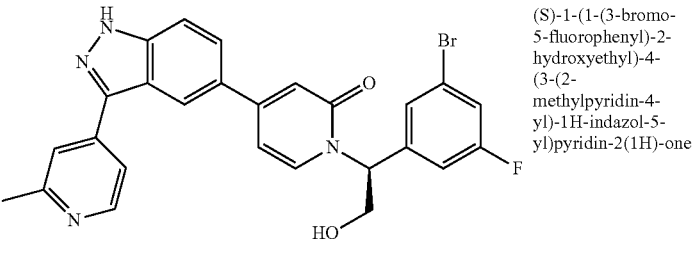<br>(Method 4) | (S)-1-(1-(3-bromo-5-fluorophenyl)-2-hydroxyethyl)-4-(3-(2-methylpyridin-4-yl)-1H-indazol-5-yl)pyridin-2(1H)-one | 519.0 | $^1$H NMR (400 MHz, CD$_3$OD) δ/ppm: 8.53 (d, J = 5.2 Hz, 1H), 8.40 (s, 1H), 7.95 (s, 1H), 7.90 (d, J = 4.8 Hz, 1H), 7.86 (d, J = 7.1 Hz, 1H), 7.80 (d, J = 8.8 Hz, 1H), 7.72 (d, J = 8.8 Hz, 1H), 7.41 (s, 1H), 7.33 (d, J = 8.1 Hz, 1H), 7.19 (d, J = 9.5 Hz, 1H), 6.91 (d, J = 8.5 Hz, 2H), 6.16-6.08 (m, 1H), 4.30 (dd, J = 12.1, 7.4 Hz, 1H), 4.22 (dd, J = 12.1, 5.2 Hz, 1H), 2.65 (s, 3H). |
| 27 | 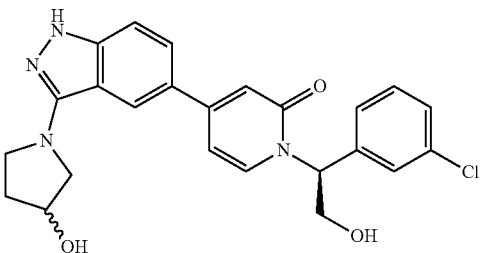<br>(Method 5) | 1-((S)-1-(3-chlorophenyl)-2-hydroxyethyl)-4-(3-(3-hydroxypyrrolidin-1-yl)-1H-indazol-5-yl)pyridin-2(1H)-one | 451.1 | $^1$H NMR (400 MHz, CD$_3$OD) δ/ppm: 8.10 (s, 1H), 7.75 (d, J = 7.2 Hz, 1H), 7.60 (dd, J = 8.9, 1.3 Hz, 1H), 7.42 (s, 1H), 7.34 (tt, J = 15.5, 7.6 Hz, 4H), 6.78 (dd, J = 10.1, 2.9 Hz, 2H), 6.19-6.11 (m, 1H), 4.61-4.52 (m, 1H), 4.28 (dd, J = 12.0, 7.6 Hz, 1H), 4.20 (dd, J = 12.1, 5.3 Hz, 1H), 3.83 (dt, J = 10.5, 6.7 Hz, 2H), 3.72 (td, J = 8.7, 3.3 Hz, 1H), 3.60 (d, J = 10.4 Hz, 1H), 2.24-2.13 (m, 1H), 2.10-2.00 (m, 1H). |
| 28 | 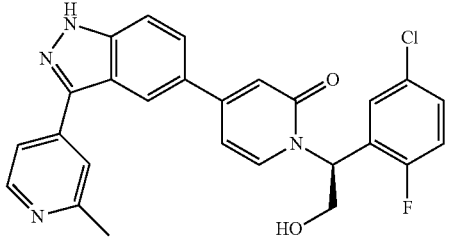<br>(Method 6) | (S)-1-(1-(5-chloro-2-fluorophenyl)-2-hydroxyethyl)-4-(3-(2-methylpyridin-4-yl)-1H-indazol-5-yl)pyridin-2(1H)-one | 475.1 | $^1$H NMR (400 MHz, CD$_3$OD) δ/ppm: 8.52 (d, J = 4.8 Hz, 1H), 8.36 (s, 1H), 7.91 (d, J = 14.3 Hz, 1H), 7.87 (s, 1H), 7.77 (d, J = 7.4 Hz, 2H), 7.70 (d, J = 8.5 Hz, 1H), 7.58 (dd, J = 6.2, 2.5 Hz, 1H), 7.44-7.35 (m, 1H), 7.22-7.10 (m, 1H), 6.93-6.82 (m, 2H), 6.26 (t, J = 5.8 Hz, 1H), 4.25 (ddd, J = 17.3, 12.1, 5.9 Hz, 2H), 2.63 (s, 3H). |

TABLE 1-continued

| Example | Structure (Synthetic Method) | Chemical Name | LC/MS [M + H]+ | 1H-NMR (400 MHz) |
|---|---|---|---|---|
| 29 | 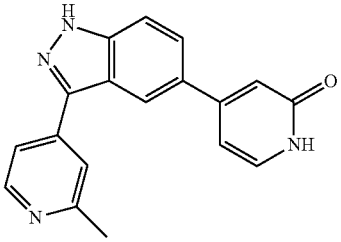 (Method 6) | 4-(3-(2-methylpyridin-4-yl)-1H-indazol-5-yl)pyridin-2(1H)-one | 302.9 | 1H NMR (400 MHz, DMSO-d6) δ 13.70 (s, 1H), 11.58 (s, 1H), 8.56 (d, J = 5.1 Hz, 1H), 8.37 (s, 1H), 7.99-7.84 (m, 2H), 7.73 (q, J = 8.8 Hz, 2H), 7.45 (d, J = 6.8 Hz, 1H), 6.72 (s, 1H), 6.67 (d, J = 6.8 Hz, 1H), 2.58 (s, 3H). |
| 30 | 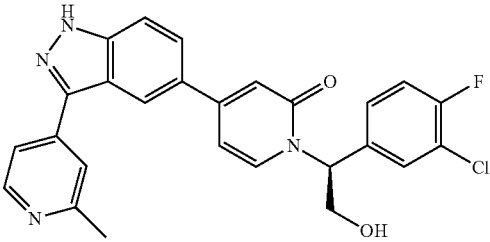 (Method 6) | (S)-1-(1-(3-chloro-4-fluorophenyl)-2-hydroxyethyl)-4-(3-(2-methylpyridin-4-yl)-1H-indazol-5-yl)pyridin-2(1H)-one | 475.0 | $^1$H NMR (400 MHz, CD$_3$OD) δ 8.52 (d, J = 4.7 Hz, 1H), 8.37 (s, 1H), 7.91 (d, J = 14.6 Hz, 1H), 7.87 (s, 1H), 7.82 (d, J = 7.2 Hz, 1H), 7.76 (t, J = 10.6 Hz, 1H), 7.71 (d, J = 8.2 Hz, 1H), 7.57 (dd, J = 6.9, 1.9 Hz, 1H), 7.42-7.34 (m, 1H), 7.26 (t, J = 8.8 Hz, 1H), 6.93-6.84 (m, 2H), 6.22-6.06 (m, 1H), 4.25 (ddd, J = 17.4, 12.1, 6.4 Hz, 2H), 2.61 (s, 3H). |
| 31 | 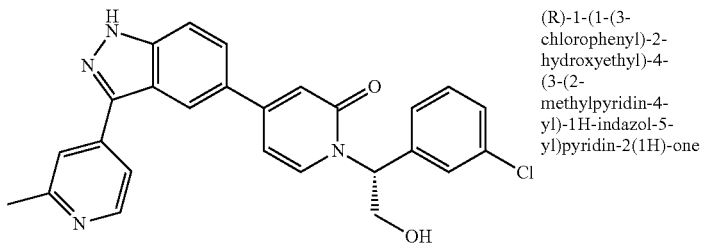 (Method 6) | (R)-1-(1-(3-chlorophenyl)-2-hydroxyethyl)-4-(3-(2-methylpyridin-4-yl)-1H-indazol-5-yl)pyridin-2(1H)-one | 457.1 | $^1$H NMR (400 MHz, DMSO-d6) δ/ppm: 13.70 (s, 1H), 8.55 (d, J = 5.2 Hz, 1H), 8.41 (s, 1H), 7.88 (m, 3H), 7.75 (m, 2H), 7.48-7.27 (m, 4H), 6.84 (m, 1H), 6.78 (m, 1H), 6.02 (m, 1H), 5.30 (t, J = 5.1 Hz, 1H), 4.23-4.13 (m, 1H), 4.12-3.98 (m, 1H), 2.58 (s, 3H). |
| 32 | 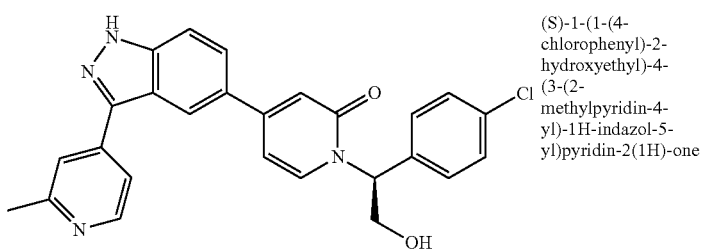 (Method 6) | (S)-1-(1-(4-chlorophenyl)-2-hydroxyethyl)-4-(3-(2-methylpyridin-4-yl)-1H-indazol-5-yl)pyridin-2(1H)-one | 457.1 | $^1$H NMR (400 MHz, CD$_3$OD) δ 8.52 (d, J = 5.3 Hz, 1H), 8.37 (s, 1H), 7.94 (s, 1H), 7.88 (d, J = 5.2 Hz, 1H), 7.81-7.75 (m, 2H), 7.71 (d, J = 8.8 Hz, 1H), 7.39 (s, 4H), 6.91 (d, J = 1.8 Hz, 1H), 6.87 (dd, J = 7.2, 2.0 Hz, 1H), 6.18 (dd, J = 7.5, 5.3 Hz, 1H), 4.29 (dd, J = 12.0, 7.6 Hz, 1H), 4.21 (dd, J = 12.1, 5.3 Hz, 1H), 2.64 (s, 3H). |
| 33 | 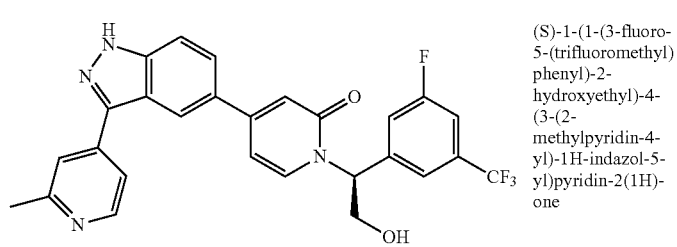 (Method 6) | (S)-1-(1-(3-fluoro-5-(trifluoromethyl)phenyl)-2-hydroxyethyl)-4-(3-(2-methylpyridin-4-yl)-1H-indazol-5-yl)pyridin-2(1H)-one | 508.5 | $^1$H NMR (400 MHz, CD$_3$OD) δ 8.52 (d, J = 5.3 Hz, 1H), 8.39 (s, 1H), 7.94 (s, 1H), 7.89 (t, J = 5.0 Hz, 2H), 7.79 (dd, J = 8.8, 1.3 Hz, 1H), 7.71 (d, J = 8.8 Hz, 1H), 7.56 (s, 1H), 7.45 (t, J = 9.8 Hz, 2H), 6.96-6.87 (m, 2H), 6.21-6.14 (m, 1H), 4.35 (dd, J = 12.1, 7.2 Hz, 1H), 4.26 (dd, J = 12.1, 5.2 Hz, 1H), 2.64 (s, 3H). |

TABLE 1-continued

| Example | Structure (Synthetic Method) | Chemical Name | LC/MS [M + H]⁺ | 1H-NMR (400 MHz) |
|---|---|---|---|---|
| 34 | 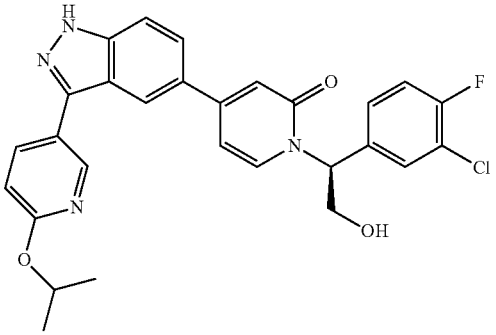<br>(Method 6) | (S)-1-(1-(3-chloro-4-fluorophenyl)-2-hydroxyethyl)-4-(3-(6-isopropoxypyridin-3-yl)-1H-indazol-5-yl)pyridin-2(1H)-one | 519.0 | $^1$H NMR (400 MHz, CD$_3$OD) δ 8.68 (d, J = 2.0 Hz, 1H), 8.24-8.14 (m, 2H), 7.78 (d, J = 7.2 Hz, 1H), 7.72 (d, J = 8.8 Hz, 1H), 7.63 (d, J = 8.8 Hz, 1H), 7.55 (dd, J = 6.9, 1.9 Hz, 1H), 7.38-7.32 (m, 1H), 7.23 (t, J = 8.8 Hz, 1H), 6.89-6.80 (m, 3H), 6.17-6.07 (m, 1H), 5.37-5.25 (m, 1H), 4.28 (dd, J = 12.0, 7.4 Hz, 1H), 4.19 (dd, J = 12.1, 5.3 Hz, 1H), 1.37 (s, 3H), 1.36 (s, 3H). |
| 35 | 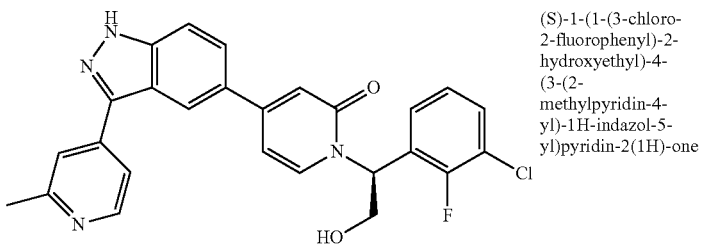<br>(Method 6) | (S)-1-(1-(3-chloro-2-fluorophenyl)-2-hydroxyethyl)-4-(3-(2-methylpyridin-4-yl)-1H-indazol-5-yl)pyridin-2(1H)-one | 474.9 | $^1$H NMR (400 MHz, CD$_3$OD) δ 8.52 (d, J = 5.3 Hz, 1H), 8.37 (s, 1H), 7.94 (s, 1H), 7.88 (d, J = 5.3 Hz, 1H), 7.77 (dd, J = 6.2, 4.3 Hz, 2H), 7.71 (d, J = 8.8 Hz, 1H), 7.53-7.45 (m, 2H), 7.22 (t, J = 8.0 Hz, 1H), 6.92-6.83 (m, 2H), 6.31 (t, J = 6.0 Hz, 1H), 4.30 (dd, J = 12.1, 6.9 Hz, 1H), 4.21 (dd, J = 12.1, 5.2 Hz, 1H), 2.64 (s, 3H). |
| 36 | 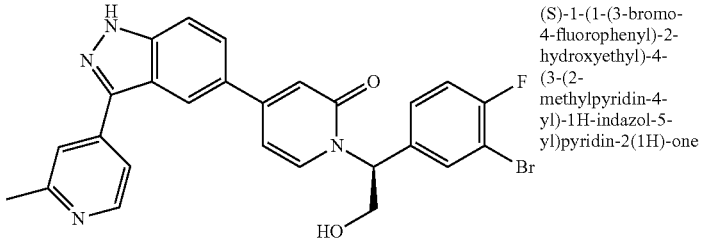<br>(Method 6) | (S)-1-(1-(3-bromo-4-fluorophenyl)-2-hydroxyethyl)-4-(3-(2-methylpyridin-4-yl)-1H-indazol-5-yl)pyridin-2(1H)-one | 519.0 | $^1$H NMR (400 MHz, CD$_3$OD) δ 8.53 (d, J = 5.3 Hz, 1H), 8.39 (s, 1H), 7.95 (s, 1H), 7.90 (d, J = 5.2 Hz, 1H), 7.83 (d, J = 7.2 Hz, 1H), 7.79 (dd, J = 8.8, 1.5 Hz, 1H), 7.75-7.69 (m, 2H), 7.46-7.40 (m, 1H), 7.24 (t, J = 8.6 Hz, 1H), 6.94-6.86 (m, 2H), 6.17-6.11 (m, 1H), 4.30 (dd, J = 12.1, 7.5 Hz, 1H), 4.20 (dd, J = 12.1, 5.3 Hz, 1H), 2.65 (s, 3H). |
| 37 | 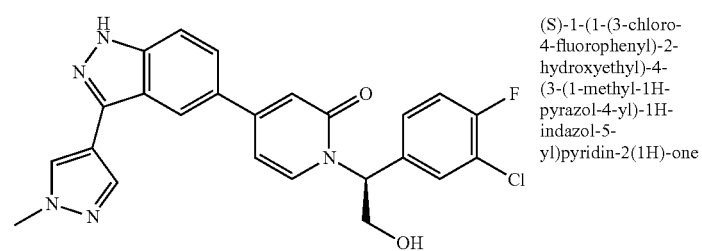<br>(Method 6) | (S)-1-(1-(3-chloro-4-fluorophenyl)-2-hydroxyethyl)-4-(3-(1-methyl-1H-pyrazol-4-yl)-1H-indazol-5-yl)pyridin-2(1H)-one | 464.0 | $^1$H NMR (400 MHz, CD$_3$OD) δ 8.27 (s, 1H), 8.21 (d, J = 10.2 Hz, 1H), 8.05 (s, 1H), 7.79 (d, J = 7.2 Hz, 1H), 7.71 (dd, J = 8.8, 1.2 Hz, 1H), 7.59 (d, J = 8.8 Hz, 1H), 7.55 (dd, J = 6.9, 2.0 Hz, 1H), 7.38-7.33 (m, 1H), 7.24 (t, J = 8.8 Hz, 1H), 6.87 (dd, J = 10.5, 3.2 Hz, 2H), 6.16-6.10 (m, 1H), 4.29 (dd, J = 12.0, 7.4 Hz, 1H), 4.20 (dd, J = 12.1, 5.3 Hz, 1H), 3.99 (s, 3H). |
| 38 | 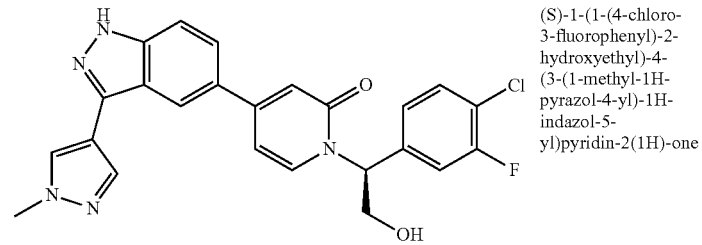<br>(Method 6) | (S)-1-(1-(4-chloro-3-fluorophenyl)-2-hydroxyethyl)-4-(3-(1-methyl-1H-pyrazol-4-yl)-1H-indazol-5-yl)pyridin-2(1H)-one | 464.0 | $^1$H NMR (400 MHz, CD$_3$OD) δ 8.29 (s, 1H), 8.22 (s, 1H), 8.06 (s, 1H), 7.79 (d, J = 7.2 Hz, 1H), 7.72 (dd, J = 8.8, 1.4 Hz, 1H), 7.60 (d, J = 8.8 Hz, 1H), 7.47 (t, J = 8.0 Hz, 1H), 7.32 (dd, J = 10.3, 1.8 Hz, 1H), 7.19 (d, J = 8.3 Hz, 1H), 6.92-6.84 (m, 2H), 6.18-6.10 (m, 1H), 4.29 (dd, J = 12.1, 7.3 Hz, 1H), 4.21 (dd, J = 12.1, 5.2 Hz, 1H), 3.99 (s, 3H). |

TABLE 1-continued

| Example | Structure (Synthetic Method) | Chemical Name | LC/MS [M + H]+ | 1H-NMR (400 MHz) |
|---|---|---|---|---|
| 39 | (Method 6) | (S)-1-(1-(3-bromo-5-fluorophenyl)-2-hydroxyethyl)-4-(3-(1-methyl-1H-pyrazol-4-yl)-1H-indazol-5-yl)pyridin-2(1H)-one | 510.2 | ¹H NMR (400 MHz, DMSO-d6) δ 13.10 (s, 1H), 8.52 (s, 1H), 8.28 (s, 1H), 8.05 (s, 1H), 7.88 (d, J = 7.2 Hz, 1H), 7.73 (d, J = 8.6 Hz, 1H), 7.61 (d, J = 8.7 Hz, 1H), 7.51 (d, J = 8.2 Hz, 1H), 7.40 (s, 1H), 7.26 (d, J = 9.5 Hz, 1H), 6.85 (s, 1H), 6.80 (d, J = 7.1 Hz, 1H), 6.04-5.94 (m, 1H), 5.35 (t, J = 4.8 Hz, 1H), 4.24-4.13 (m, 1H), 4.13-4.02 (m, 1H), 3.94 (s, 3H). |
| 40 | (Method 6) | (S)-1-(1-(3-bromo-5-fluorophenyl)-2-hydroxyethyl)-4-(3-(6-isopropoxypyridin-3-yl)-1H-indazol-5-yl)pyridin-2(1H)-one | 565.1 | 1H NMR (400 MHz, DMSO-d6) δ 13.41 (s, 1H), 8.85 (s, 1H), 8.32 (d, J = 5.9 Hz, 2H), 7.87 (d, J = 7.1 Hz, 1H), 7.76 (d, J = 8.6 Hz, 1H), 7.67 (d, J = 8.7 Hz, 1H), 7.51 (d, J = 8.0 Hz, 1H), 7.40 (s, 1H), 7.26 (d, J = 9.4 Hz, 1H), 6.95-6.77 (m, 3H), 6.04-5.92 (m, 1H), 5.33 (dd, J = 11.3, 5.3 Hz, 2H), 4.17 (d, J = 5.5 Hz, 1H), 4.11-4.00 (m, 1H), 1.35 (s, 3H), 1.31 (s, 3H). |
| 41 | (Method 6) | (S)-1-(1-(3-fluoro-5-(trifluoromethyl)phenyl)-2-hydroxyethyl)-4-(3-(1-methyl-1H-pyrazol-4-yl)-1H-indazol-5-yl)pyridin-2(1H)-one | 498.3 | ¹H NMR (400 MHz, DMSO-d6) δ 13.10 (s, 1H), 8.51 (s, 1H), 8.27 (s, 1H), 8.04 (s, 1H), 7.91 (d, J = 7.3 Hz, 1H), 7.73 (dd, J = 8.8, 1.1 Hz, 1H), 7.65 (d, J = 8.6 Hz, 1H), 7.60 (d, J = 8.8 Hz, 1H), 7.56 (d, J = 10.2 Hz, 2H), 6.85 (d, J = 1.9 Hz, 1H), 6.81 (dd, J = 7.3, 2.0 Hz, 1H), 6.10-6.01 (m, 1H), 5.38 (t, J = 5.0 Hz, 1H), 4.28-4.18 (m, 1H), 4.17-4.10 (m, 1H), 3.93 (s, 3H). |
| 42 | (Method 6) | (S)-1-(2-hydroxy-1-(3-(trifluoromethyl)phenyl)ethyl)-4-(3-(1-methyl-1H-pyrazol-4-yl)-1H-indazol-5-yl)pyridin-2(1H)-one | 480.1 | ¹H NMR (400 MHz, DMSO-d6) δ 13.10 (s, 1H), 8.51 (s, 1H), 8.27 (s, 1H), 8.04 (s, 1H), 7.88 (d, J = 7.3 Hz, 1H), 7.72 (d, J = 9.1 Hz, 2H), 7.70-7.57 (m, 4H), 6.85 (d, J = 1.5 Hz, 1H), 6.82-6.77 (m, 1H), 6.15-6.03 (m, 1H), 5.35 (d, J = 4.6 Hz, 1H), 4.23 (dd, J = 14.6, 9.6 Hz, 1H), 4.11 (dd, J = 11.1, 5.1 Hz, 1H), 3.93 (s, 3H). |

TABLE 1-continued

| Example | Structure (Synthetic Method) | Chemical Name | LC/MS [M + H]+ | 1H-NMR (400 MHz) |
|---|---|---|---|---|
| 43 | (Method 6) | (S)-1-(2-hydroxy-1-(3-(trifluoromethyl)phenyl)ethyl)-4-(3-(6-isopropoxypyridin-3-yl)-1H-indazol-5-yl)pyridin-2(1H)-one | 535.2 | ¹H NMR (400 MHz, DMSO-d6) δ 13.40 (s, 1H), 8.84 (d, J = 2.0 Hz, 1H), 8.37-8.28 (m, 2H), 7.87 (d, J = 7.3 Hz, 1H), 7.79-7.70 (m, 2H), 7.70-7.58 (m, 4H), 6.93-6.83 (m, 2H), 6.81 (d, J = 7.3 Hz, 1H), 6.12-6.04 (m, 1H), 5.37-5.29 (m, 2H), 4.27-4.18 (m, 1H), 4.16-4.06 (m, 1H), 1.34 (s, 3H), 1.32 (s, 3H). |
| 44 | (Method 6) | (S)-1-(1-(3-bromophenyl)-2-hydroxyethyl)-4-(3-(6-isopropoxypyridin-3-yl)-1H-indazol-5-yl)pyridin-2(1H)-one | 545.0 | ¹H NMR (400 MHz, DMSO-d6) δ 13.41 (s, 1H), 8.84 (d, J = 2.0 Hz, 1H), 8.32 (dd, J = 7.4, 3.3 Hz, 2H), 7.84 (d, J = 7.3 Hz, 1H), 7.75 (d, J = 8.8 Hz, 1H), 7.67 (d, J = 8.7 Hz, 1H), 7.56 (s, 1H), 7.54-7.46 (m, 1H), 7.38-7.30 (m, 2H), 6.89 (d, J = 8.6 Hz, 1H), 6.84 (s, 1H), 6.81-6.75 (m, 1H), 6.04-5.96 (m, 1H), 5.39-5.26 (m, 2H), 4.23-4.13 (m, 1H), 4.10-4.01 (m, 1H), 1.34 (s, 3H), 1.33 (s, 3H). |
| 45 | (Method 6) | (S)-1-(1-(3-bromophenyl)-2-hydroxyethyl)-4-(3-(1-methyl-1H-pyrazol-4-yl)-1H-indazol-5-yl)pyridin-2(1H)-one | 489.9 | ¹H NMR (400 MHz, DMSO-d6) δ 13.11 (s, 1H), 8.52 (s, 1H), 8.26 (s, 1H), 8.04 (s, 1H), 7.84 (d, J = 7.3 Hz, 1H), 7.72 (d, J = 8.7 Hz, 1H), 7.60 (d, J = 8.8 Hz, 1H), 7.57 (s, 1H), 7.51 (d, J = 6.8 Hz, 1H), 7.38-7.30 (m, 2H), 6.84 (d, J = 1.5 Hz, 1H), 6.78 (dd, J = 7.3, 1.7 Hz, 1H), 6.04-5.95 (m, 1H), 5.31 (s, 1H), 4.17 (d, J = 7.8 Hz, 1H), 4.07 (s, 1H), 3.91 (d, J = 18.8 Hz, 3H). |
| 46 | (Method 6) | (S)-1-(1-(3-bromo-4-fluorophenyl)-2-hydroxyethyl)-4-(3-(1-methyl-1H-pyrazol-4-yl)-1H-indazol-5-yl)pyridin-2(1H)-one | 508.0 | ¹H NMR (400 MHz, DMSO-d6) δ 13.09 (s, 1H), 8.50 (s, 1H), 8.25 (s, 1H), 8.03 (s, 1H), 7.84 (d, J = 7.3 Hz, 1H), 7.74-7.67 (m, 2H), 7.59 (d, J = 8.7 Hz, 1H), 7.41-7.33 (m, 2H), 6.83 (d, J = 1.7 Hz, 1H), 6.76 (dd, J = 10.7, 5.3 Hz, 1H), 6.03-5.94 (m, 1H), 5.31 (s, 1H), 4.16 (d, J = 4.2 Hz, 1H), 4.06 (dd, J = 15.0, 9.9 Hz, 1H), 3.92 (s, 3H). |

TABLE 1-continued

| Example | Structure (Synthetic Method) | Chemical Name | LC/MS [M + H]+ | 1H-NMR (400 MHz) |
|---|---|---|---|---|
| 47 | 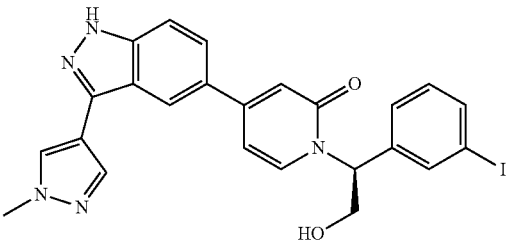<br>(Method 6) | (S)-1-(2-hydroxy-1-(3-iodophenyl)ethyl)-4-(3-(1-methyl-1H-pyrazol-4-yl)-1H-indazol-5-yl)pyridin-2(1H)-one | 537.9 | $^1$H NMR (400 MHz, DMSO-d6) δ 13.08 (s, 1H), 8.50 (s, 1H), 8.25 (s, 1H), 8.03 (s, 1H), 7.82 (d, J = 7.3 Hz, 1H), 7.75-7.68 (m, 2H), 7.66 (d, J = 8.0 Hz, 1H), 7.59 (d, J = 8.7 Hz, 1H), 7.36 (d, J = 8.5 Hz, 1H), 7.16 (t, J = 7.8 Hz, 1H), 6.82 (d, J = 1.8 Hz, 1H), 6.76 (dd, J = 7.3, 2.0 Hz, 1H), 6.00-5.93 (m, 1H), 5.31-5.24 (m, 1H), 4.19-4.11 (m, 1H), 4.07-3.99 (m, 1H), 3.92 (s, 3H). |
| 48 | 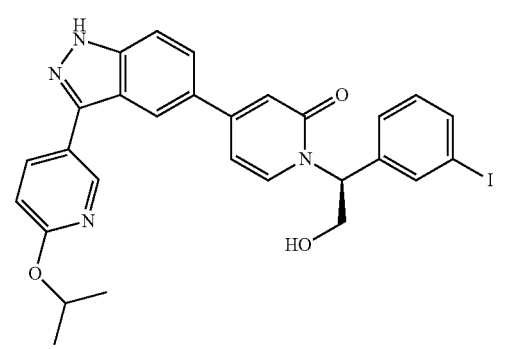<br>(Method 6) | (S)-1-(2-hydroxy-1-(3-iodophenyl)ethyl)-4-(3-(6-isopropoxypyridin-3-yl)-1H-indazol-5-yl)pyridin-2(1H)-one | 593.2 | $^1$H NMR (400 MHz, DMSO-d6) δ 13.39 (s, 1H), 8.83 (d, J = 1.8 Hz, 1H), 8.34-8.26 (m, 2H), 7.81 (d, J = 7.3 Hz, 1H), 7.73 (d, J = 12.5 Hz, 2H), 7.65 (d, J = 8.4 Hz, 2H), 7.35 (d, J = 7.5 Hz, 1H), 7.15 (t, J = 7.8 Hz, 1H), 6.87 (d, J = 8.6 Hz, 1H), 6.82 (s, 1H), 6.79 (s, 1H), 6.77 (d, J = 7.2 Hz, 1H), 6.00-5.91 (m, 1H), 5.39-5.22 (m, 2H), 4.14 (dd, J = 14.9, 9.8 Hz, 1H), 4.07-3.97 (m, 1H), 1.33 (s, 3H), 1.31 (s, 3H). |
| 49 | 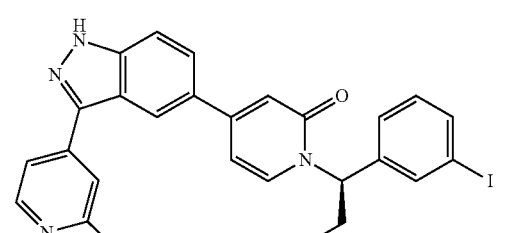<br>(Method 6) | (S)-1-(2-hydroxy-1-(3-iodophenyl)ethyl)-4-(3-(2-methylpyridin-4-yl)-1H-indazol-5-yl)pyridin-2(1H)-one | 549.0 | $^1$H NMR (400 MHz, DMSO-d6) δ 13.70 (s, 1H), 8.53 (d, J = 5.0 Hz, 1H), 8.40 (s, 1H), 7.89 (s, 1H), 7.85 (t, J = 6.6 Hz, 2H), 7.79-7.68 (m, 3H), 7.66 (d, J = 7.7 Hz, 1H), 7.36 (d, J = 7.5 Hz, 1H), 7.16 (t, J = 7.8 Hz, 1H), 6.82 (s, 1H), 6.76 (d, J = 7.0 Hz, 1H), 6.02-5.92 (m, 1H), 5.29 (s, 1H), 4.20-4.10 (m, 1H), 4.08-3.98 (m, 1H), 2.56 (s, 3H). |
| 50 | 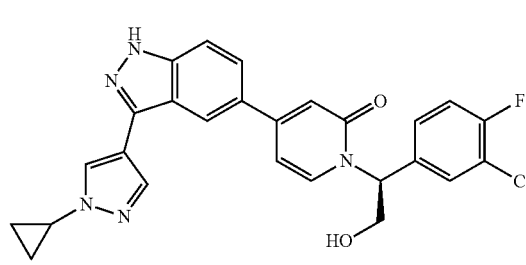<br>(Method 6) | (S)-1-(1-(3-chloro-4-fluorophenyl)-2-hydroxyethyl)-4-(3-(1-cyclopropyl-1H-pyrazol-4-yl)-1H-indazol-5-yl)pyridin-2(1H)-one | 490.0 | $^1$H NMR (400 MHz, DMSO-d6) δ 13.09 (s, 1H), 8.54 (s, 1H), 8.24 (s, 1H), 8.04 (s, 1H), 7.89-7.76 (m, 1H), 7.70 (d, J = 8.7 Hz, 1H), 7.60 (dd, J = 13.4, 5.5 Hz, 2H), 7.46-7.30 (m, 2H), 6.82 (t, J = 6.5 Hz, 1H), 6.77 (dt, J = 8.5, 4.2 Hz, 1H), 6.04-5.94 (m, 1H), 4.22-4.12 (m, 1H), 4.12-3.99 (m, 1H), 3.80 (ddd, J = 11.1, 7.4, 3.8 Hz, 1H), 3.20-3.06 (m, 1H), 1.18-1.09 (m, 2H), 1.04-0.94 (m, 2H). |
| 51 | 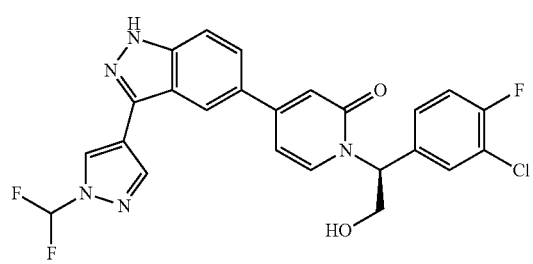<br>(Method 6) | (S)-1-(1-(3-chloro-4-fluorophenyl)-2-hydroxyethyl)-4-(3-(1-(difluoromethyl)-1H-pyrazol-4-yl)-1H-indazol-5-yl)pyridin-2(1H)-one | 500.0 | $^1$H NMR (400 MHz, CD$_3$OD) δ 8.77 (s, 1H), 8.33 (s, 1H), 8.28 (s, 1H), 7.80 (t, J = 7.6 Hz, 1H), 7.78-7.72 (m, 1H), 7.65 (d, J = 8.8 Hz, 1H), 7.56 (dd, J = 7.6, 2.7 Hz, 1H), 7.37 (ddd, J = 8.3, 4.4, 2.2 Hz, 1H), 7.25 (t, J = 8.8 Hz, 1H), 6.91 (dd, J = 8.0, 2.8 Hz, 2H), 6.15-6.10 (m, 1H), 4.34-4.24 (m, 1H), 4.23-4.14 (m, 1H). |

TABLE 1-continued

| Example | Structure (Synthetic Method) | Chemical Name | LC/MS [M + H]+ | 1H-NMR (400 MHz) |
|---|---|---|---|---|
| 52 | 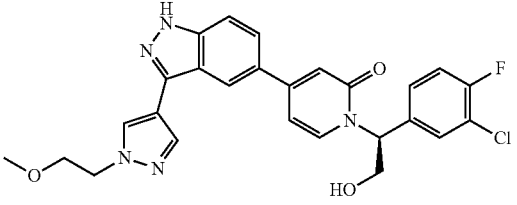<br>(Method 6) | (S)-1-(1-(3-chloro-4-fluorophenyl)-2-hydroxyethyl)-4-(3-(1-(2-methoxyethyl)-1H-pyrazol-4-yl)-1H-indazol-5-yl)pyridin-2(1H)-one | 508.0 | $^1$H NMR (400 MHz, CD$_3$OD) δ 8.33 (s, 1H), 8.23 (s, 1H), 8.10 (s, 1H), 7.80 (d, J = 7.2 Hz, 1H), 7.73 (d, J = 8.8 Hz, 1H), 7.63-7.58 (m, 1H), 7.56 (dd, J = 7.0, 2.1 Hz, 1H), 7.40-7.33 (m, 1H), 7.25 (t, J = 8.8 Hz, 1H), 6.92-6.84 (m, 2H), 6.17-6.07 (m, 1H), 4.41 (t, J = 5.2 Hz, 2H), 4.29 (dd, J = 12.1, 7.4 Hz, 1H), 4.20 (dd, J = 12.1, 5.3 Hz, 1H), 3.80 (dd, J = 14.9, 9.8 Hz, 2H), 3.35 (s, 3H). |
| 53 | 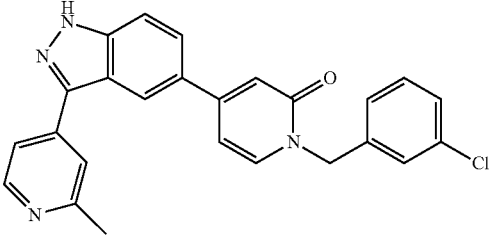<br>(Method 8) | 1-(3-chlorobenzyl)-4-(3-(2-methylpyridin-4-yl)-1H-indazol-5-yl)pyridin-2(1H)-one | 426.9 | $^1$H NMR (400 MHz, CD$_3$OD) δ/ppm: 8.51 (d, J = 5.2 Hz, 1H), 8.33 (s, 1H), 7.90 (s, 1H), 7.85 (d, J = 4.9 Hz, 1H), 7.82-7.66 (m, 3H), 7.49-7.16 (m, 4H), 6.98-6.70 (m, 2H), 5.20 (s 2H), 2.61 (s, 3H). |
| 54 | 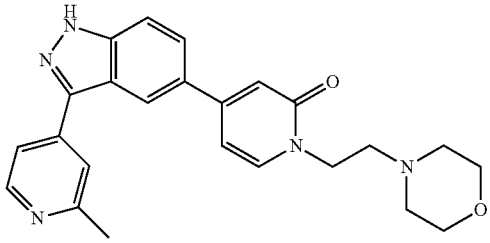<br>(Method 8) | 4-(3-(2-methylpyridin-4-yl)-1H-indazol-5-yl)-1-(2-morpholinoethyl)pyridin-2(1H)-one | 416.1 | |
| 55 | <br>(Method 8) | 1-(5-bromo-2-fluorobenzyl)-4-(3-(2-methylpyridin-4-yl)-1H-indazol-5-yl)pyridin-2(1H)-one | 488.9 | $^1$H NMR (400 MHz, DMSO-d6) δ/ppm: 13.70 (s, 1H), 8.55 (d, J = 5.1 Hz, 1H), 8.43 (s, 1H), 7.91 (s, 1H), 7.87 (t, J = 6.7 Hz, 2H), 7.79 (dd, J = 8.8, 1.3 Hz, 1H), 7.71 (d, J = 8.8 Hz, 1H), 7.56 (ddd, J = 8.6, 4.5, 2.6 Hz, 1H), 7.40 (dd, J = 6.5, 2.5 Hz, 1H), 7.29-7.21 (m, 1H), 6.84 (dd, J = 9.2, 2.1 Hz, 2H), 5.17 (s, 2H), 2.58 (s, 3H). |
| 56 | 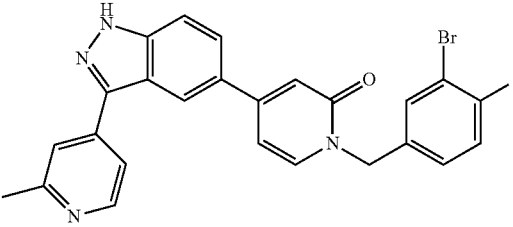<br>(Method 8) | 1-(3-bromo-4-fluorobenzyl)-4-(3-(2-methylpyridin-4-yl)-1H-indazol-5-yl)pyridin-2(1H)-one | 490.8 | $^1$H NMR (400 MHz, DMSO-d6) δ/ppm: 13.71 (s, 1H), 8.55 (d, J = 5.1 Hz, 1H), 8.41 (s, 1H), 7.95 (d, J = 7.1 Hz, 1H), 7.90 (s, 1H), 7.88 (d, J = 5.2 Hz, 1H), 7.81-7.73 (m, 2H), 7.71 (d, J = 8.8 Hz, 1H), 7.48-7.40 (m, 1H), 7.37 (t, J = 8.7 Hz, 1H), 6.85 (d, J = 1.8 Hz, 1H), 6.80 (dd, J = 7.1, 2.0 Hz, 1H), 5.12 (s, 2H), 2.58 (s, 3H). |

TABLE 1-continued

| Example | Structure (Synthetic Method) | Chemical Name | LC/MS [M + H]+ | 1H-NMR (400 MHz) |
|---|---|---|---|---|
| 57 | (Method 8) | 1-(3-iodobenzyl)-4-(3-(2-methylpyridin-4-yl)-1H-indazol-5-yl)pyridin-2(1H)-one | 519.0 | $^1$H NMR (400 MHz, DMSO-d6) δ 13.70 (s, 1H), 8.55 (d, J = 5.1 Hz, 1H), 8.42 (s, 1H), 7.91 (m, 3H), 7.72 (m, 4H), 7.37 (d, J = 7.8 Hz, 1H), 7.16 (t, J = 7.8 Hz, 1H), 6.85 (m, 1H), 6.80 (m, 1H), 5.11 (s, 2H), 2.58 (s, 3H). |
| 58 | (Method 8) | 1-(3-chloro-5-fluorobenzyl)-4-(3-(2-methylpyridin-4-yl)-1H-indazol-5-yl)pyridin-2(1H)-one | 444.9 | $^1$H NMR (400 MHz, DMSO-d6) δ/ppm: 13.69 (s, 1H), 8.54 (d, J = 5.1 Hz, 1H), 8.41 (s, 1H), 7.93 (d, J = 7.1 Hz, 1H), 7.89 (s, 1H), 7.87 (d, J = 5.2 Hz, 1H), 7.77 (dd, J = 8.8, 0.9 Hz, 1H), 7.70 (d, J = 8.8 Hz, 1H), 7.40-7.32 (m, 1H), 7.28 (s, 1H), 7.20 (d, J = 9.3 Hz, 1H), 6.85 (d, J = 1.6 Hz, 1H), 6.81 (dd, J = 7.1, 1.9 Hz, 1H), 5.14 (s, 2H), 2.56 (s, 3H). |
| 59 | (Method 8) | 4-(3-(2-methylpyridin-4-yl)-1H-indazol-5-yl)-1-(2-(trifluoromethyl)benzyl)pyridin-2(1H)-one | 460.4 | $^1$H NMR (400 MHz, DMSO-d6) δ/ppm: 13.70 (s, 1H), 8.55 (d, 5.1 Hz, 1H), 8.45 (s, 1H), 7.95-7.87 (m, 2H), 7.81 (t, J = 9.1 Hz, 3H), 7.72 (d, J = 8.8 Hz, 1H), 7.63 (t, J = 7.6 Hz, 1H), 7.50 (t, J = 7.6 Hz, 1H), 6.97-6.91 (m, 2H), 6.88 (dd, J = 7.1, 1.9 Hz, 1H), 5.35 (s, 2H), 2.57 (s, 3H). |
| 60 | (Method 8) | 1-benzyl-4-(3-(2-methylpyridin-4-yl)-1H-indazol-5-yl)pyridin-2(1H)-one | 393.0 | $^1$H NMR (400 MHz, DMSO-d6) δ/ppm: 13.71 (s, 1H), 8.52 (t, J = 9.9 Hz, 1H), 8.39 (s, 1H), 7.88 (dd, J = 7.0, 3.7 Hz, 3H), 7.76 (dd, J = 8.8, 1.1 Hz, 1H), 7.72-7.65 (m, 1H), 7.40-7.22 (m, 5H), 6.84 (d, J = 1.8 Hz, 1H), 6.76 (dd, J = 7.1, 2.0 Hz, 1H), 5.20-5.06 (s, 2H), 2.55 (s, 3H). |
| 61 | (Method 8) | 1-(3,4-difluorobenzyl)-4-(3-(2-methylpyridin-4-yl)-1H-indazol-5-yl)pyridin-2(1H)-one | 429.1 | $^1$H NMR (400 MHz, DMSO-d6) δ/ppm: 13.72 (s, 1H), 8.54 (d, J = 5.1 Hz, 1H), 8.39 (s, 1H), 7.97-7.83 (m, 3H), 7.75 (d, J = 8.4 Hz, 1H), 7.70 (d, J = 8.7 Hz, 1H), 7.43 (ddd, J = 19.4, 10.8, 5.0 Hz, 2H), 7.21 (s, 1H), 6.84 (d, J = 1.4 Hz, 1H), 6.79 (dd, J = 7.1, 1.7 Hz, 1H), 5.09 (d, J = 18.4 Hz, 2H), 2.57 (s, 3H). |

TABLE 1-continued

| Example | Structure (Synthetic Method) | Chemical Name | LC/MS [M + H]⁺ | 1H-NMR (400 MHz) |
|---|---|---|---|---|
| 62 | (Method 8) | 1-(4-chloro-3-fluorobenzyl)-4-(3-(2-methylpyridin-4-yl)-1H-indazol-5-yl)pyridin-2(1H)-one | 445.1 | ¹H NMR (400 MHz, DMSO-d6) δ/ppm: 13.72 (s, 1H), 8.54 (d, J = 5.1 Hz, 1H), 8.40 (s, 1H), 7.96-7.79 (m, 3H), 7.73 (dd, = 24.5, 8.7 Hz, 2H), 7.57 (t, J = 8.0 Hz, 1H), 7.41 (d, J = 10.2 Hz, 1H), 7.20 (d, J = 8.1 Hz, 1H), 6.87-6.76 (m, 2H), 5.14 (s, 2H), 2.56 (s, 3H). |
| 63 | (Method 8) | 1-(3-chloro-2-fluorobenzyl)-4-(3-(2-methylpyridin-4-yl)-1H-indazol-5-yl)pyridin-2(1H)-one | 445.1 | ¹H NMR (400 MHz, DMSO-d6) δ/ppm: 13.70 (s, 1H), 8.54 (d, J = 5.1 Hz, 1H), 8.41 (s, 1H), 7.87 (m, 3H), 7.82-7.65 (m, 2H), 7.56-7.47 (m, 1H), 7.19 (m, 2H), 6.88-6.77 (m, 2H), 5.21 (s, 2H), 2.57 (s, 3H). |
| 64 | (Method 8) | 4-((4-(3-(2-methylpyridin-4-yl)-1H-indazol-5-yl)-2-oxopyridin-1(2H)-yl)methyl)benzonitrile | 418.0 | ¹H NMR (400 MHz, DMSO-d6) δ/ppm: 13.69 (s, 1H), 8.54 (d, J = 5.1 Hz, 1H), 8.41 (s, 1H), 7.95-7.85 (m, 3H), 7.82 (d, J = 8.3 Hz, 2H), 7.77 (m, 1H), 7.70 (m, 1H), 7.48 (d, J = 8.3 Hz, 2H), 6.86 (m, 1H), 6.82 (m, 1H), 5.22 (s, 2H), 2.57 (s, 3H). |
| 65 | (Method 8) | 1-(3-chloro-4-fluorobenzyl)-4-(3-(2-methylpyridin-4-yl)-1H-indazol-5-yl)pyridin-2(1H)-one | 445.1 | ¹H NMR (400 MHz, DMSO-d6) δ/ppm: 13.71 (s, 1H), 8.54 (d, J = 5.1 Hz, 1H), 8.39 (s, 1H), 7.94 (d, J = 7.1 Hz, 1H), 7.91-7.84 (m, 2H), 7.76 (dd, J = 8.8, 1.1 Hz, 1H), 7.70 (d, J = 8.8 Hz, 1H), 7.62 (d, J = 7.4 Hz, 1H), 7.39 (d, J = 7.2 Hz, 2H), 6.84 (d, J = 1.6 Hz, 1H), 6.79 (dd, J = 7.1, 1.9 Hz, 1H), 5.11 (s, 2H), 2.56 (s, 3H). |
| 66 | (Method 8) | 1-(5-chloro-2-fluorobenzyl)-4-(3-(2-methylpyridin-4-yl)-1H-indazol-5-yl])pyridin-2(1H)-one | 444.9 | ¹H NMR (400 MHz, DMSO-d6) δ/ppm: 13.69 (s, 1H), 8.54 (d, J = 5.1 Hz, 1H), 8.42 (s, 1H), 7.87 (m, 3H), 7.81-7.67 (m, 2H), 7.48-7.37 (m, 1H), 7.34-7.22 (m, 2H), 6.83 (m, 2H), 5.16 (s, 2H), 2.57 (s, 3H). |

TABLE 1-continued

| Example | Structure (Synthetic Method) | Chemical Name | LC/MS [M + H]+ | 1H-NMR (400 MHz) |
|---|---|---|---|---|
| 67 | (Method 8) | 4-(3-(2-methylpyridin-4-yl)-1H-indazol-5-yl)-1-(3-(trifluoromethoxy)benzyl)pyridin-2(1H)-one | 476.3 | 1H NMR (400 MHz, DMSO-d6) δ 13.68 (s, 1H), 8.54 (d, J = 5.1 Hz, 1H), 8.41 (s, 1H), 7.98-7.83 (m, 3H), 7.81-7.65 (m, 2H), 7.49 (t, J = 8.0 Hz, 1H), 7.32 (m, 3H), 6.86 (m, 1H), 6.81 (m, 1H), 5.18 (s, 2H), 2.57 (s, 3H). |
| 68 | (Method 8) | 1-(3-fluorobenzyl)-4-(3-(2-methylpyridin-4-yl)-1H-indazol-5-yl)pyridin-2(1H)-one | 411.2 | $^1$H NMR (400 MHz, DMSO-d6) δ 13.68 (s, 1H), 8.54 (d, J = 5.0 Hz, 1H), 8.40 (s, 1H), 7.96-7.82 (m, 3H), 7.76 (d, J = 8.5 Hz, 1H), 7.70 (d, J = 8.7 Hz, 1H), 7.39 (dd, J = 14.2, 7.5 Hz, 1H), 7.22-7.05 (m, 3H), 6.84 (s, 1H), 6.79 (d, J = 7.0 Hz, 1H), 5.15 (s, 2H), 2.56 (s, 3H). |
| 69 | (Method 8) | 1-(4-bromo-3-fluorobenzyl)-4-(3-(2-methylpyridin-4-yl)-1H-indazol-5-yl)pyridin-2(1H)-one | 490.9 | $^1$H NMR (400 MHz, DMSO-d6) δ/ppm: 13.74 (s, 1H), 8.55 (d, J = 5.2 Hz, 1H), 8.40 (s, 1H), 7.92-7.88 (m, 3H), 7.76 (d, J = 8.8 Hz, 1H), 7.71-7.66 (m, 2H), 7.37 (dd, J = 9.9, 1.7 Hz, 1H), 7.15-7.10 (m, 1H), 6.85 (d, J = 1.7 Hz, 1H), 6.80 (dd, J = 7.1, 2.0 Hz, 1H), 5.13 (s, 2H), 2.57 (s, 3H). |
| 70 | (Method 8) | 4-(3-(2-methylpyridin-4-yl)-1H-indazol-5-yl)-1-(3-(trifluoromethyl)benzyl)pyridin-2(1H)-one | 460.0 | $^1$H NMR (400 MHz, DMSO-d6) δ/ppm: 13.71 (s, 1H), 8.53 (s, 1H), 8.40 (s, 1H), 7.97 (d, J = 6.3 Hz, 1H), 7.88 (s, 2H), 7.79-7.55 (m, 6H), 6.94-6.69 (m, 2H), 5.22 (s, 2H), 2.56 (s, 3H). |
| 71 | (Method 8) | 3-((4-(3-(2-methylpyridin-4-yl)-1H-indazol-5-yl)-2-oxopyridin-1(2H)-yl)methyl)benzonitrile | 417.2 | $^1$H NMR (400 MHz, DMSO-d6) δ/ppm: 13.88 (s, 1H), 8.58 (d, J = 5.3 Hz, 1H), 8.43 (s, 1H), 8.05-7.94 (m, 3H), 7.81-7.67 (m, 5H), 7.57 (t, J = 7.7 Hz, 1H), 6.86 (s, 1H), 6.81 (dd, J = 7.1, 1.8 Hz, 1H), 5.19 (s, 2H), 2.62 (s, 3H). |

TABLE 1-continued

| Example | Structure (Synthetic Method) | Chemical Name | LC/MS [M + H]+ | 1H-NMR (400 MHz) |
|---|---|---|---|---|
| 72 | (Method 8) | 1-(2,5-difluorobenzyl)-4-(3-(2-methylpyridin-4-yl)-1H-indazol-5-yl)pyridin-2(1H)-one | 429.2 | $^1$H NMR (400 MHz, DMSO-d6) δ 13.68 (s, 1H), 8.54 (d, J = 5.0 Hz, 1H), 8.41 (s, 1H), 7.92-7.81 (m, 3H), 7.77 (d, J = 8.6 Hz, 1H), 7.70 (d, J = 8.7 Hz, 1H), 7.33-7.25 (m, 1H), 7.24-7.15 (m, 1H), 7.05-6.98 (m, 1H), 6.87-6.78 (m, 2H), 5.16 (s, 2H), 2.57 (s, 3H). |
| 73 | (Method 8) | 1-(3-fluoro-5-(trifluoromethyl)benzyl)-4-(3-(2-methylpyridin-4-yl)-1H-indazol-5-yl)pyridin-2(1H)-one | 479 | $^1$H NMR (400 MHz, DMSO-d6) δ 13.69 (s, 1H), 8.54 (d, J = 4.8 Hz, 1H), 8.41 (s, 1H), 7.98 (d, J = 6.9 Hz, 1H), 7.92-7.83 (m, 2H), 7.77 (d, J = 8.6 Hz, 1H), 7.70 (d, J = 8.7 Hz, 1H), 7.62 (d, J = 7.3 Hz, 2H), 7.52 (d, J = 9.0 Hz, 1H), 6.89-6.78 (m, 2H), 5.22 (s, 2H), 2.54 (d, J = 17.6 Hz, 3H). |
| 74 | (Method 8) | 1-(1-(3-bromo-5-fluorophenyl)ethyl)-4-(3-(2-methylpyridin-4-yl)-1H-indazol-5-yl)pyridin-2(1H)-one | 502.9 | $^1$H NMR (400 MHz, DMSO-d6) δ 13.76-13.57 (s, 1H), 8.54 (d, J = 5.1 Hz, 1H), 8.41 (s, 1H), 7.90 (s, 1H), 7.87 (d, J = 5.1 Hz, 1H), 7.83 (d, J = 7.3 Hz, 1H), 7.77 (dd, J = 8.8, 1.3 Hz, 1H), 7.70 (d, J = 8.8 Hz, 1H), 7.49 (dd, J = 8.3, 1.9 Hz, 1H), 7.39 (s, 1H), 7.26 (d, J = 9.7 Hz, 1H), 6.83 (d, J = 1.9 Hz, 1H), 6.79 (dd, J = 7.3, 2.1 Hz, 1H), 6.13 (m, 1H), 2.57 (s, 3H), 1.72 (t, J = 13.4 Hz, 3H). |
| 75 | (Method 8) | 1-(3-bromo-2-fluorobenzyl)-4-(3-(2-methylpyridin-4-yl)-1H-indazol-5-yl)pyridin-2(1H)-one | 490.9 | $^1$H NMR (400 MHz, DMSO-d6) δ 13.70 (s, 1H), 8.53 (t, J = 10.1 Hz, 1H), 8.41 (s, 1H), 7.91-7.85 (m, 3H), 7.77 (dd, J = 8.8, 1.2 Hz, 1H), 7.71 (d, J = 8.8 Hz, 1H), 7.63 (dd, J = 10.4, 4.2 Hz, 1H), 7.16 (dt, J = 15.6, 7.2 Hz, 2H), 6.86-6.79 (m, 2H), 5.21 (s, 2H), 2.55 (s, 3H). |
| 76 | (Method 8) | 4-(3-(2-methylpyridin-4-yl)-1H-indazol-5-yl)-1-(3,4,5-trifluorobenzyl)pyridin-2(1H)-one | 446.9 | $^1$H NMR (400 MHz, DMSO-d6) δ/ppm: 13.71 (s, 1H), 8.54 (d, J = 5.1 Hz, 1H), 8.40 (s, 1H), 7.95-7.85 (m, 3H), 7.77 (dd, J = 8.8, 1.3 Hz, 1H), 7.70 (d, J = 8.7 Hz, 1H), 7.33 (dd, J = 8.6, 6.9 Hz, 2H), 6.85 (d, J = 1.8 Hz, 1H), 6.81 (dd, J = 7.1, 2.0 Hz, 1H), 5.11 (s, 2H), 2.57 (s, 3H). |

TABLE 1-continued

| Example | Structure (Synthetic Method) | Chemical Name | LC/MS [M + H]+ | 1H-NMR (400 MHz) |
|---|---|---|---|---|
| 77 | (Method 8) | 1-(4-fluoro-3-(trifluoromethyl)benzyl)-4-(3-(2-methylpyridin-4-yl)-1H-indazol-5-yl)pyridin-2(1H)-one | 478.9 | ¹H NMR (400 MHz, DMSO-d6) δ 13.69 (s, 1H), 8.54 (d, J = 5.1 Hz, 1H), 8.40 (s, 1H), 7.99 (d, J = 7.1 Hz, 1H), 7.90-7.84 (m, 3H), 7.78-7.68 (m, 3H), 7.56-7.46 (m, 1H), 6.89-6.76 (m, 2H), 5.19 (s, 2H), 2.56 (s, 3H). |
| 78 | (Method 8) | 1-(4-fluoro-3-(trifluoromethoxy)benzyl)-4-(3-(2-methylpyridin-4-yl)-1H-indazol-5-yl)pyridin-2(1H)-one | 495.1 | ¹H NMR (400 MHz, DMSO-d6) δ 13.69 (s, 1H), 8.54 (d, J = 5.1 Hz, 1H), 8.40 (s, 1H), 7.96 (d, J = 7.1 Hz, 1H), 7.92-7.83 (m, 2H), 7.82-7.66 (m, 2H), 7.63 (d, J = 7.3 Hz, 1H), 7.54-7.40 (m, 2H), 6.85 (d, J = 1.7 Hz, 1H), 6.81 (dd, J = 7.1, 2.0 Hz, 1H), 5.15 (s, 2H), 2.57 (s, 3H). |
| 79 | (Method 8) | 1-(3,5-difluorobenzyl)-4-(3-(2-methylpyridin-4-yl)-1H-indazol-5-yl)pyridin-2(1H)-one | 428.9 | ¹H NMR (400 MHz, DMSO-d6) δ/ppm: 13.70 (s, 1H), 8.54 (s, 1H), 8.41 (s, 1H), 7.90 (s, 3H), 7.73 (dd, J = 27.1, 8.1 Hz, 2H), 7.26-6.98 (m, 3H), 6.96-6.67 (m, 2H), 5.14 (s, 2H), 2.57 (s, 3H). |
| 80 | (Method 8) | 1-(2-fluoro-3-(trifluoromethyl)benzyl)-4-(3-(2-methylpyridin-4-yl)-1H-indazol-5-yl)pyridin-2(1H)-one | 478.7 | ¹H NMR (400 MHz, DMSO-d6) δ/ppm: 13.73 (s, 1H), 8.55 (d, J = 5.1 Hz, 1H), 8.42 (s, 1H), 7.98-7.85 (m, 3H), 7.83-7.68 (m, 3H), 7.52 (t, J = 7.1 Hz, 1H), 7.39 (t, J = 7.8 Hz, 1H), 6.85 (d, J = 5.4 Hz, 2H), 5.25 (s, 2H), 2.57 (s, 3H). |
| 81 | (Method 8) | 1-(2,3-difluorobenzyl)-4-(3-(2-methylpyridin-4-yl)-1H-indazol-5-yl)pyridin-2(1H)-one | 429.1 | ¹H NMR (400 MHz, DMSO-d6) δ/ppm: 14.46 (s, 1H), 8.74 (d, J = 6.3 Hz, 1H), 8.56 (d, J = 5.2 Hz, 2H), 8.51 (d, J = 6.2 Hz, 1H), 7.91 (d, J = 7.1 Hz, 1H), 7.83 (q, J = 8.8 Hz, 1H), 7.42-7.30 (m, 1H), 7.19 (dd, J = 12.6, 7.5 Hz, 1H), 7.01 (t, J = 7.0 Hz, 1H), 6.91 (d, J = 1.7 Hz, 1H), 6.84 (dd, J = 7.1, 1.9 Hz, 1H), 5.24 (s, 2H), 2.84 (s, 3H). |

TABLE 1-continued

| Example | Structure (Synthetic Method) | Chemical Name | LC/MS [M + H]⁺ | 1H-NMR (400 MHz) |
|---|---|---|---|---|
| 82 | (Method 8) | 1-(2-amino-3-fluorobenzyl)-4-(3-(2-methylpyridin-4-yl)-1H-indazol-5-yl)pyridin-2(1H)-one | 426.1 | |
| 83 | (Method 8) | N-(2-fluoro-6-((4-(3-(2-methylpyridin-4-yl)-1H-indazol-5-yl)-2-oxopyridin-1(2H)-yl)methyl)phenyl)methanesulfonamide | 503.9 | ¹H NMR (400 MHz, DMSO-d6) δ 13.75 (s, 1H), 9.75 (s, 1H), 8.66-8.27 (m, 2H), 8.03-7.58 (m, 5H), 7.44-7.16 (m, 2H), 7.06-6.73 (m, 3H), 5.26 (s, 2H), 3.11 (s, 3H), 2.53 (s, 3H). |
| 84 | (Method 8) | 1-(3-chloro-4-fluorobenzyl)-4-(3-(1-methyl-1H-pyrazol-4-yl)-1H-indazol-5-yl)pyridin-2(1H)-one | 434.2 | ¹H NMR (400 MHz, DMSO-d6) δ 13.12 (s, 1H), 8.51 (s, 1H), 8.26 (s, 1H), 8.04 (s, 1H), 7.94 (d, J = 7.1 Hz, 1H), 7.72 (d, J = 8.8 Hz, 1H), 7.61 (dd, J = 11.8, 8.3 Hz, 2H), 7.42-7.36 (m, 2H), 6.85 (d, J = 1.7 Hz, 1H), 6.81 (dd, J = 7.1, 1.9 Hz, 1H), 5.12 (s, 2H), 3.94 (s, 3H). |
| 85 | (Method 8) | 1-(5-bromo-2-fluorobenzyl)-4-(3-(1-methyl-1H-pyrazol-4-yl)-1H-indazol-5-yl)pyridin-2(1H)-one | 480.0 | ¹H NMR (400 MHz, DMSO-d6) δ 13.11 (s, 1H), 8.53 (s, 1H), 8.29 (s, 1H), 8.05 (s, 1H), 7.85 (d, J = 6.9 Hz, 1H), 7.73 (d, J = 8.7 Hz, 1H), 7.60 (d, J = 8.7 Hz, 1H), 7.58-7.51 (m, 1H), 7.39 (dd, J = 6.4, 2.2 Hz, 1H), 7.25 (t, J = 9.3 Hz, 1H), 6.85 (d, J = 7.8 Hz, 2H), 5.17 (s, 2H), 3.94 (s, 3H). |
| 86 | (Method 8) | 1-(3-bromo-5-fluorobenzyl)-4-(3-(1-methyl-1H-pyrazol-4-yl)-1H-indazol-5-yl)pyridin-2(1H)-one | 477.9 | ¹H NMR (400 MHz, DMSO-d6) δ 13.10 (s, 1H), 8.52 (s, 1H), 8.28 (s, 1H), 8.05 (s, 1H), 7.93 (d, J = 7.1 Hz, 1H), 7.73 (d, J = 8.8 Hz, 1H), 7.60 (d, J = 8.7 Hz, 1H), 7.49 (d, J = 8.4 Hz, 1H), 7.43 (s, 1H), 7.24 (d, J = 9.3 Hz, 1H), 6.87 (d, J = 1.6 Hz, 1H), 6.83 (dd, J = 7.1, 1.9 Hz, 1H), 5.15 (s, 2H), 3.94 (s, 3H). |

TABLE 1-continued

| Example | Structure (Synthetic Method) | Chemical Name | LC/MS [M + H]+ | 1H-NMR (400 MHz) |
|---|---|---|---|---|
| 87 | 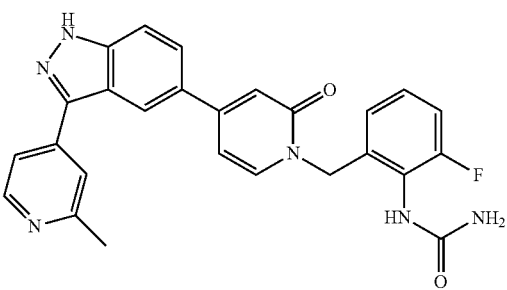 (Method 8) | 1-(2-fluoro-6-((4-(3-(2-methylpyridin-4-yl)-1H-indazol-5-yl)-2-oxopyridin-1(2H)-yl)methyl)phenyl)urea | 469.3 | $^1$H NMR (400 MHz, DMSO-d6) δ 13.79 (s, 1H), 8.57 (d, J = 5.2 Hz, 1H), 8.41 (d, J = 20.2 Hz, 1H), 8.20 (s, 1H), 7.98-7.90 (m, 2H), 7.86 (d, J = 7.1 Hz, 1H), 7.79 (d, J = 8.9 Hz, 1H), 7.73 (d, J = 8.7 Hz, 1H), 7.24-7.08 (m, 2H), 6.91-6.78 (m, 3H), 6.11 (s, 2H), 5.08 (s, 2H), 2.58 (s, 3H). |
| 88 | 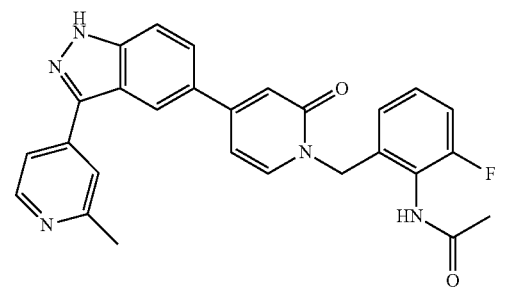 (Method 8) | N-(2-fluoro-6-((4-(3-(2-methylpyridin-4-yl)-1H-indazol-5-yl)-2-oxopyridin-1(2H)-yl)methyl)phenyl)acetamide | 468.4 | $^1$H NMR (400 MHz, DMSO-d6) δ 13.75 (s, 1H), 9.87 (d, J = 20.1 Hz, 1H), 8.55 (d, J = 5.1 Hz, 1H), 8.42 (s, 1H), 7.94-7.86 (m, 2H), 7.80 (dd, J = 11.8, 8.1 Hz, 2H), 7.72 (d, J = 8.8 Hz, 1H), 7.32-7.15 (m, 2H), 6.95 (d, J = 7.6 Hz, 1H), 6.89 (s, 1H), 6.84 (dd, J = 7.1, 1.7 Hz, 1H), 5.10 (s, 2H), 2.58 (s, 3H), 2.12 (s, 3H). |
| 89 | 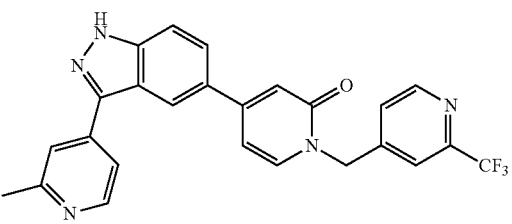 (Method 8) | 4-(3-(2-methylpyridin-4-yl)-1H-indazol-5-yl)-1-((2-(trifluoromethyl)pyridin-4-yl)methyl)pyridin-2(1H)-one | 462.1 | $^1$H NMR (400 MHz, DMSO-d6) δ 13.71 (s, 1H), 8.74 (d, J = 5.0 Hz, 1H), 8.56 (d, J = 5.1 Hz, 1H), 8.44 (s, 1H), 7.98 (d, J = 7.1 Hz, 1H), 7.93-7.87 (m, 2H), 7.85 (s, 1H), 7.81 (m, 1H), 7.72 (d, J = 8.8 Hz, 1H), 7.54 (d, J = 4.8 Hz, 1H), 6.92-6.85 (m, 2H), 5.29 (s, 2H), 2.58 (s, 3H). |
| 90 | 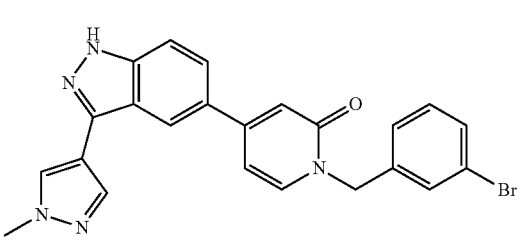 (Method 8) | 1-(3-bromobenzyl)-4-(3-(1-methyl-1H-pyrazol-4-yl)-1H-indazol-5-yl)pyridin-2(1H)-one | 460.0 | $^1$H NMR (400 MHz, DMSO-d6) δ 13.10 (s, 1H), 8.52 (s, 1H), 8.27 (s, 1H), 8.05 (s, 1H), 7.92 (d, J = 7.1 Hz, 1H), 7.72 (d, J = 8.6 Hz, 1H), 7.63-7.55 (m, 2H), 7.49 (d, J = 7.5 Hz, 1H), 7.39-7.29 (m, 2H), 6.86 (s, 1H), 6.82 (d, 1H), 5.14 (s, 2H), 3.94 (s, 3H). |
| 91 | 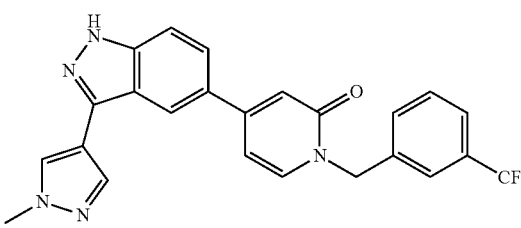 (Method 8) | 4-(3-(1-methyl-1H-pyrazol-4-yl)-1H-indazol-5-yl)-1-(3-(trifluoromethyl)benzyl)pyridin-2(1H)-one | 450.0 | $^1$H NMR (400 MHz, DMSO-d6) δ 13.11 (s, 1H), 8.53 (s, 1H), 8.29 (s, 1H), 8.06 (s, 1H), 7.97 (d, J = 7.0 Hz, 1H), 7.80-7.70 (m, 2H), 7.65 (s, 2H), 7.63-7.55 (m, 2H), 6.88 (s, 1H), 6.84 (d, J = 6.7 Hz, 1H), 5.24 (s, 2H), 3.97 (d, J = 18.5 Hz, 3H). |

TABLE 1-continued

| Example | Structure (Synthetic Method) | Chemical Name | LC/MS [M + H]+ | 1H-NMR (400 MHz) |
|---|---|---|---|---|
| 92 | (Method 8) | 1-(3-fluoro-5-(trifluoromethyl)benzyl)-4-(3-(1-methyl-1H-pyrazol-4-yl)-1H-indazol-5-yl)pyridin-2(1H)-one | 468.2 | $^1$H NMR (400 MHz, DMSO-d6) δ 13.10 (s, 1H), 8.52 (s, 1H), 8.28 (s, 1H), 8.05 (s, 1H), 7.99 (d, J = 7.0 Hz, 1H), 7.74 (d, J = 8.6 Hz, 1H), 7.68-7.57 (m, 3H), 7.54 (d, J = 9.2 Hz, 1H), 6.91-6.80 (m, 2H), 5.24 (s, 2H), 3.94 (s, 3H). |
| 93 | (Method 8) | 1-(3-iodobenzyl)-4-(3-(1-methyl-1H-pyrazol-4-yl)-1H-indazol-5-yl)pyridin-2(1H)-one | 508.0 | $^1$H NMR (400 MHz, DMSO-d6) δ 13.11 (s, 1H), 8.53 (s, 1H), 8.28 (s, 1H), 8.06 (s, 1H), 7.91 (d, J = 7.0 Hz, 1H), 7.76 (s, 1H), 7.71 (t, J = 9.9 Hz, 1H), 7.66 (d, J = 7.6 Hz, 1H), 7.60 (d, J = 8.7 Hz, 1H), 7.37 (d, J = 7.4 Hz, 1H), 7.16 (t, J = 7.7 Hz, 1H), 6.87 (s, 1H), 6.81 (d, J = 6.6 Hz, 1H), 5.11 (s, 2H), 3.94 (s, 3H). |
| 94 | (Method 8) | 1-((1H-indazol-6-yl)methyl)-4-(3-(2-methylpyridin-4-yl)-1H-indazol-5-yl)pyridin-2(1H)-one | 433.1 | $^1$H NMR (400 MHz, DMSO-d6) δ 13.71 (s, 1H), 13.03 (s, 1H), 8.55 (d, J = 5.1 Hz, 1H), 8.41 (s, 1H), 8.03 (s, 1H), 7.95-7.83 (m, 3H), 7.81-7.66 (m, 3H), 7.46 (s, 1H), 7.15 (dd, J = 8.4, 1.0 Hz, 1H), 6.87 (d, J = 1.9 Hz, 1H), 6.79 (dd, J = 7.1, 2.0 Hz, 1H), 5.28 (s, 2H), 2.57 (s, 3H). |
| 95 | (Method 8) | 4-(3-(1-methyl-1H-pyrazol-4-yl)-1H-indazol-5-yl)-1-((2-(trifluoromethyl)pyridin-4-yl)methyl)pyridin-2(1H)-one | 451.0 | $^1$H NMR (400 MHz, DMSO-d6) δ 13.11 (s, 1H), 8.74 (d, J = 4.9 Hz, 1H), 8.52 (s, 1H), 8.30 (s, 1H), 8.03 (d, J = 18.1 Hz, 1H), 7.96 (d, J = 7.0 Hz, 1H), 7.84 (s, 1H), 7.75 (d, J = 8.7 Hz, 1H), 7.61 (d, J = 8.7 Hz, 1H), 7.53 (d, J = 4.7 Hz, 1H), 6.89 (d, J = 8.4 Hz, 2H), 5.27 (s, 2H), 3.94 (s, 3H). |
| 96 | (Method 8) | 1-(1-(3-bromo-5-fluorophenyl)ethyl)-4-(3-(1-methyl-1H-pyrazol-4-yl)-1H-indazol-5-yl)pyridin-2(1H)-one | 492.1 | 1H NMR (400 MHz, CDCl$_3$) δ 8.01 (t, J = 12.9 Hz, 2H), 7.90 (s, 1H), 7.53 (d, J = 8.4 Hz, 1H), 7.47 (d, J = 8.5 Hz, 1H), 7.19 (d, J = 7.1 Hz, 1H), 7.15 (d, J = 7.8 Hz, 1H), 6.97 (d, J = 9.0 Hz, 1H), 6.92 (s, 1H), 6.54 (d, J = 6.4 Hz, 1H), 6.40 (dd, J = 13.6, 6.6 Hz, 1H), 4.09-3.84 (m, 4H), 1.72 (d, J = 7.0 Hz, 3H). |

TABLE 1-continued

| Example | Structure (Synthetic Method) | Chemical Name | LC/MS [M + H]+ | 1H-NMR (400 MHz) |
|---|---|---|---|---|
| 97 | (Method 8) | 1-(1-(3-chloro-4-fluorophenyl)ethyl)-4-(3-(1-methyl-1H-pyrazol-4-yl)-1H-indazol-5-yl)pyridin-2(1H)-one | 447.8 | $^1$H NMR (400 MHz, CD$_3$OD) δ 8.30 (s, 1H), 8.23 (s, 1H), 8.06 (s, 1H), 7.76-7.70 (m, 1H), 7.68-7.57 (m, 2H), 7.52 (dd, J = 6.9, 2.0 Hz, 1H), 7.39-7.32 (m, 1H), 7.25 (t, J = 8.8 Hz, 1H), 6.93-6.84 (m, 2H), 6.29 (q, J = 7.0 Hz, 1H), 4.00 (s, 3H), 1.79 (t, J = 9.5 Hz, 3H). |
| 98 | (Method 6) | 1-(1-(3-chlorophenyl)-2-(methylamino)ethyl)-4-(3-(1-methyl-1H-pyrazol-4-yl)-1H-indazol-5-yl)pyridin-2(1H)-one | 459.1 | $^1$H NMR (400 MHz, CD$_3$OD) δ 8.25 (s, 1H), 8.19 (s, 1H), 8.04 (s, 1H), 7.74-7.67 (m, 2H), 7.59 (d, J = 8.8 Hz, 1H), 7.45 (s, 1H), 7.40-7.32 (m, 3H), 6.90 (d, J = 1.8 Hz, 1H), 6.86 (dd, J = 7.3, 2.0 Hz, 1H), 6.34 (dd, J = 9.6, 5.5 Hz, 1H), 3.98 (s, 3H), 3.56 (dd, J = 13.0, 9.7 Hz, 1H), 3.45 (dd, J = 13.1, 5.5 Hz, 1H), 2.51 (s, 3H). |
| 99 | (Method 8) | 1-(3-bromo-5-fluorobenzyl)-4-(3-(6-isopropoxypyridin-3-yl)-1H-indazol-5-yl)pyridin-2(1H)-one | 533.1 | $^1$H NMR (400 MHz, CD$_3$OD) δ/ppm: 8.68 (d, J = 2.1 Hz, 1H), 8.18 (dd, J = 10.0, 7.6 Hz, 2H), 7.76 (d, J = 7.1 Hz, 1H), 7.72 (dd, J = 8.8, 1.3 Hz, 1H), 7.63 (d, J = 8.8 Hz, 1H), 7.36 (s, 1H), 7.26 (d, 1H), 7.11 (d, J = 9.2 Hz, 1H), 6.89-6.80 (m, 3H), 5.35-5.25 (m, 1H), 5.19 (s, 2H), 1.36 (d, J = 6.2 Hz, 6H). |
| 100 | (Method 6) | (S)-1-(1-(4-chloro-3-(fluorophenyl)-2-hydroxyethyl)-4-(3-(6-isopropoxypyridin-3-yl)-1H-indazol-5-yl)pyridin-2(1H)-one | 519.1 | 1H NMR (400 MHz, CD$_3$OD) δ 8.70 (d, J = 2.0 Hz, 1H), 8.25-8.19 (m, 2H), 7.77 (dd, J = 17.7, 8.0 Hz, 2H), 7.65 (d, J = 8.8 Hz, 1H), 7.47 (t, J = 8.0 Hz, 1H), 7.36-7.30 (m, 1H), 7.19 (d, J = 8.1 Hz, 1H), 6.92-6.81 (m, 3H), 6.17-6.10 (m, 1H), 5.37-5.27 (m, 1H), 4.28 (dd, J = 12.0, 7.4 Hz, 1H), 4.20 (dd, J = 12.1, 5.2 Hz, 1H), 1.38 (s, 3H), 1.36 (s, 3H). |

TABLE 1-continued

| Example | Structure (Synthetic Method) | Chemical Name | LC/MS [M + H]⁺ | 1H-NMR (400 MHz) |
|---|---|---|---|---|
| 101 | 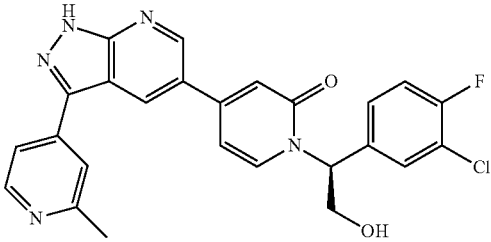 (Method 6) | (S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one | 476.0 | ¹H NMR (400 MHz, DMSO-d6) δ 14.28 (s, 1H), 8.91 (d, J = 12.1 Hz, 2H), 8.54 (d, J = 5.0 Hz, 1H), 7.94 (s, 1H), 7.91 (d, J = 7.2 Hz, 2H), 7.61 (d, J = 6.0 Hz, 1H), 7.45-7.33 (m, 2H), 6.96 (s, 1H), 6.84 (d, J = 6.1 Hz, 1H), 6.04-5.94 (m, 1H), 5.32 (s, 1H), 4.26-4.13 (m, 1H), 4.10-4.00 (m, 1H), 2.45 (s, 3H). |
| 102 | 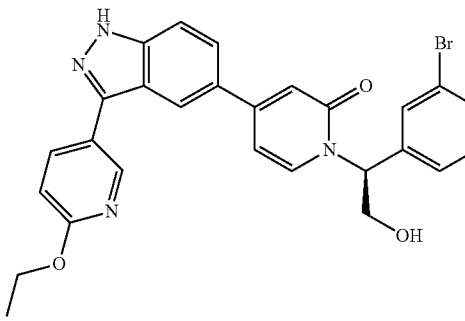 (Method 6) | (S)-1-(1-(3-bromo-5-fluorophenyl)-2-hydroxyethyl)-4-(3-(6-ethoxypyridin-3-yl)-1H-indazol-5-yl)pyridin-2(1H)-one | 549.0 | ¹H NMR (400 MHz, CD₃OD) δ 8.71 (s, 1H), 8.25 (s, 2H), 7.83 (d, J = 7.0 Hz, 1H), 7.77 (d, J = 8.8 Hz, 1H), 7.67 (d, J = 8.8 Hz, 1H), 7.40 (s, 1H), 7.32 (d, J = 8.1 Hz, 1H), 7.18 (d, J = 9.6 Hz, 1H), 6.11 (dd, J = 6.9, 5.5 Hz, 1H), 4.40 (q, J = 7.0 Hz, 2H), 4.29 (dd, J = 12.1, 7.4 Hz, 1H), 4.20 (dd, J = 12.1, 5.2 Hz, 1H), 1.42 (t, J = 7.0 Hz, 3H). |
| 103 | 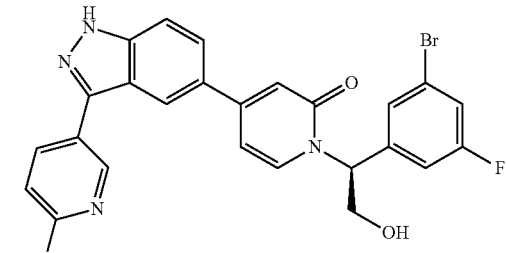 (Method 6) | (S)-1-(1-(3-bromo-5-fluorophenyl)-2-hydroxyethyl)-4-(3-(6-methoxypyridin-3-yl)-1H-indazol-5-yl)pyridin-2(1H)-one | 534.9 | ¹H NMR (400 MHz, DMSO-d6) δ 13.40 (s, 1H), 8.85 (s, 1H), 8.50-8.06 (m, 2H), 7.96-7.59 (m, 3H), 7.52-7.32 (m, 2H), 7.23 (d, J = 8.0 Hz, 1H), 6.95 (d, J = 7.5 Hz, 1H), 6.89-6.71 (m, 2H), 6.11-5.80 (m, 1H), 5.43-5.14 (m, 1H), 4.21-3.97 (m, 2H), 3.91 (s, 3H). |
| 104 | 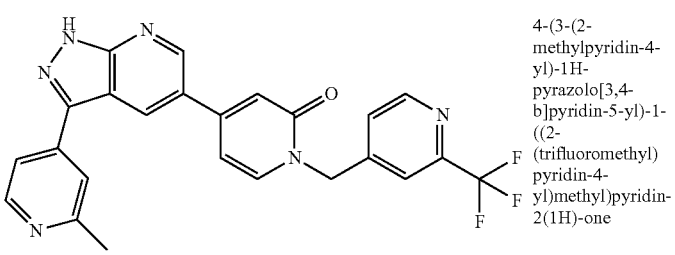 (Method 4) | 4-(3-(2-methylpyridin-4-yl)-1H-pyrazolo[3,4-b]pyridin-5-yl)-1-((2-(trifluoromethyl)pyridin-4-yl)methyl)pyridin-2(1H)-one | 463.0 | ¹H NMR (400 MHz, CD₃OD) δ 8.92 (d, J = 2.0 Hz, 1H), 8.87 (d, J = 2.0 Hz, 1H), 8.69 (d, J = 5.0 Hz, 1H), 8.53 (d, J = 5.3 Hz, 1H), 8.00 (s, 1H), 7.94 (d, J = 6.9 Hz, 2H), 7.78 (s, 1H), 7.55 (d, J = 4.8 Hz, 1H), 7.02 (d, J = 1.7 Hz, 1H), 6.98 (dd, J = 7.1, 2.0 Hz, 1H), 5.39 (s, 2H), 2.65 (s, 3H). |
| 105 | 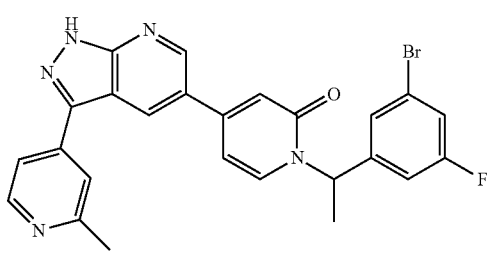 (Method 4) | 1-(1-(3-bromo-5-fluorophenyl)ethyl)-4-(3-(2-methylpyridin-4-yl)-1H-pyrazolo[3,4-b]pyridin-5-yl)pyridin-2(1H)-one | 503.9 | ¹H NMR (400 MHz, CD₃OD) δ 8.88 (d, J = 2.0 Hz, 1H), 8.83 (d, J = 2.0 Hz, 1H), 8.52 (d, J = 5.3 Hz, 1H), 7.97 (s, 1H), 7.91 (d, J = 5.3 Hz, 1H), 7.76 (d, J = 7.3 Hz, 1H), 7.38 (s, 1H), 7.31 (dd, J = 8.2, 1.9 Hz, 1H), 7.16 (d, J = 9.6 Hz, 1H), 6.97 (t, J = 5.7 Hz, 1H), 6.91 (dd, J = 7.3, 2.0 Hz, 1H), 6.27 (q, J = 7.1 Hz, 1H), 2.64 (s, 3H), 1.82 (d, J = 7.2 Hz, 3H). |

TABLE 1-continued

| Example | Structure (Synthetic Method) | Chemical Name | LC/MS [M + H]+ | 1H-NMR (400 MHz) |
|---|---|---|---|---|
| 106 | 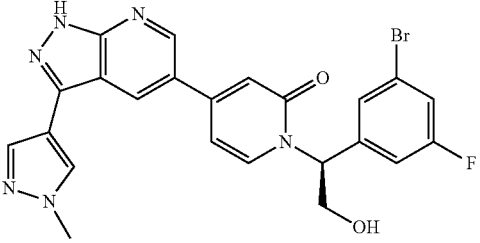<br>(Method 4) | (S)-1-(1-(3-bromo-5-fluorophenyl)-2-hydroxyethyl)-4-(3-(1-methyl-1H-pyrazol-4-yl)-1H-pyrazolo[3,4-b]pyridin-5-yl)pyridin-2(1H)-one | 509.1 | $^1$H NMR (400 MHz, DMSO-d6) δ 13.66 (s, 1H), 8.88 (d, J = 1.5 Hz, 1H), 8.74 (d, J = 1.5 Hz, 1H), 8.55 (s, 1H), 8.09 (s, 1H), 7.92 (d, J = 7.3 Hz, 1H), 7.50 (d, J = 8.2 Hz, 1H), 7.39 (s, 1H), 7.25 (d, J = 9.6 Hz, 1H), 6.95 (d, J = 1.4 Hz, 1H), 6.85 (d, J = 7.2 Hz, 1H), 6.03-5.93 (m, 1H), 5.34 (t, J = 5.0 Hz, 1H), 4.22-4.13 (m, 1H), 4.11-4.02 (m, 1H), 3.92 (s, 3H). |
| 107 | 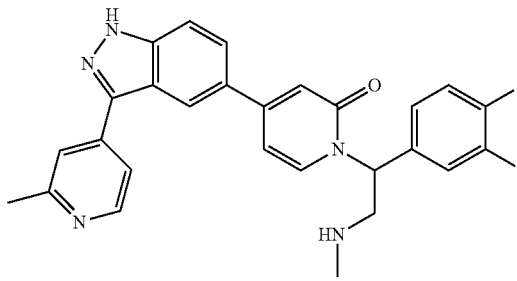<br>(Method 6) | 1-(1-(3-chloro-4-fluorophenyl)-2-(methylamino)ethyl)-4-(3-(2-methylpyridin-4-yl)-1H-indazol-5-yl)pyridin-2(1H)-one | 488.0 | $^1$H NMR (400 MHz, CD$_3$OD) δ 8.51 (d, J = 5.3 Hz, 1H), 8.34 (s, 1H), 7.91 (s, 1H), 7.86 (d, J = 5.2 Hz, 1H), 7.78-7.66 (m, 3H), 7.61 (dd, J = 6.9, 2.2 Hz, 1H), 7.46-7.39 (m, 1H), 7.29 (t, J = 8.8 Hz, 1H), 6.95-6.85 (m, 2H), 6.34 (dd, J = 9.5, 5.4 Hz, 1H), 3.65 (dd, J = 13.0, 9.7 Hz, 1H), 3.52 (dd, J = 13.1, 5.4 Hz, 1H), 2.63 (s, 3H), 2.56 (s, 3H). |
| 108 | 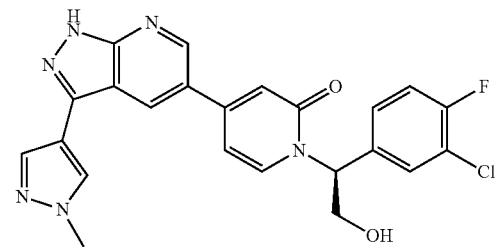<br>(Method 4) | (S)-1-(1-(3-chloro-4-fluorophenyl)-2-hydroxyethyl)-4-(3-(1-methyl-1H-pyrazol-4-yl)-1H-pyrazolo[3,4-b]pyridin-5-yl)pyridin-2(1H)-one | 465.2 | $^1$H NMR (400 MHz, DMSO-d6) δ 13.66 (s, 1H), 8.87 (d, J = 1.9 Hz, 1H), 8.73 (d, J = 1.7 Hz, 1H), 8.55 (s, 1H), 8.09 (s, 1H), 7.89 (d, J = 7.3 Hz, 1H), 7.61 (dd, J = 7.1, 1.9 Hz, 1H), 7.46-7.32 (m, 2H), 6.95 (d, J = 1.8 Hz, 1H), 6.83 (dd, J = 7.3, 2.0 Hz, 1H), 6.03-5.95 (m, 1H), 5.31 (t, J = 5.2 Hz, 1H), 4.23-4.14 (m, 1H), 4.10-4.01 (m, 1H), 3.92 (s, 3H). |
| 109 | 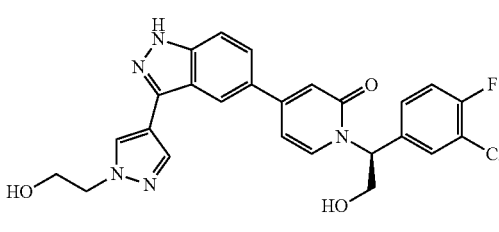<br>(Method 6) | (S)-1-(1-(3-chloro-4-fluorophenyl)-2-hydroxyethyl)-4-(3-(1-(2-hydroxyethyl)-1H-pyrazol-4-yl)-1H-indazol-5-yl)pyridin-2(1H)-one | 493.9 | $^1$H NMR (400 MHz, DMSO-d6) δ 13.08 (s, 1H), 8.48 (s, 1H), 8.25 (s, 1H), 8.06 (s, 1H), 7.83 (d, J = 7.3 Hz, 1H), 7.70 (d, J = 8.7 Hz, 1H), 7.59 (t, J = 7.2 Hz, 2H), 7.41 (t, J = 8.9 Hz, 1H), 7.37-7.32 (m, 1H), 6.81 (s, 1H), 6.76 (d, J = 7.2 Hz, 1H), 6.00-5.95 (m, 1H), 5.30 (t, J = 5.1 Hz, 1H), 4.93 (t, J = 5.3 Hz, 1H), 4.22 (t, J = 5.6 Hz, 2H), 4.16 (dd, J = 11.2, 5.9 Hz, 1H), 4.08-4.01 (m, 1H), 3.79 (dd, J = 11.0, 5.5 Hz, 2H). |
| 110 | 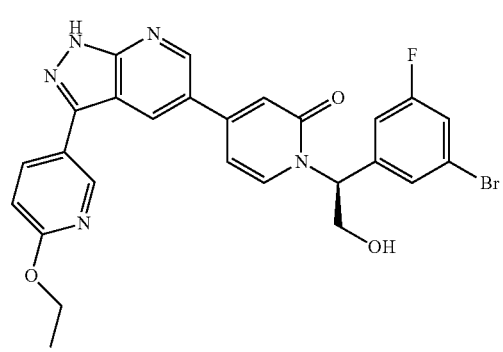<br>(Method 6) | (S)-1-(1-(3-bromo-5-fluorophenyl)-2-hydroxyethyl)-4-(3-(6-ethoxypyridin-3-yl)-1H-pyrazolo[3,4-b]pyridin-5-yl)pyridin-2(1H)-one | 500.1 | $^1$H NMR (400 MHz, DMSO-d6) δ 13.99 (s, 1H), 8.87 (m, 2H), 8.37 (d, J = 7.4 Hz, 1H), 7.91 (d, J = 6.6 Hz, 1H), 7.57-7.41 (m, 1H), 7.38 (s, 1H), 7.24 (d, J = 8.9 Hz, 1H), 7.02-6.83 (m, 2H), 5.96 (s, 1H), 5.35 (s, 1H), 4.37 (d, J = 6.7 Hz, 2H), 4.12 (d, J = 39.5 Hz, 1H), 4.07 (s, 1H), 1.50-1.27 (m, 3H). |

TABLE 1-continued

| Example | Structure (Synthetic Method) | Chemical Name | LC/MS [M + H]+ | 1H-NMR (400 MHz) |
|---|---|---|---|---|
| 111 | 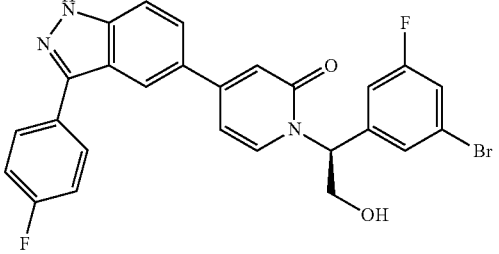<br>(Method 6) | (S)-1-(1-(3-bromo-5-fluorophenyl)-2-hydroxyethyl)-4-(3-(4-fluorophenyl)-1H-indazol-5-yl)pyridin-2(1H)-one | 522.1 | 1H NMR (400 MHz, CD3OD) δ 8.26 (s, 1H), 7.99 (dd, 8.7, 5.4 Hz, 2H), 7.83 (d, J = 7.1 Hz, 1H), 7.75 (d, J = 8.8 Hz, 1H), 7.66 (d, J = 8.8 Hz, 1H), 7.40 (s, 1H), 7.34-7.21 (m, 3H), 7.17 (d, J = 9.5 Hz, 1H), 6.95-6.79 (m, 2H), 6.17-6.04 (m, 1H), 4.29 (dd, J = 12.1, 7.4 Hz, 1H), 4.20 (dd, J = 12.1, 5.2 Hz, 1H). |
| 112 | 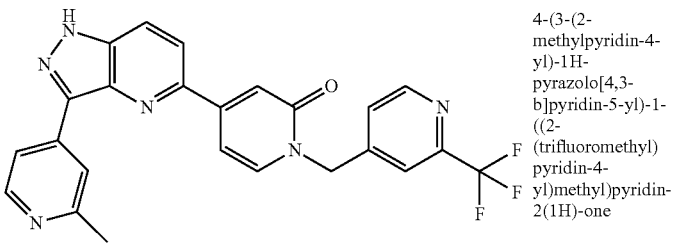<br>(Method 9) | 4-(3-(2-methylpyridin-4-yl)-1H-pyrazolo[4,3-b]pyridin-5-yl)-1-((2-(trifluoromethyl)pyridin-4-yl)methyl)pyridin-2(1H)-one | 462.9 | 1H NMR (400 MHz, DMSO-d6) δ 13.92 (s, 1H), 8.72 (d, J = 5.0 Hz, 1H), 8.60 (d, J = 5.1 Hz, 1H), 8.35-8.27 (m, 2H), 8.21 (d, J = 8.8 Hz, 1H), 8.14 (d, J = 8.9 Hz, 1H), 8.04 (d, J = 7.1 Hz, 1H), 7.84 (s, 1H), 7.54 (d, J = 4.8 Hz, 1H), 7.27 (s, 1H), 7.24 (d, J = 7.2 Hz, 1H), 5.31 (s, 2H), 2.57 (s, 3H). |
| 113 | 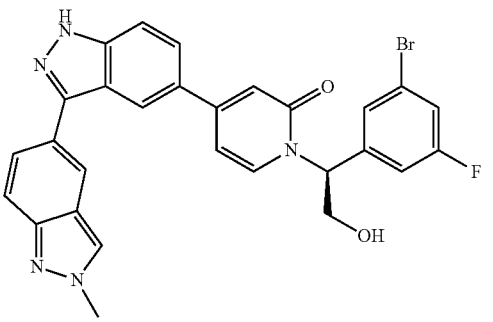<br>(Method 6) | (S)-1-(1-(3-bromo-5-fluorophenyl)-2-hydroxyethyl)-4-(2'-methyl-1H,2'H-[3,5'-biindazol]-5-yl)pyridin-2(1H)-one | 557.9 | 1H NMR (400 MHz, DMSO-d6) δ 13.34 (s, 1H), 8.43 (s, 2H), 8.41 (s, 1H), 7.97 (dd, J = 9.0, 1.5 Hz, 1H), 7.90 (d, J = 7.3 Hz, 1H), 7.77 (dd, J = 8.8, 1.4 Hz, 1H), 7.73 (d, J = 9.0 Hz, 1H), 7.69 (d, J = 8.7 Hz, 1H), 7.56-7.50 (m, 1H), 7.43 (s, 1H), 7.28 (d, J = 9.6 Hz, 1H), 6.84 (d, J = 1.9 Hz, 1H), 6.80 (dd, J = 7.3, 2.1 Hz, 1H), 6.04-5.97 (m, 1H), 5.37 (t, J = 5.1 Hz, 1H), 4.21 (s, 3H), 4.20-4.16 (m, 1H), 4.14-4.06 (m, 1H). |
| 114 | 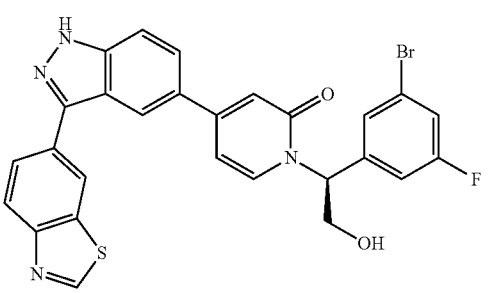<br>(Method 6) | (S)-4-(3-(benzo[d]thiazol-6-yl)-1H-indazol-5-yl)-1-(1-(3-bromo-5-fluorophenyl)-2-hydroxyethyl)pyridin-2(1H)-one | 561.0 | 1H NMR (400 MHz, DMSO-d6) δ 13.53 (s, 1H), 9.44 (s, 1H), 8.95 (d, J = 1.0 Hz, 1H), 8.50 (s, 1H), 8.28 (dd, J = 8.5, 1.4 Hz, 1H), 8.22 (d, J = 8.5 Hz, 1H), 7.91 (d, J = 7.3 Hz, 1H), 7.80 (d, J = 8.8 Hz, 1H), 7.72 (d, J = 8.7 Hz, 1H), 7.52 (d, J = 8.3 Hz, 1H), 7.42 (s, 1H), 7.28 (d, J = 9.6 Hz, 1H), 6.89 (d, J = 1.8 Hz, 1H), 6.83 (dd, J = 7.3, 2.0 Hz, 1H), 6.06-5.95 (m, 1H), 5.36 (t, J = 5.1 Hz, 1H), 4.26-4.16 (m, 1H), 4.14-4.05 (m, 1H). |
| 115 | 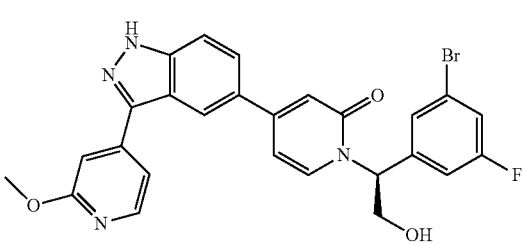<br>(Method 10) | (S)-1-(1-(3-bromo-5-fluorophenyl)-2-hydroxyethyl)-4-(3-(2-methoxypyridin-4-yl)-1H-indazol-5-yl)pyridin-2(1H)-one | 534.9 | 1H NMR (400 MHz, DMSO-d6) δ 13.71 (s, 1H), 8.37 (s, 1H), 8.27 (d, J = 5.3 Hz, 1H), 7.88 (d, J = 7.3 Hz, 1H), 7.76 (s, 1H), 7.70 (dd, J = 11.5, 7.1 Hz, 2H), 7.51 (d, J = 8.3 Hz, 1H), 7.43 (s, 1H), 7.39 (s, 1H), 7.25 (d, J = 9.6 Hz, 1H), 6.84 (s, 1H), 6.79 (d, J = 7.2 Hz, 1H), 6.02-5.92 (m, 1H), 5.34 (s, 1H), 4.21-4.11 (m, 1H), 4.12-4.02 (m, 1H), 3.91 (s, 3H). |

TABLE 1-continued

| Example | Structure (Synthetic Method) | Chemical Name | LC/MS [M + H]+ | 1H-NMR (400 MHz) |
|---|---|---|---|---|
| 116 | (Method 8) | 4-(3-(6-methoxypyridin-3-yl)-1H-indazol-5-yl)-1-((2-(trifluoromethyl)pyridin-4-yl)methyl)pyridin-2(1H)-one | 477.8 | ¹H NMR (400 MHz, DMSO-d6) δ 13.42 (s, 1H), 8.87 (d, J = 2.1 Hz, 1H), 8.72 (d, J = 5.0 Hz, 1H), 8.34 (dd, J = 8.4, 2.6 Hz, 2H), 7.94 (d, J = 7.8 Hz, 1H), 7.82 (s, 1H), 7.77 (dd, J = 8.8, 1.3 Hz, 1H), 7.67 (d, J = 8.8 Hz, 1H), 7.52 (d, J = 4.7 Hz, 1H), 6.97 (d, J = 8.6 Hz, 1H), 6.90-6.83 (m, 2H), 5.28 (s, 2H), 3.92 (s, 3H). |
| 117 | (Method 8) | 4-(3-(4-fluorophenyl)-1H-indazol-5-yl)-1-((2-(trifluoromethyl)pyridin-4-yl)methyl)pyridin-2(1H)-one | 465.0 | ¹H NMR (400 MHz, DMSO-d6) δ 13.39 (s, 1H), 8.72 (d, J = 5.0 Hz, 1H), 8.33 (s, 1H), 8.10 (dd, J = 8.7, 5.6 Hz, 2H), 7.95 (d, J = 7.0 Hz, 1H), 7.83 (s, 1H), 7.77 (dd, J = 8.8, 1.2 Hz, 1H), 7.67 (d, J = 8.8 Hz, 1H), 7.52 (d, J = 4.8 Hz, 1H), 7.39-7.28 (m, 2H), 6.84 (dd, J = 10.6, 8.6 Hz, 2H), 5.28 (s, 2H). |
| 118 | (Method 6) | (S)-1-(1-(3-bromo-5-fluorophenyl)-2-hydroxyethyl)-4-(3-(6-cyclopropoxy-pyridin-3-yl)-1H-indazol-5-yl)pyridin-2(1H)-one | 560.9 | ¹H NMR (400 MHz, DMSO-d6) δ 13.42 (s, 1H), 8.89 (d, J = 2.2 Hz, 1H), 8.43-8.27 (m, 2H), 7.86 (d, J = 7.3 Hz, 1H), 7.76 (dd, J = 8.8, 1.2 Hz, 1H), 7.66 (d, J = 8.8 Hz, 1H), 7.50 (dd, J = 8.4, 1.8 Hz, 1H), 7.38 (s, 1H), 7.24 (d, J = 9.6 Hz, 1H), 7.00 (d, J = 8.6 Hz, 1H), 6.88-6.75 (m, 2H), 6.01-5.90 (m, 1H), 5.32 (t, J = 5.2 Hz, 1H), 4.26 (s, 1H), 4.19 (d, J = 5.8 Hz, 1H), 4.07 (s, 1H), 0.78 (s, 2H), 0.72 (d, J = 2.8 Hz, 2H). |
| 119 | (Method 10) | (S)-1-(1-(3-bromo-5-fluorophenyl)-2-hydroxyethyl)-4-(3-(2-ethoxypyridin-4-yl)-1H-indazol-5-yl)pyridin-2(1H)-one | 549.2 | ¹H NMR (400 MHz, CD3OD) δ 8.33 (s, 1H), 8.22 (s, 1H), 7.85 (d, J = 7.1 Hz, 1H), 7.77 (s, 1H), 7.71 (s, 1H), 7.58 (s, 1H), 7.41 (s, 1H), 7.38-7.30 (m, 2H), 7.18 (d, J = 9.5 Hz, 1H), 6.89 (d, J = 10.8 Hz, 2H), 6.11 (d, J = 6.9 Hz, 1H), 4.39 (q, J = 6.9 Hz, 2H), 4.30 (dd, J = 12.1, 7.4 Hz, 1H), 4.21 (dd, J = 12.1, 5.2 Hz, 1H), 1.43 (t, J = 7.0 Hz, 3H). |
| 120 | (Method 6) | (S)-1-(1-(3-bromo-5-fluorophenyl)-2-hydroxyethyl)-4-(3-(1-methyl-6-oxo-1,6-dihydropyridin-3-yl)-1H-indazol-5-yl)pyridin-2(1H)-one | 535.1 | ¹H NMR (400 MHz, DMSO-d6) δ 13.32 (s, 1H), 8.40 (d, J = 2.3 Hz, 1H), 8.31 (s, 1H), 8.07 (dd, J = 9.4, 2.4 Hz, 1H), 7.94-7.86 (m, 1H), 7.73 (d, J = 8.8 Hz, 1H), 7.62 (d, J = 8.7 Hz, 1H), 7.50 (d, J = 8.3 Hz, 1H), 7.38 (s, 1H), 7.25 (d, J = 9.6 Hz, 1H), 6.84-6.76 (m, 2H), 6.54 (d, J = 9.4 Hz, 1H), 6.02-5.92 (m, 1H), 5.34 (t, J = 5.1 Hz, 1H), 4.16 (dd, J = 11.3, 5.9 Hz, 1H), 4.06 (dd, J = 11.2, 5.6 Hz, 1H), 3.57 (s, 3H). |

TABLE 1-continued

| Example | Structure (Synthetic Method) | Chemical Name | LC/MS [M + H]+ | 1H-NMR (400 MHz) |
|---|---|---|---|---|
| 121 | 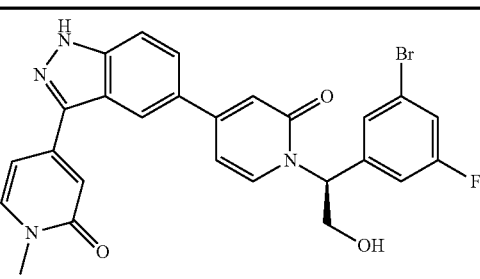 (Method 6) | (S)-1-(1-(3-bromo-5-fluorophenyl)-2-hydroxyethyl)-4-(3-(1-methyl-2-oxo-1,2-dihydropyridin-4-yl)-1H-indazol-5-yl)pyridin-2(1H)-one | 535.1 | ¹H NMR (400 MHz, DMSO-d6) δ 13.72 (s, 1H), 8.28 (d, J = 10.5 Hz, 1H), 7.87 (d, J = 7.3 Hz, 1H), 7.76 (d, J = 7.3 Hz, 2H), 7.70 (d, J = 8.7 Hz, 1H), 7.49 (d, J = 8.3 Hz, 1H), 7.38 (s, 1H), 7.24 (d, J = 9.6 Hz, 1H), 7.06 (s, 1H), 6.90 (dd, J = 7.0, 1.6 Hz, 1H), 6.81 (s, 1H), 6.77 (d, J = 7.2 Hz, 1H), 5.96 (t, J = 6.5 Hz, 1H), 5.32 (t, J = 5.1 Hz, 1H), 4.15 (dd, J = 15.2, 9.8 Hz, 1H), 4.10-4.01 (m, 1H), 3.46 (s, 3H). |
| 122 | 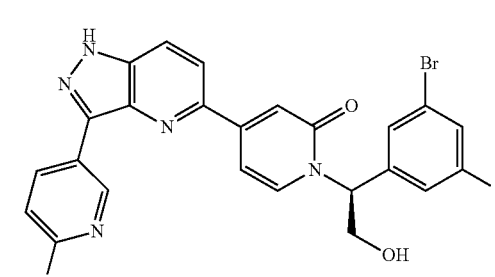 (Method 6) | (S)-1-(1-(3-bromo-5-fluorophenyl)-2-hydroxyethyl)-4-(3-(6-methoxypyridin-3-yl)-1H-pyrazolo[4,3-b]pyridin-5-yl)pyridin-2(1H)-one | 535.1 | ¹H NMR (400 MHz, DMSO-d6) δ 13.63 (s, 1H), 9.39 (d, J = 1.9 Hz, 1H), 8.67 (dd, J = 8.7, 2.3 Hz, 1H), 8.16 (d, J = 8.9 Hz, 1H), 8.10 (d, J = 8.9 Hz, 1H), 7.97 (d, J = 7.3 Hz, 1H), 7.51 (d, J = 8.3 Hz, 1H), 7.39 (s, 1H), 7.25 (d, J = 9.5 Hz, 1H), 7.20 (s, 1H), 7.16 (d, J = 7.3 Hz, 1H), 7.01 (d, J = 8.6 Hz, 1H), 6.00-5.94 (m, 1H), 5.36 (t, J = 5.2 Hz, 1H), 4.16 (dd, J = 15.4, 10.0 Hz, 1H), 4.11-4.01 (m, 1H), 3.92 (s, 3H). |
| 123 | 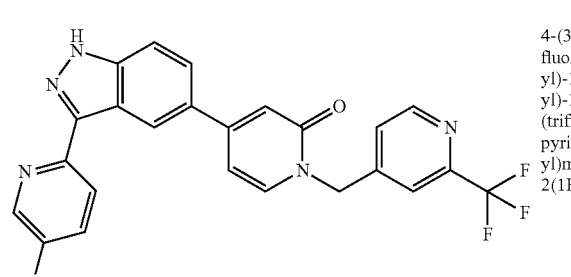 (Method 8) | 4-(3-(5-fluoropyridin-2-yl)-1H-indazol-5-yl)-1-((2-(trifluoromethyl)pyridin-4-yl)methyl)pyridin-2(1H)-one | 466.1 | ¹H NMR (400 MHz, DMSO-d6) δ 13.58 (s, 1H), 8.82 (s, 1H), 8.76 (d, J = 2.7 Hz, 1H), 8.71 (t, J = 9.8 Hz, 1H), 8.23 (dd, J = 8.8, 4.6 Hz, 1H), 7.96 (t, J = 10.4 Hz, 1H), 7.88-7.80 (m, 2H), 7.77 (d, J = 8.8 Hz, 1H), 7.68 (d, J = 8.7 Hz, 1H), 7.51 (d, J = 4.6 Hz, 1H), 6.77-6.70 (m, 2H), 5.28 (s, 2H). |
| 124 | 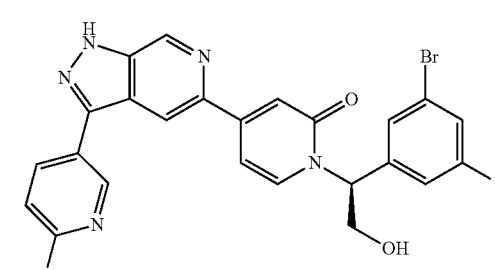 (Method 6) | (S)-1-(1-(3-bromo-5-fluorophenyl)-2-hydroxyethyl)-4-(3-(6-methoxypyridin-3-yl)-1H-pyrazolo[3,4-c]pyridin-5-yl)pyridin-2(1H)-one | 536.0 | ¹H NMR (400 MHz, DMSO-d6) δ 13.97 (d, J = 19.4 Hz, 1H), 9.26-9.10 (m, 1H), 8.96 (d, J = 2.1 Hz, 1H), 8.66 (s, 1H), 8.41 (dd, J = 8.6, 2.4 Hz, 1H), 7.88 (d, J = 7.4 Hz, 1H), 7.50 (dd, J = 6.5, 1.8 Hz, 1H), 7.36 (s, 1H), 7.32 (d, J = 1.8 Hz, 1H), 7.23 (d, J = 9.7 Hz, 1H), 7.18 (dd, J = 7.4, 2.0 Hz, 1H), 6.98 (d, J = 8.6 Hz, 1H), 6.00-5.93 (m, 1H), 5.34 (t, J = 5.2 Hz, 1H), 4.21-4.13 (m, 1H), 4.10-4.03 (m, 1H), 3.93 (s, 3H). |
| 125 | 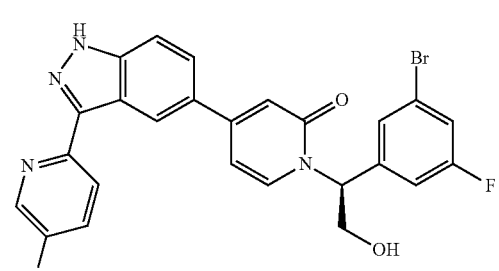 (Method 6) | (S)-1-(1-(3-bromo-5-fluorophenyl)-2-hydroxyethyl)-4-(3-(5-fluoropyridin-2-yl)-1H-indazol-5-yl)pyridin-2(1H)-one | 523.1 | ¹H NMR (400 MHz, DMSO-d6) δ 13.58 (s, 1H), 8.82 (s, 1H), 8.77 (d, J = 2.8 Hz, 1H), 8.24 (dd, J = 8.9, 4.6 Hz, 1H), 7.90 (d, J = 7.2 Hz, 1H), 7.85 (td, J = 8.8, 2.9 Hz, 1H), 7.76 (d, J = 8.8 Hz, 1H), 7.69 (d, J = 8.8 Hz, 1H), 7.51 (d, J = 8.3 Hz, 1H), 7.40 (s, 1H), 7.26 (d, J = 9.7 Hz, 1H), 6.68 (dd, J = 10.2, 2.9 Hz, 2H), 6.01-5.94 (m, 1H), 5.35 (t, J = 5.2 Hz, 1H), 4.22-4.14 (m, 1H), 4.11-4.04 (m, 1H). |

TABLE 1-continued

| Example | Structure (Synthetic Method) | Chemical Name | LC/MS [M + H]+ | 1H-NMR (400 MHz) |
|---|---|---|---|---|
| 126 | (Method 8) | 4-(3-(2-(trifluoromethyl)pyridin-4-yl)-1H-indazol-5-yl)-1-((2-(trifluoromethyl)pyridin-4-yl)methyl)pyridin-2(1H)-one | 516.1 | $^1$H NMR (400 MHz, DMSO-d6) δ 13.96 (s, 1H), 8.89 (d, J = 5.1 Hz, 1H), 8.74 (d, J = 5.0 Hz, 1H), 8.54-8.46 (m, 2H), 8.40 (s, 1H), 8.00 (d, J = 7.1 Hz, 1H), 7.88-7.82 (m, 2H), 7.77 (d, J = 8.8 Hz, 1H), 7.54 (d, J = 4.8 Hz, 1H), 6.94 (d, J = 1.7 Hz, 1H), 6.90 (dd, J = 7.1, 1.9 Hz, 1H), 5.30 (s, 2H). |
| 127 | (Method 8) | 4-(3-(2-methylpyridin-4-yl)-1H-indazol-5-yl)-1-((2-methylpyridin-4-yl)methyl)pyridin-2(1H)-one | 408.1 | $^1$H NMR (400 MHz, DMSO-d6) δ 13.72 (s, 1H), 8.56 (d, J = 5.1 Hz, 1H), 8.47-8.34 (m, 2H), 7.90 (d, J = 8.9 Hz, 3H), 7.80 (d, J = 8.8 Hz, 1H), 7.72 (d, J = 8.7 Hz, 1H), 7.12 (s, 1H), 7.04 (d, J = 4.5 Hz, 1H), 6.92-6.79 (m, 2H), 5.14 (s, 2H), 2.58 (s, 3H), 2.44 (s, 3H). |
| 128 | (Method 6) | (S)-4-(3-([1,2,4]triazolo[1,5-a]pyridin-6-yl)-1H-indazol-5-yl)-1-(1-(3-bromo-5-fluorophenyl)-2-hydroxyethyl)pyridin-2(1H)-one | 545.0 | $^1$H NMR (400 MHz, DMSO-d6) δ 13.64 (s, 1H), 9.69 (s, 1H), 8.55 (s, 1H), 8.48 (s, 1H), 8.34 (dd, J = 9.3, 1.5 Hz, 1H), 7.96 (t, J = 10.5 Hz, 1H), 7.89 (d, J = 7.3 Hz, 1H), 7.80 (d, J = 9.9 Hz, 1H), 7.71 (d, J = 8.8 Hz, 1H), 7.51 (d, J = 8.3 Hz, 1H), 7.40 (s, 1H), 7.26 (d, J = 9.7 Hz, 1H), 6.93 (d, J = 1.8 Hz, 1H), 6.84 (dd, J = 7.3, 1.9 Hz, 1H), 6.03-5.93 (m, 1H), 5.39-5.26 (m, 1H), 4.28-4.12 (m, 1H), 4.12-3.99 (m, 1H). |
| 129 | (Method 6) | (S)-1-(1-(3-bromo-5-fluorophenyl)-2-hydroxyethyl)-4-(3-(imidazo[1,2-a]pyridin-6-yl)-1H-indazol-5-yl)pyridin-2(1H)-one | 544.3 | $^1$H NMR (400 MHz, DMSO-d6) δ 13.52 (s, 1H), 9.33 (s, 1H), 8.47 (s, 1H), 8.10 (s, 1H), 7.92 (t, J = 8.2 Hz, 2H), 7.78 (d, J = 8.8 Hz, 1H), 7.70 (d, J = 8.7 Hz, 2H), 7.62 (s, 1H), 7.51 (d, J = 8.3 Hz, 1H), 7.40 (s, 1H), 7.26 (d, J = 9.8 Hz, 1H), 6.87 (s, 1H), 6.81 (d, J = 7.2 Hz, 1H), 6.01-5.96 (m, 1H), 5.35 (t, J = 5.0 Hz, 1H), 4.22-4.15 (m, 1H), 4.08 (m, 1H). |

TABLE 1-continued

| Example | Structure (Synthetic Method) | Chemical Name | LC/MS [M + H]+ | 1H-NMR (400 MHz) |
|---|---|---|---|---|
| 130 | 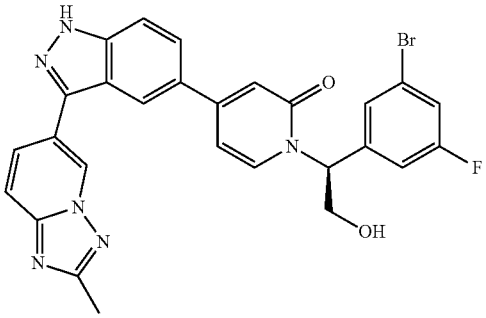 [SMILES: O=c1cc(-c2ccc3[nH]nc(-c4ccc5nccn5c4)c3c2)ccn1[C@H](CO)c1cc(F)cc(Br)c1]<br>(Method 6) | (S)-1-(1-(3-bromo-5-fluorophenyl)-2-hydroxyethyl)-4-(3-(2-methyl-[1,2,4]triazolo[1,5-a]pyridin-6-yl)-1H-indazol-5-yl)pyridin-2(1H)-one | 559.8 | $^1$H NMR (400 MHz, DMSO-d6) δ 13.61 (s, 1H), 9.52 (s, 1H), 8.47 (s, 1H), 8.27 (d, J = 9.3 Hz, 1H), 7.89 (d, J = 7.3 Hz, 1H), 7.81 (dd, J = 13.4, 9.2 Hz, 2H), 7.70 (d, J = 8.8 Hz, 1H), 7.50 (d, J = 8.3 Hz, 1H), 7.39 (s, 1H), 7.26 (d, J = 9.6 Hz, 1H), 6.91 (s, 1H), 6.84 (dd, J = 7.3, 1.6 Hz, 1H), 6.01-5.93 (m, 1H), 5.35 (t, J = 5.1 Hz, 1H), 4.22-4.13 (m, 1H), 4.11-4.02 (m, 1H), 2.49 (s, 3H). |
| 131 | 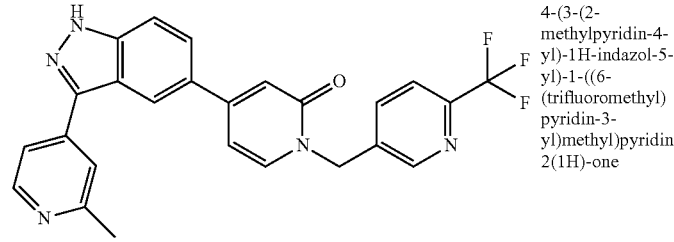<br>(Method 8) | 4-(3-(2-methylpyridin-4-yl)-1H-indazol-5-yl)-1-((6-(trifluoromethyl)pyridin-3-yl)methyl)pyridin-2(1H)-one | 462.1 | $^1$H NMR (400 MHz, DMSO-d6) δ 13.70 (s, 1H), 8.81 (s, 1H), 8.55 (d, J = 5.1 Hz, 1H), 8.41 (s, 1H), 8.02 (d, J = 7.3 Hz, 1H), 7.99 (d, J = 1.4 Hz, 1H), 7.91 (d, J = 8.4 Hz, 2H), 7.87 (d, J = 5.2 Hz, 1H), 7.78 (dd, J = 8.8, 1.3 Hz, 1H), 7.71 (d, J = 8.8 Hz, 1H), 6.88-6.83 (m, 2H), 5.28 (s, 2H), 2.57 (s, 3H). |
| 132 | 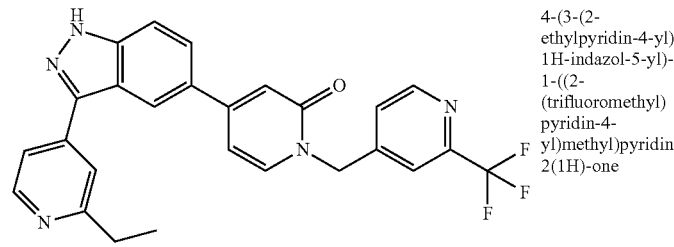<br>(Method 6) | 4-(3-(2-ethylpyridin-4-yl)-1H-indazol-5-yl)-1-((2-(trifluoromethyl)pyridin-4-yl)methyl)pyridin-2(1H)-one | 476.2 | $^1$H NMR (400 MHz, DMSO-d6) δ 13.70 (s, 1H), 8.72 (d, J = 5.0 Hz, 1H), 8.58 (d, J = 5.1 Hz, 1H), 8.42 (s, 1H), 7.96 (d, J = 7.1 Hz, 1H), 7.91-7.86 (m, 2H), 7.83 (s, 1H), 7.78 (dd, J = 8.9, 0.8 Hz, 1H), 7.71 (d, J = 8.8 Hz, 1H), 7.52 (d, J = 4.8 Hz, 1H), 6.91-6.84 (m, 2H), 5.28 (s, 2H), 2.84 (q, J = 7.6 Hz, 2H), 1.27 (t, J = 7.6 Hz, 3H). |
| 133 | 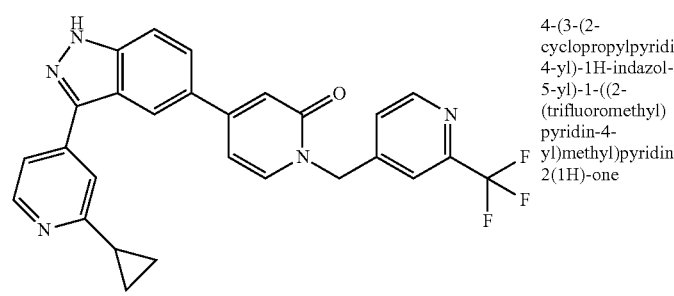<br>(Method 6) | 4-(3-(2-cyclopropylpyridin-4-yl)-1H-indazol-5-yl)-1-((2-(trifluoromethyl)pyridin-4-yl)methyl)pyridin-2(1H)-one | 488.0 | $^1$H NMR (400 MHz, DMSO-d6) δ 13.71 (s, 1H), 8.72 (d, J = 4.9 Hz, 1H), 8.49 (d, J = 5.1 Hz, 1H), 8.44 (s, 1H), 7.97 (d, J = 7.7 Hz, 2H), 7.84 (s, 1H), 7.82-7.77 (m, 2H), 7.71 (d, J = 8.7 Hz, 1H), 7.52 (d, J = 4.6 Hz, 1H), 6.89 (d, J = 7.4 Hz, 2H), 5.28 (s, 2H), 2.34-2.25 (m, 1H), 1.00-0.94 (m, 4H). |
| 134 | 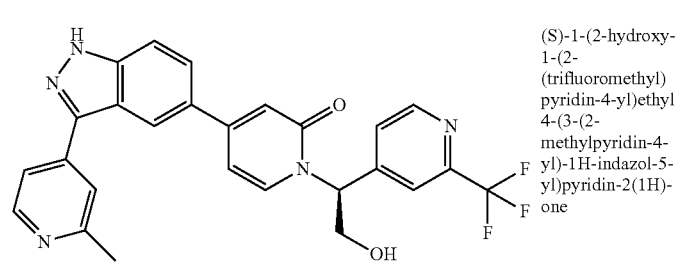<br>(Method 6) | (S)-1-(2-hydroxy-1-(2-(trifluoromethyl)pyridin-4-yl)ethyl)-4-(3-(2-methylpyridin-4-yl)-1H-indazol-5-yl)pyridin-2(1H)-one | 492.2 | $^1$H NMR (400 MHz, DMSO-d6) δ 13.71 (s, 1H), 8.72 (d, J = 4.9 Hz, 1H), 8.49 (d, J = 5.1 Hz, 1H), 8.44 (s, 1H), 7.97 (d, J = 7.7 Hz, 2H), 7.84 (s, 1H), 7.82-7.77 (m, 2H), 7.71 (d, J = 8.7 Hz, 1H), 7.52 (d, J = 4.6 Hz, 1H), 6.89 (d, J = 7.4 Hz, 2H), 5.28 (s, 2H), 2.34-2.25 (m, 1H), 1.00-0.94 (m, 4H). |

TABLE 1-continued

| Example | Structure (Synthetic Method) | Chemical Name | LC/MS [M + H]+ | 1H-NMR (400 MHz) |
|---|---|---|---|---|
| 135 | (Method 8) | 4-(3-(2-methylpyridin-4-yl)-1H-indazol-5-yl)-1-((4-(trifluoromethyl)thiazol-2-yl)methyl)pyridin-2(1H)-one | 468.3 | 1H NMR (400 MHz, DMSO-d6) δ 13.73 (s, 1H), 8.56 (d, J = 4.7 Hz, 1H), 8.46 (d, J = 13.2 Hz, 2H), 8.00 (d, J = 6.9 Hz, 1H), 7.90 (d, J = 9.2 Hz, 2H), 7.80 (d, J = 8.6 Hz, 1H), 7.73 (d, J = 8.6 Hz, 1H), 6.94-6.87 (m, 2H), 5.50 (s, 2H), 2.59 (s, 3H). |
| 136 | (Method 8) | 4-(3-(2-methylpyridin-4-yl)-1H-indazol-5-yl)-1-((2-(trifluoromethyl)pyridin-3-yl)methyl)pyridin-2(1H)-one | 462.1 | 1H NMR (400 MHz, DMSO-d6) δ 13.73 (s, 1H), 8.65 (d, J = 4.1 Hz, 1H), 8.55 (d, J = 5.0 Hz, 1H), 8.46 (s, 1H), 7.94-7.86 (m, 3H), 7.82 (d, J = 8.7 Hz, 1H), 7.76-7.65 (m, 2H), 7.39 (d, J = 8.0 Hz, 1H), 6.93 (d, J = 6.1 Hz, 2H), 5.38 (s, 2H), 2.58 (s, 3H). |
| 137 | (Method 8) | 4-(3-(2-methylpyridin-4-yl)-1H-indazol-5-yl)-1-((6-(trifluoromethyl)pyridin-2-yl)methyl)pyridin-2(1H)-one | 462.2 | 1H NMR (400 MHz, DMSO-d6) δ 13.71 (s, 1H), 8.49 (d, J = 43.2 Hz, 2H), 8.07 (s, 1H), 7.87 (d, J = 22.6 Hz, 3H), 7.81 (s, 2H), 7.71 (d, J = 7.5 Hz, 1H), 7.49 (d, J = 6.6 Hz, 1H), 6.88 (s, 2H), 5.32 (s, 2H), 2.57 (s, 3H). |
| 138 | (Method 6) | (S)-1-(1-(3-bromo-5-fluorophenyl)-2-hydroxyethyl)-4-(3-(1,3-dimethyl-1H-pyrazol-4-yl)-1H-indazol-5-yl)pyridin-2(1H)-one | 522.2 | 1H NMR (400 MHz, DMSO-d6) δ 13.09 (s, 1H), 8.50 (s, 1H), 8.18 (s, 1H), 7.87 (d, J = 7.3 Hz, 1H), 7.71 (d, J = 8.9 Hz, 1H), 7.60 (d, J = 8.7 Hz, 1H), 7.51 (d, J = 8.3 Hz, 1H), 7.39 (s, 1H), 7.25 (d, J = 9.7 Hz, 1H), 6.81 (s, 1H), 6.77 (d, J = 7.2 Hz, 1H), 5.97 (t, J = 6.5 Hz, 1H), 5.34 (t, J = 5.1 Hz, 1H), 4.22-4.12 (m, 1H), 4.11-4.01 (m, 1H), 3.85 (s, 3H), 2.43 (s, 3H). |
| 139 | (Method 8) | 4-(3-(2-methylpyridin-4-yl)-1H-indazol-5-yl)-1-((3-(trifluoromethyl)isoxazol-5-yl)methyl)pyridin-2(1H)-one | 452.1 | 1H NMR (400 MHz, CD3OD) δ 8.51 (d, J = 5.3 Hz, 1H), 8.28 (s, 1H), 7.87 (s, 1H), 7.83 (d, J = 5.3 Hz, 1H), 7.80 (d, J = 7.1 Hz, 1H), 7.70 (s, 2H), 6.87 (d, J = 1.6 Hz, 1H), 6.82 (dd, J = 7.1, 1.9 Hz, 1H), 6.74 (s, 1H), 5.43 (s, 2H), 2.65 (s, 3H). |

Example 140 (Method 11)

Preparation of 1-(1-(3-bromo-5-fluorophenyl)ethyl)-4-(3-((1r,4r)-4-hydroxycyclohexyl)-1H-indazol-5-yl)pyridin-2(1H)-one

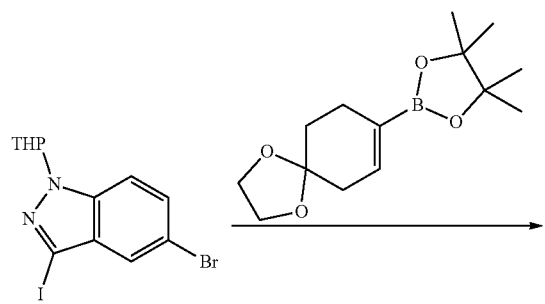

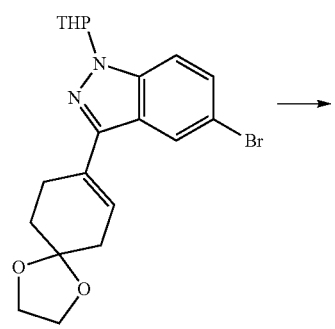

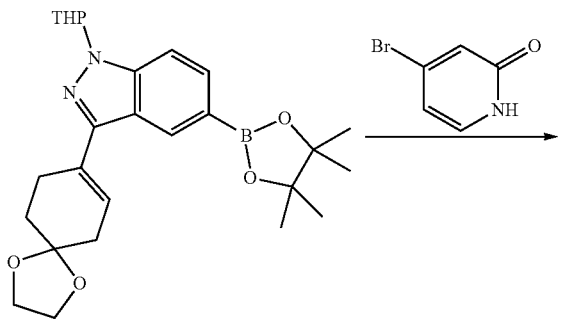

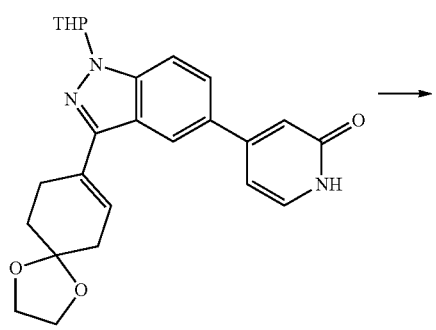

-continued

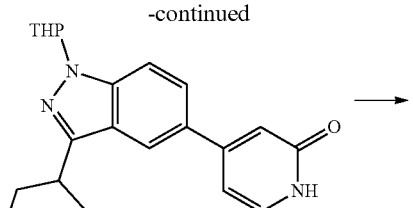

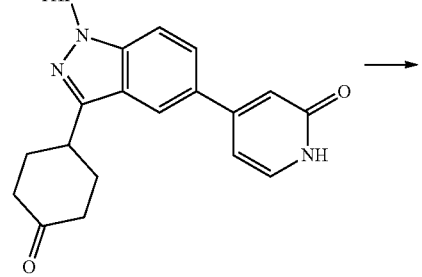

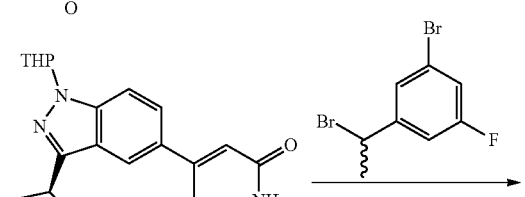

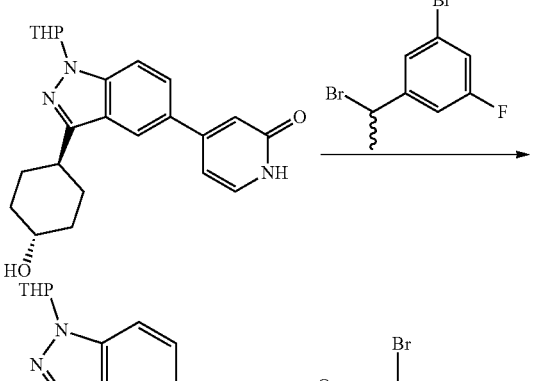

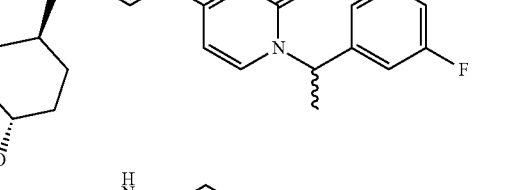

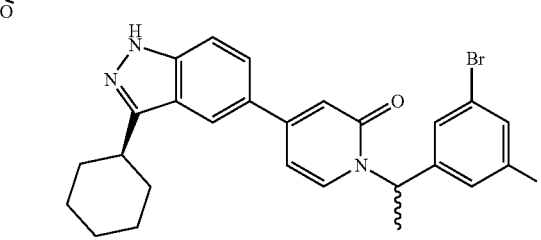

Step 1. 5-bromo-3-(1,4-dioxaspiro[4.5]dec-7-en-8-yl)-1-(tetrahydro-2H-pyran-2-yl)-1H-indazole To a solution of 5-bromo-3-iodo-1-(tetrahydro-2H-pyran-2-yl)-1H-indazole (6.27 g, 15.4 mmol) and 4,4,5,5-tetramethyl-2-(1,4-dioxaspiro[4.5]dec-7-en-8-yl)-1,3,2-dioxaborolane (4.5 g, 16.9 mmol) in dioxane/H$_2$O (100 mL/10 mL) were added sodium carbonate (3.26 g, 30.9 mmol) and Pd(dppf)Cl$_2$.DCM (628 mg, 0.77 mmol). The mixture was flushed with nitrogen, stirred at 65° C. overnight, cooled to rt, diluted with water (200 mL), and extracted with EtOAc (200 mL). The organic layer was separated, washed with water (100 mL×3), dried over anhydrous sodium sulfate, filtered off, and concentrated in vacuo. The crude product was purified by silica gel flash column chromatography (PE:EtOAc=10:1 to 5:1) to give the title compound (3.86 g, yield: 59%).

Step 2. 3-(1,4-dioxaspiro[4.5]dec-7-en-8-yl)-1-(tetrahydro-2H-pyran-2-yl)-5-(4,4,5,5-tetramethyl-1,3,2-dioxaborolan-2-yl)-1H-indazole To a solution of 5-bromo-3-(1,4-dioxaspiro[4.5]dec-7-en-8-yl)-1-(tetrahydro-2H-pyran-2-yl)-1H-indazole (4.31 g, 10.28 mmol) and B$_2$Pin$_2$ (3.13 g, 12.33 mmol) in dioxane (100 mL) were added sodium acetate (3.03 g, 30.84 mmol) and Pd(dppf)Cl$_2$-DCM (419 mg, 0.514 mmol). The mixture was flushed with nitrogen, stirred at 100° C. overnight, cooled to rt, diluted with water (200 mL), and extracted with EtOAc (200 mL). The organic layer was separated, washed with bine (100 mL), dried over anhydrous sodium sulfate, filtered off, and concentrated in vacuo. The crude product was purified by silica gel flash column chromatography (PE:EtOAc=10:1 to 4:1) to give the title compound (3.28 g, yield: 68%).

Step 3. 4-(3-(1,4-dioxaspiro[4.5]dec-7-en-8-yl)-1-(tetrahydro-2H-pyran-2-yl)-1H-indazol-5-yl)pyridin-2(1H)-one To a solution of 3-(1,4-dioxaspiro[4.5]dec-7-en-8-yl)-1-(tetrahydro-2H-pyran-2-yl)-5-(4,4,5,5-tetramethyl-1,3,2-dioxaborolan-2-yl)-1H-indazole (2.54 g, 5.45 mmol) and 4-bromopyridin-2(1H)-one (948 mg, 5.45 mmol) in dioxane/H$_2$O (30 mL/5 mL) were added sodium carbonate (1.15 g, 10.8 mmol) and Pd(dppf)Cl$_2$-DCM (222 mg, 0.273 mmol). The mixture was flushed with nitrogen, stirred at 90° C. overnight, cooled to rt, diluted with water (50 mL), and extracted with DCM (100 mL). The organic layer was separated, washed with water (50 mL×3), dried over anhydrous sodium sulfate, filtered off, and concentrated in vacuo. The crude product was purified by silica gel flash column chromatography (DCM:MeOH=50:1 to 20:1) to give the title compound (1.35 g, yield: 57%).

Step 4. 4-(3-(1,4-dioxaspiro[4.5]decan-8-yl)-1-(tetrahydro-2H-pyran-2-yl)-1H-indazol-5-yl)pyridin-2(1H)-one A solution of 4-(3-(1,4-dioxaspiro[4.5]dec-7-en-8-yl)-1-(tetrahydro-2H-pyran-2-yl)-1H-indazol-5-yl)pyridin-2(1H)-one (1.238 g, 2.85 mmol) and Pd/C (400 mg, wet, 10% Pd) in THF (20 mL) was stirred at rt under hydrogen overnight. The mixture was filtered off and the filtrate was concentrated in vacuo. The crude product was purified by silica gel flash column chromatography (DCM:MeOH=50:1 to 20:1) to give the title compound (170 mg, yield: 12%).

Step 5. 4-(3-(4-oxocyclohexyl)-1-(tetrahydro-2H-pyran-2-yl)-1H-indazol-5-yl)pyridin-2(1H)-one To a solution of 4-(3-(1,4-dioxaspiro[4.5]decan-8-yl)-1-(tetrahydro-2H-pyran-2-yl)-1H-indazol-5-yl)pyridin-2(1H)-one (170 mg, 0.39 mmol) in acetonitrile (3 mL) and water (2 mL) was added 3M HCl (aq., 0.613 mL). The mixture was stirred at rt for 2 h. The mixture was neutralized with sat. NaHCO$_3$ aqueous solution and extracted with DCM/iPrOH (10:1, 20 mL×3). The combined organic layers were dried over anhydrous sodium sulfate, filtered off, and concentrated in vacuo to give the crude title compound, which was used in the next step without further purification.

Step 6. 4-(3-((1 r,4r)-4-hydroxycyclohexyl)-1-(tetrahydro-2H-pyran-2-yl)-1H-indazol-5-yl)pyridin-2(1H)-one To a solution of 4-(3-(4-oxocyclohexyl)-1-(tetrahydro-2H-pyran-2-yl)-1H-indazol-5-yl)pyridin-2(1H)-one (~0.39 mmol) from Step 6 above in MeOH (5 mL), cooled in ice-water bath, was added sodium borohydride (29 mg, 0.78 mmol). The mixture was stirred at rt for 20 min, diluted with water (20 mL), and extracted with DCM (50 mL). The organic layer was separated, dried over anhydrous sodium sulfate, filtered off, and concentrated in vacuo to give the crude title compound, which was used in the next step without further purification.

Step 7. 1-(1-(3-bromo-5-fluorophenyl)ethyl)-4-(3-((1r,4r)-4-hydroxycyclohexyl)-1-(tetrahydro-2H-pyran-2-yl)-1H-indazol-5-yl)pyridin-2(1H)-one To a solution of the crude 4-(3-((1r,4r)-4-hydroxycyclohexyl)-1-(tetrahydro-2H-pyran-2-yl)-1H-indazol-5-yl)pyridin-2(1H)-one (~0.39 mmol) from the previous step in DMF (3 mL) were added potassium carbonate (107 mg, 0.78 mmol) and 1-bromo-3-(1-bromoethyl)-5-fluorobenzene (109 mg, 0.39 mmol). The mixture was stirred at rt overnight, diluted with water (10 mL), and extracted with DCM (20 mL×2). The combined organic layers were dried over anhydrous sodium sulfate, filtered off, and concentrated in vacuo to give the crude title compound, which was used in the next step without further purification.

Step 8. 1-(1-(3-bromo-5-fluorophenyl)ethyl)-4-(3-((1r,4r)-4-hydroxycyclohexyl)-1H-indazol-5-yl)pyridin-2(1H)-one To a solution of the crude 1-(1-(3-bromo-5-fluorophenyl)ethyl)-4-(3-((1r,4r)-4-hydroxycyclohexyl)-1-(tetrahydro-2H-pyran-2-yl)-1H-indazol-5-yl)pyridin-2(1H)-one (~0.39 mmol) in MeOH (2 mL) was added 6N HCl (aq., 2 mL). The mixture was stirred at rt overnight, diluted with water (5 mL), adjusted to pH>7 with aq. sat. NaHCO$_3$, and extracted with DCM (20 mL×2). The combined organic layers were dried over anhydrous sodium sulfate, filtered off, and concentrated in vacuo. The crude product was purified by prep-TLC (DCM:MeOH=20:1) to give the desired compound (5 mg, 4 steps yield: 2.5%). MS (ESI) m/z: 510.4 [M+1]+; $^1$HNMR (400 MHz, DMSO-d6) δ 12.74 (s, 1H), 8.16 (s, 1H), 7.78 (d, J=7.2 Hz, 1H), 7.64 (d, J=8.2 Hz, 1H), 7.54-7.44 (m, 2H), 7.36 (s, 1H), 7.23 (d, J=9.7 Hz, 1H), 6.79-6.70 (m, 2H), 6.11 (q, J=7.0 Hz, 1H), 4.56 (d, J=4.3 Hz, 1H), 3.57-3.44 (m, 1H), 3.12-2.96 (m, 1H), 2.04-1.85 (m, 4H), 1.76-1.59 (m, 5H), 1.45-1.29 (m, 2H).

Example 141

Preparation of (S)-1-(1-(3-bromo-5-fluorophenyl)-2-hydroxyethyl)-4-(3-(methylamino)-1H-indazol-5-yl)pyridin-2(1H)-one

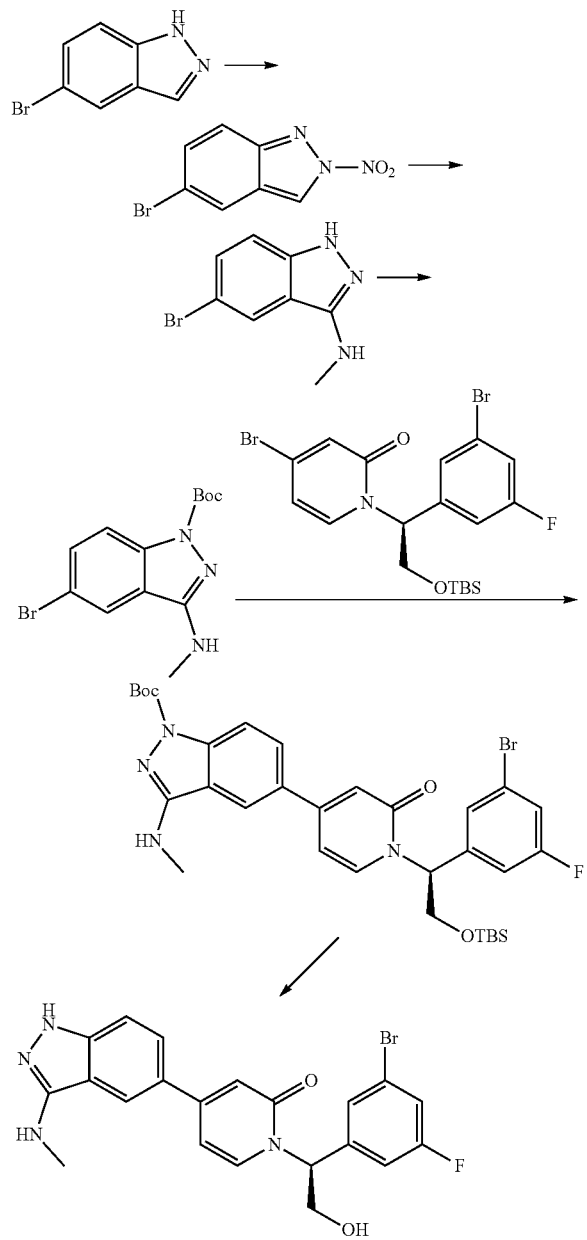

Step 1. 5-bromo-2-nitro-2H-indazole

To a stirred acetic anhydride (18.6 mL) cooled in an ice-water bath was added fuming nitric acid (8 mL) at a rate to keep the temperature between 0-5° C. under $N_2$. After addition was completed, the stirring was continued for 30 min at 0° C. 5-bromo-1H-indazole (5.9 g, 30 mmol) and acetic acid (40 mL) was added to the reaction solution concurrently in small portions under $N_2$, maintaining the temperature between 0-5° C. The reaction mixture was stirred at 0° C. and carefully poured into ice-water (250 mL) while stirring. The suspension was stirred for 30 min, and filtered. The filter cake was rinsed with $H_2O$ (50 mL), dried under vacuum to give the title compound (4.5 g, yield: 61%).

Step 2. 5-bromo-N-methyl-1H-indazol-3-amine

A solution of 5-bromo-2-nitro-2H-indazole (2 g, 8.26 mmol) in methylamine/tetrahydrofuran (2 N, 20 mL) was stirred at rt (25° C.) for 18 h under $N_2$, then heated to 65° C. under stirring for 18 h. The solution was concentrated under vacuum and the residues was diluted with EtOAc (100 mL), washed with $H_2O$ (100 mL×2) and brine (50 mL), dried over anhydrous $Na_2SO_4$, filtered off, and concentrated in vacuo. The crude product was purified by silica gel flash column chromatography (PE/EtOAc 3:1 to 1:1) to give the title compound (785 mg, yield: 42%).

Step 3. tert-butyl 5-bromo-3-(methylamino)-1H-indazole-1-carboxylate

To a solution of 5-bromo-N-methyl-1H-indazol-3-amine (226 mg, 1.00 mmol) in THF (5 mL) were added triethylamine (151 mg, 1.50 mmol), $Boc_2O$ (240 mg, 1.10 mmol) and DMAP (25 mg, 0.20 mmol) sequentially rt under $N_2$. The reaction mixture was stirred at rt for 18 h, diluted with EtOAc (30 mL), washed with $H_2O$ (30 mL) and brine (30 mL), dried over anhydrous $Na_2SO_4$, filtered off, and concentrated in vacuo. The crude product was purified by silica gel flash column chromatography (PE/EtOAc=5:1) to give the title compound (225 mg, yield: 69%).

Step 4. (S)-tert-butyl 5-(1-(1-(3-bromo-5-fluorophenyl)-2-((tert-butyldimethylsilyl)oxy)ethyl)-2-oxo-1,2-dihydropyridin-4-yl)-3-(methylamino)-1H-indazole-1-carboxylate To a solution of tert-butyl 5-bromo-3-(methylamino)-1H-indazole-1-carboxylate (225 mg, 0.69 mmol) in 1,4-dioxane (5 mL) was added 4,4,4',4',5,5,5',5'-octamethyl-2,2'-bi(1,3,2-dioxaborolane) (175 mg, 0.69 mmol), potassium acetate (270 mg, 2.76 mmol) and Pd(dppf)Cl₂.DCM (56.4 mg, 0.069 mmol) sequentially. The reaction mixture was stirred at 80° C. for 18 h under $N_2$. After cooling to rt, (S)-4-bromo-1-(1-(3-bromo-5-fluorophenyl)-2-((tert-butyldimethylsilyl)oxy)ethyl)pyridin-2(1H)-one (244 mg, 0.483 mmol), sodium carbonate (146 mg, 1.38 mmol), and $H_2O$ (1 mL) were added sequentially. The resultant mixture was stirred at 80° C. for 3 h under $N_2$, cooled rt, diluted with $H_2O$ (50 mL), and extracted with EtOAc (50 mL). The organic layer was separated, washed brine (50 mL), dried over anhydrous $Na_2SO_4$, filtered off, and concentrated. The residue was purified by prep-TLC (DCM:MeOH=10:1) to give the title compound (70 mg, yield: 21%).

Step 5. (S)-1-(1-(3-bromo-5-fluorophenyl)-2-hydroxyethyl)-4-(3-(methylamino)-1H-indazol-5-yl)pyridin-2(1H)-one To a solution of (S)-tert-butyl 5-(1-(1-(3-bromo-5-fluorophenyl)-2-((tert butyldimethylsilyl)oxy)ethyl)-2-oxo-1,2-dihydropyridin-4-yl)-3-(methylamino)-1H-indazole-1-carboxylate (70 mg, 0.104 mmol) in methanol (1.5 mL) was added 6N HCl (aq., 1.5 mL) under stirring. The solution was stirred at 55° C. for 3 h under $N_2$, basified with aq. sat. $Na_2CO_3$ (~15 mL) to pH=8-9, and extracted with dichloromethane/methanol (10:1, 20 mL×2). The combined organics were washed with H₂O (20 mL) and brine (20 mL), dried over anhydrous Na₂SO₄, filtered off, and concentrated in vacuo. The crude product was purified by prep-TLC (DCM:MeOH=10:1) to give the title compound (22 mg, yield: 46%). MS (ESI) m/z: 457.1 [M+1]⁺; ¹HNMR (400 MHz, CD₃OD) δ 8.04 (s, 1H), 7.77 (d, J=7.3 Hz, 1H), 7.63 (dd, J=8.8, 1.5 Hz, 1H), 7.37 (s, 1H), 7.33 (d, J=8.8 Hz, 1H), 7.29 (dd, J=8.2, 1.9 Hz, 1H), 7.14 (d, J=9.5 Hz, 1H), 6.83 (d, J=1.7 Hz, 1H), 6.79 (dd, J=7.3, 1.9 Hz, 1H), 6.09 (t, 1H), 4.31-4.23 (m, 1H), 4.22-4.14 (m, 1H), 2.99 (s, 3H).

Example 142

Preparation of 4-(3-(2-methylpyridin-4-yl)-1H-indazol-5-yl)-1-(1-(2-(trifluoromethyl)pyridin-4-yl)ethyl)pyridin-2(1H)-one

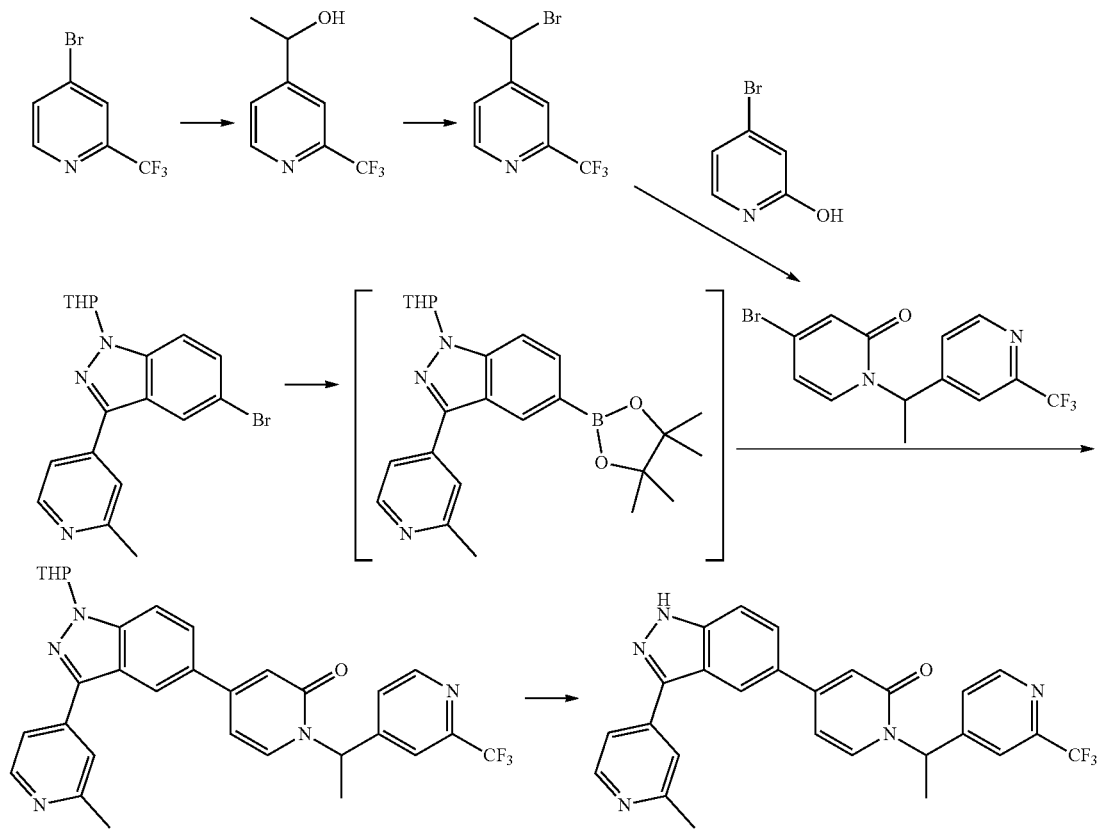

Step 1. 1-(2-(trifluoromethyl)pyridin-4-yl)ethanol

To a solution of 4-bromo-2-(trifluoromethyl)pyridine (190 g, 840.7 mmol) in THF (1300 mL) cooled to 0° C. under nitrogen was added isopropylmagnesium chloride (THF, 2N, 462 mL, 924.8 mmol) dropwise over 30 min while maintaining the temperature below 5° C. After addition, the mixture was stirred below 10° C. for 30 min and recooled to 0° C. Acetaldehyde (55.48 g, 1261 mmol) was added dropwise while maintaining the temperature below 10° C. After addition, the mixture was stirred below 10° C. for 30 min before quenching with aqeous NH₄Cl (saturated, 500 mL). The mixture was concentrated in vacuo to remove most THF. The aqueous phase was extracted with EtOAc (1.0 L×3). The combined organic extracts were washed with H₂O (500 mL×3), brine (500 mL×2), dried over anhydrous sodium sulfate, filtered off, and concentrated in vacuo to give the crude title compound (150 g, yield: 93%), which was used in the next step without further purification.

Step 2.
4-(1-bromoethyl)-2-(trifluoromethyl)pyridine

To a solution of 1-(2-(trifluoromethyl)pyridin-4-yl)ethanol (200 g, 1047 mmol) in THF (2000 mL) cooled with an ice-water bath, was added carbon tetrabromide (524 g, 1570.6 mmol) portionwise (~50 g each time) under N₂. The mixture was stirred for 10 min and triphenylphosphine (412 g, 1570.6 mmol) was added portionwise (~50 g each time). The reaction mixture was stirred at room temperature for 1 h. Additional carbon tetrabromide (174.7 g, 523.5 mmol) and triphenylphosphine (137.3 g, 523.5 mmol) was added portionwise (~50 g each time) sequentially to the reaction mixture. The reaction mixture was stirred at room temperature for another 1 h. The reaction mixture was filtered off and the filtrate was concentrated in vacuo. The residue was triturated with PE:EtOAc (10:1, 2.5 L), stirred for 30 min, and filtered. The filtrate was concentrated in vacuo and the residue was purified by purified silica gel flash column chromatography (PE:EtOAc=10:1) to give the title compound (260 g, yield: 65%).

Step 3. 4-bromo-1-(1-(2-(trifluoromethyl)pyridin-4-yl)ethyl)pyridin-2(1H)-one

A solution of 4-bromopyridin-2-ol (164.4 g, 945 mmol) in THF (2.4 L) was cooled to −20° C. under N₂ and KHMDS (1N in THF, 945 mL, 945 mmol) was added dropwise over 15 min while maintaining the temperature below 0° C. After complete addition, the reaction mixture was stirred at room temperature for 30 min before adding 4-(1-bromoethyl)-2-(trifluoromethyl)pyridine (240 g, 945 mmol). The mixture was refluxed overnight, cooled to room temperature, and quenched with saturated aqueous NH$_4$Cl (1.0 L), and concentrated in vacuo to remove THF. The residual aqueous solution was extracted with EtOAc (1500 mL×3). The combined organic layers were washed with H$_2$O (500 mL×3), brine (500 mL×2), dried over anhydrous sodium sulfate, filtered off, and concentrated under vacuum to give the crude compound, which was triturated with Et$_2$O (700 mL) to give pure title compound (220 g). The residue from the ether washings was purified by silica gel flash column chromatography (PE:EtOAc=10:1 to 1:2) to give additinal pure ttitle compound (26 g). (total: 246 g, yield: 75%).

Step 4. 4-(3-(2-methylpyridin-4-yl)-1-(tetrahydro-2H-pran-2-yl)-1H-indazol-5-yl)-1-(1-(2-(trifluoromethyl)pyridin-4-yl)ethyl)pyridin-2(1H)-one To a solution of 5-bromo-3-(2-methylpyridin-4-yl)-1-(tetrahydro-2H-pyran-2-yl)-1H-indazole (260 g, 698 mmol) in 1,4-dioxane (2.5 L) were added sequentially 4,4,4',4',5,5,5',5'-octamethyl-2,2'-bi(1,3,2-dioxaborolane) (168.5 g, 663.5 mmol), potassium acetate (205.3 g, 2095 mmol) and Pd(dppf)Cl$_2$-DCM (11.4 g, 14 mmol). The reaction mixture was stirred at 100° C. overnight under N$_2$ and cooled to room temperature. To the reaction mixture, 4-bromo-1-(1-(2-(trifluoromethyl)pyridin-4-yl)ethyl)pyridin-2(1H)-one (194 g, 558.7 mmol), sodium carbonate (148 g, 1396 mmol) and H$_2$O (500 mL). The reaction mixture was stirred at 100° C. overnight under N$_2$. After cooling to room temperature, the mixture was concentrated under vacuum. The residue was diluted with H$_2$O (500 mL) and the aquous layer was extracted with DCM/isopropanol (3:1, 1 L×4). The combined organic extracts were washed with H$_2$O (500 mL×3), brine (500 mL×2), dried over anhydrous sodium sulfate, filtered off and concentrated in vacuo. The residue was purified by silica gel flash column chromatography (DCM:MeOH=30:1) to give title compound, which was used directly in the next step.

Step 5. 4-(3-(2-methylpyridin-4-yl)-1H-indazol-5-yl)-1-(1-(2-(trifluoromethyl)pyridin-4-yl)ethyl)pyridin-2(1H)-one To a solution of 4-(3-(2-methylpyridin-4-yl)-1-(tetrahydro-2H-pyran-2-yl)-1H-indazol-5-yl)-1-(1-(2-(trifluoromethyl)pyridin-4-yl)ethyl)pyridin-2(1H)-one from Step 4 above (~600 mmol) in MeOH (1.0 L) was added aqueous HCl (6N, 2 L). The mixture was stirred at 65° C. for 5 h. The solid formed after cooling to room temperature was obtained by filtration and the solid was suspended in water (500 mL), saturated aqueous Na$_2$CO$_3$ was added until pH>7. The mixture was extracted with DCM/isopropanol (3:1, 1.0 L×3). The combined organic extracts were washed with H$_2$O (500 mL×3), brine (500 mL×2), dried over anhydrous sodium sulfate, filtered off, and concentrated in vacuo. The residue was purified by silica gel flash column chromatography (DCM:MeOH=20:1) to give the title compound (250 g, yield: 78% in two steps). MS (ESI) m/z: 476.2 [M+1]$^+$; $^1$HNMR (400 MHz, DMSO-d6) δ 13.70 (s, 1H), 8.74 (d, J=5.1 Hz, 1H), 8.54 (d, J=5.2 Hz, 1H), 8.43 (s, 1H), 7.91 (s, 1H), 7.90-7.86 (m, 2H), 7.84-7.75 (m, 2H), 7.71 (d, J=8.8 Hz, 1H), 7.56 (d, J=4.7 Hz, 1H), 6.88-6.83 (m, 2H), 6.15 (d, J=7.2 Hz, 1H), 2.57 (s, 3H), 1.81 (d, J=7.2 Hz, 3H).

Example 142A and 142B (Method 12)

Preparation of (S)-4-(3-(2-methylpyridin-4-yl)-1H-indazol-5-yl)-1-(1-(2-(trifluoromethyl)pyridin-4-v1)ethyl)pyridin-2(1H)-one and (R)-4-(3-(2-methylpyridin-4-yl)-1H-indazol-5-yl)-1-(1-(2-(trifluoromethyl)pyridin-4-yl)ethyl)pyridin-2(1H)-one Two enantiomers of compound of Example 145 (1.50 g) was separated by Chiral HPLC using (S,S) WHELK-01 chiral column (0.46 cm I.D.×25 cm L) eluting with methanol to give two pure enantiomers. 145A (710 mg, isomer 1 with retention time of 7.03 min, ee % is 100%). MS (ESI) m/z: 476.2 [M+1]$^+$; $^1$HNMR (400 MHz, DMSO-d6) δ 13.70 (s, 1H), 8.75 (d, J=5.1 Hz, 1H), 8.55 (d, J=5.2 Hz, 1H), 8.43 (s, 1H), 7.94-7.86 (m, 3H), 7.83 (s, 1H), 7.80 (dd, J=8.9, 1.2 Hz, 1H), 7.72 (d, J=8.8 Hz, 1H), 7.57 (d, J=4.7 Hz, 1H), 6.90-6.82 (m, 2H), 6.16 (d, J=7.2 Hz, 1H), 2.58 (s, 3H), 1.82 (d, J=7.2 Hz, 3H); 145B (675 mg, isomer 2 with retention time of 9.23 min, ee % is 99.5%): MS (ESI) m/z: 476.2 [M+1]+; $^1$HNMR (400 MHz, DMSO-d6) δ 13.70 (s, 1H), 8.74 (d, J=5.1 Hz, 1H), 8.54 (d, J=5.2 Hz, 1H), 8.43 (s, 1H), 7.95-7.86 (m, 3H), 7.82 (s, 1H), 7.79 (dd, J=8.8, 1.2 Hz, 1H), 7.71 (d, J=8.8 Hz, 1H), 7.56 (d, J=4.7 Hz, 1H), 6.93-6.80 (m, 2H), 6.15 (q, J=7.2 Hz, 1H), 2.57 (s, 3H), 1.81 (d, J=7.2 Hz, 3H).

Example 143

Preparation of 6-methyl-4-(3-(2-methylpyridin-4-yl)-1H-indazol-5-yl)-1-((2-(trifluoromethyl)pyridin-4-yl)methyl)pyridin-2(1H)-one

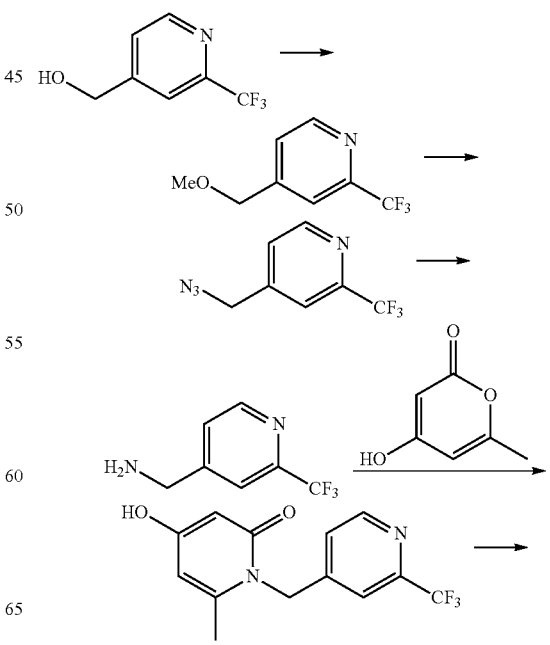

-continued

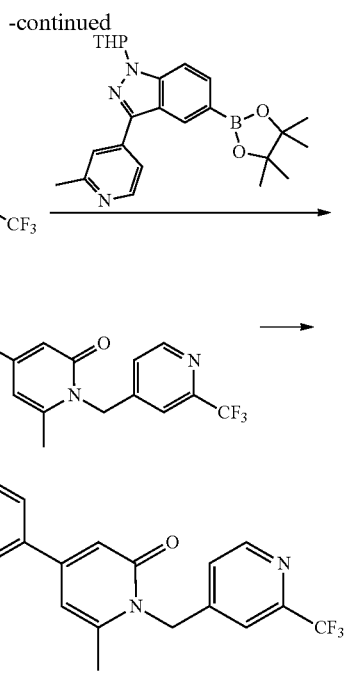

Step 1. 4-(azidomethyl)-2-(trifluoromethyl)pyridine

To a solution of (2-(trifluoromethyl)pyridin-4-yl)methanol (1 g, 5.65 mmol) in DCM (20 ml) was added TEA (857 mg, 8.48 mmol). To the reaction solution cooled to 0° C. in an ice-water bath was added MsCl (776 mg, 6.78 mmol) dropwise. The mixture was stirred at 0° C. in for 1 h. The reaction solution was diluted with DCM (20 mL) and $H_2O$ (20 mL). The organic phase was separated, washed with saturated aqueous $NaHCO_3$ (20 mL), $H_2O$ (20 mL×2), dried over anhydrous $Na_2SO_4$, filtered off, and concentrated in vacuo. The residue was dissolved in DMF (10 mL) and $NaN_3$ (1.1 g, 17 mmol) was added. The reaction mixture was stirred at room temperature overnight. The mixture was diluted with $H_2O$ (20 mL), and extracted with EtOAc (20 mL×2). The combined organic layers were washed with $H_2O$ (30 mL×2), brine (30 mL), dried over anhydrous $Na_2SO_4$, filtered off, and concentrated under vacuum to give the crude title compound (~1.2 g, crude), which was used in the next step without further purification.

Step 2. (2-(trifluoromethyl)pyridin-4-yl)methanamine

To a solution of 4-(azidomethyl)-2-(trifluoromethyl)pyridine (1.2 g, crude) in MeOH (10 ml) cooled to 0° C. in an ice-water bath was added $SnCl_2.2H_2O$ (3.82 g, 17.95 mmol) slowly. The reaction mixture was stirred at room temperature for 3 h. After diluted with $H_2O$ (50 ml) and neutralized and pH adjusted to 8-9 by saturated aqueous $Na_2CO_3$, the mixture was extracted with DCM/i-PrOH (10:1, 20 mL×2). The combined organic layers were washed with brine (20 mL), dried over anhydrous $Na_2SO_4$, filtered off, and concentrated under vacuum to give the crude title compound (300 mg, yield: 30%), which was used without further purification.

Step 3. 4-hydroxy-6-methyl-1-((2-(trifluoromethyl)pyridin-4-yl)methyl)pyridin-2(1H)-one A mixture of 4-hydroxy-6-methyl-2H-pyran-2-one (214 mg, 1.7 mmol), (2-(trifluoromethyl)pyridin-4-yl)methanamine (300 mg, 1.7 mmol) and $H_2O$ (2 ml) in a capped vial was stirred at 80° C. overnight under $N_2$. The mixture was cooled to room temperature. Water was decanded and the soid was triturated with $H_2O$, collected by filtration, and dried under vacuum to give the crude title compound (~500 mg, crude), used without further purification.

Step 4. 6-methyl-2-oxo-1-((2-(trifluoromethyl)pyridin-4-yl)methyl)-1,2-dihydropyridin-4-yl trifluoromethanesulfonate To a solution of 4-hydroxy-6-methyl-1-((2-(trifluoromethyl)pyridin-4-yl)methyl)pyridin-2(1H)-one (~500 mg, crude) in DCM (5 mL) was added TEA (202 mg, 2.0 mmol). The reaction solution was cooled to 0° C. in ice-water bath and $Tf_2O$ (564 mg, 2.0 mmol) was added dropwise. The mixture was stirred at room temperature for 1 h before quenching with ice (20 mL). The organic layer was separated, which was washed with saturated $NaHCO_3$ (15 mL), $H_2O$ (15 mL), brine (15 mL), dried over anhydrous $Na_2SO_4$, filtered off, and concentrated under vacuum to give the title compound (420 mg, yield: 58%).

Step 5. 6-methyl-4-(3-(2-methylpyridin-4-yl)-1-(tetrahydro-2H-pyran-2-v)-1H-indazol-5-yl)-1-((2-(trifluoromethyl)pyridin-4-yl)methyl)pyridin-2(1H)-one A mixture of 6-methyl-2-oxo-1-((2-(trifluoromethyl)pyridin-4-yl)methyl)-1,2-dihydropyridin-4-yl trifluoromethanesulfonate (420 mg, 1 mmol), 3-(2-methylpyridin-4-yl)-1-(tetrahydro-2H-pyran-2-yl)-5-(4,4,5,5-tetramethyl-1,3,2-dioxaborolan-2-yl)-1H-indazole (420 mg, 1 mmol), $Pd(dppf)Cl_2$-DCM (40 mg, 0.05 mmol) and $Na_2CO_3$ (212 mg, 2 mmol) in dioxane (5 mL) and $H_2O$ (0.5 mL) was stirred at 100° C. under $N_2$ overnight. After cooling to room temperature, the mixture was diluted with $H_2O$ (20 mL), and extracted with DCM/iPrOH (10:1, 20 mL×2). The combined organic layers were washed with brine (20 mL), dried over anhydrous $Na_2SO_4$, filtered off, and concentrated under vacuum. The product was purified by prep-TLC (DCM/MeOH=20:1) to give the title compound (70 mg, yield: 12.5%).

Step 6. 6-methyl-4-(3-(2-methylpyridin-4-yl)-1H-indazol-5-yl)-1-((2-(trifluoromethyl)pyridin-4-yl)methyl)pyridin-2(1H)-one A solution of 6-methyl-4-(3-(2-methylpyridin-4-yl)-1-(tetrahydro-2H-pyran-2-yl)-1H-indazol-5-yl)-1-((2-(trifluoromethyl)pyridin-4-yl)methyl)pyridin-2(1H)-one (70 mg, 0.125 mmol) in 6N HCl (2.0 ml) and MeOH (1.0 ml) was stirred at 60° C. overnight. The reaction solution was cooled to room temperature and neutralized by saturated aqueous $Na_2CO_3$ to pH=8-9. The mixture was extracted with DCM/MeOH (10:1, 30 mL). The organic layers were washed with $H_2O$ (15 mL×2), brine (15 mL), dried over anhydrous $Na_2SO_4$, filtered off, and concentrated under vacuum. The residue was purified by prep-TLC (DCM/iPrOH=10/1) to give the title compound (20 mg, 34% yield). MS (ESI) m/z: 476.0 [M+1]$^+$; $^1$HNMR (400 MHz, DMSO-d6) δ 13.73 (d, J=21.1 Hz, 1H), 8.72 (t, J=12.9 Hz, 1H), 8.55 (d, J=4.8 Hz, 1H), 8.43 (s, 1H), 7.87 (d, J=7.8 Hz, 2H), 7.82-7.67 (m, 3H), 7.36 (d, J=4.0 Hz, 1H), 6.83 (t, J=14.9 Hz, 2H), 5.45 (d, J=21.0 Hz, 2H), 2.47 (s, 3H), 2.41-2.25 (m, 3H).

Example 144

Preparation of 4-(3-(2-methylpyridin-4-yl)-1H-pyrazolo[3,4-c]pyridin-5-yl)-1-((2-(trifluoromethyl)pyridin-4-yl)methyl)pyridin-2(1H)-one

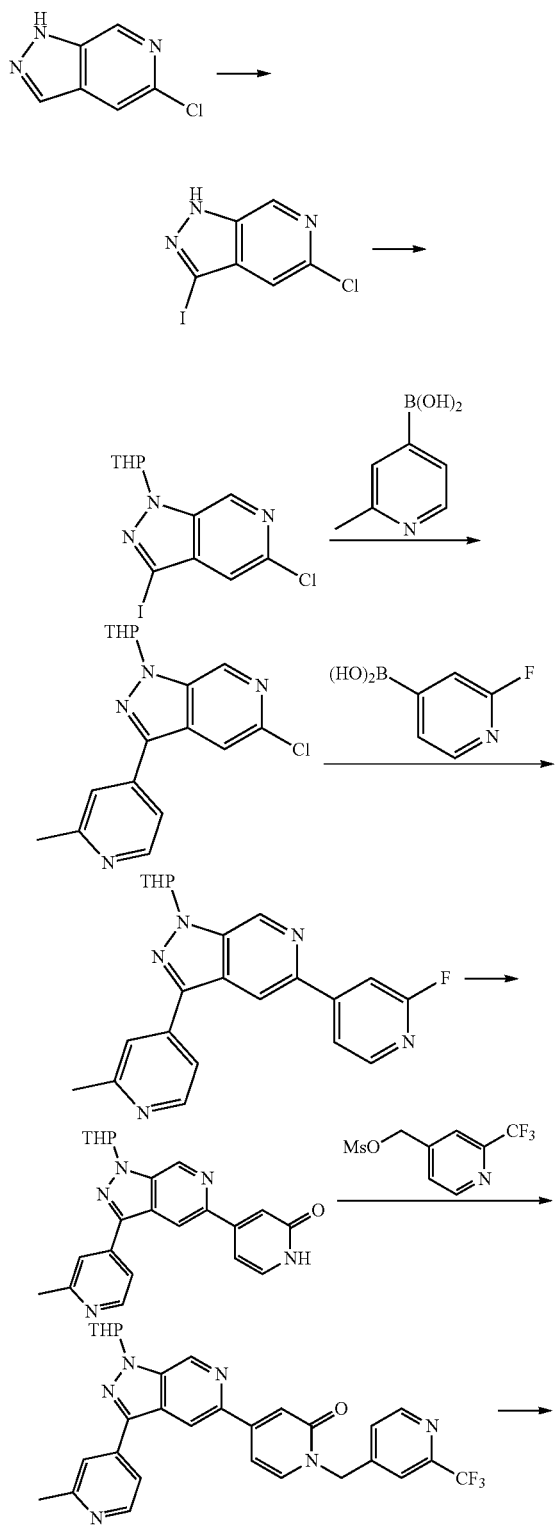

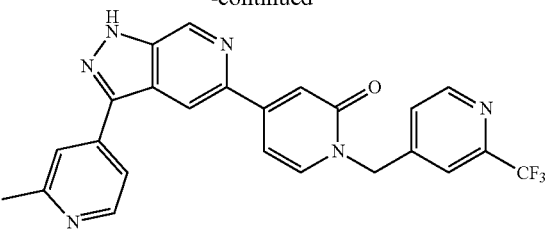

Step 1. 5-chloro-3-iodo-1H-pyrazolo[3,4-c]pyridine

To a solution of 5-chloro-1H-pyrazolo[3,4-c]pyridine (5 g, 32.6 mmol) in DMF (40 mL) was added iodine (17 g, 65.2 mmol), KOH (9.2 g, 163 mmol) portionwise under ice-water bath cooling. The reaction was stirred at room temperature overnight. The reaction mixture was concenteated under vacuum. The residue was dissolved in EtOAc (150 mL), which was washed with saturated $Na_2S_2O_3$ (50 mL) and $H_2O$ (100 mL). The aqueous layer was extracted with EtOAc (150 mL×4). The combined organic layers were washed with brine (150 mL×4), dried over anhydrous $Na_2SO_4$, filtered off, and concentrated under vacuum to give the crude title compound (4.84 g, yield: 53%), which was used without further purification.

Step 2. 5-chloro-3-iodo-1-(tetrahydro-2H-pyran-2-yl)-1H-pyrazolo[3,4-c]pyridine

To a solution of 5-chloro-3-iodo-1H-pyrazolo[3,4-c]pyridine (1 g, 3.58 mmol) in THF (10 mL) was added dihydropyrane (900 mg, 10.7 mmol) and PPTS (90 mg, 0.36 mmol). The reaction was stirred at 70° C. overnight. The reaction mixture was diluted with EtOAc (20 mL), washed with $H_2O$ (15 mL×2), brine (15 mL), dried over anhydrous $Na_2SO_4$, filtered off, and concentrated under vacuum. The residue was purified by silica gel flash column chromatography (PE: EtOAc=15:1~10:1) to give the title compound (1.08 g, yield: 82%).

Step 3. 5-chloro-3-(2-methylpyridin-4-yl)-1-(tetrahydro-2H-pyran-2-yl)-1H-pyrazolo[3,4-c]pyridine A mixture of 5-chloro-3-iodo-1-(tetrahydro-2H-pyran-2-yl)-1H-pyrazolo[3,4-c]pyridine (1.08 g, 3 mmol), (2-methylpyridin-4-yl)boronic acid (493 mg, 3.6 mmol), Pd(dppf)Cl$_2$-DCM (123 mg, 0.15 mmol) and $Na_2CO_3$ (636 mg, 6 mmol) in dioxane (20 mL) and $H_2O$ (4 mL) was stirred at 65° C. under $N_2$ overnight. After cooling to room temperature, it was diluted with EtOAc (50 mL), which was washed with $H_2O$ (50 mL×2), brine (15 mL), dried over anhydrous $Na_2SO_4$, filtered off, and concentrated under vacuum. The residue was purified by silica gel flash column chromatography (PE:EtOAc=10:1-2:1) to give the title compound (661 mg, yield: 67%).

Step 4. 5-(2-fluoropyridin-4-yl)-3-(2-methylpyridin-4-yl)-1-(tetrahydro-2H-pyran-2-yl)-1H-pyrazolo[3,4-c]pyridine A mixture of 5-chloro-3-(2-methylpyridin-4-yl)-1-(tetrahydro-2H-pyran-2-yl)-1H-pyrazolo[3,4-c]pyridine (661 mg, 2 mmol), (2-fluoropyridin-4-yl)boronic acid (338 mg, 2.4 mmol), Pd(dppf)Cl$_2$-DCM (164 mg, 0.2 mmol) and $Cs_2CO_3$ (1.63 g, 5 mmol) in dioxane (10 mL) and $H_2O$ (2 mL) was stirred at 110° C. under N₂ for 24 h. After cooling to room temperature, it was diluted with EtOAc (50 mL), which was washed with H₂O (50 mL×2), brine (15 mL), dried over anhydrous Na₂SO₄, filtered off, and concentrated under vacuum. The residue was purified by silica gel flash column chromatography (PE:EtOAc=10:1-EtOAc) to give the title compound (338 mg, yield: 43%).

Step 5. 4-(3-(2-methylpyridin-4-yl)-1-(tetrahydro-2H-pyran-2-yl)-1H-pyrazolo[3,4-c]pyridin-5-yl)pyridin-2(1H)-one A solution of 5-(2-fluoropyridin-4-yl)-3-(2-methylpyridin-4-yl)-1-(tetrahydro-2H-pyran-2-yl)-1H-pyrazolo[3,4-c]pyridine (338 mg, 0.87 mmol) in AcOH (10 mL) and H₂O (1 mL) was degassed with N₂ and stirred at 85° C. overnight. The reaction mixture was concentrated under vacuum. The residue was diluted with H₂O (10 mL), and neutralized by saturated aqueous Na₂CO₃ to pH of 8-9. The mixture was extracted with DCM/MeOH (10:1, 30 mL×2). The combined organic layers were washed with H₂O (30 mL×2), brine (30 mL×2), dried over anhydrous Na₂SO₄, filtered off, and concentrated. The residue was purified by silica gel flash column chromatography (DCM/MeOH=100:1-10:1) to give the title compound (84 mg, yield: 25%).

Step 6. 4-(3-(2-methylpyridin-4-yl)-1-(tetrahydro-2H-pyran-2-yl)-1H-pyrazolo[3,4-c]pyridin-5-yl)-1-((2-(trifluoromethyl)pyridin-4-yl)methyl)pyridin-2(1H)-one A mixture of 4-(3-(2-methylpyridin-4-yl)-1-(tetrahydro-2H-pyran-2-yl)-1H-pyrazolo[3,4-c]pyridin-5-yl)pyridin-2(1H)-one (87 mg, 0.23 mmol), (2-(trifluoromethyl)pyridin-4-yl)methyl methanesulfonate (85 mg, 0.35 mmol), K₂CO₃ (64 mg, 0.46 mmol) in DMF (5 ml) was degassed with N₂ and stirred at room temperature overnight. The reaction mixture was diluted with EtOAc (30 mL), washed with H₂O (15 mL×2), brine (15 mL), dried over anhydrous Na₂SO₄, filtered off, and concentrated under vacuum. The residue was purified by prep-TLC (DCM/MeOH=20:1) to give the title compound (78 mg, yield: 63%).

Step 7. 4-(3-(2-methylpyridin-4-yl)-1H-pyrazolo[3,4-c]pyridin-5-yl)-1-((2-(trifluoromethyl)pyridin-4-yl)methyl)pyridin-2(1H)-one A solution of 4-(3-(2-methylpyridin-4-yl)-1-(tetrahydro-2H-pyran-2-yl)-1H-pyrazolo[3,4-c]pyridin-5-yl)-1-((2-(trifluoromethyl)pyridin-4-yl)methyl)pyridin-2(1H)-one (78 mg, 0.143 mmol) in 6N HCl (4 mL) and MeOH (2 mL) was stirred at 65° C. for 3 h. The reaction solution was cooled to room temperature and neutralized by saturated Na₂CO₃ to pH of 8-9. The mixture was extracted with DCM/MeOH (10:1, 30 mL), which was washed with H₂O (15 mL×2), brine (15 mL), dried over anhydrous Na₂SO₄, filtered off, and concentrated under vacuum. The residue was purified by prep-TLC (DCM/MeOH=10/1) to give the title compound (55 mg, 83% yield). MS (ESI) m/z: 462.8 [M+1]⁺; ¹HNMR (400 MHz, DMSO-d6) δ 14.32 (s, 1H), 9.25 (s, 1H), 8.75 (d, J=4.1 Hz, 2H), 8.60 (d, J=5.1 Hz, 1H), 7.99 (dd, J=10.0, 6.6 Hz, 3H), 7.83 (s, 1H), 7.55 (d, J=4.8 Hz, 1H), 7.40 (d, J=1.8 Hz, 1H), 7.26 (dd, J=7.2, 1.9 Hz, 1H), 5.33 (s, 2H), 2.62 (s, 3H).

Example 96A and 96B

Preparation of (S)-1-(1-(3-bromo-5-fluorophenyl)ethyl)-4-(3-(1-methyl-1H-pyrazol-4-yl)-1H-indazol-5-yl)pyridin-2(1H)-one and (R)-1-(1-(3-bromo-5-fluorophenyl)ethyl)-4-(3-(1-methyl-1H-pyrazol-4-yl)-1H-indazol-5-yl)pyridin-2(1H)-one Two enantiomers of compound of Example 96 was separated by a method similar to Method 12. 96A (isomer 1 with shorter retention time). MS (ESI) m/z: 492.1 [M+1]⁺; ¹HNMR (400 MHz, DMSO-d6) δ 13.09 (s, 1H), 8.52 (s, 1H), 8.26 (s, 1H), 8.03 (s, 1H), 7.81 (d, J=7.3 Hz, 1H), 7.71 (dd, J=8.8, 1.2 Hz, 1H), 7.58 (d, J=8.6 Hz, 1H), 7.50 (d, J=8.3 Hz, 1H), 7.38 (s, 1H), 7.26 (d, J=9.7 Hz, 1H), 6.8 (d, J=1.8 Hz, 1H), 6.79 (dd, J=7.3, 2.0 Hz, 1H), 6.14 (q, J=7.1 Hz, 1H), 3.92 (s, 3H), 1.74 (d, J=7.2 Hz, 3H); 96B (isomer 2 with longer retention time): MS (ESI) m/z: 492.1 [M+1]⁺; ¹HNMR (400 MHz, DMSO-d6) δ 13.09 (s, 1H), 8.52 (s, 1H), 8.26 (s, 1H), 8.03 (s, 1H), 7.81 (d, J=7.3 Hz, 1H), 7.71 (dd, J=8.8, 1.2 Hz, 1H), 7.59 (d, J=8.7 Hz, 1H), 7.50 (d, J=8.3 Hz, 1H), 7.38 (s, 1H), 7.26 (d, J=9.7 Hz, 1H), 6.84 (d, J=1.8 Hz, 1H), 6.79 (dd, J=7.3, 2.0 Hz, 1H), 6.14 (q, J=7.1 Hz, 1H), 3.92 (s, 3H), 1.74 (d, J=7.2 Hz, 3H).

Table 2 lists examples that were prepared according to the procedures as described in methods 11 as indicated below the structure of each example by using the corresponding intermediates and reagents under appropriate conditions that could be accomplished by the skilled persons.

TABLE 2

| 145 | | (S)-1-(1-(3-bromo-5-fluorophenyl)-2-hydroxyethyl)-4-(3-(tetrahydro-2H-pyran-4-yl)-1H-indazol-5-yl)pyridin-2(1H)-one | 512.1 | 1H NMR (400 MHz, DMSO-d6) δ 12.83 (s, 1H), 8.20 (s, 1H), 7.85 (d, J = 7.3 Hz, 1H), 7.67 (d, J = 8.6 Hz, 1H), 7.53 (d, J = 8.7 Hz, 1H), 7.48 (d, J = 8.3 Hz, 1H), 7.37 (s, 1H), 7.23 (d, J = 9.6 Hz, 1H), 6.76 (d, J = 5.1 Hz, 1H), 6.73 (d, J = 7.3 Hz, 1H), 6.01-5.90 (m, 1H), 5.33 (t, J = 4.9 Hz, 1H), 4.20-4.11 (m, 1H), 4.11-4.01 (m, 1H), 3.95 (d, J = 10.9 Hz, 2H), 3.56-3.46 (m, 2H), 3.41-3.37 (m, 1H), 1.94-1.82 (m, 4H). |
|---|---|---|---|---|
| 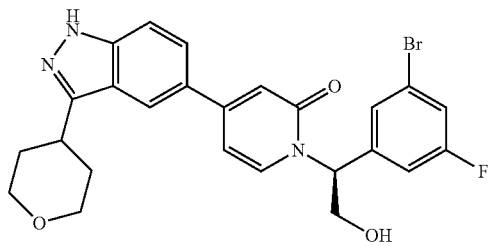 | | | | |
| (Method 11) | | | | |

TABLE 2-continued

| | | | | |
|---|---|---|---|---|
| 146 | 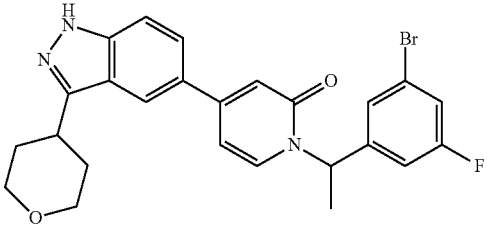 (Method 11) | 1-(1-(3-bromo-5-fluorophenyl)ethyl)-4-(3-(tetrahydro-2H-pyran-4-yl)-1H-indazol-5-yl)pyridin-2(1H)-one | 496.2 | $^1$H NMR (400 MHz, DMSO-d6) δ 12.82 (s, 1H), 8.19 (s, 1H), 7.77 (d, J = 5.3 Hz, 1H), 7.65 (d, J = 7.3 Hz, 1H), 7.57-7.41 (m, 2H), 7.35 (s, 1H), 7.22 (d, J = 8.2 Hz, 1H), 6.75 (d, J = 10.8 Hz, 2H), 6.12 (s, 1H), 3.94 (m, 2H), 3.50 (m, 2H), 3.42-3.36 (m, 1H), 2.01-1.80 (m, 4H), 1.72 (d, J = 4.4 Hz, 3H). |
| 147 | 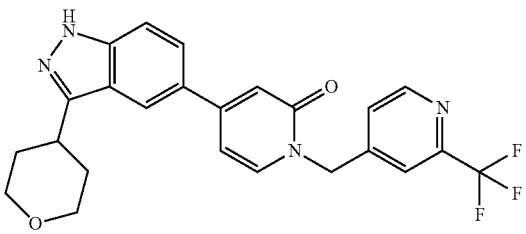 (Method 11) | 4-(3-(tetrahydro-2H-pyran-4-yl)-1H-indazol-5-yl)-1-((2-(trifluoromethyl)pyridin-4-yl)methyl)pyriidn-2(1H)-one | 455.2 | $^1$H NMR (400 MHz, DMSO-d6) δ 12.85 (s, 1H), 8.74 (s, 1H), 8.26 (s, 1H), 7.95 (d, J = 7.9 Hz, 1H), 7.83 (s, 1H), 7.72 (dd, J = 8.8, 1.5 Hz, 1H), 7.57 (s, 2H), 6.88-6.79 (m, 2H), 5.29 (s, 2H), 4.05-3.94 (m, 2H), 3.64-3.50 (m, 2H), 3.43-3.36 (m, 1H), 1.93 (m, 4H). |
| 148 | 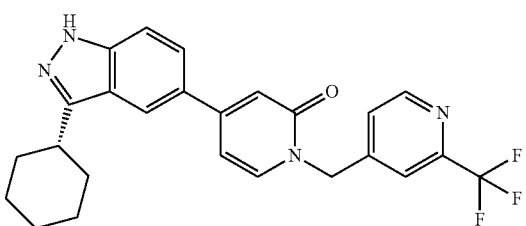 (Method 11) | 4-(3-((1r,4r)-4-hydroxycyclohexyl)-1H-indazol-5-yl)-1-((2-(trifluoromethyl)pyridin-4-yl)methyl)pyridin-2(1H)-one | 469.2 | $^1$H NMR (400 MHz, DMSO-d6) δ 12.75 (s, 1H), 8.72 (d, J = 4.7 Hz, 1H), 8.20 (s, 1H), 7.92 (d, J = 7.4 Hz, 1H), 7.81 (s, 1H), 7.67 (d, J = 8.5 Hz, 1H), 7.56-7.35 (m, 2H), 6.93-6.67 (m, 2H), 5.26 (s, 2H), 4.57 (d, J = 3.6 Hz, 1H), 3.57-3.44 (m, 1H), 3.10-2.98 (m, 1H), 2.04-1.88 (m, 4H), 1.76-1.62 (m, 2H), 1.47-1.28 (m, 2H). |
| 149 | 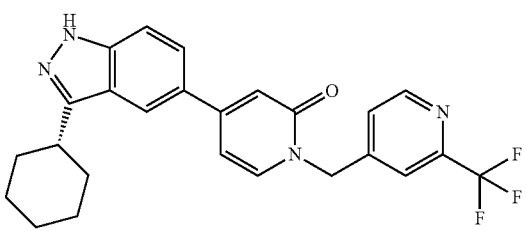 (Method 11) | 4-(3-((1s,4s)-4-hydroxycyclohexyl)-1H-indazol-5-yl)-1-((2-(trifluoromethyl)pyridin-4-yl)methyl)pyridin-2(1H)-one | 469.2 | $^1$H NMR (400 MHz, DMSO-d6) δ 12.76 (s, 1H), 8.71 (d, J = 5.0 Hz, 1H), 8.17 (s, 1H), 7.95-7.90 (m, 1H), 7.82 (s, 1H), 7.67 (dd, J = 8.8, 1.3 Hz, 1H), 7.51 (dd, J = 8.9, 4.9 Hz, 2H), 6.84-6.75 (m, 2H), 5.27 (s, 2H), 4.37 (d, J = 3.2 Hz, 1H), 3.86 (s, 1H), 3.20-3.10 (m, 1H), 2.17-2.03 (m, 2H), 2.02-1.87 (m, 1H), 1.81-1.55 (m, 6H). |
| 150 | 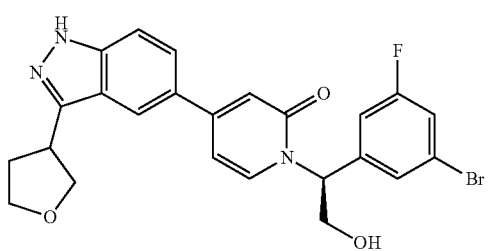 (Method 11) | 1-((S)-1-(3-bromo-5-fluorophenyl)-2-hydroxyethyl)-4-(3-(tetrahydrofuran-3-yl)-1H-indazol-5-yl)pyridin-2(1H)-one | 498.1 | $^1$H NMR (400 MHz, CD$_3$OD) δ 8.14 (s, 1H), 7.83 (d, J = 7.1 Hz, 1H), 7.70 (dd, J = 8.8, 1.4 Hz, 1H), 7.57 (d, J = 8.8 Hz, 1H), 7.39 (s, 1H), 7.31 (dd, J = 8.1, 1.8 Hz, 1H), 7.17 (d, J = 9.5 Hz, 1H), 6.90-6.81 (m, 2H), 6.15-6.07 (m, 1H), 4.29 (m, 1H), 4.25-4.17 (m, 2H), 4.11 (m, 1H), 4.06-4.01 (m, 1H), 4.00-3.91 (m, 2H), 2.54-2.44 (m, 1H), 2.32 (m, 1H). |

TABLE 2-continued

| | | | |
|---|---|---|---|
| 151 | (structure shown) (Method 11) | 1-((S)-1-(3-bromo-5-fluorophenyl)-2-hydroxyethyl)-4-(3-(3-hydroxypyrrolidin-1-yl)-1H-indazol-5-yl)pyridin-2(1H)-one | 512.1 | $^1$H NMR (400 MHz, CD$_3$OD) δ 8.13 (s, 1H), 7.83-7.78 (m, 1H), 7.65 (d, J = 8.8 Hz, 1H), 7.37 (d, J = 11.0 Hz, 2H), 7.33-7.28 (m, 1H), 7.16 (d, J = 9.5 Hz, 1H), 6.81 (t, J = 7.3 Hz, 2H), 6.13-6.06 (m, 1H), 4.57 (d, J = 2.1 Hz, 1H), 4.28 (dd, J = 12.1, 7.4 Hz, 1H), 4.20 (dd, J = 12.1, 5.2 Hz, 1H), 3.90-3.56 (m, 4H), 2.24-2.14 (m, 1H), 2.11-2.00 (m, 1H). |

Enzymatic Assay

Compounds were tested in a LanthaScreen™ time-resolved fluorescence energy transfer (TR-FRET) enzymatic assay from Invitrogen. The assay used human ERK2 (Mitogen Activated Kinase 1, Invitrogen, Cat. PV3311) recombinantly expressed as GST-tagged full-length protein purified from E. coli and activated in vitro with MAP2K1. The substrate was a recombinant truncated version (residues 19-96) of ATF2 fused with Green Fluorescent Protein (Invitrogen, Cat. PV4445). Test compounds were prepared and diluted in DMSO in 3-fold serial dilutions to 100× of the final testing concentrations. The compounds were then further diluted to 4× by the kinase reaction buffer (Invitrogen, Cat. PV3189). The enzymatic reaction for compound testing was performed in a white 384-well polypropylene plate (Packard, Cat. 6005214) with a total reaction volume of 10 μl containing 20 ng/ml ERK2, 400 nM substrate, and 5 μM ATP that is around its K$_m$. The assay started with loading 2.5 μl of ERK2 diluted in kinase reaction buffer to wells, followed by addition of equal volume of 4× compounds for 15-min incubation at the room temperature for pre-treatment. The enzymatic reaction was initiated by addition of 5 μl of mixture of the substrate and ATP prepared in kinase reaction buffer. After one hour reaction, 10 μl mixture of EDTA (final 10 mM) and terbium-labeled anti-pATF2 (pThr71) antibody (final 2 nM) (Invitrogen, Cat. PV4451) prepared in TR-FRET antibody dilution buffer (Invitrogen, Cat. PV3574) was added to stop the enzymatic reaction and produce TR-FRET signals. After 30 minutes of incubation at room temperature, the plate was read in Tecan Infinite F200 Pro with the following settings: Excitation 340 nm (30)/Emission1 495 nm (10)/Emission2 520 nm (25). The TR-FRET values were dimensionless numbers that were calculated as the ratio of the acceptor (Green Fluorescent Protein) signal to the donor (Terbium) signal. Percent of control was calculated as the percentage of compound-treated vs 1% DMSO vehicle-treated. The dose-response curves were generated and the ICsos were calculated by nonlinear sigmoid curve fitting using GraphPad Prism.

The IC$_{50}$ values of ERK2 biochemical activity for the examples disclosed herein are listed in Table 3, A: ≤10 nM; B: >10 nM and ≤50 nM; C: >50 nM and ≤100 nM; D.>100 nM.

Colo205 Cell Proliferation Assay

Compounds disclosed herein were tested for the inhibition of ERK2 by a Colo205 cell proliferation assay commonly known as MTT assay. In this assay, a complete media was prepared by adding 10% fetal bovine serum to RPMI-1640 medium (Life technology). Colon cancer cells (Colo205 cell line) were added to each of 88 wells of a 96 well plate at a seeding density of 5,000 cells/well/90 μL. The cells were allowed to attach to the plate by incubating at 37° C. for 24 hours. The compound was dissolved in DMSO (SIGMA). A solution of test compound was prepared in complete media by serial dilution to obtain the following concentrations: 500 μM, 150 μM, 50 μM, 15 μM, 5 μM, 1.5 μM, 0.5 μM, 0.15 μM and 0.05 μM. The test compound solution (10 μL) was added to each of 80 cell-containing wells. The final concentrations of the compound were following: 50 μM, 15 μM, 5 μM, 1.5 μM, 0.5 μM, 0.15 μM, 0.05 μM, 0.015 μM and 0.005 μM. The final concentration of DMSO is 0.5%. To the 8 remaining cell-containing wells, only complete media (containing 0.5% DMSO) was added to form a control group in order to measure maximal proliferation. To the remaining 8 empty wells, complete media was added to for a vehicle control group in order to measure background. The plates were incubated at 37° C. for 72 hours. 10 μL WST-8 solution (DOJINDO, Cell Counting KIT-8) was added to each well. The plates were further incubated at 37° C. for 2 hours, and then read for the absorbance using a microplate reader at 450 nm. The ERK2 enzymatic inhibition IC$_{50}$ values for the compounds disclosed herein ranged from 0.1 nM to 10 μM.

The IC$_{50}$ values of growth inhibition in Colo 205 cells for Compounds disclosed are listed in Table 3, A': ≤0.5 μM; B': >0.5 μM and ≤1 μM; C': >1.0 μM and ≤5 uM; D': >5 μM.

TABLE 3

| Example | ERK2 Activity* | Colo 205 Cell Activity** |
|---|---|---|
| 1 | A | A' |
| 2 | A | B' |
| 3 | B | C' |
| 4 | A | B' |
| 5 | B | C' |
| 6 | A | A' |
| 7 | B | C' |
| 8 | A | B' |
| 9 | A | B' |
| 10 | B | D' |
| 11 | B | D' |
| 12 | B | C' |
| 13 | A | B' |
| 14 | B | C' |
| 15 | A | A' |
| 16 | A | B' |
| 17 | A | B' |
| 18 | A | A' |
| 19 | A | C' |
| 20 | B | C' |
| 21 | A | C' |
| 22 | B | D' |
| 23 | C | C' |
| 24 | C | C' |
| 25 | A | A' |

TABLE 3-continued

| Example | ERK2 Activity* | Colo 205 Cell Activity** |
|---|---|---|
| 26 | A | A' |
| 27 | A | C' |
| 28 | A | A' |
| 29 | A | C' |
| 30 | A | A' |
| 31 | A | C' |
| 32 | A | A' |
| 33 | A | A' |
| 34 | B | C' |
| 35 | A | A' |
| 36 | A | A' |
| 37 | A | A' |
| 38 | A | B' |
| 39 | A | A' |
| 40 | A | A' |
| 41 | A | A' |
| 42 | A | B' |
| 43 | A | C' |
| 44 | A | B' |
| 45 | A | A' |
| 46 | A | A' |
| 47 | A | A' |
| 48 | A | B' |
| 49 | A | A' |
| 50 | A | B' |
| 51 | A | A' |
| 52 | A | C' |
| 53 | A | B' |
| 54 |  | D' |
| 55 | A | A' |
| 56 | A | B' |
| 57 | A | A' |
| 58 | A | B' |
| 59 | A | C' |
| 60 | A | B' |
| 61 | A | B' |
| 62 | A | B' |
| 63 | A | B' |
| 64 | A | C' |
| 65 | A | B' |
| 66 | A | B' |
| 67 | A | C' |
| 68 | A | C' |
| 69 | A | B' |
| 70 | A | B' |
| 71 | A | C' |
| 72 | A | B' |
| 73 | A | B' |
| 74 | A | B' |
| 75 | A | B' |
| 76 | A | B' |
| 77 | A | A' |
| 78 | B | C' |
| 79 | A | B' |
| 80 | A | C' |
| 81 | A | A' |
| 82 | A | B' |
| 83 | A | C' |
| 84 | A | A' |
| 85 | A | A' |
| 86 | A | A' |
| 87 | A | D' |
| 88 | A | C' |
| 89 | A | A' |
| 90 | A | A' |
| 91 | A | B' |
| 92 | A | A' |
| 93 | A | A' |
| 94 | A | C' |
| 95 | A | C' |
| 96 | A | B' |
| 97 | B | C' |
| 98 | A | A' |
| 99 | A | C' |
| 100 | B | C' |
| 101 | A | A' |
| 102 | A | A' |
| 103 | A | A' |
| 104 | B | B' |
| 105 | A | B' |
| 106 | A | B' |
| 107 | A | A' |
| 108 | A | C' |
| 109 | A | D' |
| 110 | A | B' |
| 111 | A | A' |
| 112 | A | C' |
| 113 | A | A' |
| 114 | A | A' |
| 115 | A | A' |
| 116 | A | C' |
| 117 | A | C' |
| 118 | A | A' |
| 119 | A | A' |
| 120 | A | C' |
| 121 | A | C' |
| 122 | A | C' |
| 123 | B | D' |
| 124 | A | B' |
| 125 |  | B' |
| 126 |  | D' |
| 127 |  | C' |
| 128 |  | A' |
| 129 |  | A' |
| 130 |  | A' |
| 131 |  | C' |
| 132 |  | C' |
| 133 |  | C' |
| 134 |  | C' |
| 135 |  | C' |
| 136 |  | C' |
| 137 |  | B' |
| 138 |  | B' |
| 139 |  | C' |
| 140 | A | C' |
| 141 |  | C' |
| 142 | A | A' |
| 142A |  | C' |
| 142B |  | A' |
| 143 | A | B' |
| 144 | A | C' |
| 96A | A | C' |
| 96B | A | A' |
| 145 | A | B' |
| 146 | A | C' |
| 147 | A | A' |
| 148 | A | C' |
| 149 | B | D' |
| 150 |  | C' |
| 151 |  | C' |

*A: <10 µM; B: >10 µM and ≤50 µM; C: >50 µM and ≤100 µM; D: >100 µM.
**A': ≤0.5 µM; B': >0.5 µM and ≤1 µM; C': >1.0 µM and ≤5 µM; D': >5 µM.

INDUSTRIAL APPLICABILITY

The compound of the present invention can be applied to the field of medicine.

What is claimed is:
1. A compound of formula I:

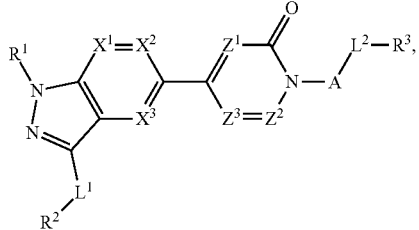

and/or a stereoisomer, a stable isotope, or a pharmaceutically acceptable salt thereof, wherein:

$R^1$ is selected from H and C1-C4 alkyl, $R^2$ is selected from H, D, —CN, halo, and an optionally substituted group selected from C1-C6 alkyl, C3-C8 cycloalkyl, C4-C8 cycloalkenyl, saturated or unsaturated 4-8 membered heterocyclyl containing 1-2 heteroatoms selected from N, O, and S as ring members, aryl, heteroaryl containing 1-4 heteroatoms selected from N, O, and S as ring members, and wherein the optional substituents for $R^2$ are 1-4 substituents independently selected from D, halo, —OH, =O, —CN, —$N_3$, —$CO_2R^4$, —C(O)N($R^{5a}R^{5b}$), —C(=$NR^6$)N($R^{5a}R^{5b}$), —C(O)$R^4$, —$SO_{0-2}R^7$, —SO(=$NR^6$)$R^7$, —$SO_{1-2}$N($R^{5a}R^{5b}$), —N($R^{5a}R^{5b}$), —N($R^{5a}$)C(O)$R^7$, —N($R^{5a}$)C(=$NR^6$)$R^7$, —N($R^{5a}$)$SO_{1-2}R^7$, —N($R^{5c}$)C(O)N($R^{5a}R^{5b}$), —N($R^{5c}$)C(=$NR^6$)N($R^{5a}R^{5b}$), —N($R^{5c}$)$SO_{1-2}$N($R^{5a}R^{5b}$), —N($R^{5a}$)$CO_2R^7$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, and wherein the optional substituents are 1-4 substituents independently selected from D, halo, —$OR^4$, and —N($R^{5c}$)$SO_{1-2}$N($R^{5a}R^{5b}$), wherein $R^4$, $R^{5a}$, $R^{5b}$ and $R^{5c}$ are independently selected from H and C1-C4 alkyl optionally substituted with 1-3 groups independently selected from D, halo, —OH, —$NH_2$, —NHMe and —$NMe_2$; $R^6$ is independently selected from H, —CN, —OH, C1-C4 alkyl and C1-C4 alkoxy; $R^7$ is C1-C4 alkyl optionally substituted with 1-3 groups independently selected from D, halo, —OH, —$NH_2$, —NHMe and —$NMe_2$; and two substituents on the same or adjacent carbon atoms of $R^2$ are optionally taken together to form a 5-6 membered ring that is saturated or aromatic and optionally contains 1-2 heteroatoms selected from N, O and S and is optionally substituted with 1-2 groups independently selected from D, -Me, halo, —OH, =O, C1-C4 alkoxy, —$NH_2$, C1-C4 alkylamino and di(C1-C4 alkyl)amino;

$R^3$ is selected from C3-C8 cycloalkyl, 5-8-membered heterocyclyl containing 1-2 heteroatoms selected from N, O, and S as ring members, aryl and heteroaryl containing 1-4 heteroatoms selected from N, O and S as ring members, wherein $R^3$ is optionally substituted with 1-3 substituents selected from of D, halo, —OH, =O, —CN, —$N_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —$CO_2R^8$, —C(O)N($R^{9a}R^{9b}$), —C(=$NR^{10}$)N($R^{9a}R^{9b}$), —C(O)$R^8$, —$SO_{0-2}R^{11}$, —SO(=$NR^{10}$)$R^{11}$, —$SO_{1-2}$N($R^{9a}R^{9b}$), —N($R^{9a}R^{9b}$), —N($R^{9a}$)C(O)$R^8$, —N($R^{9a}$)C(=$NR^{10}$)$R^8$, —N($R^{9a}$)$SO_{1-2}R^{11}$, —N($R^{9c}$)C(O)N($R^{9a}R^{9b}$), —N($R^{9c}$)C(=$NR^{10}$)N($R^{9a}R^{9b}$), —N($R^{9c}$)$SO_{1-2}$N($R^{9a}R^{9b}$) and —N($R^{9a}$)$CO_2R^{11}$; wherein $R^8$, $R^{9a}$, $R^{9b}$ and $R^{9c}$ are independently selected from H and C1-C4 alkyl, each of which is optionally substituted with 1-3 groups independently selected from D, halo, —OH, —$NH_2$, —NHMe, —$NMe_2$ and C1-C4 alkoxy; $R^{10}$ is independently selected from H, —CN, —OH, C1-C4 alkyl, and C1-C4 alkoxy; $R^{11}$ is C1-C4 alkyl optionally substituted with 1-3 groups independently selected from D, halo, —OH, —$NH_2$, —NHMe, —$NMe_2$ and C1-C4 alkoxy;

A is a bond, or is selected from C1-C4 alkylene, C2-C4 alkenylene, C2-C4 alkynylene, C3-C7 cycloalkyl and 4-7 membered heterocyclyl containing 1-2 heteroatoms selected from N, O, and S as ring members, wherein A is optionally substituted with 1-3 substituents independently selected from D, halo, —OH, =O, —CN, —$N_3$, —$R^{12}$, —$CO_2R^{12}$, —C(O)N($R^{13a}R^{13b}$), —C(=$NR^{14}$)N($R^{13a}R^{13b}$), —C(O)$R^{12}$, —$SO_{0-2}R^{14}$, —SO(=$NR^{15}$)$R^{14}$, —$SO_{1-2}$N($R^{13a}R^{13b}$), —N($R^{13a}R^{13b}$), —N($R^{13a}$)C(O)$R^{12}$, —N($R^{13a}$)C(=$NR^{15}$)$R^{14}$, —N($R^{13a}$)$SO_{1-2}R^{14}$, —N($R^{13c}$)C(O)N($R^{13a}R^{13b}$), —N($R^{13c}$)C(=$NR^{15}$)N($R^{13a}R^{13b}$), —N($R^{13c}$)$SO_{1-2}$N($R^{13a}R^{13b}$) and —N($R^{13a}$)$CO_2R^{14}$; wherein $R^{14}$ is selected from C1-C4 alkyl optionally substituted with 1-3 groups independently selected from D, halo, —OH, —$NH_2$, —NHMe, —$NMe_2$, —$OPO_3H_2$ and C1-C4 alkoxy; $R^{12}$, $R^{13a}$, $R^{13b}$ and $R^{13c}$ are independently selected from H and C1-C4 alkyl optionally substituted with 1-3 groups independently selected from D, halo, —OH, —$NH_2$, —NHMe, —$NMe_2$, —$OPO_3H_2$ and C1-C4 alkoxy; $R^{15}$ is selected from H, —CN, —OH, C1-C4 alkyl and C1-C4 alkoxy;

$L^1$ and $L^2$ are selected from a bond, —N($R^{16}$)—, —O—, —C(O)—, —S(O)$_{0-2}$— and —C($R^{17a}R^{17b}$)—, wherein $R^{16}$, $R^{17a}$, and $R^{17b}$ are independently selected from H and C1-C4 alkyl optionally substituted with 1-3 groups independently selected from D, halo, —OH, —$NH_2$, —NHMe, —$NMe_2$, —$OPO_3H_2$ and C1-C4 alkoxy;

optionally A and $L^2$ cyclize to form a C5-C7 cycloalkyl ring, a 4-7 membered heterocyclic ring containing 1-2 heteroatoms selected from N, O, and S, phenyl or a 5-6 membered heteroaryl ring containing 1-4 heteroatoms selected from N, O, and S as ring members, wherein the optional ring formed is optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl, —$CO_2R^{18}$, —CON($R^{19a}R^{19b}$), —$SO_2R^{20}$, —$SO_2$N($R^{19a}R^{19b}$)) and —N($R^{19a}R^{19b}$), wherein $R^{18}$, $R^{19a}$ and $R^{19b}$ are independently selected from H and C1-4 alkyl; $R^{20}$ is C1-C4 alkyl;

$X^1$, $X^2$, and $X^3$ are independently selected from N and $CR^{21}$, wherein $R^{21}$ is selected from H, D, halo, —CN, C1-C4 alkyl, C1-C4 haloalkyl, C1-C4 alkoxy and C1-C6 haloalkoxy;

$Z^1$ is selected from $CR^{22}$, wherein $R^{22}$ is selected from H, D, OH, halo, CN, C1-C4 alkyl, C1-C4 haloalkyl, C1-C4 alkoxy and C1-C6 haloalkoxy;

$Z^2$ is selected from N and $CR^{23}$, wherein $R^{23}$ is selected from H, D, —OH, —CN, C1-C4 alkyl, C1-C4 haloalkyl, C1-C4 alkoxy, and C1-C6 haloalkoxy, each of which is optionally substituted with 1-3 groups independently selected from D, halo, —CN, =O, —OH, C1-C4 alkoxy, C1-C4 alkyl, C1-C4 haloalkyl, C1-C4 hydroxyalkyl, C1-C4 haloalkoxy, —COOR$^{24}$, —SO$_2$R$^{25}$, —N(R$^{26a}$R$^{26b}$), —N(R$^{26a}$)C(O)R$^{25}$, —N(R$^{26a}$)SO$_2$R$^{25}$, —N(R$^{26a}$)COOR$^{25}$, —CON(R$^{26a}$R$^{26b}$) and —SO$_2$N(R$^{26a}$R$^{26b}$), wherein R$^{24}$, R$^{26a}$ and R$^{26b}$ are independently selected from H and C1-C4 alkyl; R$^{25}$ is C1-C4 alkyl;

Z$^3$ is selected from N and CR$^{27}$, wherein R$^{27}$ is selected from H, D, —OH, halo, —CN, C1-C4 alkyl, C1-C4 haloalkyl, C1-C4 alkoxy and C1-C6 haloalkoxy;

optionally R$^{23}$ cyclizes with A to form a 5-7 membered heterocyclic ring containing 1-2 heteroatoms selected from N, O, and S, optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl —CO$_2$R$^{28}$, —CON(R$^{29a}$R$^{29b}$), —SO$_2$R$^{30}$, —SO$_2$N($^{29a}$R$^{29b}$) and —N(R$^{29a}$R$^{29b}$), wherein R$^{28}$, R$^{29a}$ and R$^{29b}$ are independently selected from H and C1-C4 alkyl; R$^{30}$ is C1-C4 alkyl; and optionally R$^{23}$ cyclizes with R$^{27}$ to form a C5-C7 cycloalkyl ring, a 5-7 membered heterocyclic ring containing 1-2 heteroatoms selected from N, O, and S, phenyl or a 5-6 membered heteroaryl containing 1-4 heteroatoms selected from N, O, and S as ring members, wherein the optional ring formed by R$^{23}$ cyclizing with R$^{27}$ is optionally substituted with 1-2 groups independently selected from D, —CN, =O, —OH, C1-4 alkyl, C1-C4 haloalkyl, C1-C4 alkoxy, C1-C4 haloalkoxy, C1-C4 aminoalkyl, C1-C4 hydroxyalkyl, —CO$_2$R$^{31}$, —CON(R$^{32a}$R$^{32b}$), —SO$_2$R$^{33}$, —SO$_2$N($^{32a}$R$^{32b}$) and —N(R$^{32a}$R$^{32b}$), wherein R$^{31}$, R$^{32a}$ and R$^{32b}$ are independently selected from H and C1-C4 alkyl; R$^{33}$ is C1-C4 alkyl.

2. The compound according to claim 1, and/or a stereoisomer, a stable isotope, or a pharmaceutically acceptable salt thereof, wherein X$^1$, X$^2$, and X$^3$ are CH.

3. The compound according to claim 1, and/or a stereoisomer, a stable isotope, or a pharmaceutically acceptable salt thereof, wherein X$^1$, X$^2$, and X$^3$ are N.

4. The compound according to claim 1, and/or a stereoisomer, a stable isotope, or a pharmaceutically acceptable salt thereof, wherein X$^1$ is N, X$^2$ and X$^3$ are CH.

5. The compound according to claim 1, and/or a stereoisomer, a stable isotope, or a pharmaceutically acceptable salt thereof, wherein X$^2$ is N, X$^1$ and X$^3$ are CH.

6. The compound according to claim 1, and/or a stereoisomer, a stable isotope, or a pharmaceutically acceptable salt thereof, wherein X$^3$ is N, X$^1$ and X$^2$ are CH.

7. The compound according to claim 1, and/or a stereoisomer, a stable isotope, or a pharmaceutically acceptable salt thereof, wherein Z$^1$, Z$^2$, and Z$^3$ are CH.

8. The compound according to claim 1, and/or a stereoisomer, a stable isotope, or a pharmaceutically acceptable salt thereof, wherein R$^1$ is H.

9. The compound according to claim 1, and/or a stereoisomer, a stable isotope, or a pharmaceutically acceptable salt thereof, wherein L$^1$ is a bond.

10. The compound according to claim 1, and/or a stereoisomer, a stable isotope, or a pharmaceutically acceptable salt thereof, wherein R$^2$ is selected from C3-C8 cycloalkyl, 5-8 membered heterocyclyl containing 1-2 heteroatoms selected from N, O, and S as ring members, phenyl, 5-6 membered heteroaryl containing 1-3 heteroatoms selected from N, O, and S as ring members, and is optionally substituted with 1-3 groups independently selected from =O, D, halo, —CN, —OH, C1-C4 alkoxy, C1-C4 alkyl, C1-C4 haloalkyl, C1-C4 hydroxyalkyl, C1-C4 haloalkoxy, —COOR$^{34}$, —SO$^2$R$^{35}$, —N(R$^{36a}$R$^{36b}$), —N(R$^{36a}$)C(O)R$^{35}$, —N(R$^{36a}$)SO$_2$R$^{35}$, —N(R$^{36a}$)COOR$^{35}$, —CON(R$^{36a}$R$^{36b}$) and —SO$_2$N(R$^{36a}$R$^{36b}$), wherein R$^{34}$, R$^{36a}$ and R$^{36b}$ are independently selected from H and C1-C4 alkyl; R$^{35}$ is C1-C4 alkyl.

11. The compound according to claim 1, and/or a stereoisomer, a stable isotope, or a pharmaceutically acceptable salt thereof, wherein R$^2$ is selected from phenyl, pyridine, pyridone, pyrazine, pyridazine, pyrazole, triazole, tetrazole, thiazole, oxazole, imidazole, isothiazole, isoxazole, furan, 1,2,5-oxadiazole and thiophene, each of which is optionally substituted with one or two groups independently selected from =O, D, halo, —CN, hydroxy, C1-C4 alkoxy, C1-C4 alkyl, C1-C4 haloalkyl, C1-C4 hydroxyalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —N(R$^{36a}$)SO$_2$R$^{35}$, —N(R$^{36a}$)COOR$^{35}$, —CON(R$^{36a}$R$^{36b}$) and —SO$_2$N(R$^{36a}$R$^{36b}$), wherein R$^{34}$, R$^{36a}$ and R$^{36b}$ are independently selected from H and C1-C4 alkyl; R$^{35}$ is C1-C4 alkyl.

12. The compound according to claim 1, and/or a stereoisomer, a stable isotope, or a pharmaceutically acceptable salt thereof, wherein R$^2$ is selected from cyclobutyl, cyclopentyl, cyclohexyl, cyclohexenyl, tetrahydropyran, dihydropyran, tetrahydrofuran, oxetane, azetidine, pyrrolidine, piperidine, piperazine, morpholine, tetrahydrothiopyran, and tetrahydrothiofuran, each of which is optionally substituted with one or two groups independently selected from =O, D, halo, —CN, —OH, C1-C4 alkoxy, C1-C4 alkyl, C1-C4 haloalkyl, C1-C4 hydroxyalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —N(R$^{36a}$)SO$_2$R$^{35}$, —N(R$^{36a}$)COOR$^{35}$, —CON(R$^{36a}$R$^{36b}$) and —SO$_2$N(R$^{36a}$R$^{36b}$), wherein R$^{34}$, R$^{36a}$ and R$^{36b}$ are independently selected from H and C1-C4 alkyl; R$^{35}$ is C1-C4 alkyl.

13. The compound of claim 1, and/or a stereoisomer, a stable isotope, or a pharmaceutically acceptable salt thereof, wherein R$^3$ is phenyl and is optionally substituted with up to three groups independently selected from halo, D, —CN, C1-C4 alkoxy, C1-C4 alkyl, C1-C4 haloalkyl, C1-C4 haloalkoxy, —SR$^{35}$, —SO$_2$R$^{35}$, —N(R$^{36a}$R$^{36b}$), —N(R$^{36a}$)C(O)R$^{35}$ and —SO$_2$N(R$^{36a}$R$^{36b}$), wherein R$^{36a}$ and R$^{36b}$ are independently selected from H, C1-C4 alkyl and C1-C4 haloalkyl; R$^{35}$ is C1-C4 alkyl.

14. The compound of claim 1, and/or a stereoisomer, a stable isotope, or a pharmaceutically acceptable salt thereof, wherein R$^3$ is oxazolyl, isoxazolyl, thiophenyl, thiazolyl, pyridinyl, pyrimidinyl, pyrazinyl or pyridazinyl, and is optionally substituted with up to three groups independently selected from D, halo, —CN, C1-C4 alkoxy, C1-C4 alkyl, C1-C4 haloalkyl, C1-C4 haloalkoxy, —SO$_2$R$^{35}$, —N(R$^{36a}$R$^{36b}$), —N(R$^{36a}$)C(O)R$^{35}$ and —SO$_2$N(R$^{36a}$R$^{36b}$), wherein R$^{36a}$ and R$^{36b}$ are independently selected from H, C1-C4 alkyl and C1-C4 haloalkyl; R$^{35}$ is C1-C4 alkyl.

15. The compound according to claim 1, and/or a stereoisomer, a stable isotope, or a pharmaceutically acceptable salt thereof, wherein A is selected from cyclopropane-1,1-diyl, cyclopropane-1,2-diyl, —CHR$^{37}$— and —C(R$^{37}$)$_2$—, wherein R$^{37}$ is selected from H, D and C1-C2 alkyl optionally substituted with up to three groups independently selected from D, —OH, halo, —NH$_2$, C1-C2 alkylamino, di(C1-C2 alky)amino and C1-C4 alkoxy.

16. The compound of claim 15, and/or a stereoisomer, a stable isotope, or a pharmaceutically acceptable salt thereof, wherein A is

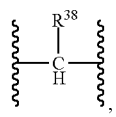

wherein $R^{38}$ is methyl or ethyl, and is optionally substituted with at least one substituent selected from fluoro, amino, hydroxy, methylamino, ethylamino, dimethylamino, —OP(O)(OH)$_2$, methoxy and ethoxy.

17. The compound of claim 15, and/or a stereoisomer, a stable isotope, or a pharmaceutically acceptable salt thereof, wherein A is —C(R$^{39}$)$_2$—, wherein R$^{39}$ is H or D.

18. The compound of claim 1, and/or a stereoisomer, a stable isotope, or a pharmaceutically acceptable salt thereof, wherein $Z^2$ is CR$^{23}$, wherein R$^{23}$ is selected from H, C1-C4 alkyl, C3-C7 cycloalkyl and 5-8 membered heterocyclyl containing 1-2 heteroatoms selected from N, O, and S as ring members, and is optionally substituted with up to three groups independently selected from halo, —CN, C1-C4 alkoxy, C1-C4 alkyl, C1-C4 haloalkyl, C1-C4 haloalkoxy, —SO$_2$R$^{35}$, —N(R$^{38a}$R$^{36b}$), —N(R$^{36a}$)C(O)R$^{35}$, —SO$_2$N(R$^{38a}$R$^{36b}$) and —N(R$^{38a}$)SO$_2$R$^{35}$, wherein R$^{36a}$ and R$^{36b}$ are independently selected from H, C1-C4 alkyl and C1-C4 haloalkyl; R$^{35}$ is C1-C4 alkyl.

19. The compound of claim 1, and/or a stereoisomer, a stable isotope, or a pharmaceutically acceptable salt thereof, wherein $Z^1$, $Z^2$, and $Z^3$ are CR$^{38}$, wherein CR$^{38}$ is independently selected from H, methyl, and halo.

20. The compound of claim 1, which is a compound of Formula IA, and/or a stereoisomer, a stable isotope, or a pharmaceutically acceptable salt thereof:

(IA)

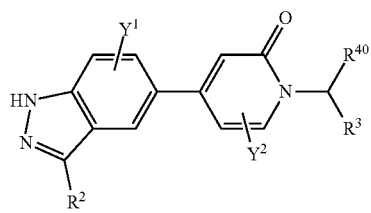

wherein $R^2$ is phenyl, pyridinyl, pyrimidinyl, triazinyl, pyrazolyl, imidazolyl, isoxazolyl, isothiazolyl, oxazolyl, oxadizolyl, triazolyl or thiazolyl, which is optionally substituted with up to two groups independently selected from D, F, Cl, Br, —CN, -Me, -Et, —Pr, i-Pr, butyl, isobutyl, sec-butyl, t-butyl, —CHF$_2$CF$_3$, cyclopropyl, —OMe, —OEt, —Pr$^i$, —OPr, —OBu, —OBu$^i$, —OBu$^s$, —OBu$_t$, —OCF$_3$, —O(cyproyl), —(CH$_2$)$_2$OH, —(CH$_2$)$_2$OMe, —(CH$_2$)C(OH)CH$_2$OH, —(CH$_2$)$_2$NHSO$_2$NH$_2$, —C(OH)(CH$_3$)$_3$, —O(CH$_2$)$_2$OH, —O(CH$_2$)$_2$OMe, —O(CH$_2$)C(OH)CH$_2$OH and —O(CH$_2$)$_2$NHSO$_2$NH$_2$;

or $R^2$ is a non-aromatic cycloalkyl or heterocyclic group which is optionally substituted with 1-3 groups groups independently selected from D, F, Cl, —CN, —NH$_2$, —NHMe, —NMe$_2$, -Me, -Et, —Pr$^i$, —NHSO$_2$Me, —NHCOMe, =O, —OH, —OMe, —CH$_2$OH, and —CF$_3$;

$Y^1$ and $Y^2$ are independently H, F, Cl or Me;

wherein $R^3$ is phenyl, pyridine or thienyl, optionally substituted with 1-2 groups independently selected from D, —NH$_2$, halo, —CN, C1-C4 alkyl, C1-C4 alkoxy, C1-C4 haloalkyl, C1-C4 haloalkoxy, —COOR$^{34}$, —SO$_2$R$^{35}$, —N(R$^{36a}$R$^{36b}$), —N(R$^{36a}$)C(O)R$^{35}$, —SO$_2$N(R$^{36a}$R$^{36b}$) and —N(R$^{36a}$)SO$_2$R$^{35}$, wherein R$^{34}$, R$^{36a}$ and R$^{36b}$ are independently selected from H and C1-C4 alkyl; R$^{35}$ is C1-C4 alkyl; and $R^{40}$ is selected from H, D and —CH$_2$R*, wherein R* is selected from H, —OH, F, —NH$_2$, —NHMe, —NMe$_2$, —OP(O)(OH)$_2$ and —OMe.

21. The compound of claim 1, which is a compound of Formula IB, and/or a stereoisomer, a stable isotope, or a pharmaceutically acceptable salt thereof:

(IB)

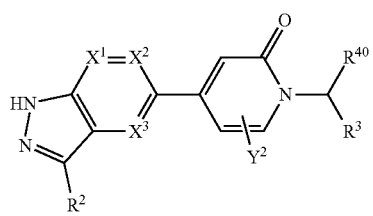

wherein $X^1$, $X^2$ and $X^3$ are independently selected from —CH— and —N—, or the structure

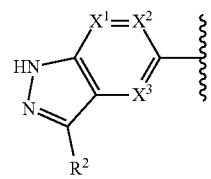

in Formula IB is selected from:

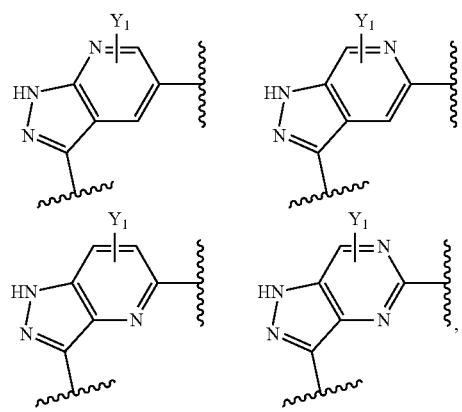

wherein $Y^1$ is H, F, Cl, or Me;
wherein $Y^2$ is H, F, Cl, or Me;
wherein $R^2$ is phenyl, pyridinyl, pyrimidinyl, triazinyl, pyrazolyl, imidazolyl, isoxazolyl, isothiazolyl, oxazolyl, oxadizolyl, triazolyl or thiazolyl, which is optionally substituted with up to two groups independently selected from D, F, Cl, Br, —CN, -Me, -Et, —Pr, i-Pr, butyl, isobutyl, sec-butyl, t-butyl, —CHF$_2$CF$_3$, cyclopropyl, —OMe, —OEt, —Pr$^i$, —OPr, —OBu, —OBu$^i$, —OBu$^s$, —OBu$^t$, —OCF$_3$, —O(cyproyl), —(CH$_2$)$_2$OH, —(CH$_2$)$_2$OMe, —(CH$_2$)C(OH)CH$_2$OH, —(CH$_2$)$_2$NHSO$_2$NH$_2$, —C(OH)(CH$_3$)$_3$, —O(CH$_2$)$_2$OH, —O(CH$_2$)$_2$OMe, —O(CH$_2$)C(OH)CH$_2$OH and —O(CH$_2$)$_2$NHSO$_2$NH$_2$;

or R² is a non-aromatic cycloalkyl or heterocyclic group which is optionally substituted with 1-3 groups groups independently selected from D, F, Cl, —CN, —NH₂, —NHMe, —NMe₂, -Me, -Et, —Pr$^i$, —NHSO₂Me, —NHCOMe, =O, —OH, —OMe, —CH₂OH, and —CF₃;

wherein R³ is phenyl, pyridine or thienyl, optionally substituted with 1-2 groups independently selected from D, —NH₂, halo, —CN, C1-C4 alkyl, C1-C4 alkoxy, C1-C4 haloalkyl, C1-C4 haloalkoxy, —COOR³⁴, —SO₂R³⁵, —N(R³⁶ᵃR³⁶ᵇ), —N(R³⁶ᵃ)C(O)R³⁵, —SO₂N(R³⁶ᵃR³⁶ᵇ) and —N(R³⁶ᵃ)SO₂R³⁵, wherein R³⁴, R³⁶ᵃ and R³⁶ᵇ are independently selected from H and C1-C4 alkyl; R³⁵ is C1-C4 alkyl; and wherein R⁴⁰ is selected from H, D and —CH₂R*, wherein R* is selected from H, —OH, F, —NH₂, —NHMe, —NMe₂, —OP(O)(OH)₂ and —OMe.

22. The compound of claim 1, which is a compound of Formula IC, and/or a stereoisomer, a stable isotope, or a pharmaceutically acceptable salt thereof:

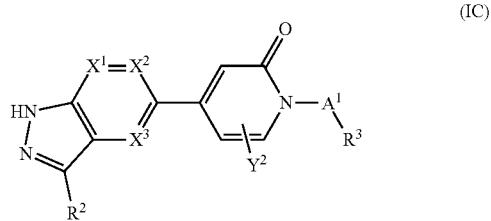

(IC)

wherein A1 is selected from —CR⁴¹R⁴²—, wherein R⁴¹ and R⁴² are independently selected from H, D, F, —CH₃, —CD₃, -Et, and —Pr;

wherein X¹, X² and X³ are independently selected from —CH— and —N—, or the structure

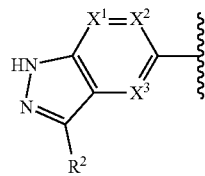

in Formula IC is selected from:

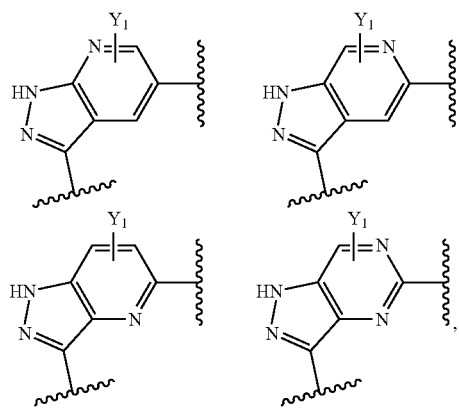

wherein Y¹ is H, F, Cl, or Me;

wherein Y² is H, F, Cl, or Me;

wherein R² is phenyl, pyridinyl, pyrimidinyl, triazinyl, pyrazolyl, imidazolyl, isoxazolyl, isothiazolyl, oxazolyl, oxadizolyl, triazolyl or thiazolyl, which is optionally substituted with up to two groups independently selected from D, F, Cl, Br, —CN, -Me, -Et, —Pr, i-Pr, butyl, isobutyl, sec-butyl, t-butyl, —CHF₂CF₃, cyclopropyl, —OMe, —OEt, —Pr$^i$, —OPr, —OBu, —OBu$^i$, —OBu$^s$, —OBu$^t$, —OCF₃, —O(cyclopropyl), —(CH₂)₂OH, —(CH₂)₂OMe, —(CH₂)C(OH)CH₂OH, —(CH₂)₂NHSO₂NH₂, —C(OH)(CH₃)₃, —O(CH₂)₂OH, —O(CH₂)₂OMe, —O(CH₂)C(OH)CH₂OH and —O(CH₂)₂NHSO₂NH₂;

or R² is a non-aromatic cycloalkyl or heterocyclic group which is optionally substituted with 1-3 groups groups independently selected from D, F, Cl, —CN, —NH₂, —NHMe, —NMe₂, -Me, -Et, —Pr$^i$, —NHSO₂Me, —NHCOMe, =O, —OH, —OMe, —CH₂OH, and —CF₃; and wherein R³ is phenyl, pyridine or thienyl, optionally substituted with 1-2 groups independently selected from D, —NH₂, halo, —CN, C1-C4 alkyl, C1-C4 alkoxy, C1-C4 haloalkyl, C1-C4 haloalkoxy, —COOR³⁴, —SO₂R³⁵, —N(R³⁶ᵃR³⁶ᵇ), —N(R³⁶ᵃ)C(O)R³⁵, —SO₂N(R³⁶ᵃR³⁶ᵇ) and —N(R³⁶ᵃ)SO₂R³⁵, wherein R³⁴, R³⁶ᵃ and R³⁶ᵇ are independently selected from H and C1-C4 alkyl; R³⁵ is C1-C4 alkyl.

23. The compound of claim 20, and/or a stereoisomer, a stable isotope, or a pharmaceutically acceptable salt thereof, wherein R² is selected from:

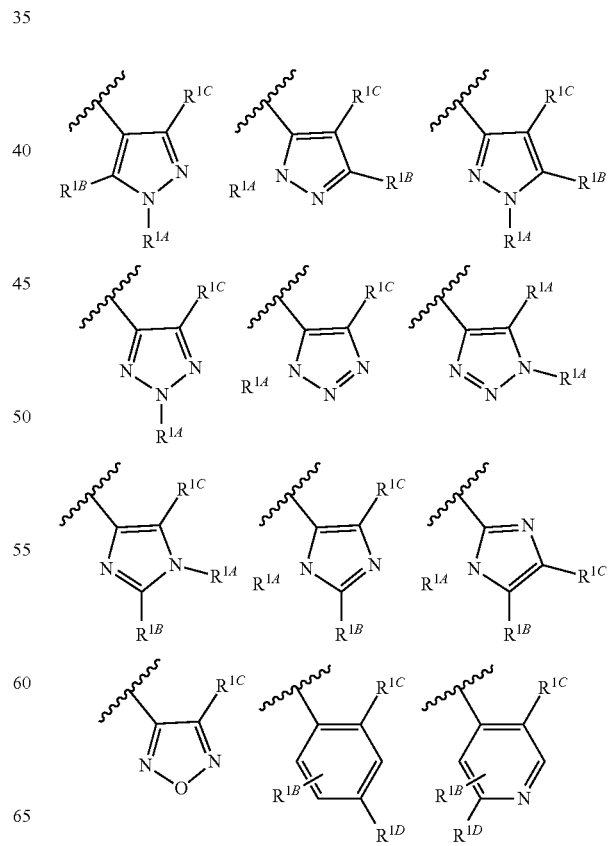

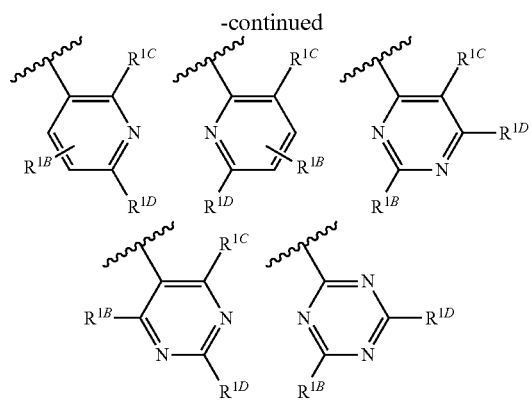

wherein $R^{1A}$ is independently selected from H, D, Me, Et, propyl, isopropyl, butyl, isobutyl, sec-butyl, t-butyl, —CH$_2$F —CF$_2$H, —CF$_3$, and cyclopropyl; and $R^{1B}$, $R^{1C}$ and $R^{1D}$ are independently selected from H, D, Me, Et, propyl, isopropyl, butyl, isobutyl, sec-butyl, t-butyl, —CH$_2$F—CF$_2$H, —CF$_3$, cyclopropyl, —OMe, —OEt, —OPr, —OPr$^i$, —OBu, —OBu$^i$, —OBu$^s$, —OBu$^t$, —OCF$_3$, —O(cycloproyl), —C(OH)Me$_2$, —CN, Cl and F.

24. The compound of claim 20, and/or a stereoisomer, a stable isotope, or a pharmaceutically acceptable salt thereof, wherein $R^2$ is selected from:

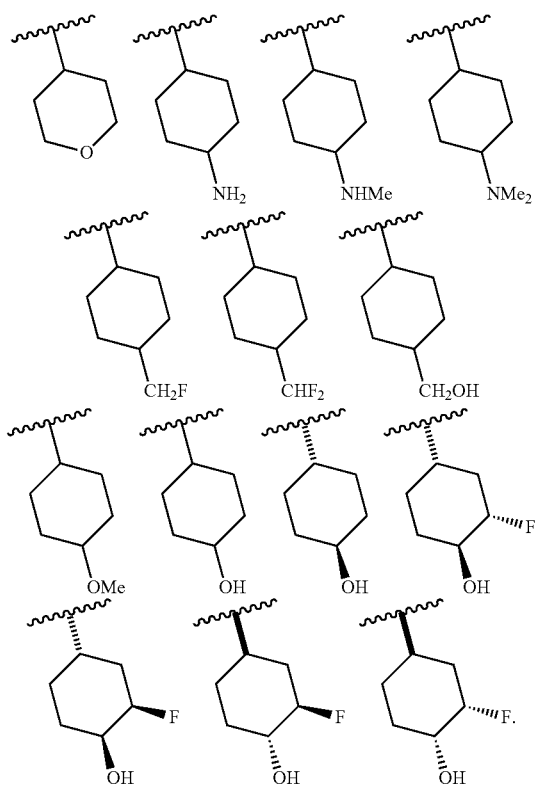

25. The compound of claim 1, which is selected from the following compounds, stereoisomers, stable isotopes and pharmaceutically acceptable salts thereof:

(S)-1-(1-(3-chlorophenyl)-2-hydroxyethyl)-4-(3-(2-methyl-pyridin-4-yl)-1H-indazol-5-yl)pyridin-2(1H)-one, (S)-1-(1-(4-chloro-3-fluorophenyl)-2-hydroxyethyl)-4-(3-(2-methylpyridin-4-yl)-1H-indazol-5-yl)pyridin-2(1H)-one, (S)-1-(1-(3-chlorophenyl)-2-hydroxyethyl)-4-(3-(tetra-hydro-2H-pyran-4-yl)-1H-indazol-5-yl)pyridin-2(1H)-one, (S)-1-(1-(3-chlorophenyl)-2-hydroxyethyl)-4-(3-(1,3-di-methyl-1H-pyrazol-4-yl)-1H-indazol-5-yl)pyridin-2(1H)-one, (S)-1-(1-(3-chlorophenyl)-2-hydroxyethyl)-4-(3-(6-iso-propoxypyridin-3-yl)-1H-indazol-5-yl)pyridin-2(1H)-one, (S)-1-(1-(3-chlorophenyl)-2-hydroxyethyl)-4-(3-(1-methyl-1H-pyrazol-4-yl)-1H-indazol-5-yl)pyridin-2(1H)-one, (S)-1-(1-(3-chlorophenyl)-2-hydroxyethyl)-4-(3-(2-iso-propoxypyridin-4-yl)-1H-indazol-5-yl)pyridin-2(1H)-one, (S)-1-(1-(3-chloro-4-fluorophenyl)-2-hydroxyethyl)-4-(3-(6-(2-hydroxypropan-2-yl)pyridin-3-yl)-1H-inda-zol-5-yl)pyridin-2(1H)-one, (S)-1-(1-(3-chloro-4-fluorophenyl)-2-hydroxyethyl)-4-(3-(2-(2-hydroxypropan-2-yl)pyridin-4-yl)-1H-inda-zol, (S)-1-(1-(3-chlorophenyl)-2-hydroxyethyl)-4-(3-methyl-1H-indazol-5 yl)pyridin-2(1H)-one, (S)-1-(1-(3-chlorophenyl)-2-hydroxyethyl)-4-(1H-inda-zol-5-yl)pyridin-2(1H)-one, (S)-1-(1-(3-chlorophenyl)-2-hydroxyethyl)-4-(3-ethyl-1H-indazol-5-yl)pyridin-2(1H)-one, (S)-4-(3-amino-1H-indazol-5-yl)-1-(1-(3-chlorophenyl)-2-hydroxyethyl)pyridin-2(1H)-one, (S)-1-(1-(3-chlorophenyl)-2-hydroxyethyl)-4-(3-(2-meth-ylpyridin-4-yl)-1H-pyrazolo[3,4-b]pyridin-5-yl)pyri-din-2(1H)-one, (S)-1-(1-(4-chloro-3-fluorophenyl)-2-hydroxyethyl)-4-(3-(2-methylpyridin-4-yl)-1H-pyrazolo[3,4-b]pyridin-5-yl)pyridin-2(1H)-one, (S)-1-(1-(3-bromo-5-fluorophenyl)-2-hydroxyethyl)-4-(3-(2-methylpyridin-4-yl)-1H-indazol-5-yl)pyridin-2(1H)-one, (S)-1-(1-(3-chlorophenyl)-2-hydroxyethyl)-4-(3-(methyl-amino)-1H-indazol-5-yl)pyridin-2(1H)-one, 1-((S)-1-(3-chlorophenyl)-2-hydroxyethyl)-4-(3-(3-hy-droxypyrrolidin-1-yl)-1H-indazol-5-yl)pyridin-2(1H)-one, (S)-1-(1-(3-chlorophenyl)-2-hydroxyethyl)-4-(3-((1-methyl-1H-pyrazol-5-yl)amino)-1H-indazol-5-yl)pyri-din-2(1H)-one, (S)-1-(1-(3-bromophenyl)-2-hydroxyethyl)-4-(3-(2-methylpyridin-4-yl)-1H-indazol-5-yl)pyridin-2(1H)-one, (S)-1-(1-(5-chloro-2-fluorophenyl)-2-hydroxyethyl)-4-(3-(2-methylpyridin-4-yl)-1H-indazol-5-yl)pyridin-2(1H)-one, (S)-1-(1-(3-chloro-4-fluorophenyl)-2-hydroxyethyl)-4-(3-(2-methylpyridin-4-yl)-1H-indazol-5-yl)pyridin-2(1H)-one, (R)-1-(1-(3-chlorophenyl)-2-hydroxyethyl)-4-(3-(2-methylpyridin-4-yl)-1H-indazol-5-yl)pyridin-2(1H)-one, (S)-1-(1-(4-chlorophenyl)-2-hydroxyethyl)-4-(3-(2-meth-ylpyridin-4-yl)-1H-indazol-5-yl)pyridin-2(1H)-one, (S)-1-(1-(3-fluoro-5-(trifluoromethyl)phenyl)-2-hydroxy-ethyl)-4-(3-(2-methylpyridin-4-yl)-1H-indazol-5-yl)pyridin-2(1H)-one, (S)-1-(1-(3-chloro-4-fluorophenyl)-2-hydroxyethyl)-4-(3-(6-isopropoxypyridin-3-yl)-1H-indazol-5-yl)pyridin-2(1H)-one,
(S)-1-(1-(3-chloro-2-fluorophenyl)-2-hydroxyethyl)-4-(3-(2-methylpyridin-4-yl)-1H-indazol-5-yl)pyridin-2(1H)-one,
(S)-1-(1-(3-bromo-4-fluorophenyl)-2-hydroxyethyl)-4-(3-(2-methylpyridin-4-yl)-1H-indazol-5-yl)pyridin-2(1H)-one,
(S)-1-(1-(3-chloro-4-fluorophenyl)-2-hydroxyethyl)-4-(3-(1-methyl-1H-pyrazol-4-yl)-1H-indazol-5-yl)pyridin-2(1H)-one,
(S)-1-(1-(4-chloro-3-fluorophenyl)-2-hydroxyethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(6-isopropoxypyridin-3-yl)-1H-indazol-5-yl)pyridin-2(1H)-one,
(S)-1-(1-(3-fluoro-5-(trifluoromethyl)phenyl)-2-hydroxyethyl)-4-(3-(1-methyl-1H-pyrazol-4-yl)-1H-indazol-5-yl)pyridin-2(1H)-one,
(S)-1-(2-hydroxy-1-(3-(trifluoromethyl)phenyl)ethyl)-4-(3-(1-methyl-1H-pyrazol-4-yl)-1H-indazol-5-yl)pyridin-2(1H)-one,
(S)-1-(2-hydroxy-1-(3-(trifluoromethyl)phenyl)ethyl)-4-(3-(6-isopropoxypyridin-3-yl)-1H-indazol-5-yl)pyridin-2(1H)-one,
(S)-1-(1-(3-bromophenyl)-2-hydroxyethyl)-4-(3-(6-isopropoxypyridin-3-yl)-1H-indazol-5-yl)pyridin-2(1H)-one,
(S)-1-(1-(3-bromophenyl)-2-hydroxyethyl)-4-(3-(1-methyl-1H-pyrazol-4-yl)-1H-indazol-5-yl)pyridin-2(1H)-one,
(S)-1-(1-(3-bromo-4-fluorophenyl)-2-hydroxyethyl)-4-(3-(1-methyl-1H-pyrazol-4-yl)-1H-indazol-5-yl)pyridin-2(1H)-one,
(S)-1-(2-hydroxy-1-(3-iodophenyl)ethyl)-4-(3-(1-methyl-1H-pyrazol-4-yl)-1H-indazol-5-yl)pyridin-2(1H)-one,
(S)-1-(2-hydroxy-1-(3-iodophenyl)ethyl)-4-(3-(6-isopropoxypyridin-3-yl)-1H-indazol-5-yl)pyridin-2(1H)-one,
(S)-1-(2-hydroxy-1-(3-iodophenyl)ethyl)-4-(3-(2-methylpyridin-4-yl)-1H-indazol-5-yl)pyridin-2(1H)-one,
(S)-1-(1-(3-chlorophenyl)-2-hydroxyethyl)-4-(3-(1-methyl-1H-pyrazol-5-yl)-1H-indazol-5-yl)pyridin-2(1H)-one,
(S)-1-(1-(3-chlorophenyl)-2-hydroxyethyl)-4-(3-(1,5-dimethyl-1H-pyrazol-4-yl)-1H-indazol-5-yl)pyridin-2(1H)-one,
(S)-1-(1-(3-chlorophenyl)-2-hydroxyethyl)-4-(4-fluoro-3-(2-methyl-pyridin-4-yl)-1H-indazol-5-yl)pyridin-2(1H)-one,
(S)-1-(1-(3-chlorophenyl)-2-hydroxyethyl)-4-(6-fluoro-3-(2-methylpyridin-4-yl)-1H-indazol-5-yl)pyridin-2(1H)-one,
1-(3-bromo-5-fluorobenzyl)-4-(3-(2-methylpyridin-4-yl)-1H-indazol-5-yl)pyridin-2(1H)-one,
1-(3-chlorobenzyl)-4-(3-(2-methylpyridin-4-yl)-1H-indazol-5-yl)pyridin-2(1H)-one,
1-(5-bromo-2-fluorobenzyl)-4-(3-(2-methylpyridin-4-yl)-1H-indazol-5-yl)pyridin-2(1H)-one,
1-(3-bromo-4-fluorobenzyl)-4-(3-(2-methylpyridin-4-yl)-1H-indazol-5-yl)pyridin-2(1H)-one,
1-(3-iodobenzyl)-4-(3-(2-methylpyridin-4-yl)-1H-indazol-5-yl)pyridin-2(1H)-one
1-(3-chloro-5-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(2-(trifluoromethyl)benzyl)pyridin-2(1H)-one,
1-benzyl-4-(3-(2-methylpyridin-4-yl)-1H-indazol-5-yl)pyridin-2(1H)-one,
1-(3,4-difluorobenzyl)-4-(3-(2-methylpyridin-4-yl)-1H-indazol-5-yl)pyridin-2(1H)-one,
1-(4-chloro-3-fluorobenzyl)-4-(3-(2-methylpyridin-4-yl)-1H-indazol-5-yl)pyridin-2(1H)-one,
1-(3-chloro-2-fluorobenzyl)-4-(3-(2-methylpyridin-4-yl)-1H-indazol-5-yl)pyridin-2(1H)-one,
4-((4-(3-(2-methylpyridin-4-yl)-1H-indazol-5-yl)-2-oxopyridin-1 (2H)-yl)methyl)benzonitrile,
1-(3-chloro-4-fluorobenzyl)-4-(3-(2-methylpyridin-4-yl)-1H-indazol-5-yl)pyridin-2(1H)-one,
1-(5-chloro-2-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3-(trifluoromethoxy)benzyl)pyridin-2(1H)-one,
1-(3-fluorobenzyl)-4-(3-(2-methylpyridin-4-yl)-1H-indazol-5-yl)pyridin-2(1H)-one,
1-(4-bromo-3-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3-(trifluoromethyl)benzyl)pyridin-2(1H)-one,
3-((4-(3-(2-methylpyridin-4-yl)-1H-indazol-5-yl)-2-oxopyridin-1 (2H)-yl)methyl)benzonitrile,
1-(2,5-difluorobenzyl)-4-(3-(2-methylpyridin-4-yl)-1H-indazol-5-yl)pyridin-2(1H)-one,
1-(3-fluoro-5-(trifluoromethyl)benzyl)-4-(3-(2-methylpyridin-4-yl)-1H-indazol-5-yl)pyridin-2(1H)-one,
1-(1-(3-bromo-5-fluorophenyl)ethyl)-4-(3-(2-methylpyridin-4-yl)-1H-indazol-5-yl)pyridin-2(1H)-one,
1-(3-bromo-2-fluorobenzyl)-4-(3-(2-methylpyridin-4-yl)-1H-indazol-5-yl)pyridin-2(1H)-one,
4-(3-(2-methylpyridin-4-yl)-1H-indazol-5-yl)-1-(3,4,5-trifluorobenzyl)pyridin-2(1H)-one,
1-(4-fluoro-3-(trifluoromethyl)benzyl)-4-(3-(2-methylpyridin-4-yl)-1H-indazol-5-yl)pyridin-2(1H)-one,
1-(4-fluoro-3-(trifluoromethoxy)benzyl)-4-(3-(2-methylpyridin-4-yl)-1H-indazol-5-yl)pyridin-2(1H)-one,
1-(3,5-difluorobenzyl)-4-(3-(2-methylpyridin-4-yl)-1H-indazol-5-yl)pyridin-2(1H)-one,
1-(2-fluoro-3-(trifluoromethyl)benzyl)-4-(3-(2-methylpyridin-4-yl)-1H-indazol-5-yl)pyridin-2(1H)-one,
1-(2,3-difluorobenzyl)-4-(3-(2-methylpyridin-4-yl)-1H-indazol-5-yl)pyridin-2(1H)-one,
1-(2-amino-3-fluorobenzyl)-4-(3-(2-methylpyridin-4-yl)-1H-indazol-5-yl)pyridin-2(1H)-one,
N-(2-fluoro-6-((4-(3-(2-methylpyridin-4-yl)-1H-indazol-5-yl)-2-oxopyridin-1 (2H)-yl)methyl)phenyl)methanesulfonamide,
1-(3-chloro-4-fluorobenzyl)-4-(3-(1-methyl-1H-pyrazol-4-yl)-1H-indazol-5-yl)pyridin-2(1H)-one,
1-(5-bromo-2-fluorobenzyl)-4-(3-(1-methyl-1H-pyrazol-4-yl)-1H-indazol-5-yl)pyridin-2(1H)-one,
1-(3-bromo-5-fluorobenzyl)-4-(3-(1-methyl-1H-pyrazol-4-yl)-1H-indazol-5-yl)pyridin-2(1H)-one,
1-(2-fluoro-6-((4-(3-(2-methylpyridin-4-yl)-1H-indazol-5-yl)-2-oxopyridin-1 (2H)-yl)methyl)phenyl)urea,
N-(2-fluoro-6-((4-(3-(2-methylpyridin-4-yl)-1H-indazol-5-yl)-2-oxopyridin-1 (2H)-yl)methyl)phenyl)acetamide, 4-(3-(2-methylpyridin-4-yl)-1H-indazol-5-yl)-1-((2-(trifluoromethyl)pyridin-4-yl)methyl)pyridin-2(1H)-one, 1-(3-bromobenzyl)-4-(3-(1-methyl-1H-pyrazol-4-yl)-1H-indazol-5-yl)pyridin-2(1H)-one, 4-(3-(1-methyl-1H-pyrazol-4-yl)-1H-indazol-5-yl)-1-(3-(trifluoromethyl)benzyl)pyridin-2(1H)-one, 1-(3-fluoro-5-(trifluoromethyl)benzyl)-4-(3-(1-methyl-1H-pyrazol-4-yl)-1H-indazol-5-yl)pyridin-2(1H)-one, 1-(3-iodobenzyl)-4-(3-(1-methyl-1H-pyrazol-4-yl)-1H-indazol-5-yl)pyridin-2(1H)-one, 1-((1H-indazol-6-yl)methyl)-4-(3-(2-methylpyridin-4-yl)-1H-indazol-5-yl)pyridin-2(1H)-one, 4-(3-(1-methyl-1H-pyrazol-4-yl)-1H-indazol-5-yl)-1-((2-(trifluoromethyl)pyridin-4-yl)methyl)pyridin-2(1H)-one, 1-(1-(3-bromo-5-fluorophenyl)ethyl)-4-(3-(1-methyl-1H-pyrazol-4-yl)-1H-indazol-5-yl)pyridin-2(1H)-one, 1-(1-(3-chloro-4-fluorophenyl)ethyl)-4-(3-(1-methyl-1H-pyrazol-4-yl)-1H-indazol-5-yl)pyridin-2(1H)-one, 1-(1-(3-chlorophenyl)-2-(methylamino)ethyl)-4-(3-(1-methyl-1H-pyrazol-4-yl)-1H-indazol-5-yl)pyridin-2(1H)-one, (S)-1-(1-(3-chlorophenyl)-2-hydroxyethyl)-4-(3-(2-methylpyridin-4-yl)-1H-pyrazolo[4,3-b]pyridin-5-yl)pyridin-2(1H)-one, (S)-1-(1-(3-chlorophenyl)-2-hydroxyethyl)-4-(3-(2-methylpyridin-4-yl)-1H-pyrazolo[3,4-c]pyridin-5-yl)pyridin-2(1H)-one, 1-(3-bromo-5-fluorobenzyl)-4-(3-(2-isopropoxypyridin-4-yl)-1H-indazol-5-yl)pyridin-2(1H)-one, 1-(3-bromo-5-fluorobenzyl)-4-(3-(6-isopropoxypyridin-3-yl)-1H-indazol-5-yl)pyridin-2(1H)-one, S)-1-(1-(4-chloro-3-fluorophenyl)-2-hydroxyethyl)-4-(3-(6-isopropoxypyridin-3-yl)-1H-indazol-5-yl)pyridin-2(1H)-one, 4-(3-(2-methylpyridin-4-yl)-1H-indazol-5-yl)pyridin-2(1H)-one, 4-(3-(2-methylpyridin-4-yl)-1H-indazol-5-yl)-1-(2-morpholinoethyl)pyridin-2(1H)-one, (S)-1-(1-(3-chloro-4-fluorophenyl)-2-hydroxyethyl)-4-(3-(tetrahydro-2H-pyran-4-yl)-1H-indazol-5-yl)pyridin-2(1H)-one, (S)-1-(1-(3-chloro-4-fluorophenyl)-2-hydroxyethyl)-4-(3-(1-cyclopropyl-1H-pyrazol-4-yl)-1H-indazol-5-yl)pyridin-2(1H)-one, (S)-1-(1-(3-chloro-4-fluorophenyl)-2-hydroxyethyl)-4-(3-(1-(difluoromethyl)-1H-pyrazol-4-yl)-1H-indazol-5-yl)pyridin-2(1H)-one, (S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one, (S)-1-(1-(3-chloro-4-fluorophenyl)-2-hydroxyethyl)-4-(3-(1-(2-m ethoxyethyl)-1H-pyrazol-4-yl)-1H-indazol-5-yl)pyridin-2(1H)-one, (S)-1-(1-(3-bromo-5-fluorophenyl)-2-hydroxyethyl)-4-(3-(6-ethoxypyridin-3-yl)-1H-indazol-5-yl)pyridin-2(1H)-one, (S)-1-(1-(3-chloro-4-fluorophenyl)-2-hydroxyethyl)-4-(3-(2-methylpyridin-4-yl)-1H-pyrazolo[3,4-b]pyridin-5-yl)pyridin-2(1H)-one, (S)-1-(1-(3-bromo-5-fluorophenyl)-2-hydroxyethyl)-4-(3-(6-ethoxypyridin-3-yl)-1H-indazol-5-yl)pyridin-2(1H)-one, (S)-1-(1-(3-bromo-5-fluorophenyl)-2-hydroxyethyl)-4-(3-(6-methoxypyridin-3-yl)-1H-indazol-5-yl)pyridin-2(1H)-one, 4-(3-(2-methylpyridin-4-yl)-1H-pyrazolo[3,4-1-b]pyridin-5-yl)-1-((2-(trifluoromethyl)pyridin-4-yl)methyl)pyridin-2(1H)-one, 1-(1-(3-bromo-5-fluorophenyl)ethyl)-4-(3-(2-methylpyridin-4-yl)-1H-pyrazolo[3,4-b]pyridin-5-yl)pyridin-2(1H)-one, (S)-1-(1-(3-bromo-5-fluorophenyl)-2-hydroxyethyl)-4-(3-(1-methyl-1H-pyrazol-4-yl)-1H-pyrazolo[3,4-b]pyridin-5-yl)pyridin-2(1H)-one, 1-(1-(3-chloro-4-fluorophenyl)-2-(methylamino)ethyl)-4-(3-(2-methylpyridin-4-yl)-1H-indazol-5-yl)pyridin-2(1H)-one, (S)-1-(1-(3-chloro-4-fluorophenyl)-2-hydroxyethyl)-4-(3-(1-methyl-1H-pyrazol-4-yl)-1H-pyrazolo[3,4-b]pyridin-5-yl)pyridin-2(1H)-one, (S)-1-(1-(3-chloro-4-fluorophenyl)-2-hydroxyethyl)-4-(3-(1-(2-hydroxyethyl)-1H-pyrazol-4-yl)-1H-indazol-5-yl)pyridin-2(1H)-one, (S)-1-(1-(3-bromo-5-fluorophenyl)-2-hydroxyethyl)-4-(3-(6-ethoxypyridin-3-yl)-1H-pyrazolo[3,4-b]pyridin-5-yl)pyridin-2(1H)-one, (S)-1-(1-(3-bromo-5-fluorophenyl)-2-hydroxyethyl)-4-(3-(4-fluorophenyl)-1H-indazol-5-yl)pyridin-2(1H)-one, 4-(3-(2-methylpyridin-4-yl)-1H-pyrazolo[4,3-b]pyridin-5-yl)-1-((2-(trifluoromethyl)pyridin-4-yl)methyl)pyridin-2(1H)-one, (S)-1-(1-(3-bromo-5-fluorophenyl)-2-hydroxyethyl)-4-(2'-methyl-1H,2'H-[3,5'-biindazol]-5-yl)pyridin-2(1H)-one, (S)-4-(3-(benzo[d]thiazol-6-yl)-1H-indazol-5-yl)-1-(1-(3-bromo-5-fluorophenyl)-2-hydroxyethyl)pyridin-2(1H)-one, (S)-1-(1-(3-bromo-5-fluorophenyl)-2-hydroxyethyl)-4-(3-(2-methoxypyridin-4-yl)-1H-indazol-5-yl)pyridin-2(1H)-one, 4-(3-(6-methoxypyridin-3-yl)-1H-indazol-5-yl)-1-((2-(trifluoromethyl)pyridin-4-yl)methyl)pyridin-2(1H)-one, 4-(3-(4-fluorophenyl)-1H-indazol-5-yl)-1-((2-(trifluoromethyl)pyridin-4-yl)methyl)pyridin-2(1H)-one, (S)-1-(1-(3-bromo-5-fluorophenyl)-2-hydroxyethyl)-4-(3-(6-cyclopropoxypyridin-3-yl)-1H-indazol-5-yl)pyridin-2(1H)-one, (S)-1-(1-(3-bromo-5-fluorophenyl)-2-hydroxyethyl)-4-(3-(2-ethoxypyridin-4-yl)-1H-indazol-5-yl)pyridin-2(1H)-one, (S)-1-(1-(3-bromo-5-fluorophenyl)-2-hydroxyethyl)-4-(3-(1-methyl-6-oxo-1,6-dihydropyridin-3-yl)-1H-indazol-5-yl)pyridin-2(1H)-one, (S)-1-(1-(3-bromo-5-fluorophenyl)-2-hydroxyethyl)-4-(3-(1-methyl-2-oxo-1,2-dihydropyridin-4-yl)-1H-indazol-5-yl)pyridin-2(1H)-one, (S)-1-(1-(3-bromo-5-fluorophenyl)-2-hydroxyethyl)-4-(3-(6-methoxypyridin-3-yl)-1H-pyrazolo[4,3-b]pyridin-5-yl)pyridin-2(1H)-one, 4-(3-(5-fluoropyridin-2-yl)-1H-indazol-5-yl)-1-((2-(trifluoromethyl)pyridin-4-yl)methyl)pyridin-2(1H)-one, (S)-1-(1-(3-bromo-5-fluorophenyl)-2-hydroxyethyl)-4-(3-(6-methoxypyridin-3-yl)-1H-pyrazolo[3,4-c]pyridin-5-yl)pyridin-2(1H)-one, (S)-1-(1-(3-bromo-5-fluorophenyl)-2-hydroxyethyl)-4-(3-(5-fluoropyridin-2-yl)-1H-indazol-5-yl)pyridin-2(1H)-one, 4-(3-(2-(trifluoromethyl)pyridin-4-yl)-1H-indazol-5-yl)-1-((2-(trifluoromethyl)pyridin-4-yl)methyl)pyridin-2(1H)-one, 4-(3-(2-methylpyridin-4-yl)-1H-indazol-5-yl)-1-((2-methylpyridin-4-yl)methyl)pyridin-2(1H)-one,
(S)-4-(3-([1,2,4]triazolo[1,5-a]pyridin-6-yl)-1H-indazol-5-yl)-1-(1-(3-bromo-5-fluorophenyl)-2-hydroxyethyl)pyridin-2(1H)-one,
(S)-1-(1-(3-bromo-5-fluorophenyl)-2-hydroxyethyl)-4-(3-(imidazo[1,2-a]pyridin-6-yl)-1H-indazol-5-yl)pyridin-2(1H)-one,
(S)-1-(1-(3-bromo-5-fluorophenyl)-2-hydroxyethyl)-4-(3-(2-methyl-[1,2,4]triazolo[1,5-a]pyridin-6-yl)-1H-indazol-5-yl)pyridin-2(1H)-one,
4-(3-(2-methylpyridin-4-yl)-1H-indazol-5-yl)-1-((6-(trifluoromethyl)pyridin-3-yl)methyl)pyridin-2(1H)-one,
4-(3-(2-ethylpyridin-4-yl)-1H-indazol-5-yl)-1-((2-(trifluoromethyl)pyridin-4-yl)methyl)pyridin-2(1H)-one,
4-(3-(2-cyclopropylpyridin-4-yl)-1H-indazol-5-yl)-1-((2-(trifluoromethyl)pyridin-4-yl)methyl)pyridin-2(1H)-one,
(S)-1-(2-hydroxy-1-(2-(trifluoromethyl)pyridin-4-yl)ethyl)-4-(3-(2-methylpyridin-4-yl)-1H-indazol-5-yl)pyridin-2(1H)-one,
4-(3-(2-methylpyridin-4-yl)-1H-indazol-5-yl)-1-((4-(trifluoromethyl)thiazol-2-yl)methyl)pyridin-2(1H)-one,
4-(3-(2-methylpyridin-4-yl)-1H-indazol-5-yl)-1-((2-(trifluoromethyl)pyridin-3-yl)methyl)pyridin-2(1H)-one,
4-(3-(2-methylpyridin-4-yl)-1H-indazol-5-yl)-1-((6-(trifluoromethyl)pyridin-2-yl)methyl)pyridin-2(1H)-one,
(S)-1-(1-(3-bromo-5-fluorophenyl)-2-hydroxyethyl)-4-(3-(1,3-dimethyl-1H-pyrazol-4-yl)-1H-indazol-5-yl)pyridin-2(1H)-one,
4-(3-(2-methylpyridin-4-yl)-1H-indazol-5-yl)-1-((3-(trifluoromethyl)isoxazol-5-yl)methyl)pyridin-2(1H)-one,
1-(1-(3-bromo-5-fluorophenyl)ethyl)-4-(3-((1r,4r)-4-hydroxycyclohexyl)-1H-indazol-5-yl)pyridin-2(1H)-one,
(S)-1-(1-(3-bromo-5-fluorophenyl)-2-hydroxyethyl)-4-(3-(methylamino)-1H-indazol-5-yl)pyridin-2(1H)-one,
4-(3-(2-methylpyridin-4-yl)-1H-indazol-5-yl)-1-(1-(2-(trifluoromethyl)pyridin-4-yl)ethyl)pyridin-2(1H)-one,
(S)-4-(3-(2-methylpyridin-4-yl)-1H-indazol-5-yl)-1-(1-(2-(trifluoromethyl)pyridin-4-yl)ethyl)pyridin-2(1H)-one,
(R)-4-(3-(2-methylpyridin-4-yl)-1H-indazol-5-yl)-1-(1-(2-(trifluoromethyl)pyridin-4-yl)ethyl)pyridin-2(1H)-one,
6-methyl-4-(3-(2-methylpyridin-4-yl)-1H-indazol-5-yl)-1-((2-(trifluoromethyl)pyridin-4-yl)methyl)pyridin-2(1H)-one,
4-(3-(2-methylpyridin-4-yl)-1H-pyrazolo[3,4-c]pyridin-5-yl)-1-((2-(trifluoromethyl)pyridin-4-yl)methyl)pyridin-2(1H)-one,
(S)-1-(1-(3-bromo-5-fluorophenyl)ethyl)-4-(3-(1-methyl-1H-pyrazol-4-yl)-1H-indazol-5-yl)pyridin-2(1H)-one,
(R)-1-(1-(3-bromo-5-fluorophenyl)ethyl)-4-(3-(1-methyl-1H-pyrazol-4-yl)-1H-indazol-5-yl)pyridin-2(1H)-one,
(S)-1-(1-(3-bromo-5-fluorophenyl)-2-hydroxyethyl)-4-(3-(tetrahydro-2H-pyran-4-yl)-1H-indazol-5-yl)pyridin-2(1H)-one,
1-(1-(3-bromo-5-fluorophenyl)ethyl)-4-(3-(tetrahydro-2H-pyran-4-yl)-1H-indazol-5-yl)pyridin-2(1H)-one,
4-(3-(tetrahydro-2H-pyran-4-yl)-1H-indazol-5-yl)-1-((2-(trifluoromethyl)pyridin-4-yl)methyl)pyridin-2(1H)-one,
4-(3-((1r,4r)-4-hydroxycyclohexyl)-1H-indazol-5-yl)-1-((2-(trifluoromethyl)pyridin-4-yl)methyl)pyridin-2(1H)-one,
4-(3-((1s,4s)-4-hydroxycyclohexyl)-1H-indazol-5-yl)-1-((2-(trifluoromethyl)pyridin-4-yl)methyl)pyridin-2(1H)-one,
1-((S)-1-(3-bromo-5-fluorophenyl)-2-hydroxyethyl)-4-(3-(tetrahydrofuran-3-yl)-1H-indazol-5-yl)pyridin-2(1H)-one, and
1-((S)-1-(3-bromo-5-fluorophenyl)-2-hydroxyethyl)-4-(3-(3-hydroxypyrrolidin-1-yl)-1H-indazol-5-yl)pyridin-2(1H)-one.

26. A pharmaceutical composition comprising a compound according to claim 1, and/or a stereoisomer, a stable isotope, or a pharmaceutically acceptable salt thereof, admixed with at least one pharmaceutically acceptable carrier.

27. The pharmaceutical composition of claim 26, further comprising at least one therapeutic co-agent.

28. The pharmaceutical composition of claim 27, wherein the at least one therapeutic co-agent is selected from anti-cancer compounds, analgesics, and anti-inflammatory compounds.

29. A method to treat cancer, comprising administering to a subject in need of such treatment a therapeutically effective amount of a compound according to claim 1, and/or a stereoisomer, a stable isotope, or a pharmaceutically acceptable salt thereof, or a pharmaceutical composition of claim 26.

30. The method of claim 29, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, kidney cancer, lung cancers leukemias multiple myeloma, lymphoid disorders, skin cancers neuroblastoma, ovarian cancer, pancreatic cancer, prostate cancer, rectal cancer, sarcoma, testicular cancer, and thyroid cancer.

31. A method to treat an inflammatory disease in a patient comprising administering to a subject in need of such treatment a therapeutically effective amount of a compound according to claim 1, and/or a stereoisomer, a stable isotope, or a pharmaceutically acceptable salt thereof, or a pharmaceutical composition of claim 26, wherein the inflammatory disease is selected from rheumatoid arthritis, psoriasis, and eczema.

* * * * *

UNITED STATES PATENT AND TRADEMARK OFFICE
CERTIFICATE OF CORRECTION

PATENT NO. : 11,242,334 B2
APPLICATION NO. : 16/640813
DATED : February 8, 2022
INVENTOR(S) : Jintao Zhang et al.

Page 1 of 2

It is certified that error appears in the above-identified patent and that said Letters Patent is hereby corrected as shown below:

In the Claims

• Claim 1, Column 154, Line 53, "–SO$_2$N($^{19a}$R$^{19b}$))" should read -- SO$_2$N($^{19a}$R$^{19b}$) --.

• Claim 18, Column 157, Lines 23-24, "–N(R$^{38a}$R$^{36b}$), –N(R$^{36a}$)C(O)R$^{35}$, –SO$_2$N(R$^{38a}$R$^{36b}$) and –N(R$^{38a}$)SO$_2$R$^{35}$" should read -- –N(R$^{36a}$R$^{36b}$), –N(R$^{36a}$)C(O)R$^{35}$, –SO$_2$N(R$^{36a}$R$^{36b}$) and –N(R$^{36a}$)SO2R$^{35}$ --.

• Claim 20, Column 157, Line 59, "groups groups" should read -- groups --.

• Claim 21, Column 159, Line 2, "groups groups" should read -- groups --.

• Claim 22, Column 159, Line 33, "wherein A1 is selected from" should read -- wherein A$^1$ is selected from --.

• Claim 22, Column 160, Line 17, "groups groups" should read -- groups --.

• Claim 23, Column 160, Lines 36-44, the structure of the compound:

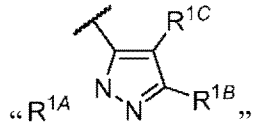

Should read as:

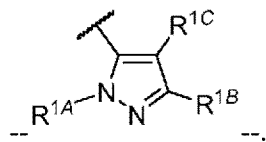

• Claim 23, Column 160, Lines 44-50, the structure of the compound:

Signed and Sealed this
Eighteenth Day of October, 2022

Katherine Kelly Vidal
*Director of the United States Patent and Trademark Office*

CERTIFICATE OF CORRECTION (continued)
U.S. Pat. No. 11,242,334 B2

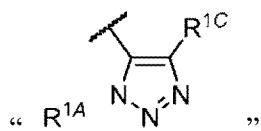

Should read as:

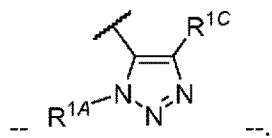

• Claim 23, Column 160, Lines 52-58, the structure of the compound:

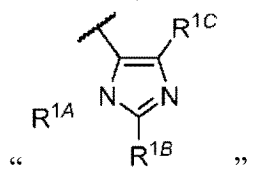

Should read as:

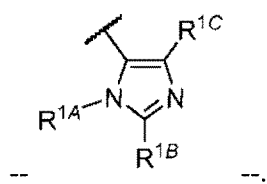

• Claim 23, Column 160, Lines 52-58, the structure of the compound:

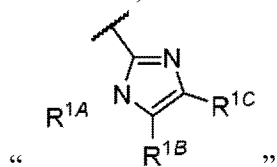

Should read as:

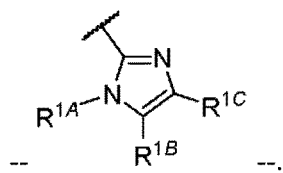

• Claim 25, Column 165, Line 54, "(1-(2-m ethoxyethyl)" should read -- (1-(2-methoxyethyl) --.

• Claim 25, Column 166, Line 1, "4-(3-(2-methylpyridin-4-yl)-1H-pyrazolo[3,4-1-b]pyri-" should read -- 4-(3-(2-methylpyridin-4-yl)-1H-pyrazolo[3,4-b]pyri- --.